United States Patent
Rothberg et al.

(10) Patent No.: US 10,288,566 B2
(45) Date of Patent: *May 14, 2019

(54) INTEGRATED DEVICE WITH EXTERNAL LIGHT SOURCE FOR PROBING DETECTING AND ANALYZING MOLECULES

(71) Applicant: Quantum-Si Incorporated, Guilford, CT (US)

(72) Inventors: Jonathan M. Rothberg, Guilford, CT (US); Ali Kabiri, Madison, CT (US); Jason W. Sickler, Madison, CT (US); Brett J. Gyarfas, Guilford, CT (US); Jeremy Lackey, Guilford, CT (US); Gerard Schmid, Guilford, CT (US); Lawrence C. West, San Jose, CA (US); Keith G. Fife, Palo Alto, CA (US); Benjamin Cipriany, Branford, CT (US); Farshid Ghasemi, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/845,996

(22) Filed: Dec. 18, 2017

(65) Prior Publication Data

US 2018/0120229 A1    May 3, 2018

Related U.S. Application Data

(63) Continuation of application No. 14/821,688, filed on Aug. 7, 2015, now Pat. No. 9,885,657.

(Continued)

(51) Int. Cl.
  *G01N 21/64*   (2006.01)
  *C12Q 1/6874*  (2018.01)
  *C12Q 1/6869*  (2018.01)

(52) U.S. Cl.
  CPC ....... *G01N 21/6408* (2013.01); *C12Q 1/6869* (2013.01); *C12Q 1/6874* (2013.01);
  (Continued)

(58) Field of Classification Search
  CPC .......... G01N 21/6408; G01N 21/6428; G01N 21/6454; G01N 21/648; G01N 2021/6419;
  (Continued)

(56) References Cited

U.S. PATENT DOCUMENTS

| 5,198,543 A | 3/1993 | Blanco et al. |
| 5,302,509 A | 4/1994 | Cheeseman |

(Continued)

FOREIGN PATENT DOCUMENTS

| EP | 1681356 A1 | 7/2006 |
| EP | 2182523 A1 | 5/2010 |

(Continued)

OTHER PUBLICATIONS

U.S. Appl. No. 15/641,949, filed Jul. 5, 2017, Rothberg et al.

(Continued)

*Primary Examiner* — Hina F Ayub
(74) *Attorney, Agent, or Firm* — Wolf, Greenfield & Sacks, P.C.

(57) ABSTRACT

System and methods for analyzing single molecules and performing nucleic acid sequencing. An integrated device includes multiple pixels with sample wells configured to receive a sample, which when excited, emits radiation. The integrated device includes at least one waveguide configured to propagate excitation energy to the sample wells from a (Continued)

region of the integrated device configured to couple with an excitation energy source. A pixel may also include at least one element for directing the emission energy towards a sensor within the pixel. The system also includes an instrument that interfaces with the integrated device. The instrument may include an excitation energy source for providing excitation energy to the integrated device by coupling to an excitation energy coupling region of the integrated device. One of multiple markers distinguishable by temporal parameters of the emission energy may label the sample and configuration of the sensor within a pixel may allow for detection of a temporal parameter associated with the marker labeling the sample.

17 Claims, 97 Drawing Sheets

Related U.S. Application Data

(60) Provisional application No. 62/164,464, filed on May 20, 2015, provisional application No. 62/035,258, filed on Aug. 8, 2014.

(52) U.S. Cl.
CPC ....... *G01N 21/648* (2013.01); *G01N 21/6428* (2013.01); *G01N 21/6454* (2013.01); *G01N 2021/6419* (2013.01); *G01N 2021/6421* (2013.01); *G01N 2021/6439* (2013.01); *G01N 2021/6463* (2013.01); *G01N 2201/0696* (2013.01); *G01N 2201/08* (2013.01); *G01N 2201/12* (2013.01)

(58) Field of Classification Search
CPC ... G01N 2021/6421; G01N 2021/6439; G01N 2021/6463; G01N 2201/0696; G01N 2201/08; G01N 2201/12; C12Q 1/6869; C12Q 1/6874
See application file for complete search history.

(56) References Cited

U.S. PATENT DOCUMENTS

| | | |
|---|---|---|
| 5,471,515 A | 11/1995 | Fossum et al. |
| 5,674,743 A | 10/1997 | Ulmer |
| 5,822,472 A | 10/1998 | Danielzik et al. |
| 5,912,155 A | 6/1999 | Chatterjee et al. |
| 6,078,705 A | 6/2000 | Neuschafer et al. |
| 6,137,117 A | 10/2000 | Feldstein et al. |
| 6,159,686 A * | 12/2000 | Kardos .................. B82Y 15/00 250/484.2 |
| 6,198,869 B1 | 3/2001 | Kraus et al. |
| 6,210,896 B1 | 4/2001 | Chan |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,280,939 B1 | 8/2001 | Allen |
| 6,327,410 B1 | 12/2001 | Walt et al. |
| 6,355,420 B1 | 3/2002 | Chan |
| 6,399,320 B1 | 6/2002 | Markau et al. |
| 6,399,335 B1 | 6/2002 | Kao et al. |
| 6,437,345 B1 | 8/2002 | Bruno-Raimondi et al. |
| 6,607,883 B1 | 8/2003 | Frey et al. |
| 6,716,394 B2 | 4/2004 | Jensen et al. |
| 6,825,921 B1 | 11/2004 | Modlin et al. |
| 6,893,816 B1 * | 5/2005 | Beattie ................. B01J 19/0046 422/68.1 |
| 6,936,702 B2 | 8/2005 | Williams et al. |
| 7,033,762 B2 | 4/2006 | Nelson et al. |
| 7,052,847 B2 | 5/2006 | Korlach et al. |
| 7,057,026 B2 | 6/2006 | Barnes et al. |
| 7,153,672 B1 | 12/2006 | Eickbush et al. |
| 7,158,224 B2 | 1/2007 | Montagu |
| 7,170,050 B2 | 1/2007 | Turner et al. |
| 7,179,654 B2 | 2/2007 | Verdonk et al. |
| 7,270,951 B1 | 9/2007 | Stemple et al. |
| 7,345,764 B2 | 3/2008 | Bulovic et al. |
| 7,393,640 B2 | 7/2008 | Kumar et al. |
| 7,405,281 B2 | 7/2008 | Xu et al. |
| 7,462,452 B2 | 12/2008 | Williams et al. |
| 7,595,883 B1 | 9/2009 | El Gamal et al. |
| 7,630,073 B2 | 12/2009 | Lundquist et al. |
| 7,731,902 B2 | 6/2010 | Nagatomo et al. |
| 7,738,086 B2 | 6/2010 | Shepard et al. |
| 7,745,116 B2 | 6/2010 | Williams |
| 7,820,983 B2 | 10/2010 | Lundquist et al. |
| 7,871,777 B2 | 1/2011 | Schneider et al. |
| 7,873,085 B2 | 1/2011 | Babushkin et al. |
| 7,875,440 B2 | 1/2011 | Williams et al. |
| 7,968,702 B2 | 6/2011 | Wegener et al. |
| 7,973,146 B2 | 7/2011 | Shen et al. |
| 7,981,604 B2 | 7/2011 | Quake |
| 8,058,030 B2 | 11/2011 | Smith et al. |
| 8,133,672 B2 | 3/2012 | Bjornson et al. |
| 8,153,375 B2 | 4/2012 | Travers et al. |
| 8,174,696 B2 | 5/2012 | Ebbesen et al. |
| 8,274,034 B2 | 9/2012 | Vogel et al. |
| 8,274,040 B2 | 9/2012 | Zhong et al. |
| 8,278,728 B2 | 10/2012 | Murshid |
| 8,323,939 B2 | 12/2012 | Hanzel et al. |
| 8,343,746 B2 | 1/2013 | Rank et al. |
| 8,349,605 B1 * | 1/2013 | Lear .................. G01N 21/552 435/288.7 |
| 8,465,699 B2 | 6/2013 | Fehr et al. |
| 8,481,264 B2 | 7/2013 | Bjornson et al. |
| 8,501,406 B1 | 8/2013 | Gray et al. |
| 8,501,922 B2 | 8/2013 | Otto et al. |
| 8,502,169 B2 | 8/2013 | Rigneault et al. |
| 8,580,539 B2 | 11/2013 | Korlach |
| 8,865,077 B2 | 10/2014 | Chiou et al. |
| 8,921,086 B2 | 12/2014 | Hanzel et al. |
| 9,062,091 B2 | 6/2015 | Bjornson et al. |
| 9,127,259 B2 | 9/2015 | Bjornson et al. |
| 9,784,679 B2 | 10/2017 | Rothberg et al. |
| 9,885,657 B2 * | 2/2018 | Rothberg ............. C12Q 1/6874 |
| 2002/0031836 A1 | 3/2002 | Feldstein |
| 2002/0110839 A1 * | 8/2002 | Bach ...................... B82Y 5/00 435/7.9 |
| 2003/0215938 A1 | 11/2003 | Sandell et al. |
| 2004/0169842 A1 | 9/2004 | Dosluoglu et al. |
| 2005/0079526 A1 * | 4/2005 | Senisterra ........... G01N 21/253 435/6.12 |
| 2007/0194247 A1 | 8/2007 | Reid et al. |
| 2007/0247628 A1 | 10/2007 | Kivelae |
| 2007/0281288 A1 | 12/2007 | Belkin et al. |
| 2008/0008418 A1 | 1/2008 | Smith et al. |
| 2008/0050747 A1 | 2/2008 | Korlach et al. |
| 2010/0009872 A1 | 1/2010 | Eid et al. |
| 2010/0173394 A1 | 7/2010 | Colston et al. |
| 2010/0255487 A1 | 10/2010 | Beechem et al. |
| 2010/0323406 A1 | 12/2010 | Vatta et al. |
| 2011/0136201 A1 | 6/2011 | Mao et al. |
| 2011/0165652 A1 | 7/2011 | Hardin et al. |
| 2011/0221889 A1 | 9/2011 | Knox et al. |
| 2011/0236983 A1 | 9/2011 | Beechem et al. |
| 2012/0094332 A1 | 4/2012 | Lee et al. |
| 2012/0183977 A1 * | 7/2012 | Bunce ............... G01N 33/54366 435/7.92 |
| 2012/0322692 A1 | 12/2012 | Pham et al. |
| 2013/0023039 A1 | 1/2013 | Zaccarin et al. |
| 2013/0071849 A1 | 3/2013 | Kong et al. |
| 2013/0217007 A1 | 8/2013 | Kamtekar et al. |
| 2013/0278930 A1 | 10/2013 | Liu et al. |
| 2014/0061677 A1 | 3/2014 | Jakoby et al. |
| 2014/0199016 A1 | 7/2014 | Grott et al. |
| 2014/0307230 A1 | 10/2014 | Hajjar et al. |
| 2014/0308004 A1 | 10/2014 | Doany et al. |
| 2015/0003780 A1 | 1/2015 | Taira |
| 2015/0124336 A1 | 5/2015 | Kaufman |

(56) References Cited

U.S. PATENT DOCUMENTS

| | | | |
|---|---|---|---|
| 2015/0141267 A1 | 5/2015 | Rothberg et al. | |
| 2015/0141268 A1 | 5/2015 | Rothberg et al. | |
| 2015/0293021 A1* | 10/2015 | Finkelstein | G01N 21/6452 506/13 |
| 2015/0309261 A1 | 10/2015 | Kobyakov et al. | |
| 2016/0041095 A1 | 2/2016 | Rothberg et al. | |
| 2016/0047747 A1* | 2/2016 | Lafferty | C12Q 1/6874 506/38 |
| 2016/0084761 A1 | 3/2016 | Rothberg et al. | |
| 2016/0133668 A1 | 5/2016 | Rothberg et al. | |
| 2016/0153888 A1* | 6/2016 | Hook | G01N 21/6458 435/288.7 |
| 2016/0370291 A1 | 12/2016 | Rothberg et al. | |
| 2016/0370292 A1 | 12/2016 | Rothberg et al. | |
| 2017/0003227 A1* | 1/2017 | Peumans | G01N 21/6452 |
| 2017/0082544 A1* | 3/2017 | Van Dorpe | G01N 21/6428 |
| 2017/0168236 A1* | 6/2017 | Huang | G02B 6/34 |
| 2017/0299518 A1 | 10/2017 | Rothberg et al. | |

FOREIGN PATENT DOCUMENTS

| | | |
|---|---|---|
| EP | 2339632 A1 | 6/2011 |
| EP | 2391639 | 12/2011 |
| EP | 2134871 B1 | 3/2012 |
| WO | WO 91/06678 A1 | 5/1991 |
| WO | WO 2005/073407 A1 | 8/2005 |
| WO | WO 2007/015168 A2 | 2/2007 |
| WO | WO 2013/171197 A1 | 11/2013 |

OTHER PUBLICATIONS

PCT/US2014/066014, Jan. 28, 2015, Invitation to Pay Additional Fees.
PCT/US2014/066014, Apr. 7, 2015, International Search Report and Written Opinion.
PCT/US2014/066014, May 26, 2016, International Preliminary Report on Patentability.
PCT/US2015/044360, Nov. 20, 2015, Invitation to Pay Additional Fees.
PCT/US2015/044360, Feb. 3, 2016, International Search Report and Written Opinion.
PCT/US2015/044378, Oct. 30, 2015, Invitation to Pay Additional Fees.
PCT/US2015/044378, Jan. 15, 2016, International Search Report and Written Opinion.
PCT/US2015/044379, Nov. 2, 2015, Invitation to Pay Additional Fees.
PCT/US2015/044379, Jan. 15, 2016, International Search Report and Written Opinion.
PCT/US2014/066013, Jan. 28, 2015, Invitation to Pay Additional Fees.
PCT/US2014/066013, Apr. 7, 2015, International Search Report and Written Opinion.
PCT/US2014/066013, May 26, 2016, International Preliminary Report on Patentability.
PCT/US2014/066010, Jan. 28, 2015, Invitation to Pay Additional Fees.
PCT/US2014/066010, Apr. 7, 2015, International Search Report and Written Opinion.
PCT/US2014/066010, May 26, 2016, International Preliminary Report on Patentability.
International Preliminary Report on Patentability for International Application No. PCT/US2014/066014 dated May 26, 2016.
International Preliminary Report on Patentability for International Application No. PCT/US2014/066013 dated May 26, 2016.
International Preliminary Report on Patentability for International Application No. PCT/US2014/066010 dated May 26, 2016.
International Search Report and Written Opinion for International Application No. PCT/US2014/066014 dated Apr. 7, 2015.
International Search Report and Written Opinion for International Application No. PCT/US2015/044360 dated Feb. 3, 2016.
International Search Report and Written Opinion for International Application No. PCT/US2015/044378 dated Jan. 15, 2016.
International Search Report and Written Opinion for International Application No. PCT/US2015/044379 dated Jan. 15, 2016.
International Search Report and Written Opinion for International Application No. PCT/US2014/066013 dated Apr. 7, 2015.
International Search Report and Written Opinion for International Application No. PCT/US2014/066010 dated Apr. 7, 2015.
Invitation to Pay Additional Fees for International Application No. PCT/US2014/066014 dated Jan. 28, 2015.
Invitation to Pay Additional Fees for International Application No. PCT/US2015/044360 dated Nov. 20, 2015.
Invitation to Pay Additional Fees for International Application No. PCT/US2015/044378 dated Oct. 30, 2015.
Invitation to Pay Additional Fees for International Application No. PCT/US2015/044379 dated Nov. 2, 2015.
Invitation to Pay Additional Fees for International Application No. PCT/US2014/066013 dated Jan. 28, 2015.
Invitation to Pay Additional Fees for International Application No. PCT/US2014/066010 dated Jan. 28, 2015.
[No Author Listed] 5.2 Megapixels, 1-inch, 250fps, global-shutter CMOS image sensor, Anafocus, Oct. 2012, 4 pages, Sevilla, Spain.
[No Author Listed] Description of our technology, CrackerBio, 4 pages, Taiwan.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed May 9, 2014].
[No Author Listed] OLED-on-CMOS for Sensors and Microdisplays, IPMS Fraunhofer Institut Photonische Mikrosysteme, 2 pages, Dresden, Germany.
Achermann, Exciton—Plasmon Interactions in Metal— Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.
Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.
Aouani et al., Plasmonic Antennas for Directional Sorting of Fluorescence Emission, Nano Letters, May 18, 2011, 11(6):2400-6.
Aouani et al., Saturated excitation of fluorescence to quantify excitation enhancement in aperture antennas, Optics Express, Jul. 30, 2012, 20(16):18085-90.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.

(56) References Cited

OTHER PUBLICATIONS

Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional Si3N4 waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.org/abs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule Fret Efficiency Determination for Surface Immobilized DNA Using Maximum Likelihood Calculated Lifetimes, J. Phys. Chem, Mar. 22, 2007, 111(11):2986-90.
Eggeling et al., Monitoring conformational dynamics of a single molecule by selective fluorescence spectroscopy. Proc. Natl. Acad. Sci. 1998;95:1556-61.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459. [last accessed Dec. 17, 2013].
Fu et al., A microfabricated fluorescence-activated cell sorter. Nature Biotechnology. Nov. 1999; 17(11): 1109-1111.
Gorin et al., Fabrication of silicon nitride waveguides for visible-light using PECVD: a study of the effect of plasma frequency on optical properties, Optics Express, Sep. 1, 2008, 16(18):13509-16.
Gryczynski et al., Two-photon excitation by the evanescent wave from total internal reflection. Anal Biochem., Apr. 5, 1997;247(1):69-76.
Haase et al., Upconverting Nanoparticles, Angewandte Chemie International Edition, Jun. 20, 2011, 50(26):5808-29.
Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.
Hansard et al., Time-of-Flight Cameras: Principles, Methods and Applications, Nov. 2012, 102 pages, Springer-Verlag, London, UK.
He et al., DNA Sequencing by Capillary Electrophoresis with Four-Decay Fluorescence Detection, Anal. Chem., Dec. 15, 2000, 72(24):5865-73.
Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.
Heucke et al., Placing Individual Molecules in the Center of Nanoapertures, Nano Letters, Feb. 12, 2014, 14(2):391-5.
Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.
Ishii et al., Self-matched high-voltage rectangular wave pulse generator, Rev. Sci. Instrum, Nov. 1985, 56(11):2116-8.
Jun et al., Plasmonic beaming and active control over fluorescent emission, Nature Communications, Apr. 19, 2011, 6 pages.
Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.
Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.
Kano et al., Two-photon-excited fluorescence enhanced by a surface plasmon. Opt Lett. Nov. 15, 1996;21(22):1848-50.
Karow, PacBio Aims to Boost Throughput of SMRT Technology with Microchip Co-development Deal, In Sequence and Clinical Sequencing News, Jul. 24, 2012, 3 pages, GenomeWeb.
Klein et al., Controlling plasmonic hot spots by interfering Airy beams, Optics Letters, Aug. 15, 2012, 37(16): 3402-4.
Korlach et al., Real-time DNA sequencing from single polymerase molecules. Methods Enzymol. May 2010;472:431-55. doi:10.1016/S0076-6879(10)72001-2.
Kreye et al, P-200: Evaluation of different OLED-Stacks for Active-Matrix OLED Microdisplays on CMOS-Substrates, SID 06 Digest, Jun. 2006, 37(1); 979-81.
Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.
Lenne et al., Fluorescence fluctuations analysis in nanoapertures: physical concepts and biological applications, Histochem Cell Biol, Sep. 2008, 130:795-805.
Leslie et al., Convex Lens-Induced Confinement for Imaging Single Molecules, Anal. Chem., Jul. 15, 2010, 82(14):6224-9.
Levy et al., An 852×600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.
Lezec et al., Beaming Light from a Subwavelength Aperture, Science, Aug. 2, 2002, 297(5582):820-2.
Li et al., Employing ~100% Excitons in OLEDs by Utilizing a Fluorescent Molecule with Hybridized Local and Charge-Transfer Excited State, Advanced Functional Materials, Mar. 19, 2014, 24(11):1609-14.
Lin et al., Cosine-Gauss Plasmon Beam: A Localized Long-Range Nondiffracting Surface Wave, Physical Review Letters, Aug. 31, 2012, 109(9):093904-1-5.
McGinty et al., Wide-field fluorescence lifetime imaging of cancer, Biomedical Optics Express, Sep. 1, 2010, 1(2): 627-40.
Misra et al., White organic LEDs and their recent advancements, Semiconductor Science and Technology, Apr. 25, 2006, 21(7):R35-47.
Mitchell et al., Nanosecond Fluorescence Lifetime Imaging with gated CCD detection and pulsed laser excitation, Photonic Research Systems Ltd., May 1, 2013, 13 pages, Newhaven East Sussex UK.
Murshid et al., Array of concentric CMOS photodiodes for detection and de-multiplexing of spatially modulated optical channels, Optics & Laser Technology, Sep. 2009, 41(6):764-9.
Murshid et al., CMOS Detectors: Concentric photodiode array enables spatial-domain multiplexing, Laser Focus World, Apr. 1, 2009, 10 pages, http://www.laserfocusworld.com/articles/print/volume-45/issue-4/features/cmos-detectors-concentric-photodiode-array-enables-spatial-domain-multiplexing.html, [last accessed Dec. 12, 2013].
Murshid et al., Concentric octagonal CMOS photodiodes for direct detection of spatially multiplexed optical fiber channels, Optical Society of America, Oct. 2008, 1 page.
Nozik, Multiple exciton generation in semiconductor quantum dots, Chemical Physics Letters, May 20, 2008, 457(1-3):3-11.
Park et al., A dual-modality optical coherence tomography and fluorescence lifetime imaging microscopy system for simultaneous morphological and biochemical tissue characterization, Biochemical Optics Express, Aug. 2, 2010, 1(1):186-200.
Pfeifer et al., Improved optical outcoupling of OLED microdisplays by nanostructured substrates, IEEE Semiconductor Conference Dresden, Sep. 18-27, 2011, 4 pages, Dresden, Germany.
Poddubny et al., Photonic quasicrystalline and aperiodic structures, Physica E: Low-dimensional Systems and Nanostructures, May 2010, 42(7): 1871-95.

(56) References Cited

OTHER PUBLICATIONS

Pons et al., Solution-phase single quantum dot fluorescence resonance energy transfer. J Am Chem Soc., Nov. 29, 2006;128(47):15324-31.
Pudavar, Fluorescence Lifetime Imaging (FILM), Leica Microsystems Inc., Oct. 25, 2009, 60 pages, Exton, PA.
Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.
Ramuz et al., Coupling light from an organic light emitting diode (OLED) into a single-mode waveguide: Toward monolithically integrated optical sensors, Journal of Applied Physics, Apr. 2009, 105(8):084508-1-7.
Ran et al., Design of a 16 gray scales 320×240 pixels OLED-on-silicon driving circuit, Journal of Semiconductors, Jan. 2009, 30(1):015010-1-4.
Reckziegel et al., Optical sensors based on monlithic integrated organic light-emitting diodes (OLEDs), Proceedings of SPIE Optical Sensors, Apr. 28, 2008, vol. 7003: 8 pages.
Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.
Richter et al., OLED-on-CMOS based bidirectional microdisplay for near-to-eye and sensor applications, IEEE Semiconductor Conference Dresden, Sep. 27-28, 2011, 3 pages, Dresden, Germany.
Rigneault et al., Enhancement of Single-Molecule Fluorescence Detection in Subwavelength Apertures, Physical Review Letters, Sep. 9, 2005, 95(11): 117401-1-4.
Romero-Garcia et al., Silicon nitride back-end optics for biosensor applications, Proc. of SPIE Integrated Optics: Physics and Simulations, May 7, 2013, vol. 8781: 87810W-1-11.
Romero-Garcia et al., Visible wavelength silicon nitride focusing grating coupler with AlCu/TiN reflector. Optics Letters. Jul. 15, 2013, 38(14):2521-3.
Rui et al., Demonstration of beam steering via dipole-coupled plasmonic spiral antenna, Scientific Reports, Jul. 19, 2013, 7 pages.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent Lifetime Multiplexing Analysis, IEEE Biomed Circuits Syst., Sep. 1, 2008, 2(3): 204-11.
Schalberger et al., 60.4: Distinguished Paper: A Fully Integrated 1" AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html, [last accessed May 9, 2014].
Taitt et al., Evanescent wave fluorescence biosensors. Biosens Bioelectron. Jun. 2005;20(12):2470-87. Epub Dec. 8, 2004.
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013, 21(8): 10121-10132.
Toma et al., Surface plasmon-coupled emission on plasmonic Bragg gratings, Optics Express, Jun. 18, 2012, 20(13):14042-53.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.
Unfricht et al., Grating-coupled surface plasmon resonance: a cell and protein microarray platform. Proteomics. Nov. 2005;5(17):4432-42.
Vogel et al., OLED-on-CMOS Integration for Optoelectronic Sensor Applications, Proc. of SPIE Silicon Photonics II, Mar. 1, 2007, vol. 6477:8 pages.
Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.
Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.
Walpole, Slab-coupled optical waveguide lasers: a review, Proc. SPIE Novel In-Plane Semiconductor Lasers III, May 11, 2004, vol. 5365, 124-32.
Wenger et al., Emission and excitation contributions to enhanced single molecule fluorescence by gold nanometric apertures, Optics Express, Mar. 3, 2008, 16(5):3008-20.
Wenger et al., Enhanced fluorescence from metal nanoapertures: physical characterizations and biophotonic applications, Proc. SPIE Plasmonics in Biology and Medicine VII, Feb. 16, 2010, 8 pages.
Wenger, Aperture optical antennas, Optical Antennas, Feb. 2013, 25pages, Cambridge University Press, Cambridge, UK.
Willoughby, Elastically Averaged Precision Alignment, Massachusetts Institute of Technology, Jun. 2005, 158 pages, Cambridge, MA.
Xiong et al., Aluminum nitrade as a new material for chip-scale optomechanics and nonlinear optics, New Journal of Physics, Sep. 17, 2012, 14: 21 pages.
Yan-Yan et al., OLED-on-silicon chip with new pixel circuit, J. Cent. South Univ., May 2012 19(5):1276-82.
Yu et al., Light Propagation with Phase Discontinuities: Generalized Laws of Reflection and Refraction, Science, Oct. 21, 2011, 334 (6054):333-7.
Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2012.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.
Zong et al., Equivalent Circuit Model of Top-emitting OLED for the Designing of OLED-on-Silicon Microdisplay, Advanced Materials Research, Nov. 2011, 383-90:7037-42.

* cited by examiner

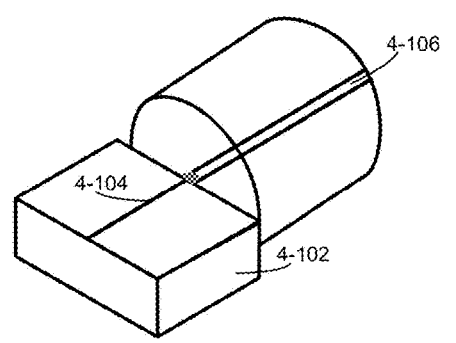
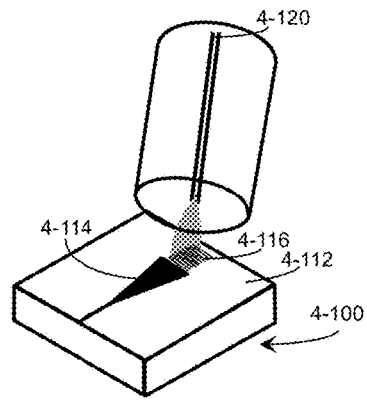
FIG. 4-1A
FIG. 4-1B
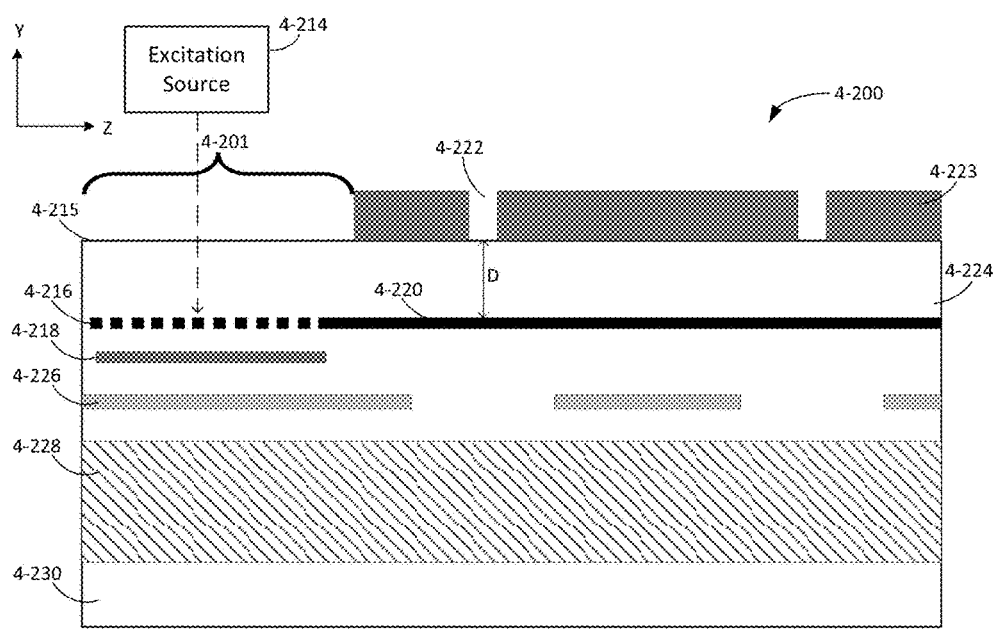
FIG. 4-2

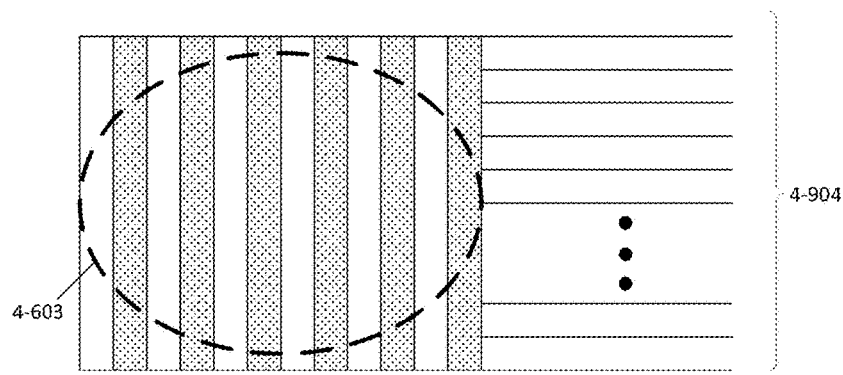
FIG. 4-9A
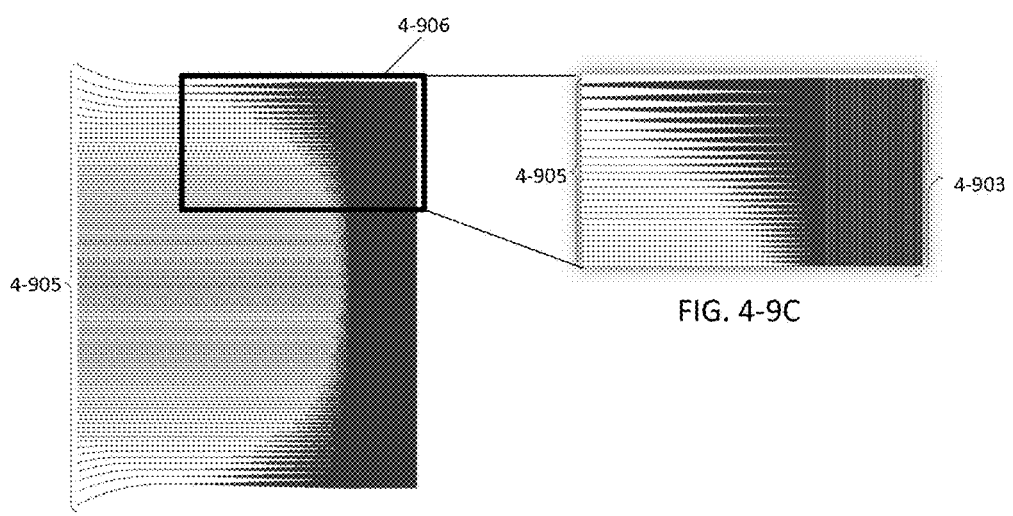
FIG. 4-9B
FIG. 4-9C

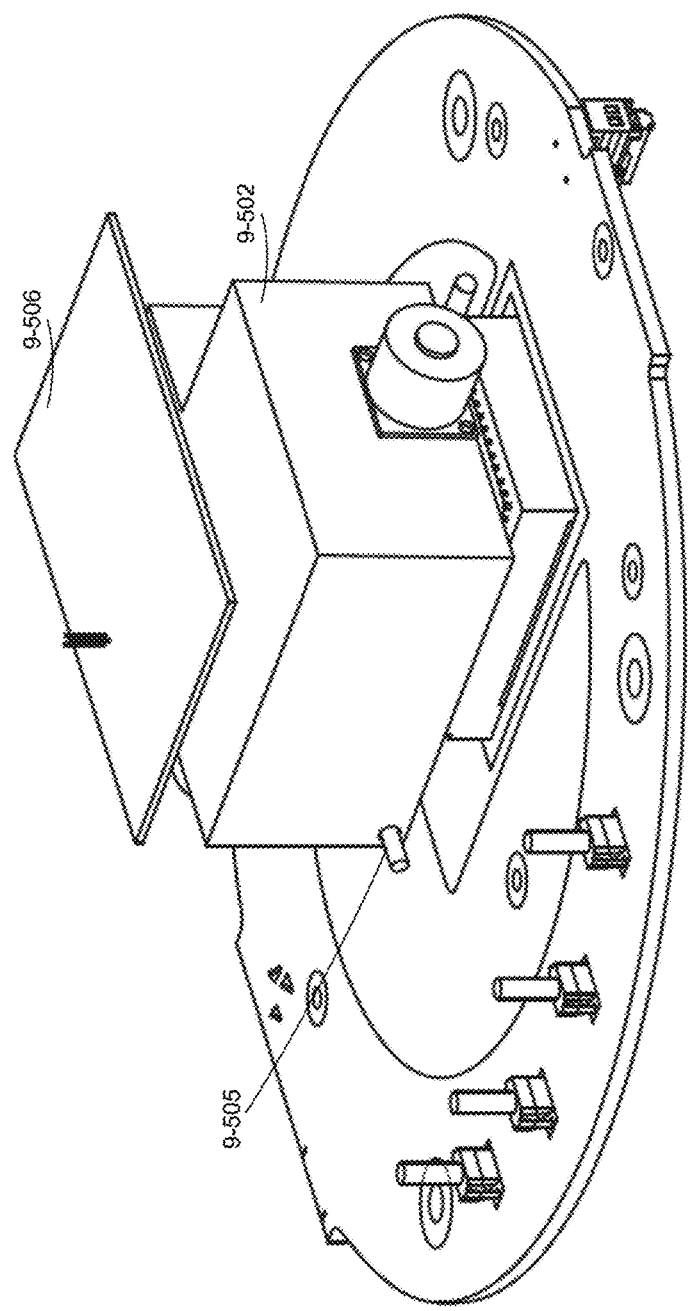

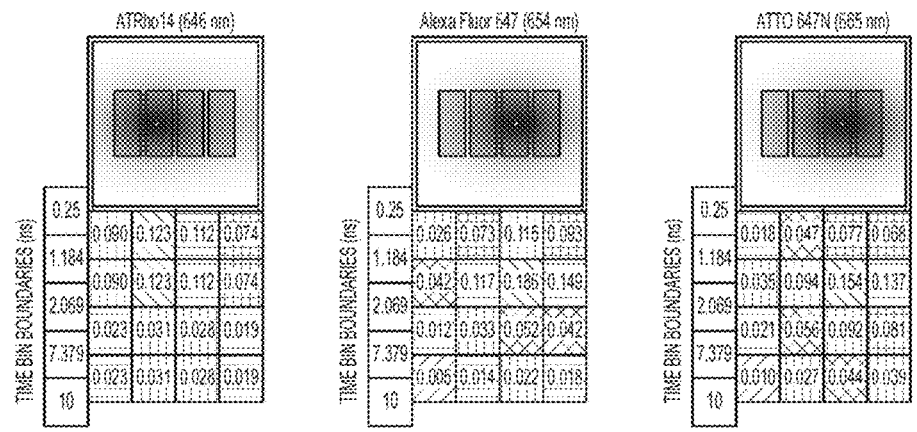
FIG. 10-14
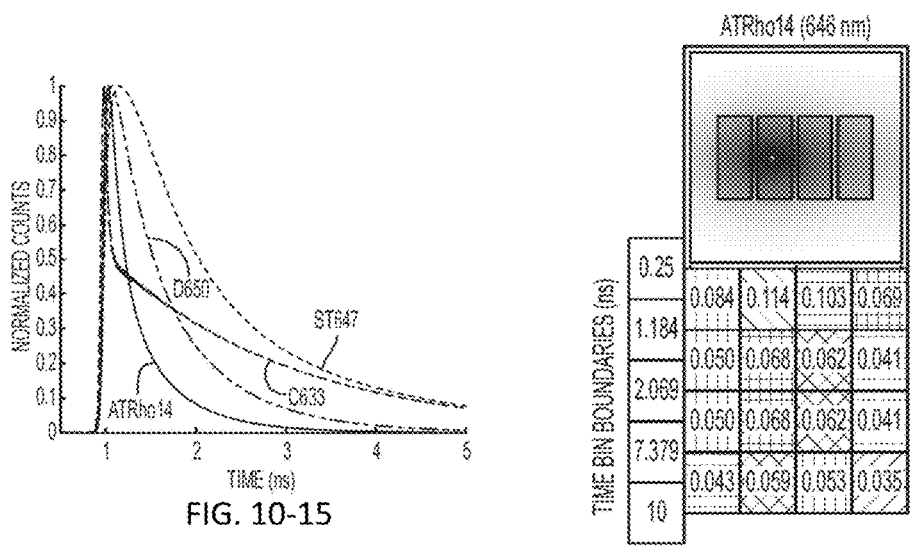
FIG. 10-15
FIG. 10-16

INTEGRATED DEVICE WITH EXTERNAL LIGHT SOURCE FOR PROBING DETECTING AND ANALYZING MOLECULES

RELATED APPLICATIONS

This application is a continuation of U.S. patent application Ser. No. 14/821,688, titled "INTEGRATED DEVICE WITH EXTERNAL LIGHT SOURCE FOR PROBING DETECTING AND ANALYZING MOLECULES," filed Aug. 7, 2015, which claims priority to U.S. Provisional Patent Application No. 62/035,258, titled "INTEGRATED DEVICE WITH EXTERNAL LIGHT SOURCE FOR PROBING, DETECTING, AND ANALYZING MOLECULES," filed Aug. 8, 2014, and U.S. Provisional Patent Application No. 62/164,464, titled "INTEGRATED DEVICE WITH EXTERNAL LIGHT SOURCE FOR PROBING, DETECTING, AND ANALYZING MOLECULES," filed May 20, 2015, each of which is hereby incorporated by reference in its entirety.

This application is related to the following U.S. applications:

U.S. Provisional Patent Application 62/164,506, titled "INTEGRATED DEVICE FOR TEMPORAL BINNING OF RECEIVED PHOTONS", filed May 20, 2015;

U.S. Provisional Patent Application 62/164,485, titled "PULSED LASER," filed May 20, 2015;

U.S. Provisional Patent Application 62/164,482, titled "METHODS FOR NUCLEIC ACID SEQUENCING," filed May 20, 2015;

U.S. Provisional Patent Application 62/035,242, titled "OPTICAL SYSTEM AND ASSAY CHIP FOR PROBING, DETECTING AND ANALYZING MOLECULES," filed Aug. 8, 2014, which is hereby incorporated by reference in its entirety;

U.S. non-provisional patent application Ser. No. 14/821,656, titled "INTEGRATED DEVICE FOR TEMPORAL BINNING OF RECEIVED PHOTONS," filed Aug. 7, 2015; and U.S. non-provisional patent application Ser. No. 14/821,686, titled "OPTICAL SYSTEM AND ASSAY CHIP FOR PROBING, DETECTING AND ANALYZING MOLECULES," filed Aug. 7, 2015.

Each of the above-listed related applications is hereby incorporated by reference in its entirety.

FIELD OF THE APPLICATION

The present application is directed generally to devices, methods and techniques for performing rapid, massively parallel, quantitative analysis of biological and/or chemical samples, and methods of fabricating said devices.

BACKGROUND

Detection and analysis of biological samples may be performed using biological assays ("bioassays"). Bioassays conventionally involve large, expensive laboratory equipment requiring research scientists trained to operate the equipment and perform the bioassays. Moreover, bioassays are conventionally performed in bulk such that a large amount of a particular type of sample is necessary for detection and quantitation.

Some bioassays are performed by tagging samples with luminescent markers that emit light of a particular wavelength. The markers are illuminated with a light source to cause luminescence, and the luminescent light is detected with a photodetector to quantify the amount of luminescent light emitted by the markers. Bioassays using luminescent markers conventionally involve expensive laser light sources to illuminate samples and complicated luminescent detection optics and electronics to collect the luminescence from the illuminated samples.

SUMMARY

The technology described herein relates to apparatus and methods for analyzing specimens rapidly using an active-source-pixel, integrated device that can be interfaced with a mobile computing instrument. The integrated device may be in the form of a disposable or recyclable lab-on-chip or a packaged module that is configured to receive a small amount of a specimen and execute, in parallel, a large number of analyses of samples within the specimen. The integrated device may be used to detect the presence of particular chemical or biological analytes in some embodiments, to evaluate a chemical or biological reactions in some embodiments, and to determine genetic sequences in some embodiments. According to some implementations, the integrated device may be used for single-molecule gene sequencing.

According to some implementations, a user deposits a specimen in a chamber on the integrated device, and inserts the integrated device into a receiving instrument. The receiving instrument, alone or in communication with a computer, automatically interfaces with the integrated device, receives data from the integrated device, processes the received data, and provides results of the analysis to the user. As may be appreciated, integration and computing intelligence on the chip, receiving instrument, and or computer reduce the skill level required from the user.

According to some embodiments of the present application, an integrated device is provided, comprising a plurality of pixels. A pixel of the plurality of pixels comprises a sample well configured to receive excitation energy from an excitation source external to the integrated device and at least one sensor positioned to receive luminescence from a sample positioned in the sample well and generate a signal that provides identification information of the sample based on the received luminescence.

In some embodiments, the signal is indicative of a temporal parameter of the received luminescence. In some embodiments, the temporal parameter is a lifetime associated with the luminescence from the sample. In some embodiments, the signal is indicative of a spectrum of the luminescence. In some embodiments, the signal is indicative of a characteristic wavelength of the luminescence. In some embodiments, the signal and the excitation energy indicates an absorption spectrum of the sample. In some embodiments, the signal and the excitation energy indicates a characteristic wavelength absorbed by the sample.

According to some embodiments of the present application, an integrated device is provided, comprising a pixel region comprising a plurality of pixels. A pixel of the plurality of pixels has a sample well on a surface of the integrated device, wherein the sample well is configured to receive a sample, at least one sensor configured to receive luminescence from the sample well, and at least one waveguide for delivering excitation energy to a vicinity of the sample well. The integrated device comprises an excitation source coupling region comprising a coupling component configured to receive excitation energy from an external excitation energy source and couple the excitation energy into the waveguide.

According to some embodiments of the present application, a system is provided, comprising an excitation source module comprising an excitation source configured to emit a pulse of excitation energy having a first duration of time and an integrated device. The integrated device a sample well configured to receive a sample which, when coupled to the pulse of excitation energy emits luminescence, a sensor that detects the luminescence over a second duration of time, wherein the second duration of time occurs after the first duration of time, a first energy path along which the pulse of excitation energy moves from the excitation source to an energy source coupling component, a second energy path along which the pulse of excitation energy moves from the energy source coupling component to the sample well, and a third energy path along which the luminescence moves from the sample well to the sensor.

According to some embodiments of the present application, a method of detecting the presence of a molecule in a sample is provided. The method comprises introducing a sample labeled with one of a plurality of luminescent markers into a sample well, wherein at least a portion of the plurality of luminescent markers having a different luminescent lifetime values. The method further comprises irradiating the sample well with a pulse of light, measuring the time of arrival of photons emitted from sample well, and determining the identity of a marker based on the time of arrival of the photons.

According to some embodiments of the present application, an integrated device comprising a sample well and a sensor is provided. The sample well is configured to receive a sample labeled with one of a plurality of luminescent markers, each of the plurality of luminescent markers has a different luminescent lifetime value. The sensor is configured to detect luminescence from one of the plurality of luminescent markers over a plurality of time durations, wherein the plurality of time durations is selected to differentiate among the plurality of luminescent markers.

According to some embodiments of the present application, an integrated device comprising a sample well and a plurality of sensors is provided. The sample well is configured to receive a sample labeled with one of a plurality of luminescent markers. Each of the plurality of luminescent markers emit luminescence within one of a plurality of spectral ranges and a portion of the plurality luminescent markers that emit luminescence at one of the plurality of spectral ranges each have different luminescent lifetime values. Each sensor of the plurality of sensors is configured to detect one of the plurality of spectral ranges over a plurality of time durations and the plurality of time durations are selected to differentiate among the portion of the plurality of luminescent markers.

According to some embodiments, a system comprising a plurality of excitation sources and an integrated device is provided. The plurality of excitation sources is configured to emit a plurality of excitation energies, wherein each of the plurality of excitation sources emits pulses of one of the plurality of excitation energies. The integrated device includes a sample well configured to receive a sample labeled with one of a plurality of luminescent markers. A portion of the plurality of luminescent markers emit luminescence after being illuminated by one of the plurality of excitation energies each have different lifetime values. The integrated device further includes a sensor configured to detect luminescence from one of the plurality of luminescent markers over a plurality of time durations after a pulse of one of the plurality of excitation energies, wherein a timing of the pulse of one of the plurality of excitation energies and the plurality of time durations differentiate among the plurality of luminescent markers.

According to some embodiments of the present application, a method of forming an integrated device is provided. The method comprises forming a plurality of sensor regions, wherein a sensor region of the plurality of sensor regions includes a plurality of sensors, forming a plurality of sample wells, wherein a sample well of the plurality of sample wells aligns with a corresponding one of the plurality of sensor regions, and forming at least one waveguide configured to couple excitation energy separate from the plurality of sample wells and direct excitation energy to at least one sample well.

According to some embodiments of the present application, an instrument is provided. The instrument comprises at least one excitation source for providing at least one excitation energy, an excitation source positioning system for aligning the at least one excitation energy emitted by the at least one excitation source to a coupling region of an integrated device, and readout circuitry configured to receive at least one readout signal representative of emission energy detected by a sensor on the integrated device.

According to some embodiments of the present application, a method for sequencing a target nucleic acid molecule is provided. The method comprises providing an integrated device that includes a sample well containing the target nucleic acid molecule, a polymerizing enzyme, and a plurality of types of nucleotides or nucleotide analogs. Each type of nucleotide or nucleotide analog of the plurality of types of nucleotides or nucleotide analogs is labeled with one or a plurality of markers. The method further comprises performing an extension reaction at a priming location of the target nucleic acid molecule in the presence of a polymerizing enzyme to sequentially incorporate at least a portion of the nucleotides or nucleotide analogs into a growing strand that is complementary to the target nucleic acid molecule, wherein upon excitation by excitation energy the markers labelling the nucleotides or nucleotide analogs produce emissions from the sample well upon incorporation into the growing strand and emission lifetimes are distinguishable for the plurality of types of nucleotides or nucleotide analogs. The method further comprises identifying the nucleotides or nucleotide analogs based on signals received from the sensor that are indicative of the emission lifetimes, thereby sequencing the target nucleic acid molecule.

According to some embodiments of the present application, a method for nucleic acid sequencing is provided. The method comprises providing an integrated device comprising a plurality of sample wells and an excitation energy source that is operatively coupled to the plurality of sample wells. Am individual sample well of the plurality of sample wells comprises a target nucleic molecule, a polymerizing enzyme and nucleotides or nucleotide analogs. One marker of a plurality of markers labels each of the nucleotides or nucleotide analogs. The method further comprises subjecting the target nucleic acid molecule to a polymerization reaction to yield a growing strand that is complementary to the target nucleic acid molecule in the presence of the nucleotides or nucleotide analogs and the polymerizing enzyme. The plurality of markers emits emissions upon excitation by excitation energy from the excitation source while the nucleotides or nucleotide analogs are incorporated into the growing strand. The method further comprises detecting lifetimes of the emissions while performing the extension reaction, wherein the lifetimes of the emissions are distinguishable for the plurality of markers, and identifying a sequence of the target nucleic acid molecule based on the lifetimes of the emissions.

According to some embodiments of the present application, a method of analyzing a specimen is provided. The method comprises depositing the specimen on a surface of an integrated device having a plurality of pixels, wherein each pixel has a sample well configured to receive a sample labeled with a first marker of a plurality of markers and a sensor region having at least one sensor, aligning the integrated device with an instrument having at least one excitation energy source for coupling excitation energy to a sample well of a first pixel and readout circuitry for receiving readout signals from the at least one sensor of the sensor region of the first pixel, illuminating the first marker with excitation energy, and detecting, from the readout signals from the at least one sensor of the sensor region of the first pixel, a lifetime of the emission energy generated from an emission by the first marker.

The term "pixel" may be used in the present disclosure to refer to a unit cell of an integrated device. The unit cell may include a sample well and a sensor. The unit cell may further include at least one excitation-coupling optical structure (which may be referred to as a "first structure") that is configured to enhance coupling of excitation energy from the excitation source to the sample well. The unit cell may further include at least one emission-coupling structure that is configured to enhance coupling of emission from the sample well to the sensor. The unit cell may further include integrated electronic devices (e.g., CMOS devices). There may be a plurality of pixels arranged in an array on an integrated device.

The term "optical" may be used in the present disclosure to refer to visible, near infrared, and short-wavelength infrared spectral bands.

The term "tag" may be used in the present disclosure to refer to a tag, probe, or reporter and include a marker attached to a sample to be analyzed or a marker attached to a reactant that may bind with a sample.

The phrase "excitation energy" may be used in the present disclosure to refer to any form of energy (e.g., radiative or non-radiative) delivered to a sample and/or marker within the sample well. Radiative excitation energy may comprise optical radiation at one or more characteristic wavelengths.

The phrase "characteristic wavelength" may be used in the present disclosure to refer to a central or predominant wavelength within a limited bandwidth of radiation. In some cases, it may refer to a peak wavelength of a bandwidth of radiation. Examples of characteristic wavelengths of fluorophores are 563 nm, 595 nm, 662 nm, and 687 nm.

The phrase "characteristic energy" may be used in the present disclosure to refer to an energy associated with a characteristic wavelength.

The term "emission" may be used in the present disclosure to refer to emission from a marker and/or sample. This may include radiative emission (e.g., optical emission) or non-radiative energy transfer (e.g., Dexter energy transfer or Förster resonant energy transfer). Emission results from excitation of a sample and/or marker within the sample well.

The phrase "emission from a sample well" or "emission from a sample" may be used in the present disclosure to refer to emission from a marker and/or sample within a sample well.

The term "self-aligned" may be used in the present disclosure to refer to a microfabrication process in which at least two distinct elements (e.g., a sample well and an emission-coupling structure, a sample well and an excitation-source) may be fabricated and aligned to each other without using two separate lithographic patterning steps in which a first lithographic patterning step (e.g., photolithography, ion-beam lithography, EUV lithography) prints a pattern of a first element and a second lithographic patterning step is aligned to the first lithographic patterning step and prints a pattern of the second element. A self-aligned process may comprise including the pattern of both the first and second element in a single lithographic patterning step, or may comprise forming the second element using features of a fabricated structure of the first element.

The term "sensor" may be used in the present disclosure to refer to one or more integrated circuit devices configured to sense emission from the sample well and produce at least one electrical signal representative of the sensed emission.

The term "nano-scale" may be used in the present disclosure to refer to a structure having at least one dimension or minimum feature size on the order of 150 nanometers (nm) or less, but not greater than approximately 500 nm.

The term "micro-scale" may be used in the present disclosure to refer to a structure having at least one dimension or minimum feature size between approximately 500 nm and approximately 100 micronmicrons.

The phrase "enhance excitation energy" may be used in the present disclosure to refer to increasing an intensity of excitation energy at an excitation region of a sample well. The intensity may be increased by concentrating and/or resonating excitation energy incident on the sample well, for example. In some cases, the intensity may be increased by anti-reflective coatings or lossy layers that allow the excitation energy to penetrate further into the excitation region of a sample well. An enhancement of excitation energy may be a comparative reference to an embodiment that does not include structures to enhance the excitation energy at an excitation region of a sample well.

The terms "about," "approximately," and "substantially" may be used in the present disclosure to refer to a value, and are intended to encompass the referenced value plus and minus acceptable variations. The amount of variation could be less than 5% in some embodiments, less than 10% in some embodiments, and yet less than 20% in some embodiments. In embodiments where an apparatus may function properly over a large range of values, e.g., a range including one or more orders of magnitude, the amount of variation could be a factor of two. For example, if an apparatus functions properly for a value ranging from 20 to 350, "approximately 80" may encompass values between 40 and 160.

The term "adjacent" may be used in the present disclosure to refer to two elements arranged within close proximity to one another (e.g., within a distance that is less than about one-fifth of a transverse or vertical dimension of a pixel). In some cases there may be intervening structures or layers between adjacent elements. In some cases adjacent elements may be immediately adjacent to one another with no intervening structures or elements.

The term "detect" may be used in the present disclosure to refer to receiving an emission at a sensor from a sample well and producing at least one electrical signal representative of or associated with the emission. The term "detect" may also be used in the present disclosure to refer to determining the presence of, or identifying a property of, a particular sample or marker in the sample well based upon emission from the sample well.

The foregoing and other aspects, embodiments, and features of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

Figure 1:
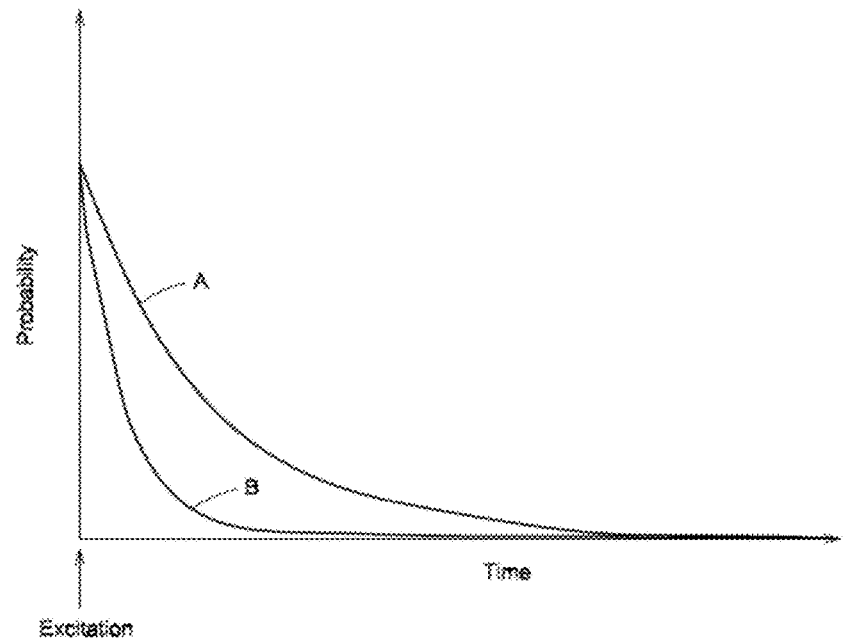

FIG. 1-1 depicts a plot of probability for emitting a photon from a marker as a function of time.

Figures 1, 2, 2A:
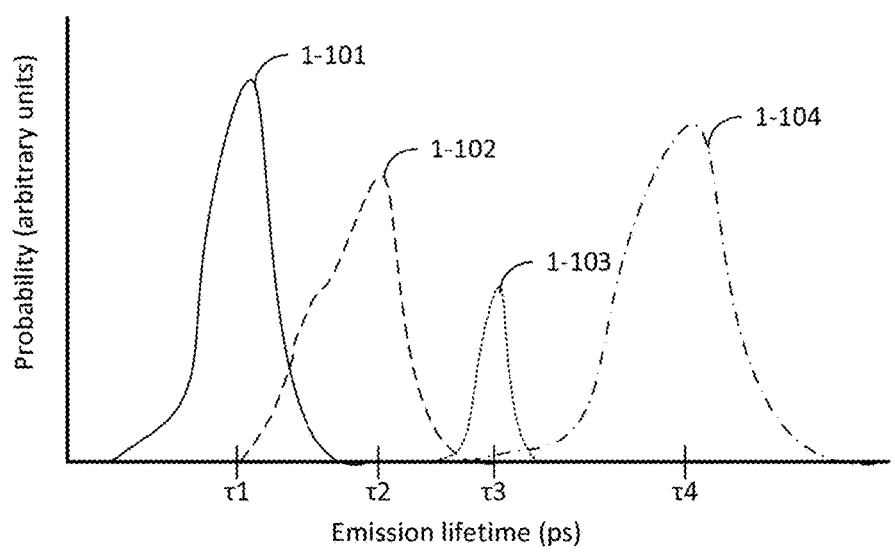

FIG. 1-2A depicts emission timing spectra, according to some embodiments.

Figures 1, 2, 2B:
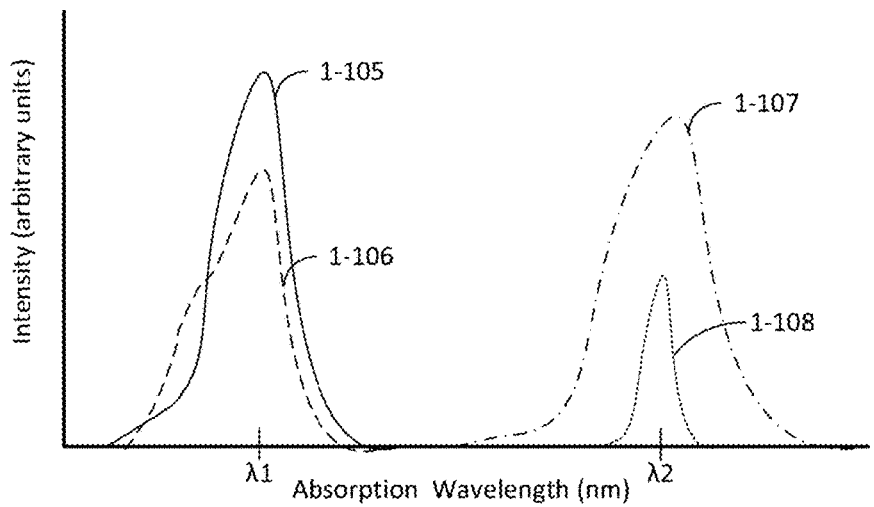

FIG. 1-2B depicts absorption wavelength spectra, according to some embodiments.

Figures 1, 2, 2C:
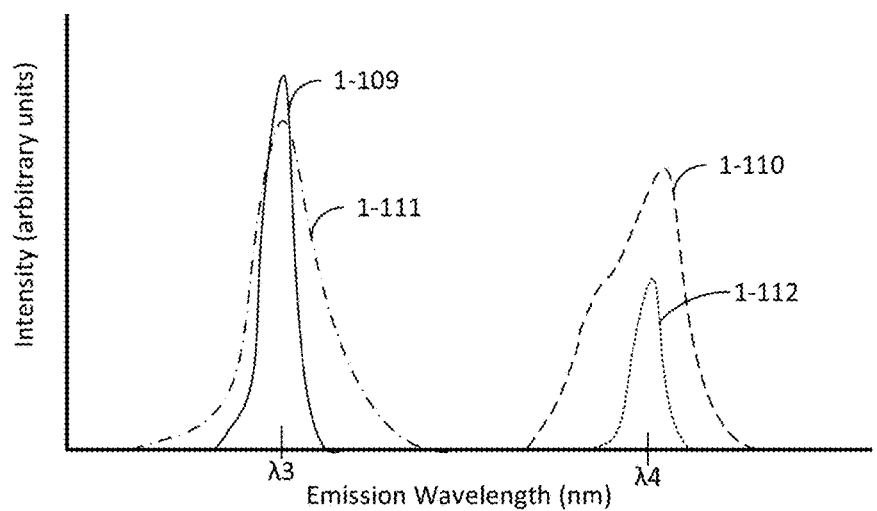

FIG. 1-2C depicts emission wavelength spectra, according to some embodiments.

FIG. 1-3A depicts a phase space for emission wavelength and emission lifetime.

FIG. 1-3B depicts a phase space for absorption wavelength and emission lifetime.

FIG. 1-4 depicts a phase space for emission wavelength, absorption wavelength, and emission lifetime.

Figures 1A, 2:
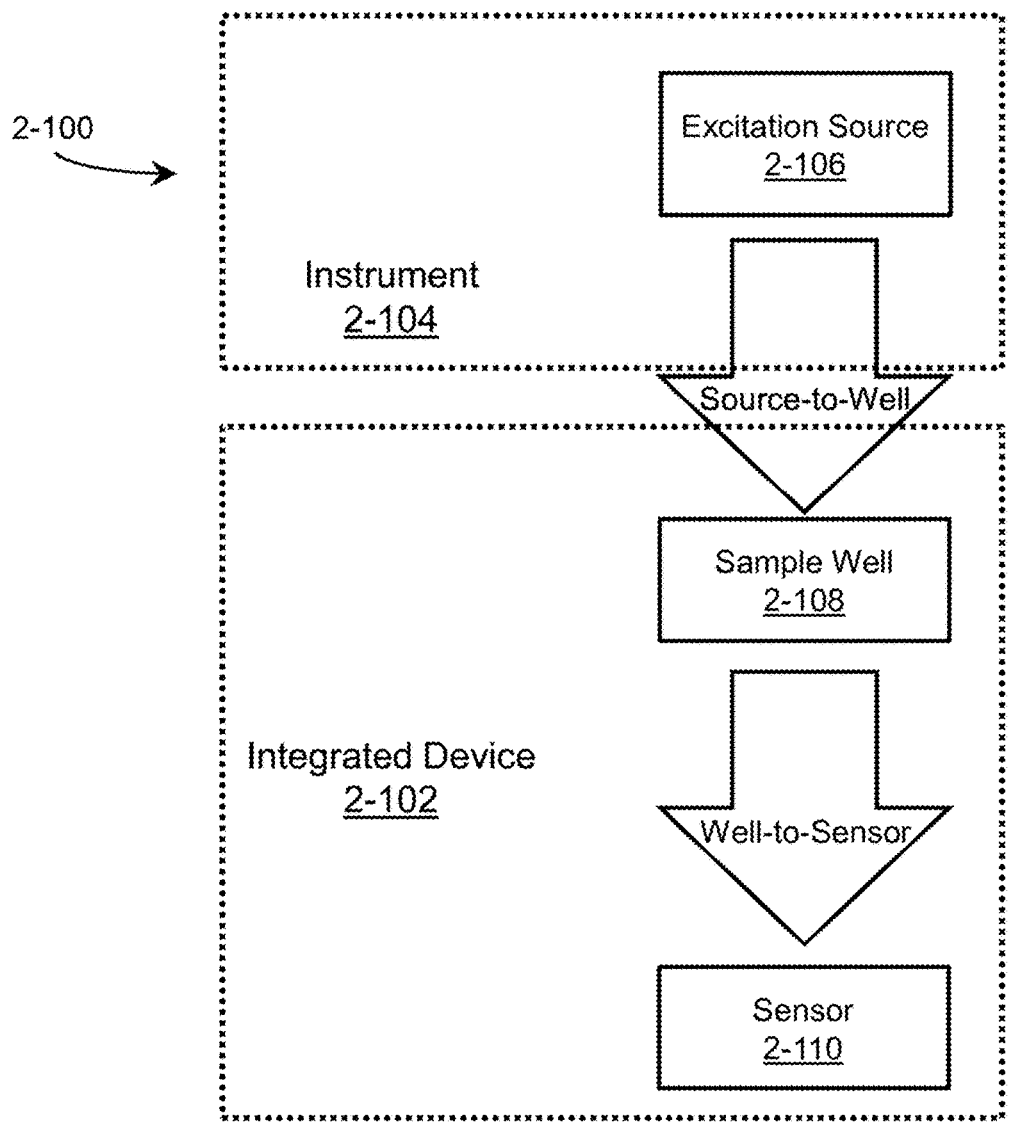

FIG. 2-1A is a block diagram representation of an apparatus that may be used for rapid, mobile analysis of biological and chemical specimens, according to some embodiments.

Figures 1B, 2:
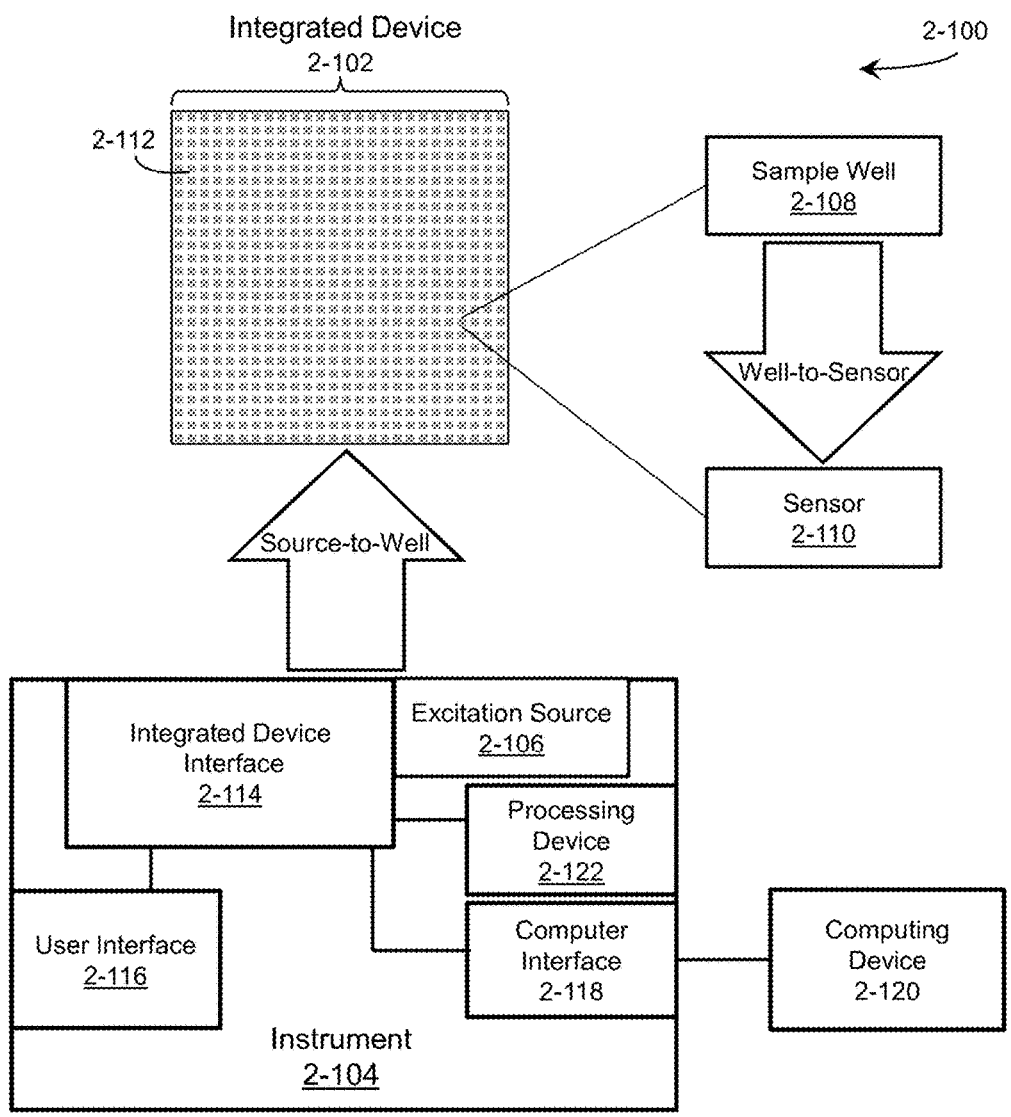
Figure 2:
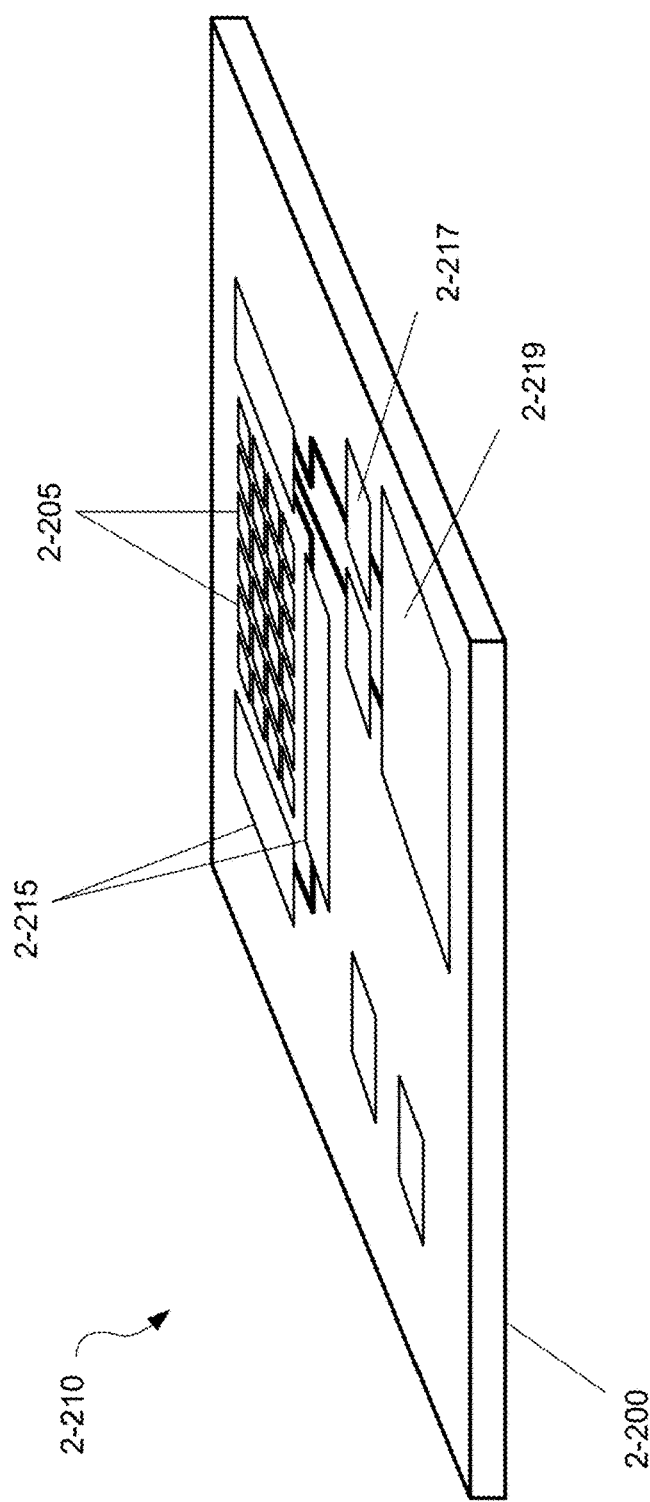
Figures 1A, 3:
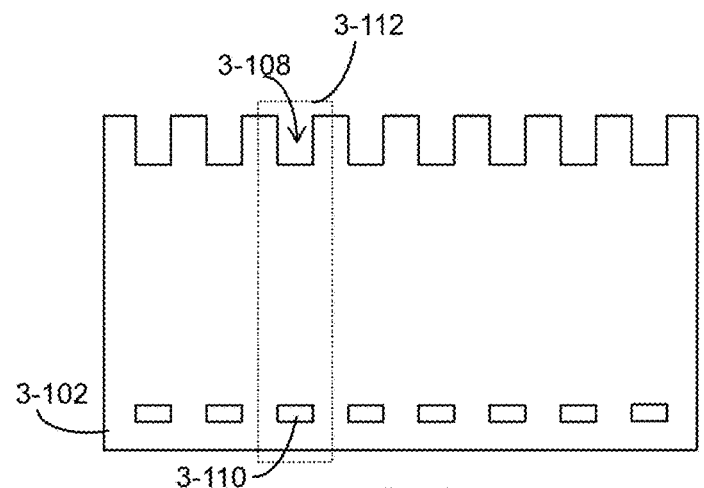
Figures 1B, 3:
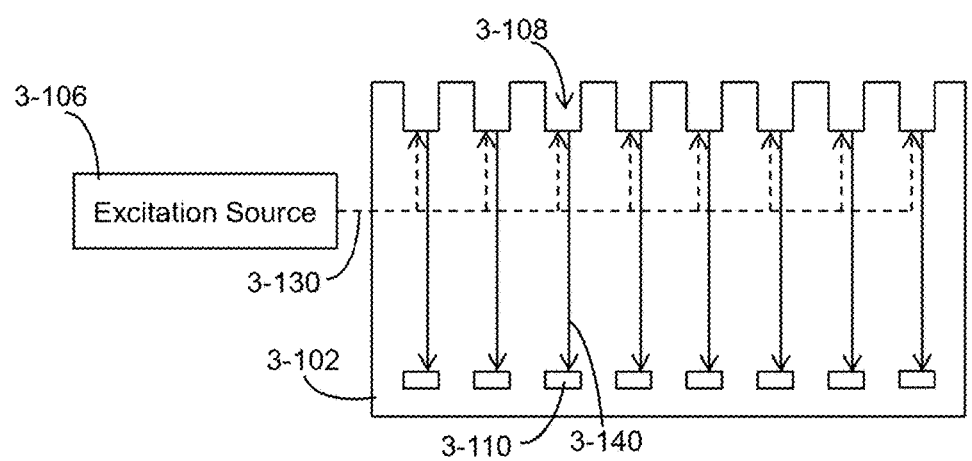
Figures 2, 3:
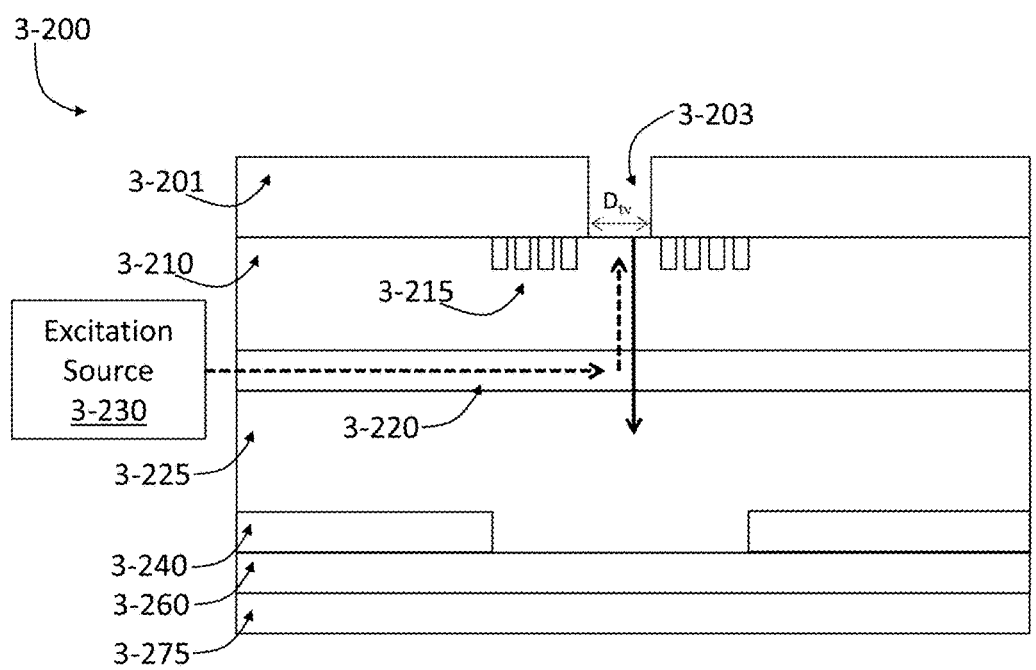

FIG. 2-1B is a block diagram of an integrated device and an instrument, according to some embodiments.

FIG. 2-2 depicts an integrated device, according to some embodiments.

Figures 1, 2, 3, 3A:
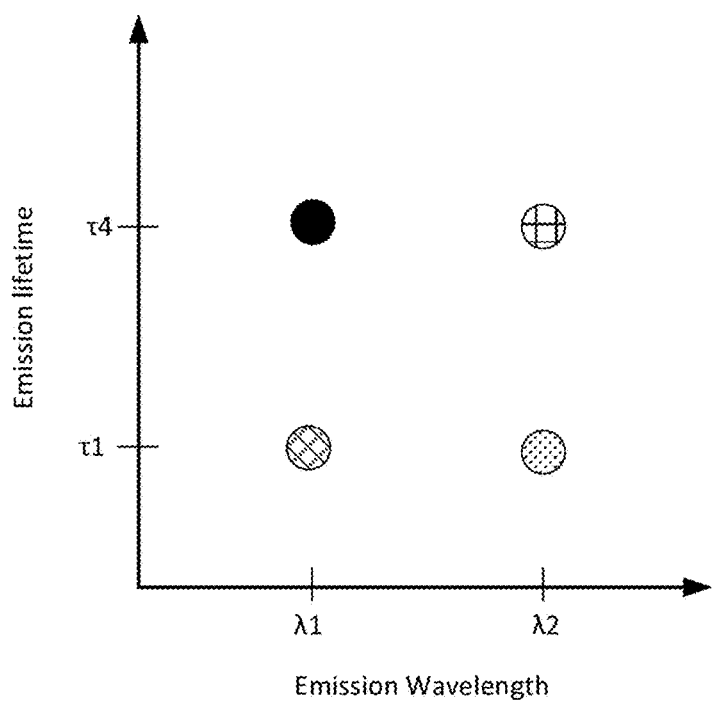

FIG. 3-1A depicts a row of pixels of an integrated device, according to some embodiments.

FIG. 3-1B depicts excitation energy coupling to sample wells in a row of pixels and emission energy from each sample well directed towards sensors, according to some embodiments.

FIG. 3-2 depicts an integrated device and an excitation source, according to some embodiments.

Figures 1, 2, 3, 3B:
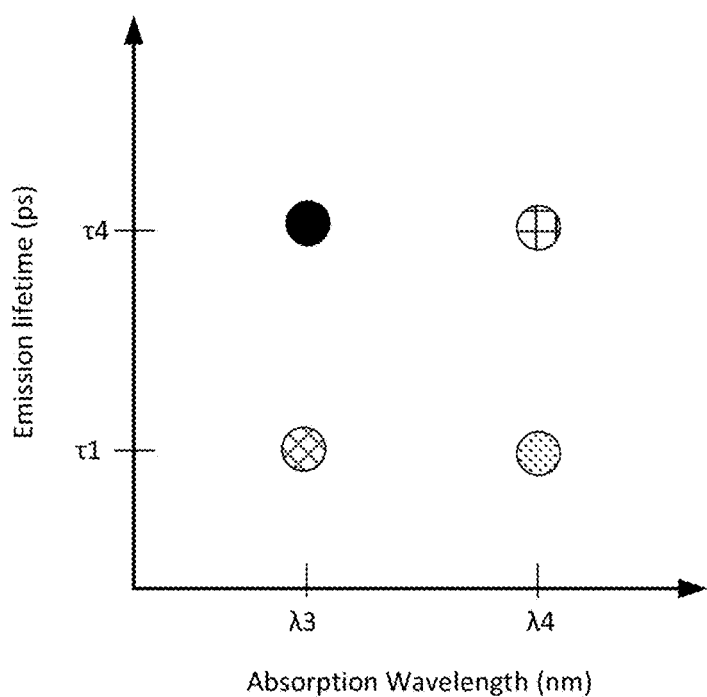
Figures 1, 2, 3, 4:
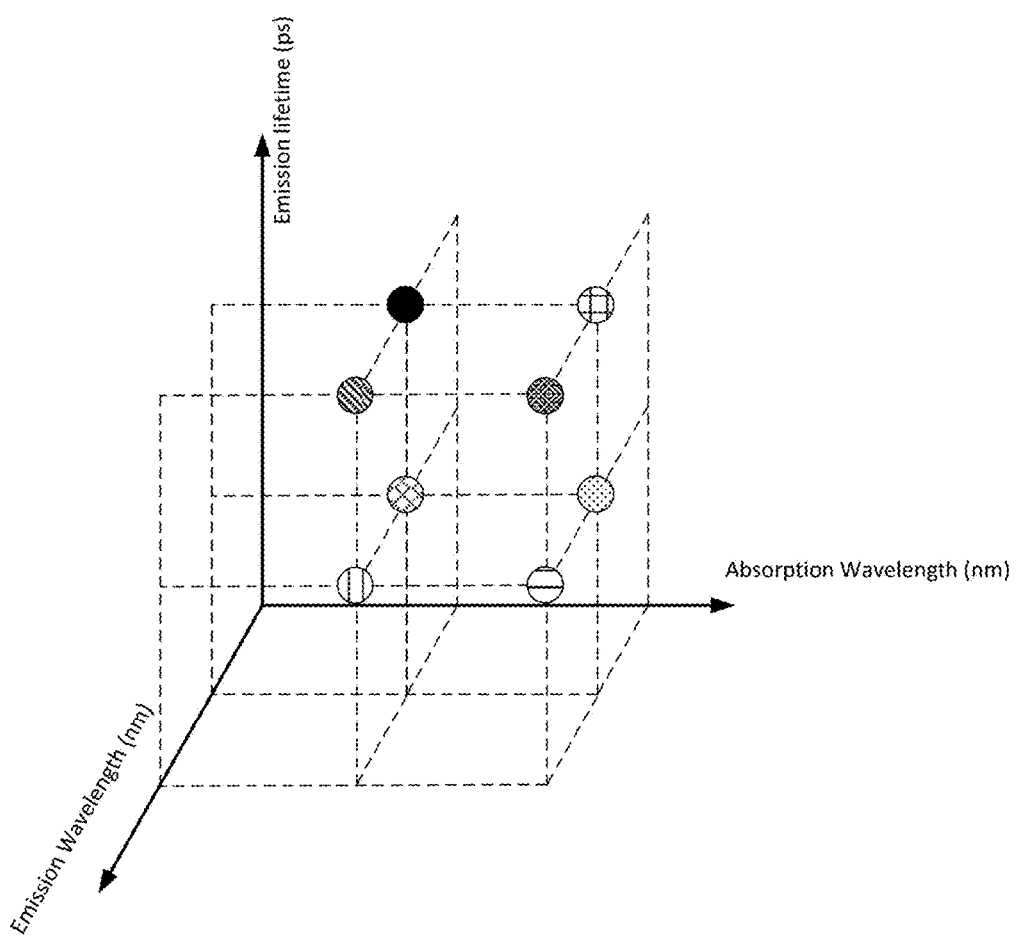

FIG. 4-1A depicts edge-coupling of an excitation source to a waveguide, according to some embodiments.

FIG. 4-1B depicts a grating coupler for coupling an integrated device to an excitation source, according to some embodiments.

FIG. 4-2 depicts an integrated device and an excitation source, according to some embodiments.

FIG. 4-3A depicts an exemplary excitation coupling region, according to some embodiments.

FIG. 4-3B depicts simulations of light intensity for the excitation coupling region shown in FIG. 4-3A.

Figures 3A, 4:
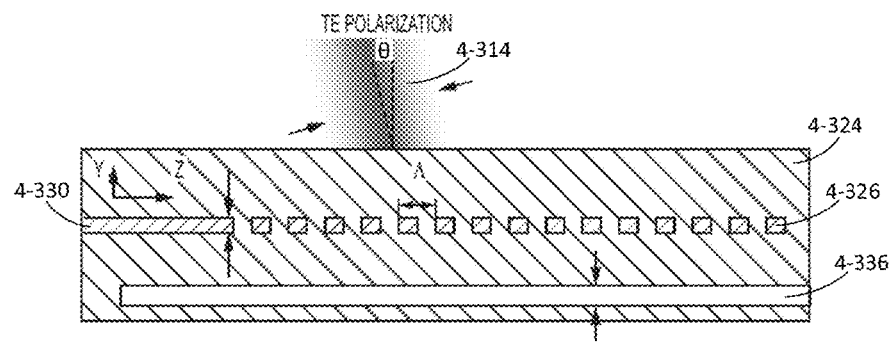
Figures 3B, 4:
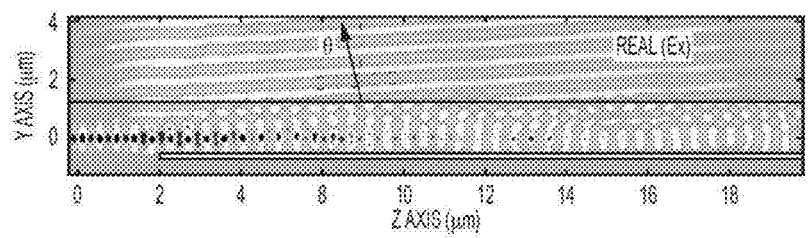
Figures 3C, 4:
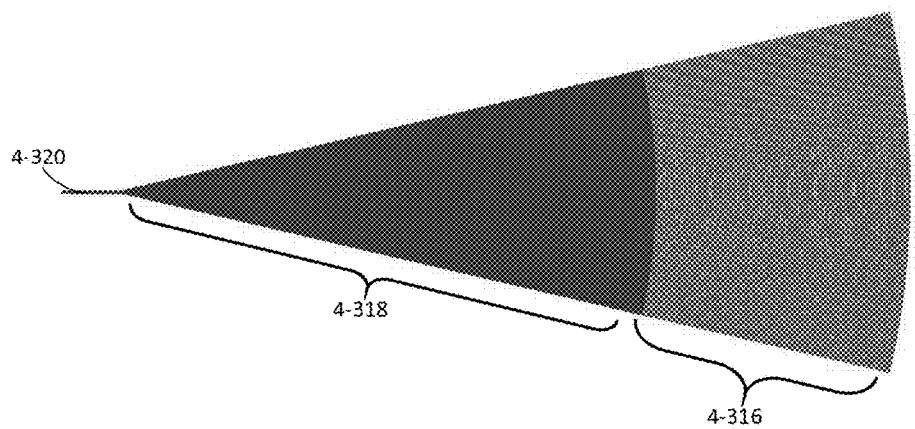
Figure 4:
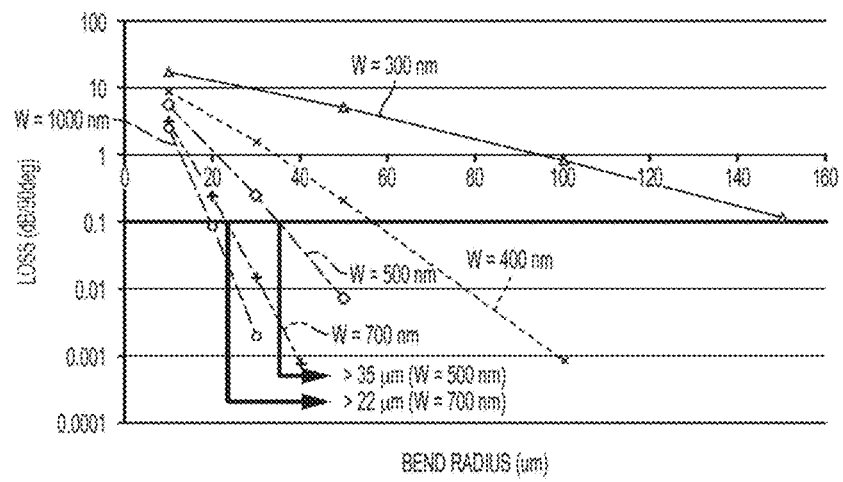

FIG. 4-3C depicts a grating coupler and waveguide, according to some embodiments.

FIG. 4-4 plots loss as a function of bend radius for different waveguide configurations.

Figures 4, 5:
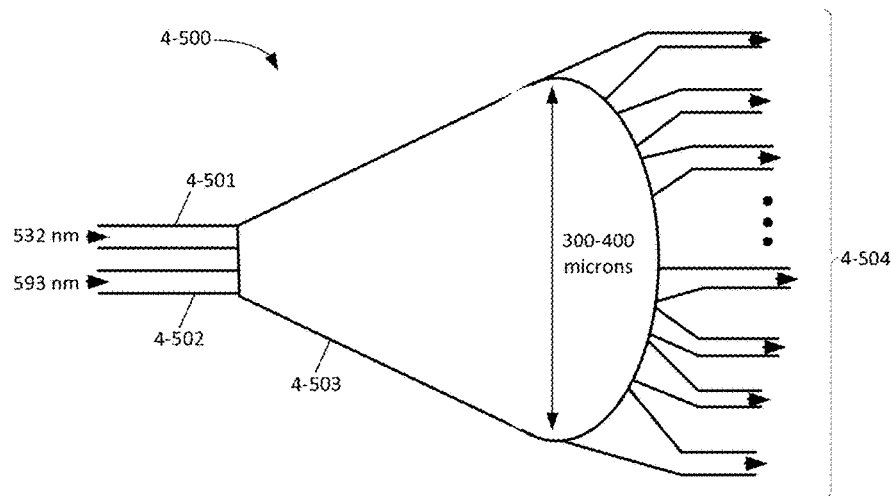

FIG. 4-5 depicts a star coupler, according to some embodiments.

Figures 4, 5, 6:
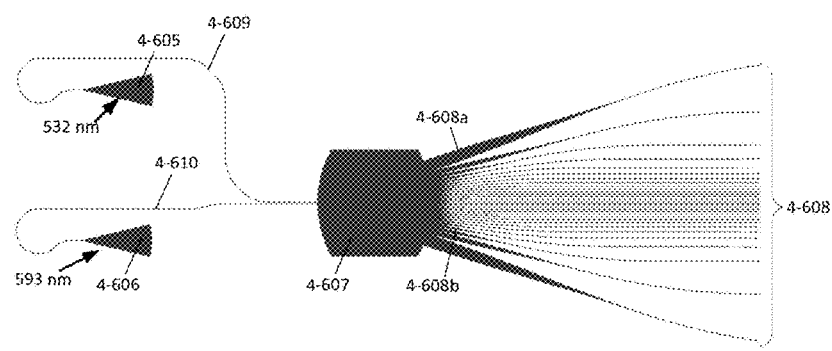

FIG. 4-6 depicts a star coupler for coupling input light from two grating couplers, according to some embodiments.

FIG. 4-7 depicts configurations for MMI splitters, according to some embodiments.

FIG. 4-8 depicts simulations of light intensity through a MMI splitter.

FIG. 4-9A depicts a grating coupler, according to some embodiments.

FIGS. 4-9B and 4-9C depicts a grating coupler, according to some embodiments.

FIG. 5-1 depicts a sample well formed in a pixel region of an integrated device, according to one embodiment.

FIG. 5-2 depicts excitation energy incident on a sample well, according to some embodiments.

FIG. 5-3 illustrates attenuation of excitation energy along a sample well that is formed as a zero-mode waveguide, according to some embodiments.

FIG. 5-4 depicts a sample well that includes a divot, which increases excitation energy at an excitation region associated with the sample well in some embodiments.

FIG. 5-5 compares excitation intensities for sample wells with and without a divot, according to one embodiment.

Figures 1, 5:
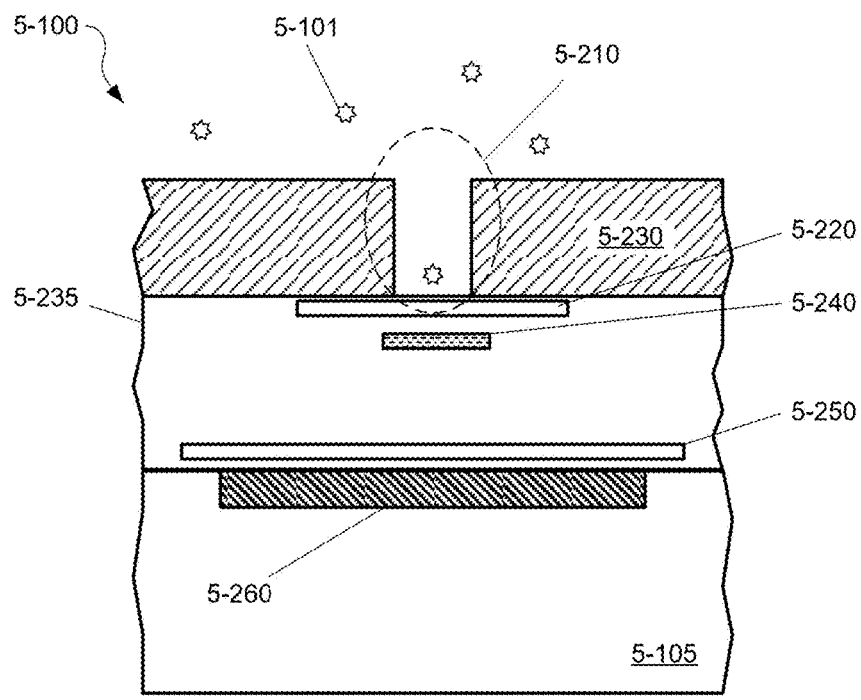
Figures 2, 5:
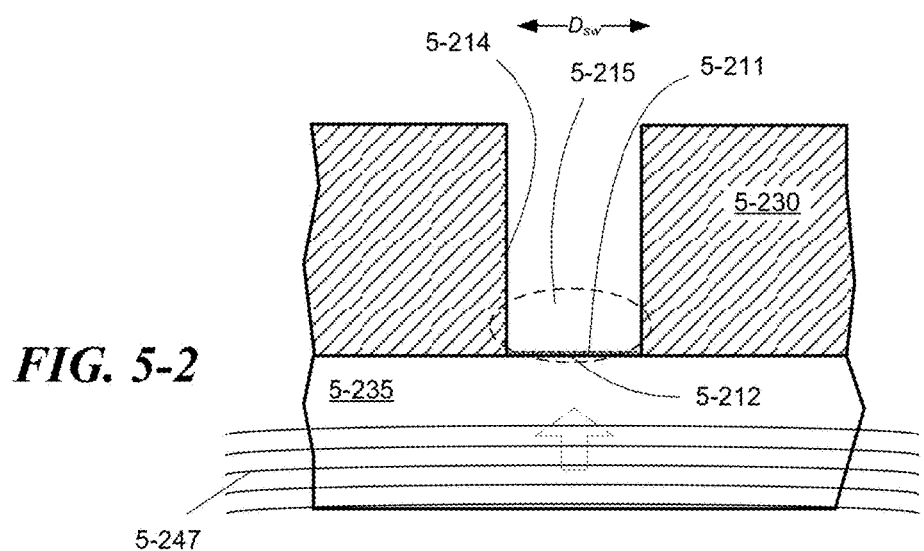
Figures 3, 5:
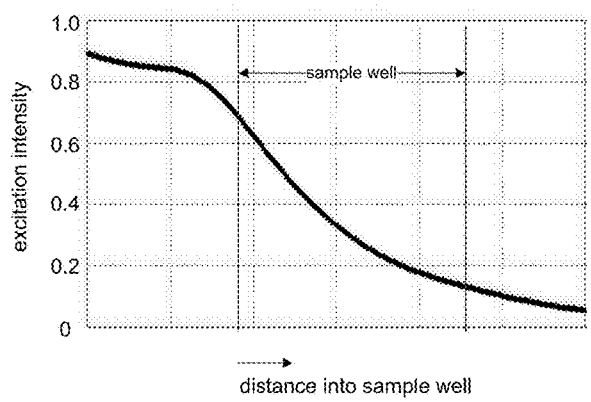
Figures 4, 5:
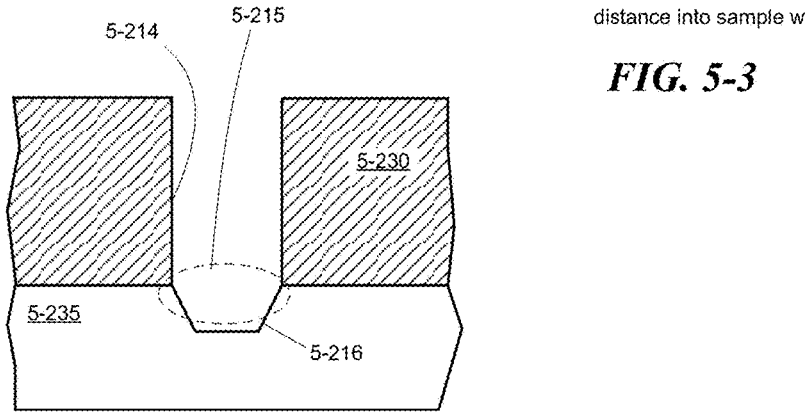
Figure 5:
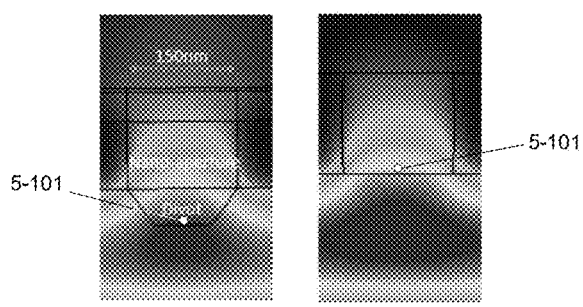
Figures 5, 6, 6A:
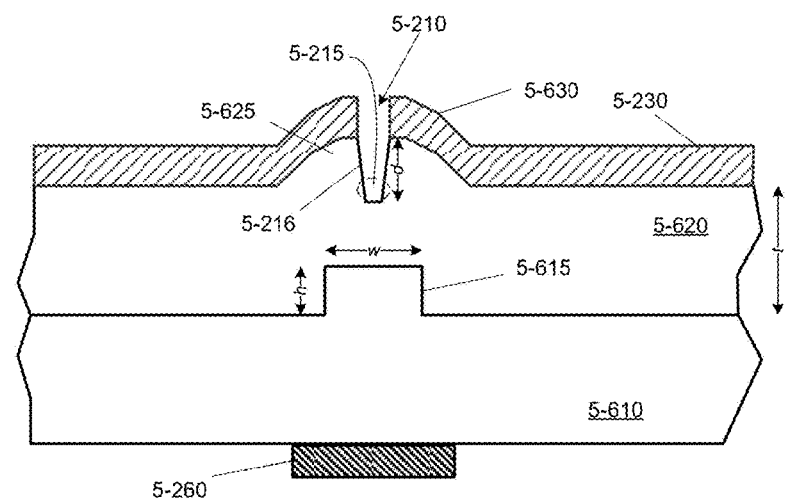

FIG. 5-6A depicts a sample well and divot formed at a protrusion, according to some embodiments.

Figures 5, 6, 6B:
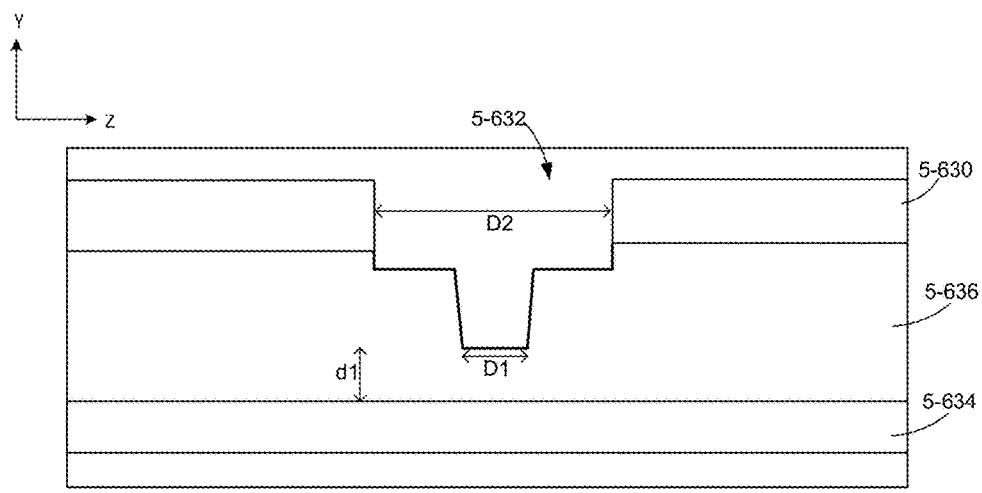

FIG. 5-6B depicts a sample well and divot, according to some embodiments.

FIG. 5-7A depicts a sample well having tapered sidewalls, according to some embodiments.

FIG. 5-7B depicts a sample well having curved sidewalls and a divot with a smaller transverse dimension, according to some embodiments.

FIG. 5-7C and FIG. 5-7D depict a sample well formed from surface plasmonic structures.

FIG. 5-7E depicts a sample well that includes an excitation-energy-enhancing structure formed along sidewalls of the sample well, according to some embodiments.

FIG. 5-7F depicts a sample well formed in a multi-layer stack, according to some embodiments.

FIG. 5-8 illustrates surface coating formed on surfaces of a sample well, according to some embodiments.

FIG. 5-9A through FIG. 5-9E depict structures associated with a lift-off process of forming a sample well, according to some embodiments.

FIG. 5-9F depicts a structure associated with an alternative lift-off process of forming a sample well, according to some embodiments.

FIG. 5-10A through FIG. 5-10D depict structures associated with a direct etching process of forming a sample well, according to some embodiments.

FIG. 5-11 depicts a sample well that may be formed in multiple layers using a lift-off process or a direct etching process, according to some embodiments.

FIG. 5-12 depicts a structure associated with an etching process that may be used to form a divot, according to some embodiments.

FIG. 5-13A through FIG. 5-13C depict structures associated with an alternative process of forming a divot, according to some embodiments.

FIG. 5-14A through FIG. 5-14D depict structures associated with a process for depositing an adherent and passivating layers, according to some embodiments.

FIG. 5-15 depicts a structure associated with a process for depositing an adherent centrally within a sample well, according to some embodiments.

FIG. 5-16 depicts a sample well with a divot, according to some embodiments.

FIG. 6-1A depicts a simulation of excitation radiation from a waveguide coupled to a sample well, according to some embodiments.

FIG. 6-1B depicts a simulation of excitation radiation coupled to a sample well, according to some embodiments.

FIGS. 6-2A, 6-2B, and 6-2C depict an integrated device with microcavities, according to some embodiments.

FIG. 6-3A depicts an integrated device with a microcavity, according to some embodiments.

FIG. 6-3B depicts an integrated device with microcavities, according to some embodiments.

FIG. 6-3C depicts an integrated device with a microcavity, according to some embodiments.

Figures 1A, 6:
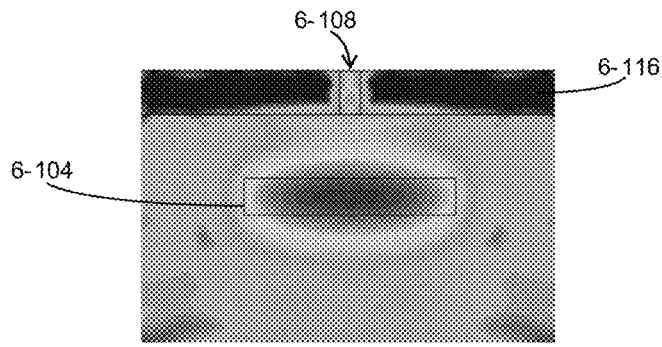
Figures 1B, 6:
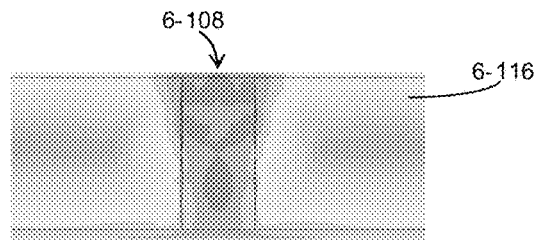
Figures 2A, 6:
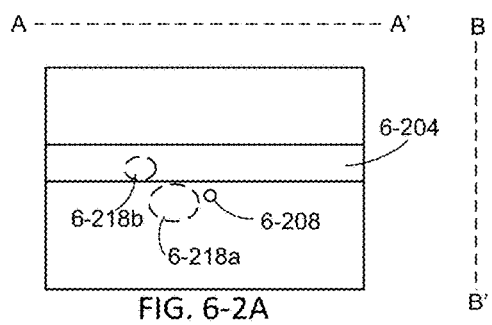
Figures 2B, 6:
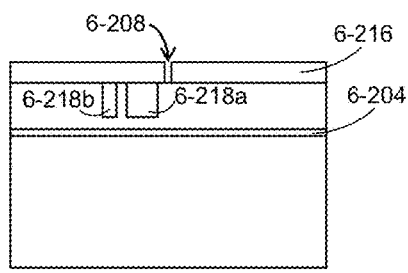
Figures 2C, 6:
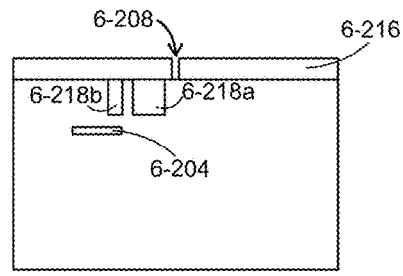
Figures 3A, 6:
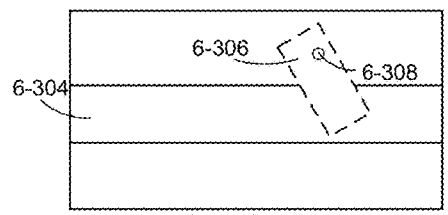
Figures 3B, 6:
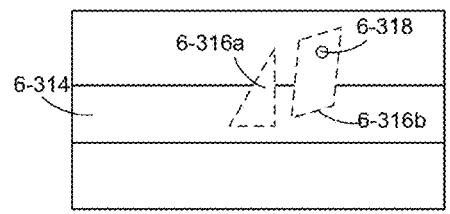
Figures 3C, 6:
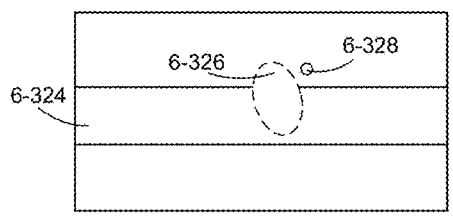
Figures 3D, 6:
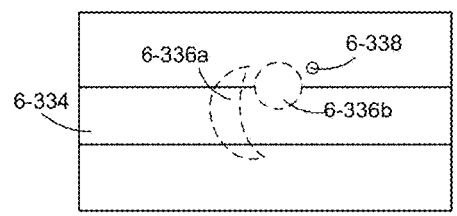
Figures 4, 6:
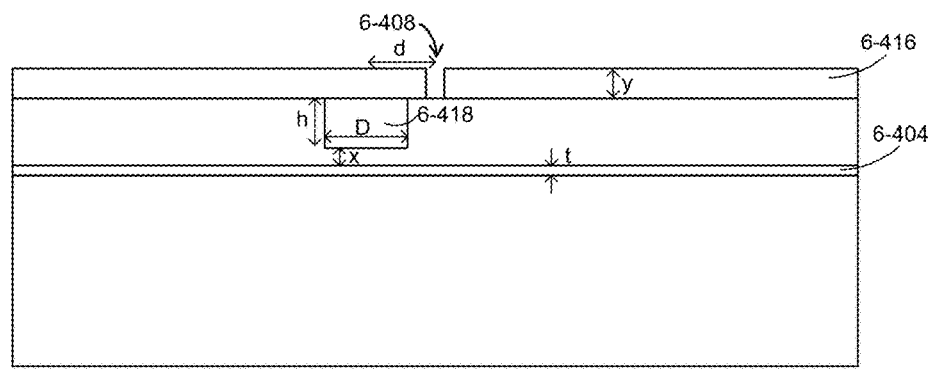
Figures 5, 6:
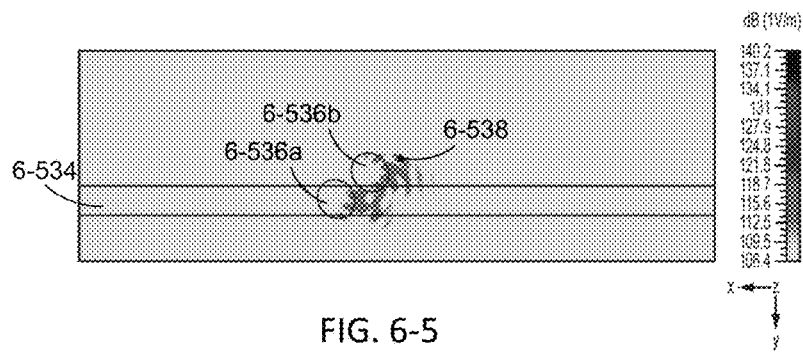
Figures 6, 6A:
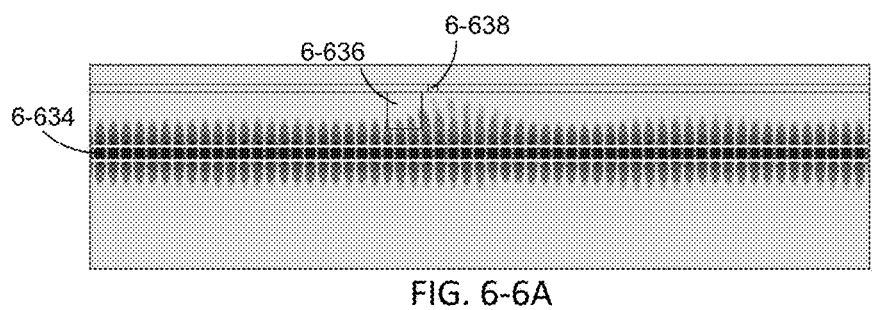
Figures 6, 6B:
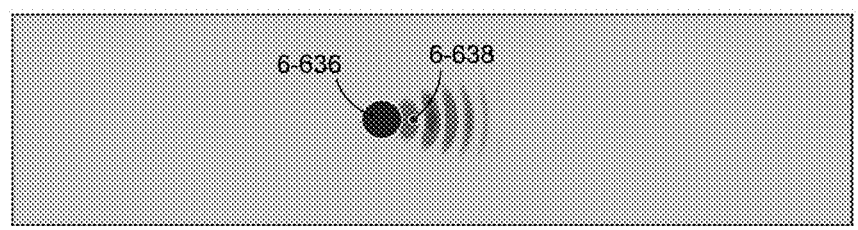

FIG. 6-3D depicts an integrated device with microcavities, according to some embodiments.

FIG. 6-4 depicts an integrated device with a microcavity, according to some embodiments.

FIG. 6-5 depicts a simulation of excitation radiation propagating in an integrated device with a microcavity, according to some embodiments.

FIGS. 6-6A, 6-6B, and 6-6C depict a simulation of excitation radiation propagating in an integrated device with a microcavity, according to some embodiments.

Figures 6, 6C:
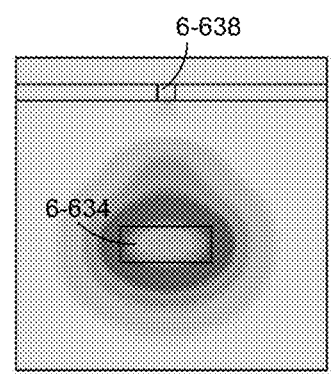
Figures 6, 6D:
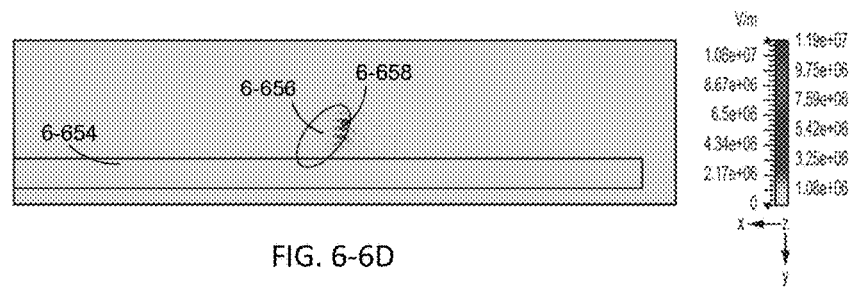
Figures 6, 7, 7A:
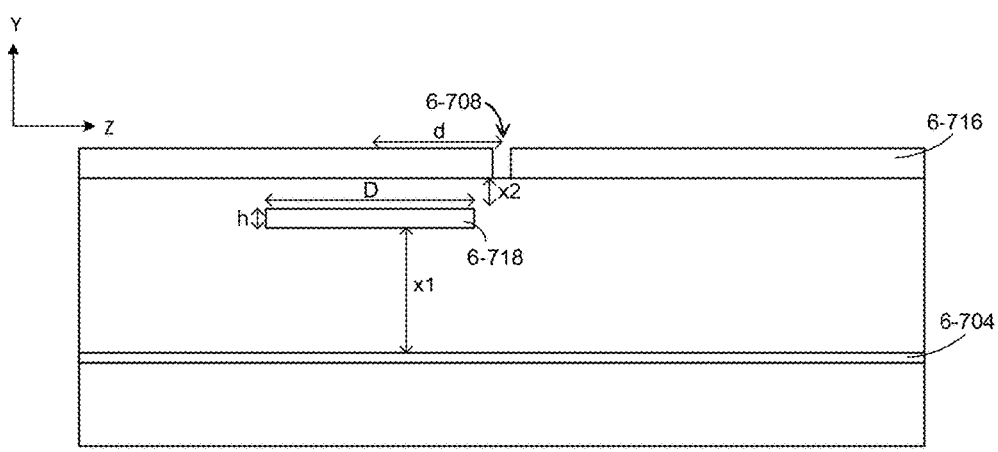
Figures 6, 7, 7B:
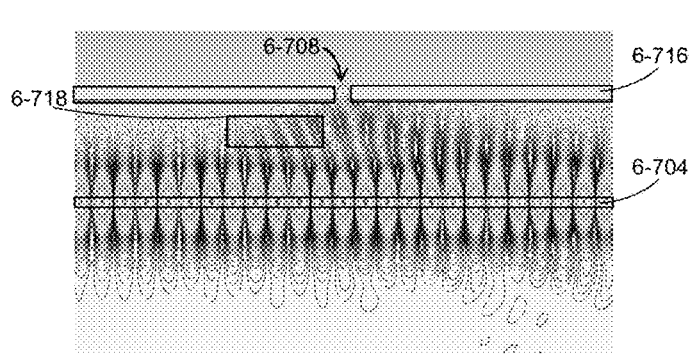
Figures 6, 7, 7C:
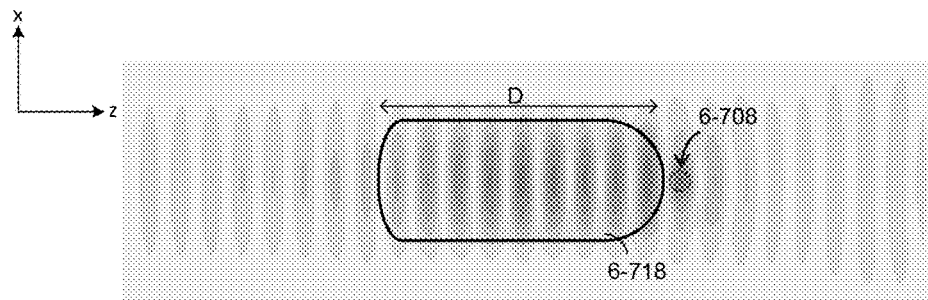
Figures 6, 7, 7D:
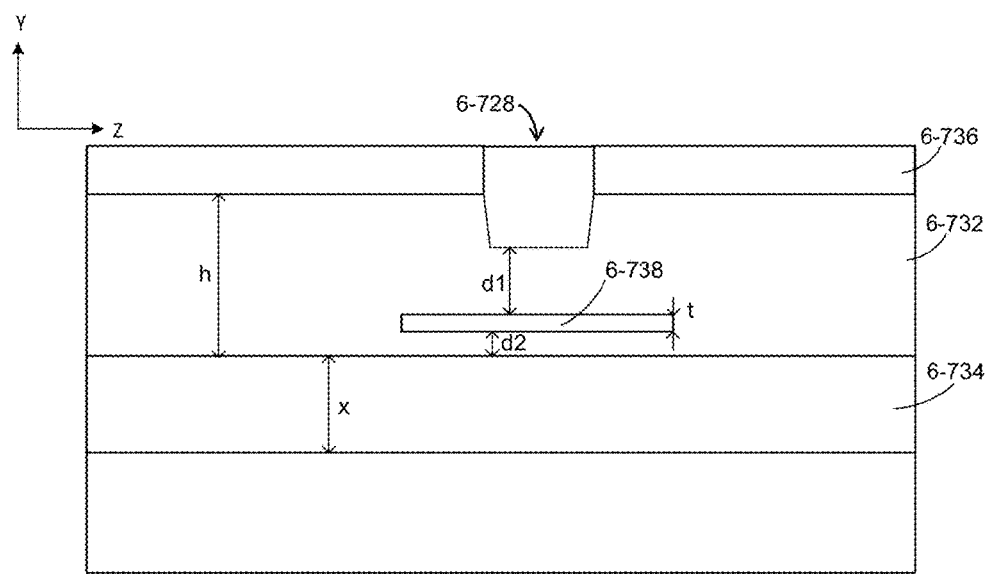

FIG. 6-6D depict a simulation of excitation radiation propagating in an integrated device with a microcavity, according to some embodiments.

Figures 4, 5, 6, 7:
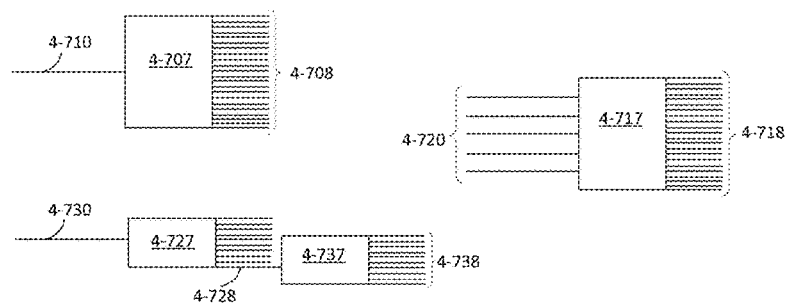
Figures 5, 6, 7, 7A:
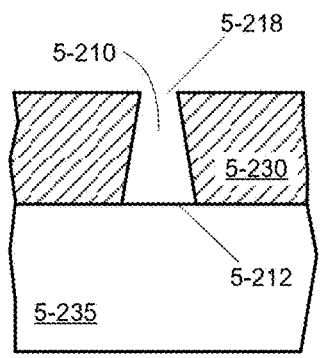

FIG. 6-7A depicts an integrated device with a microcavity, according to some embodiments.

Figures 5, 6, 7, 7B:
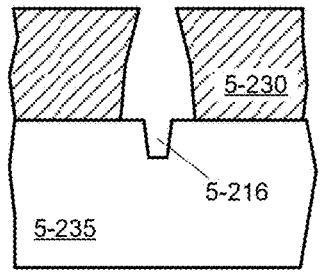

FIG. 6-7B depicts a simulation of excitation radiation propagating in an integrated device with a microcavity, according to some embodiments.

Figures 5, 6, 7, 7C:
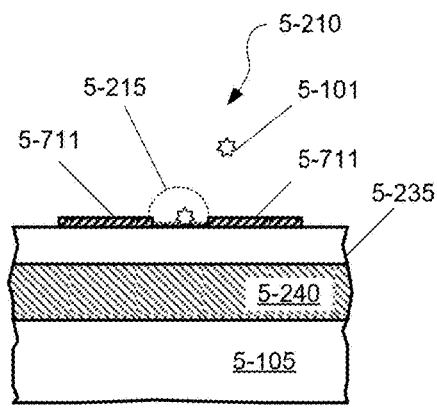

FIG. 6-7C depicts a simulation of excitation radiation propagating in an integrated device with a microcavity, according to some embodiments.

Figures 5, 6, 7, 7D:
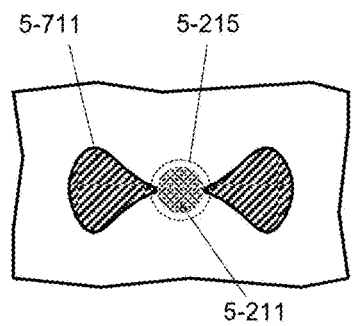
Figures 5, 6, 7, 7E:
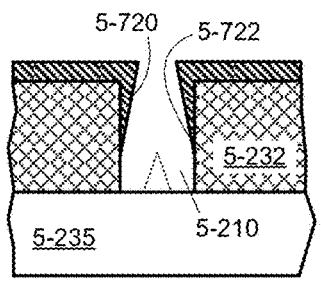
Figures 5, 6, 7, 7F:
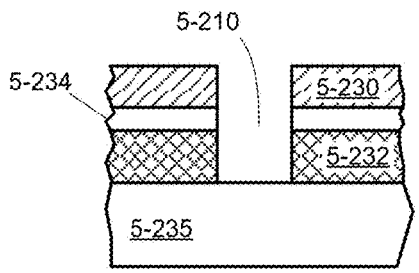
Figures 5, 6, 7, 8:
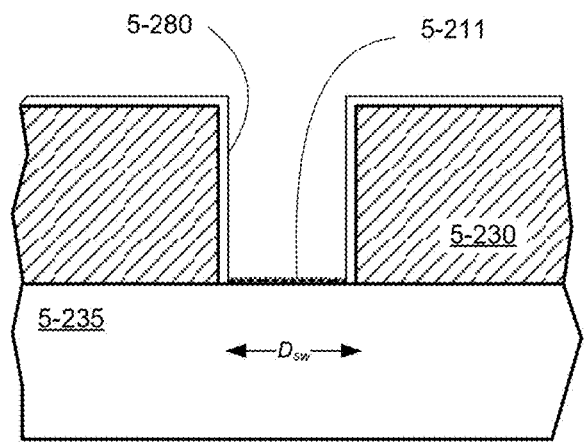

FIG. 6-7D depicts an integrated device with a sample well, a waveguide, and a microcavity, according to some embodiments.

FIGS. 6-8A and 6-8B depict an integrated device with a tapered waveguide, according to some embodiments.

FIGS. 6-9A and 6-9B depict an integrated device with a tapered waveguide, according to some embodiments.

FIG. 6-10 depicts a plot of loss as a function of taper length.

FIG. 6-11A depicts an integrated device with sample well dips, according to some embodiments.

FIGS. 6-11B and 6-11C depict an integrated device with sample well dips, according to some embodiments.

FIG. 6-12 depicts an array of sample wells of an integrated device, according to some embodiments.

FIG. 6-13 depicts an integrated device with a waveguide having a variable dimension, according to some embodiments.

FIG. 6-14 depicts an integrated device with a waveguide having a variable dimension, according to some embodiments.

FIGS. 7-1A, 7-1B, and 7-1C depict components to couple emission energy from a sample well of an integrated device, according to some embodiments.

FIG. 7-2A depicts a simulation of emission energy from a sample well.

FIG. 7-2B depicts a plot of emission energy at an angle from a sample well.

FIG. 7-3 depicts a plot of absorptance and reflectance as a function of wavelength.

Figures 1A, 7:
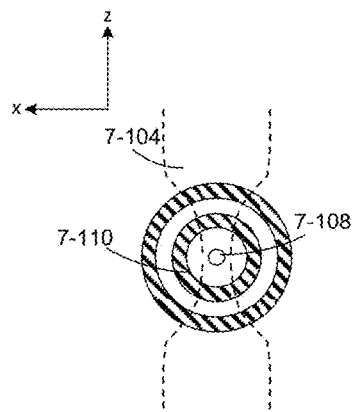
Figures 1B, 7:
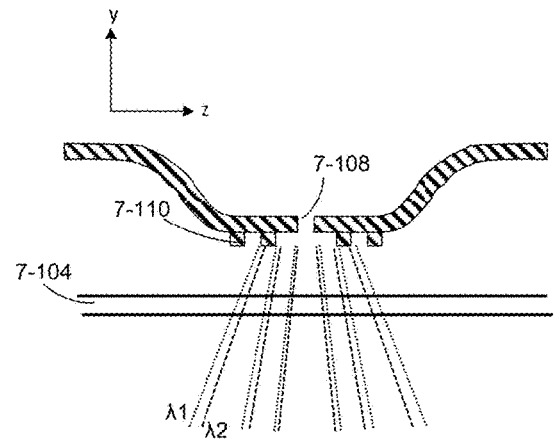
Figures 1C, 7:
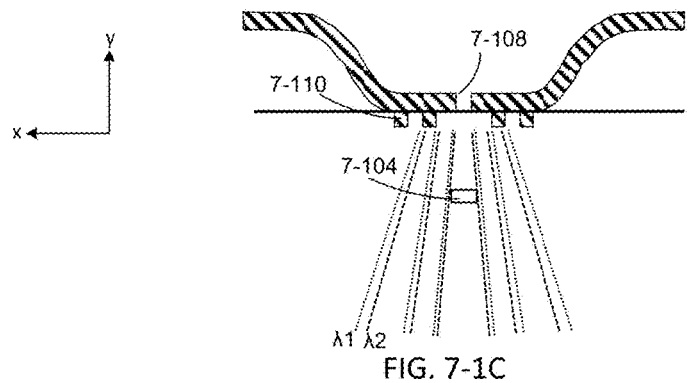
Figures 2A, 7:
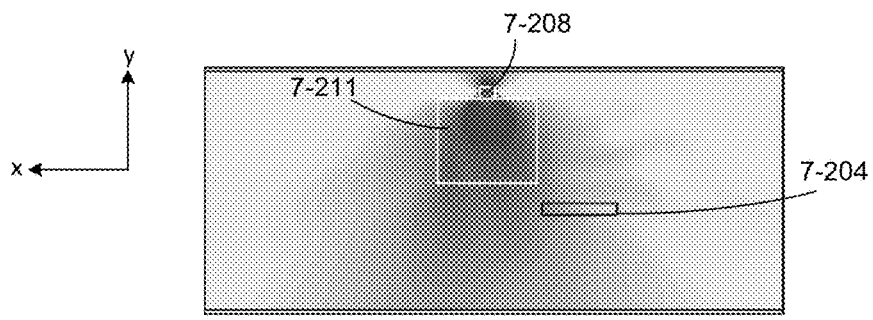
Figures 2B, 7:
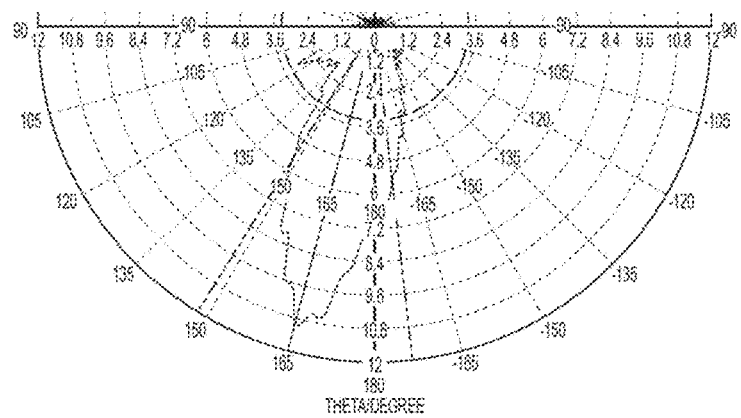
Figures 3, 7:
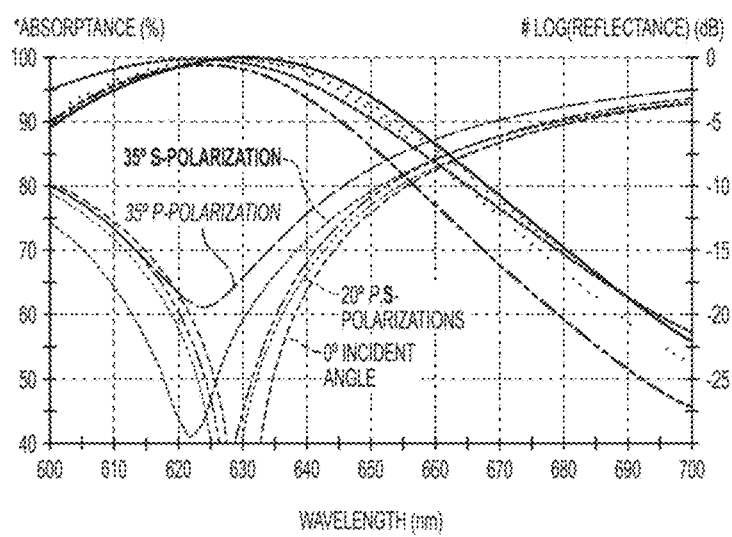
Figures 4A, 7:
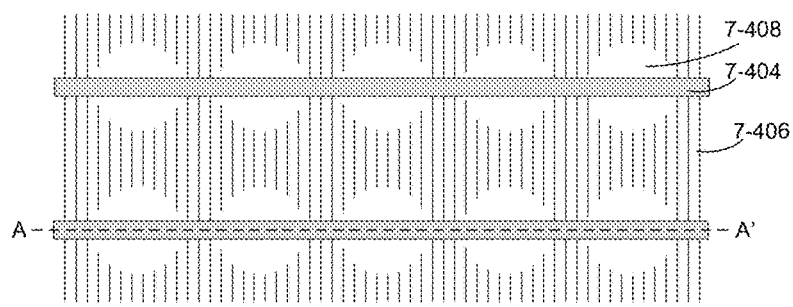
Figures 4B, 7:
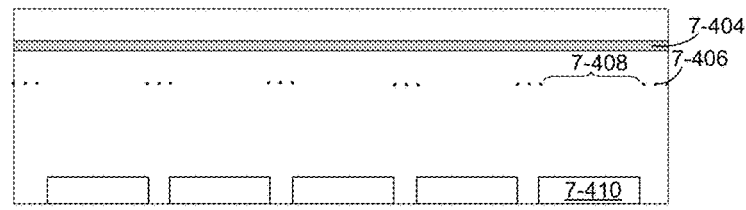
Figures 5, 7:
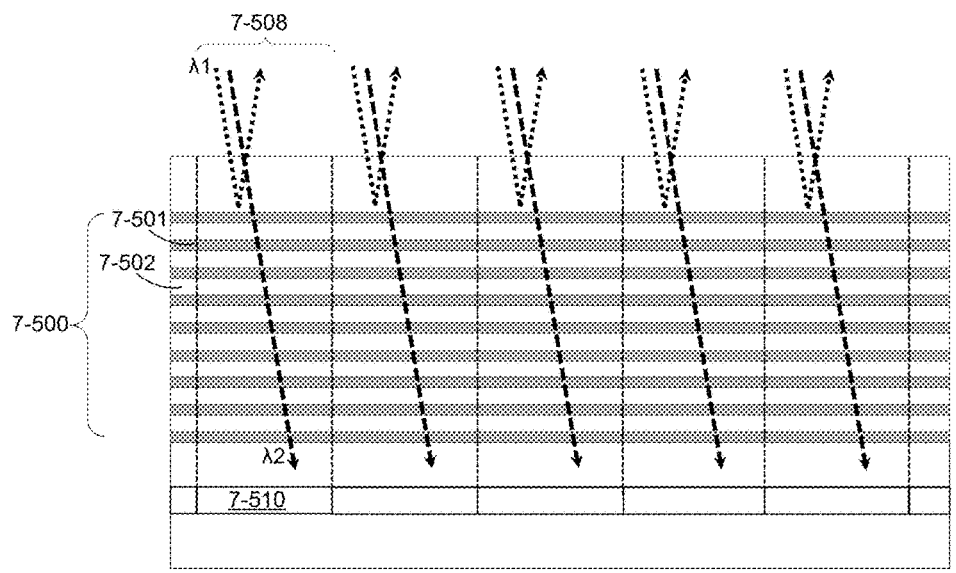
Figures 6, 7:
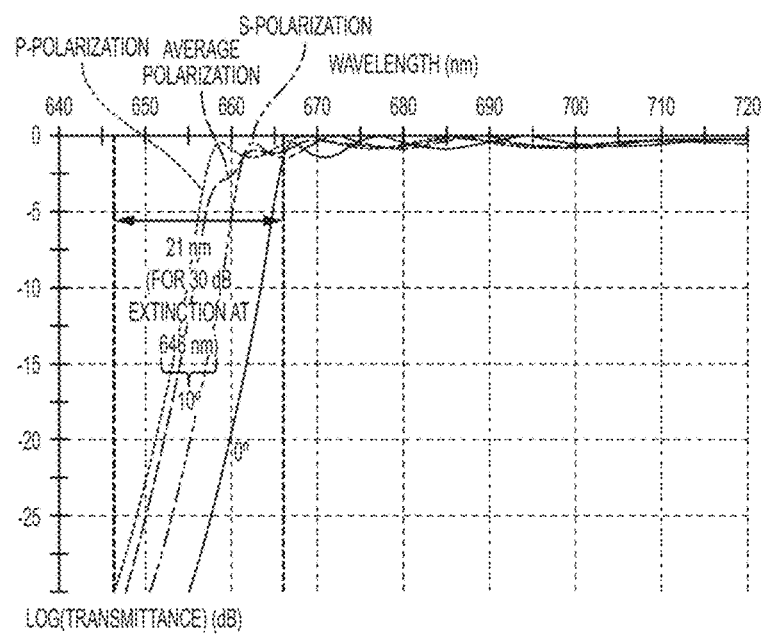
Figure 7:
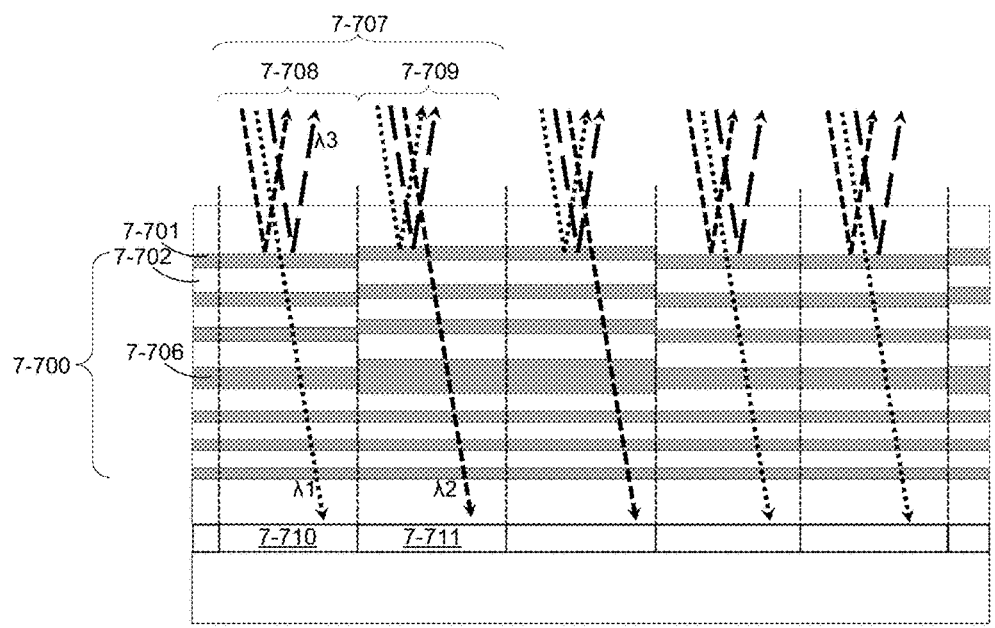
Figures 7, 8:
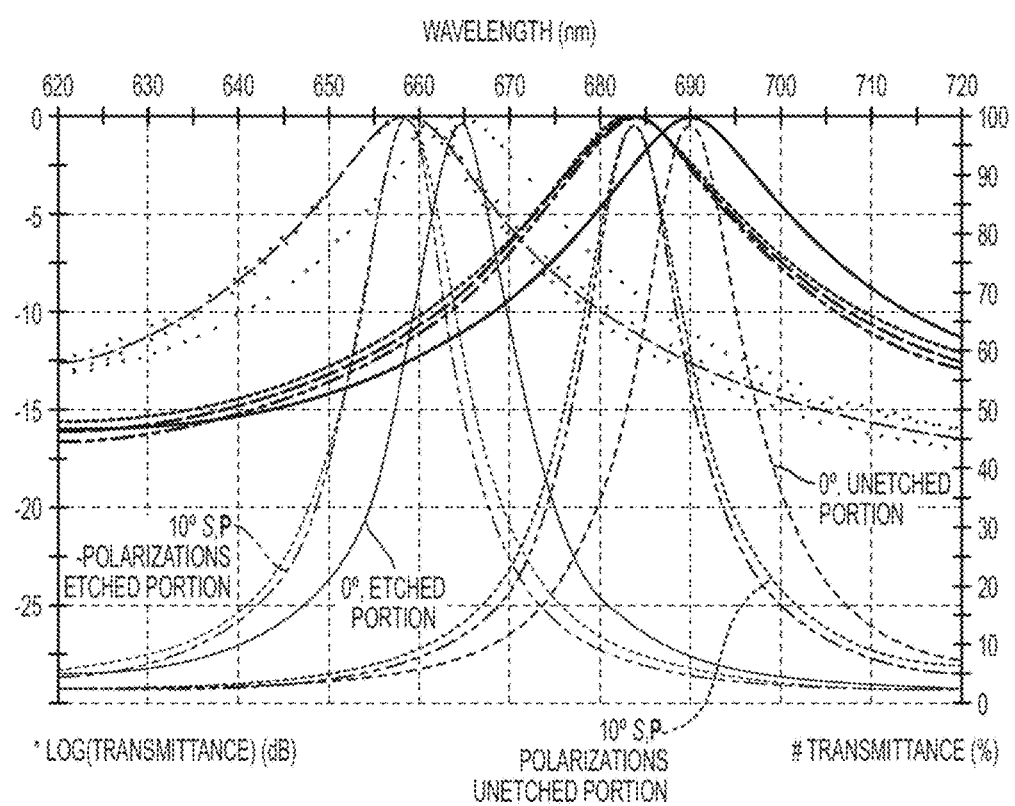
Figures 7, 8, 9, 9A:
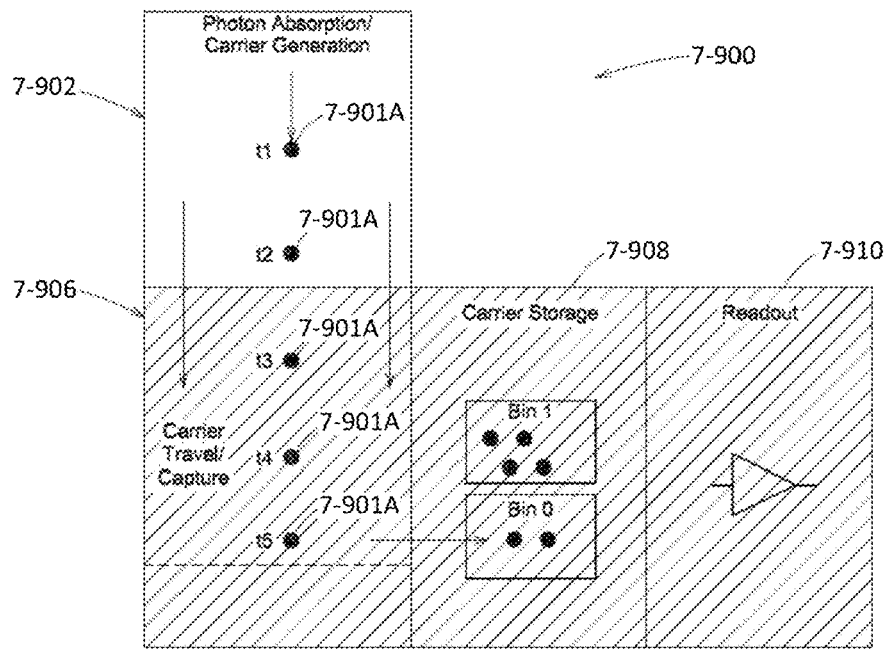
Figures 7, 8, 9, 9B:
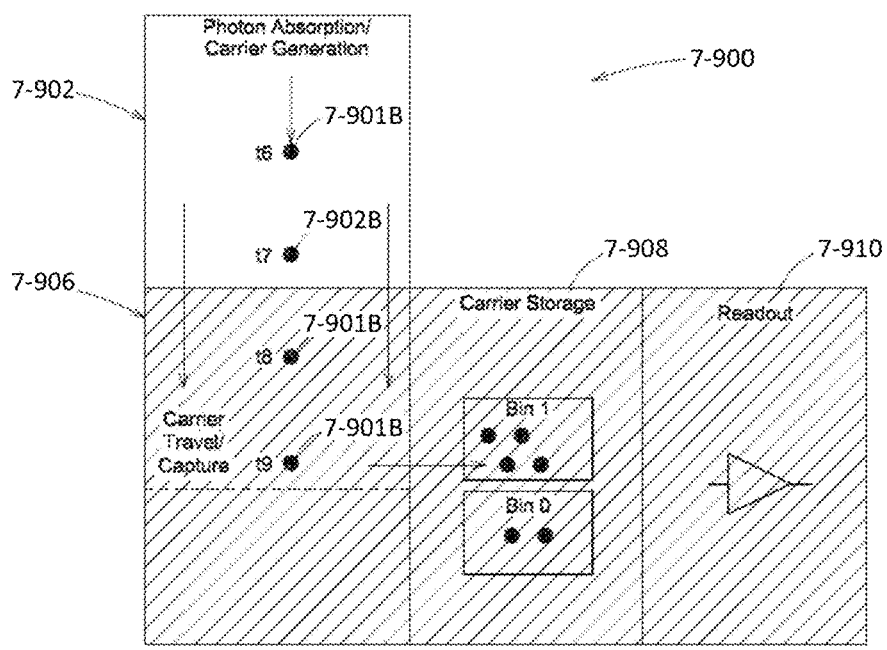

FIGS. 7-4A and 7-4B depict a polarization filter, according to some embodiments.

FIG. 7-5 depicts a wavelength filter, according to some embodiments.

FIG. 7-6 depicts a plot of transmittance as a function of wavelength.

FIG. 7-7 depicts a multi-wavelength filter, according to some embodiments.

Figures 4, 5, 6, 7, 8:
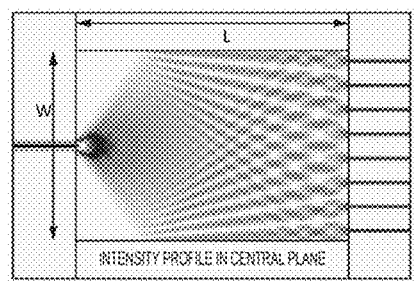

FIG. 7-8 depicts a plot of transmittance as a function of wavelength.

FIGS. 7-9A and 7-9B depict a sensor with time bins, according to some embodiments.

Figures 0A, 8:
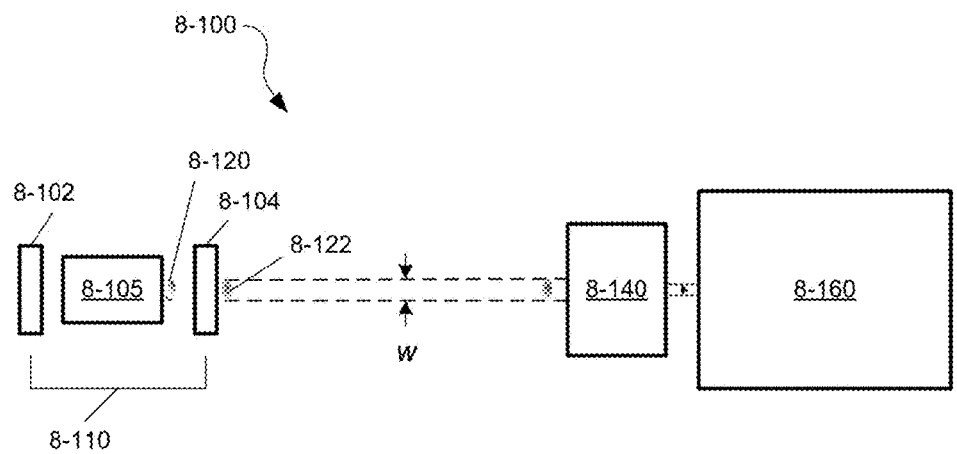

FIG. 8-0A depicts an exemplary system for providing light pulses, according to some embodiments.

Figures 0B, 8:
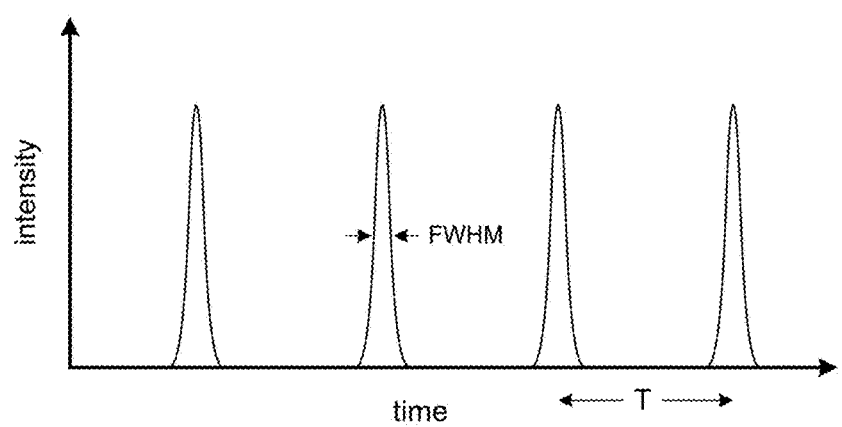
Figures 1, 8:
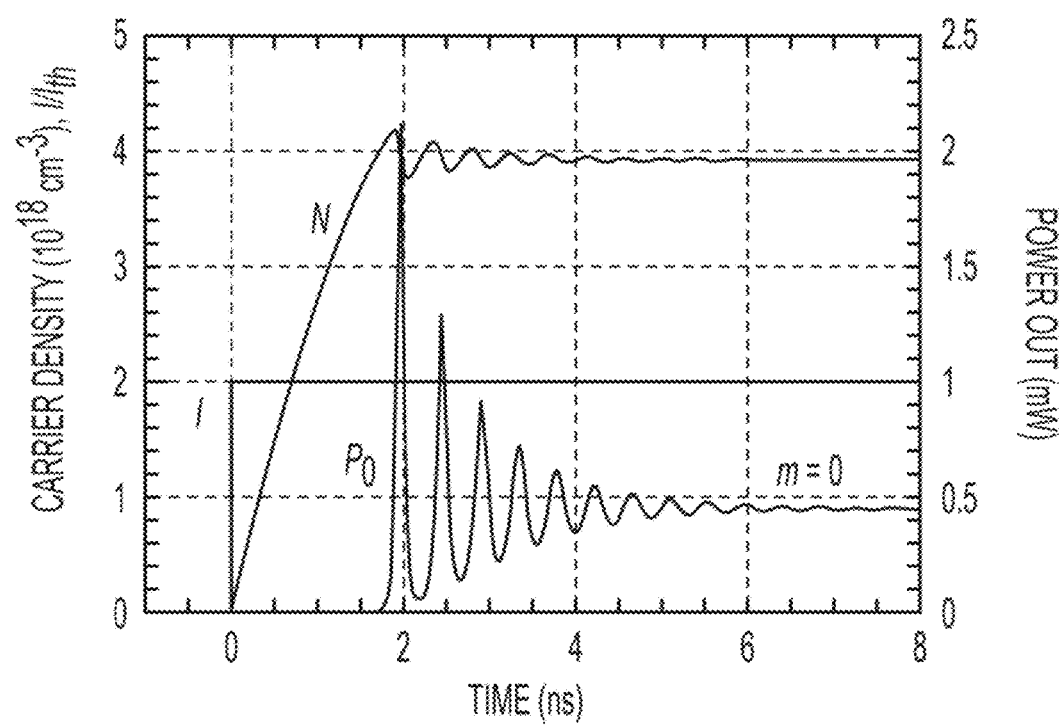
Figures 2, 8:
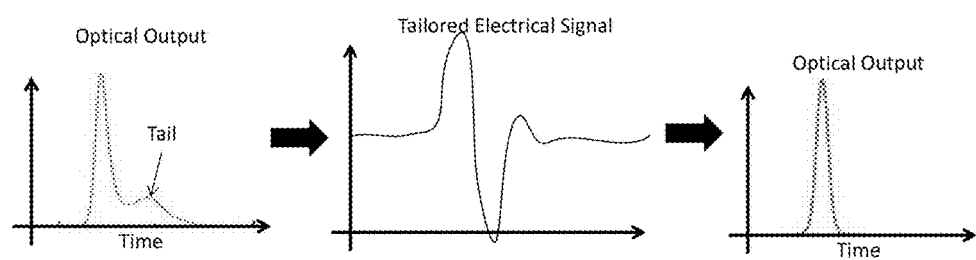
Figures 3, 8:
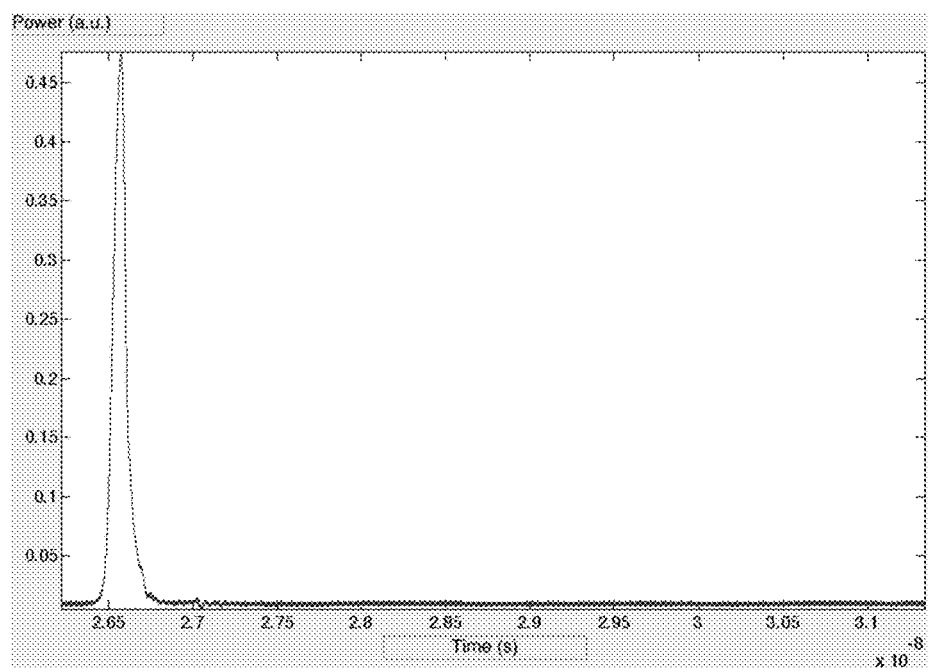
Figures 4, 8:
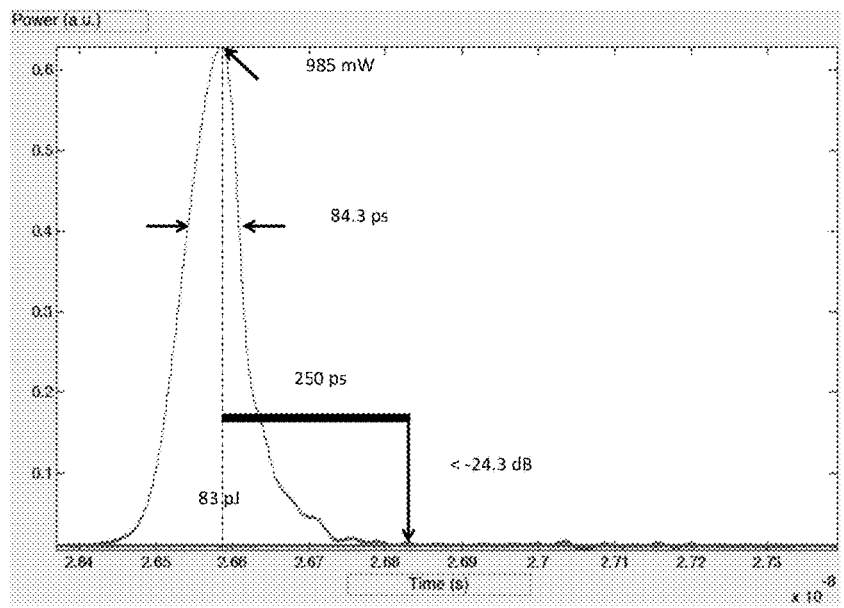
Figures 5, 8:
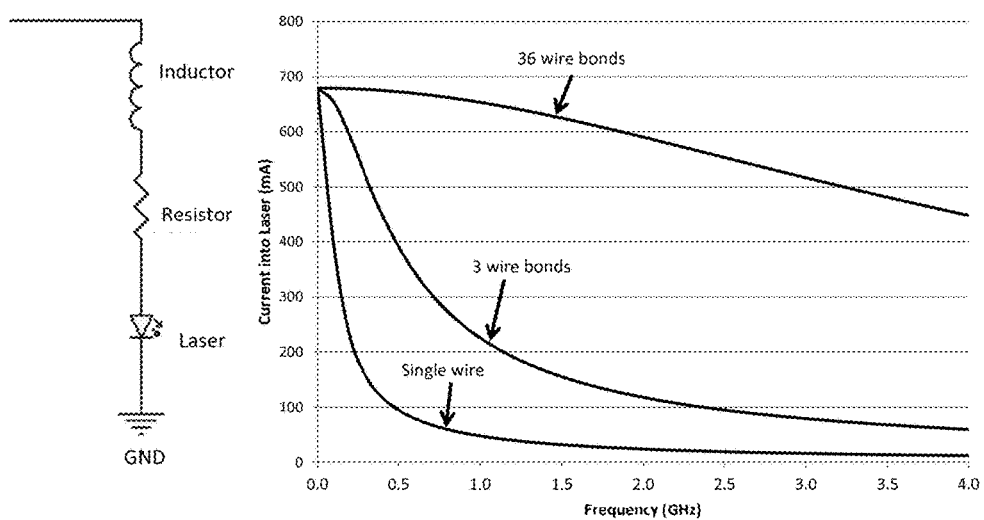
Figures 6A, 8:
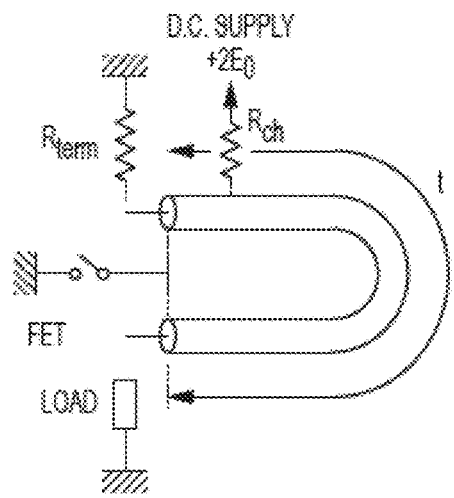
Figures 6B, 8:
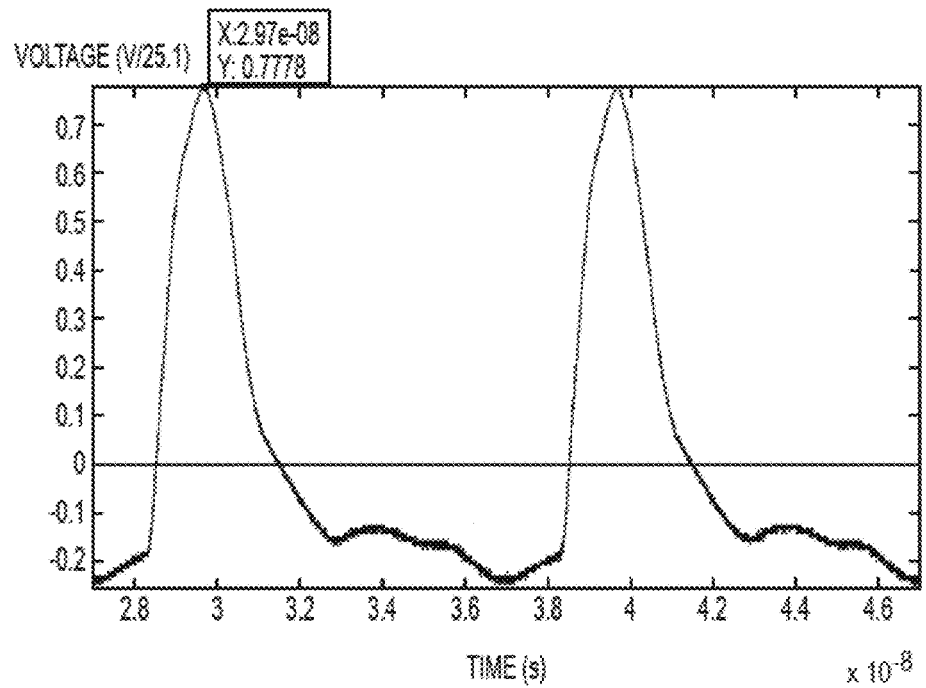
Figures 7, 8:
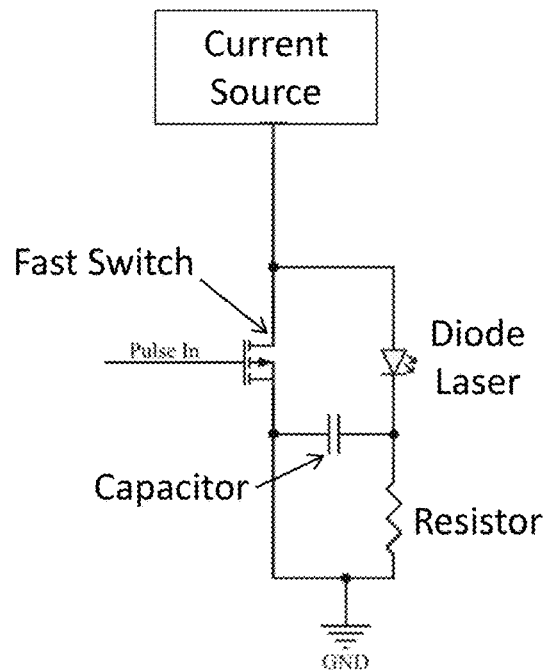
Figure 8:
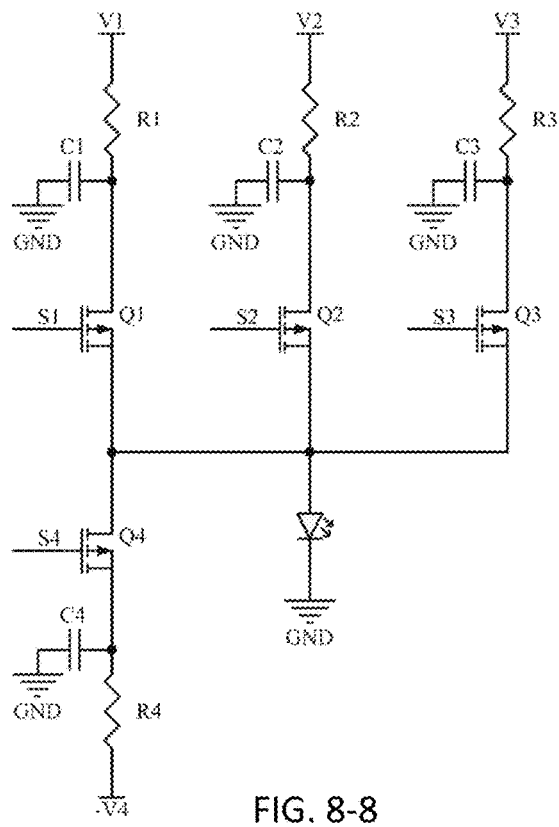
Figures 8, 9, 9A:
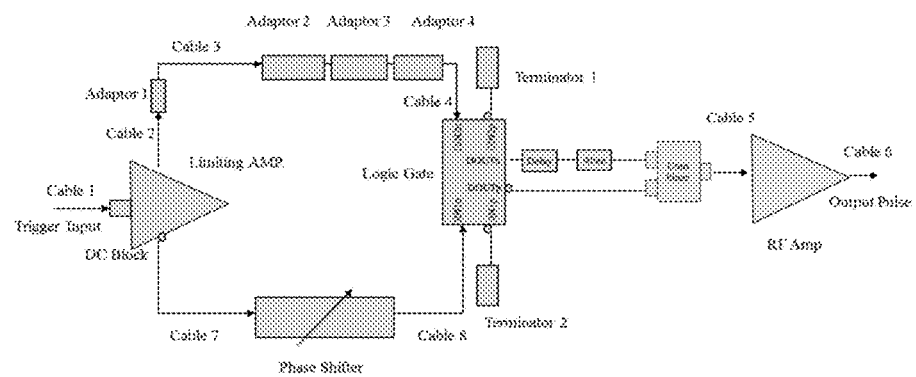
Figures 8, 9, 9B:
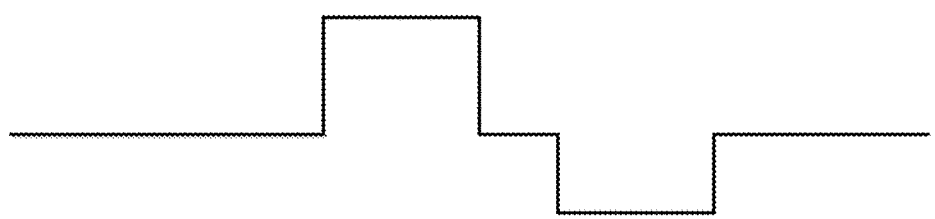
Figures 8, 9, 10, 10A:
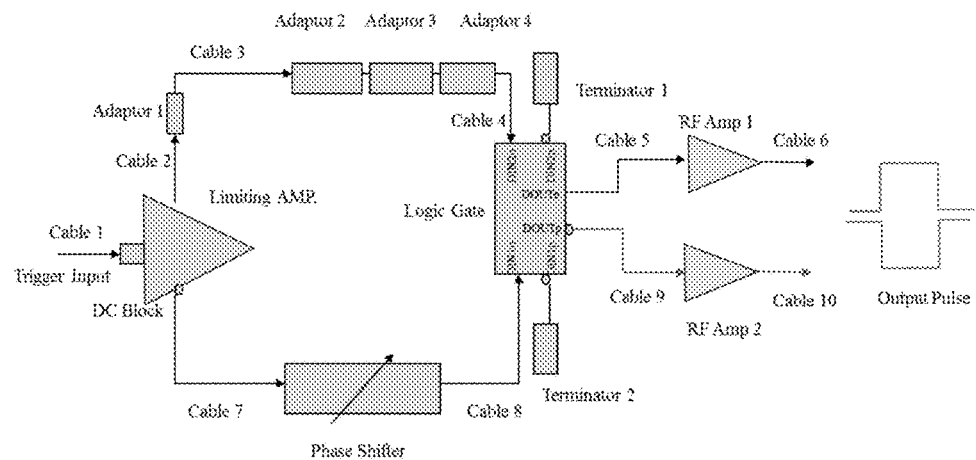
Figures 8, 9, 10, 10B:
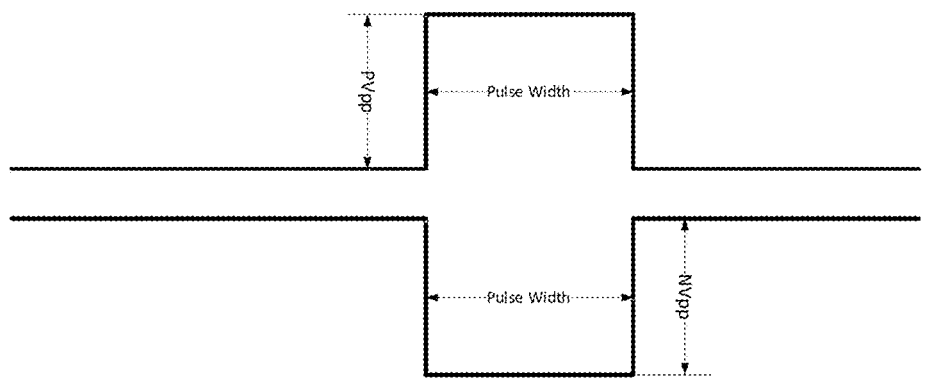
Figures 8, 9, 10, 11, 11A:
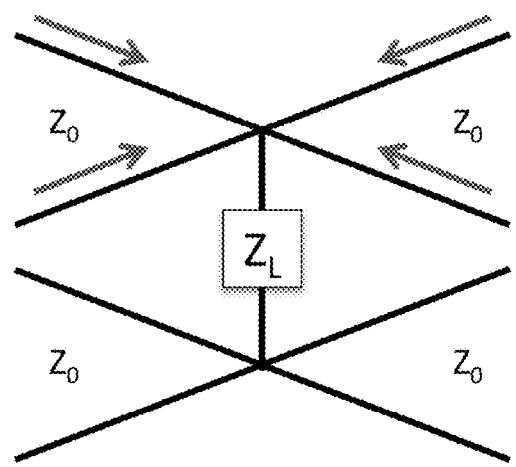
Figures 8, 9, 10, 11, 11B:
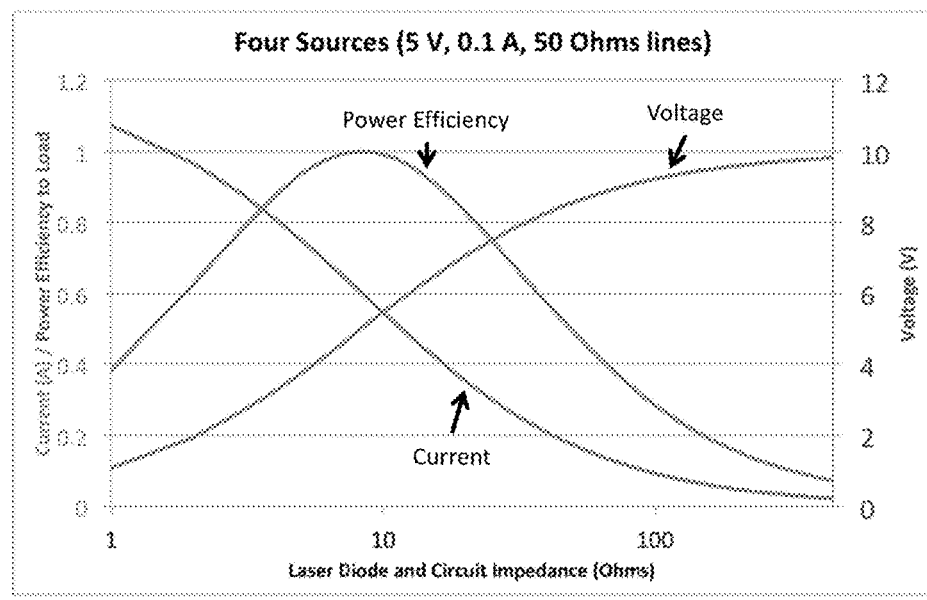
Figures 1, 9:
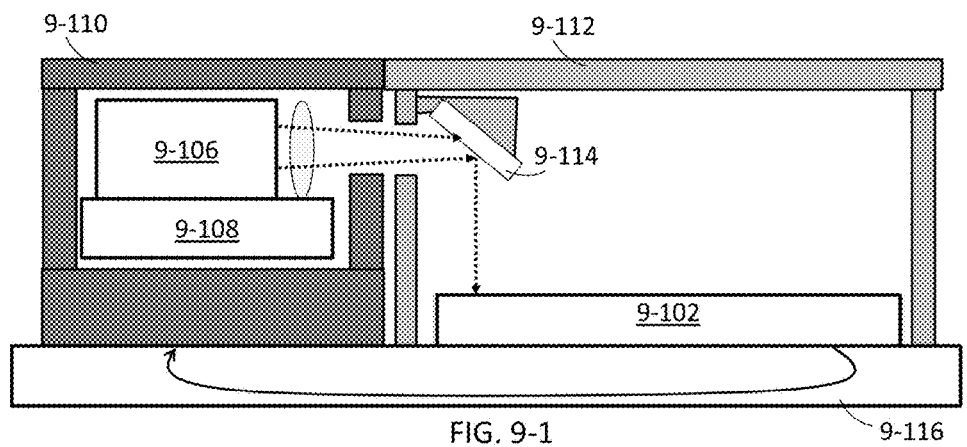
Figures 2, 9:
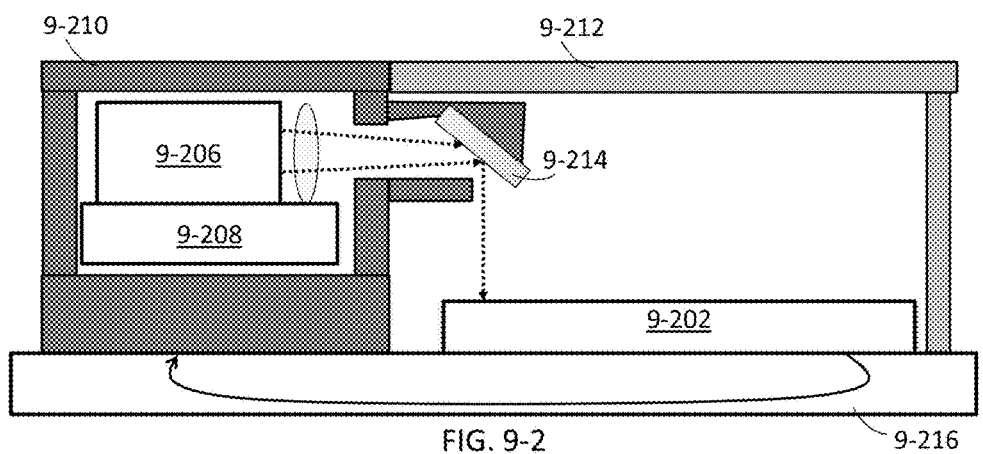
Figures 3, 9:
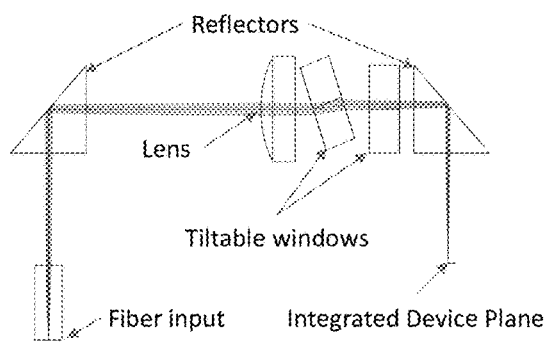
Figures 4, 9:
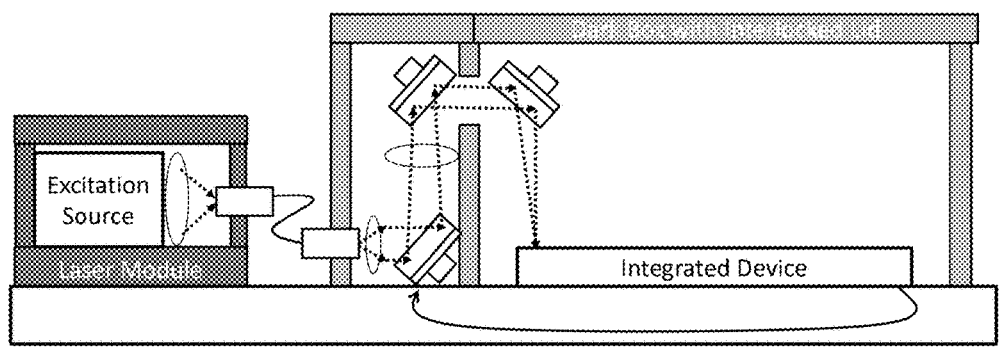
Figures 5, 9:
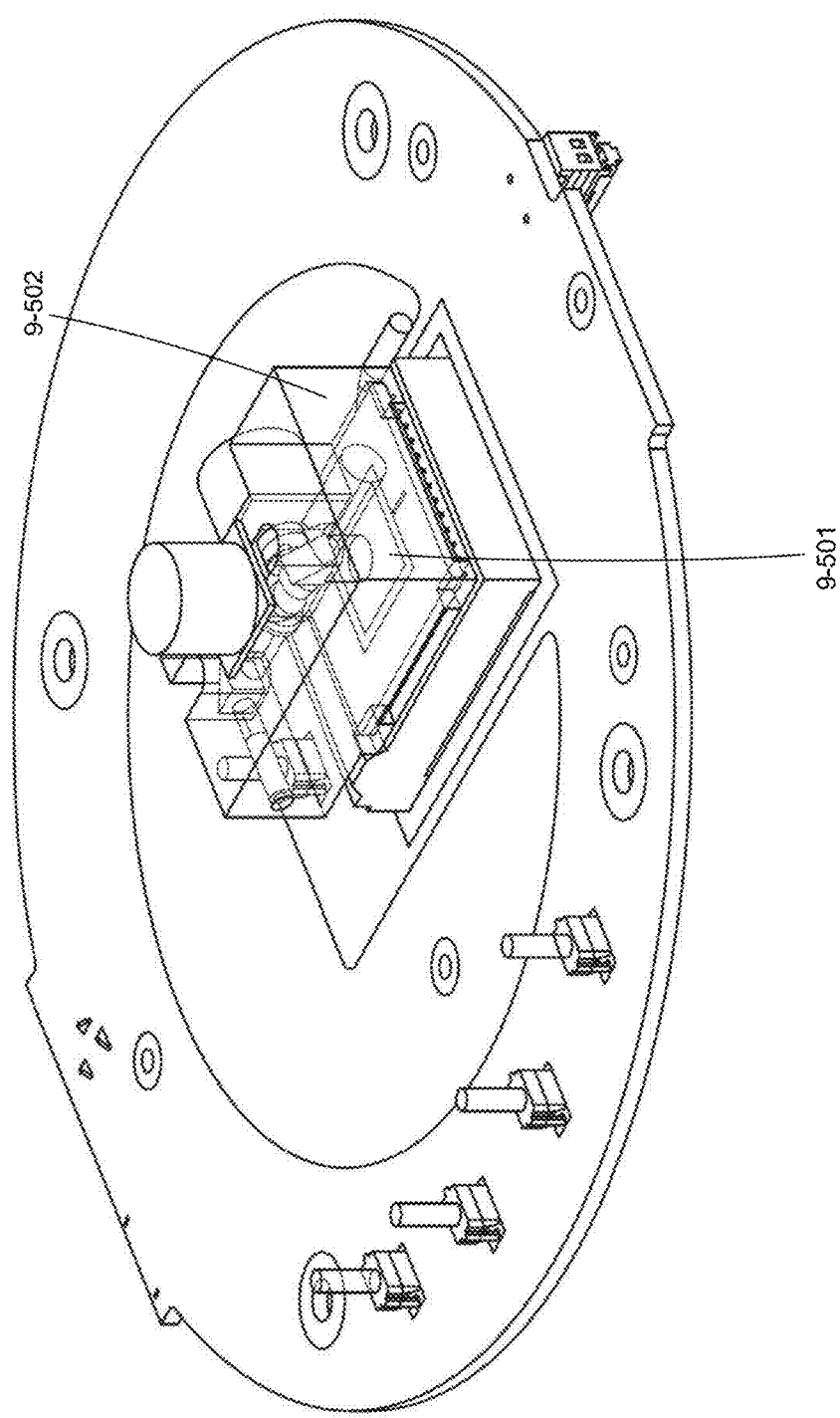
Figures 6, 9:
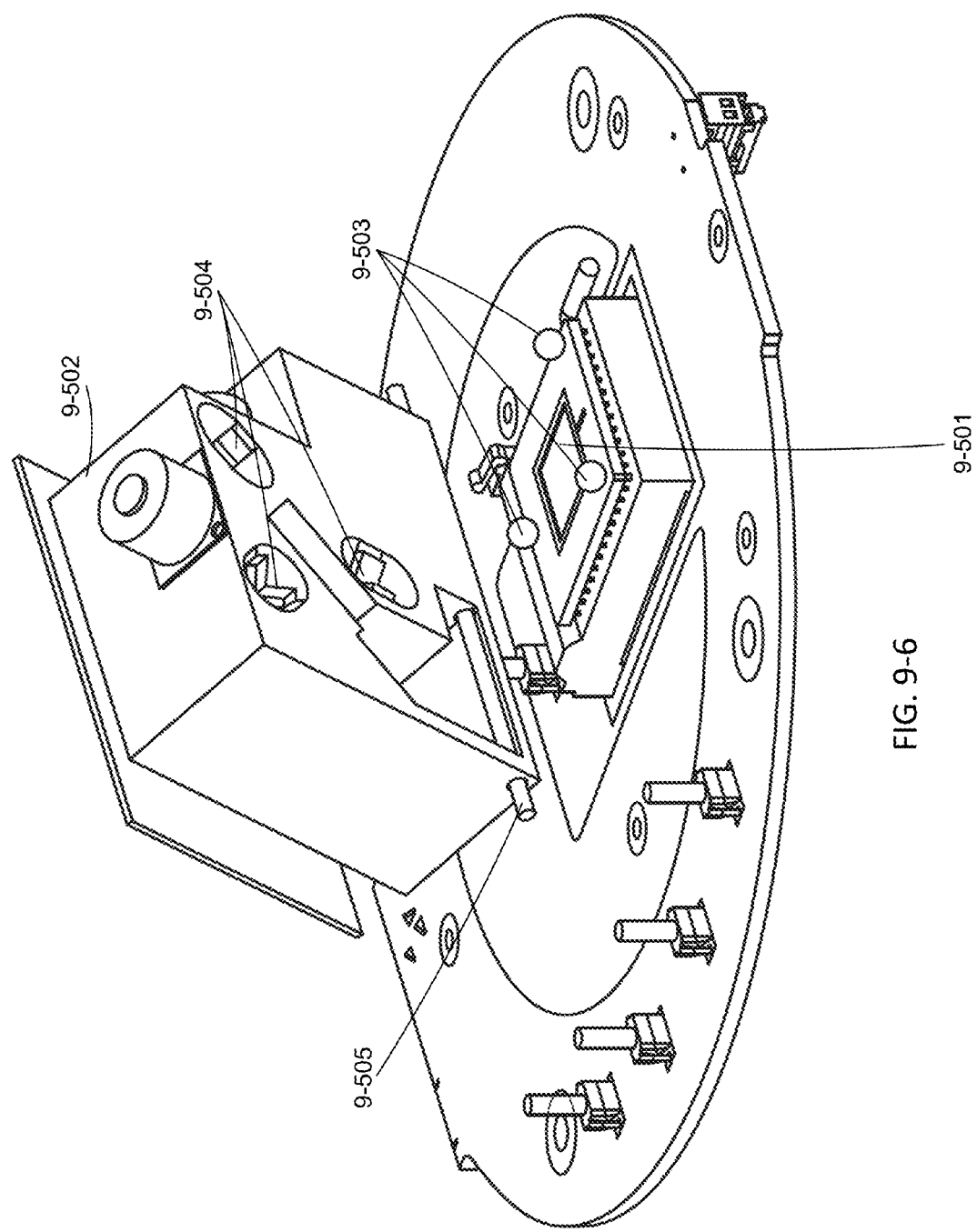
Figures 8, 9:
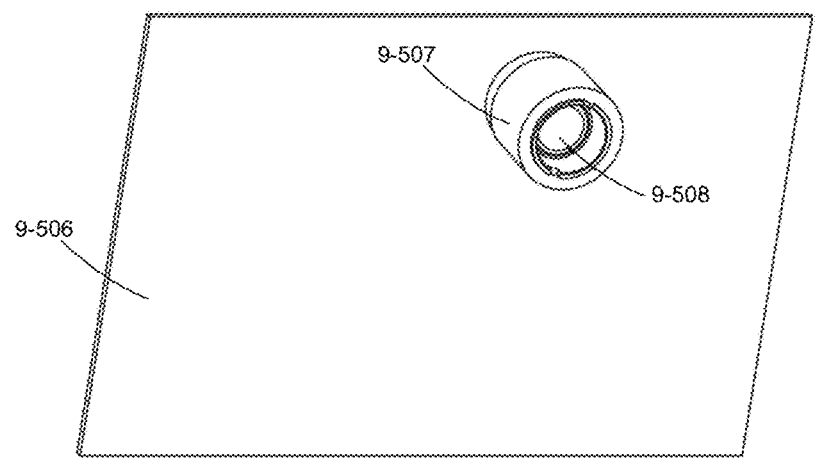
Figure 9:
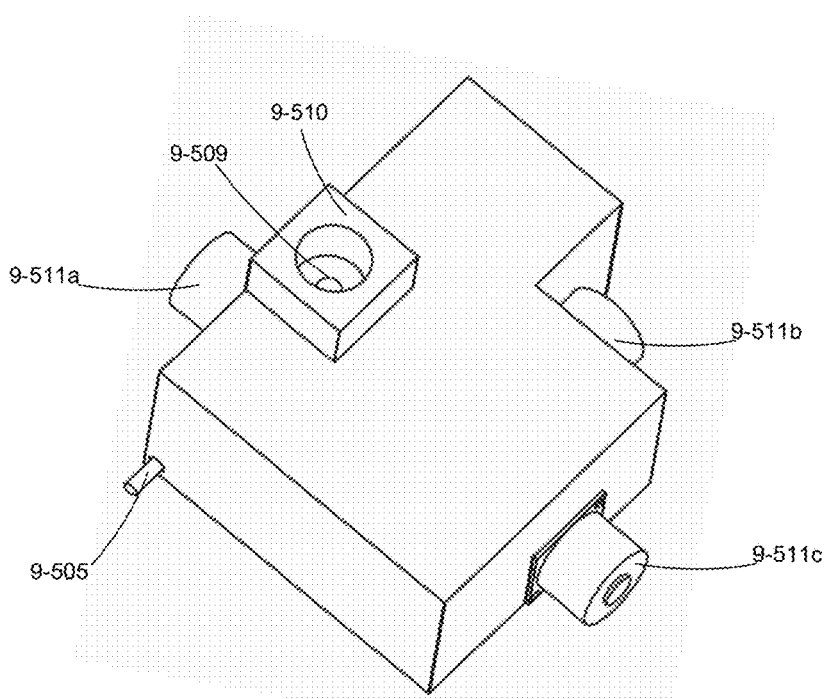
Figures 9, 10:
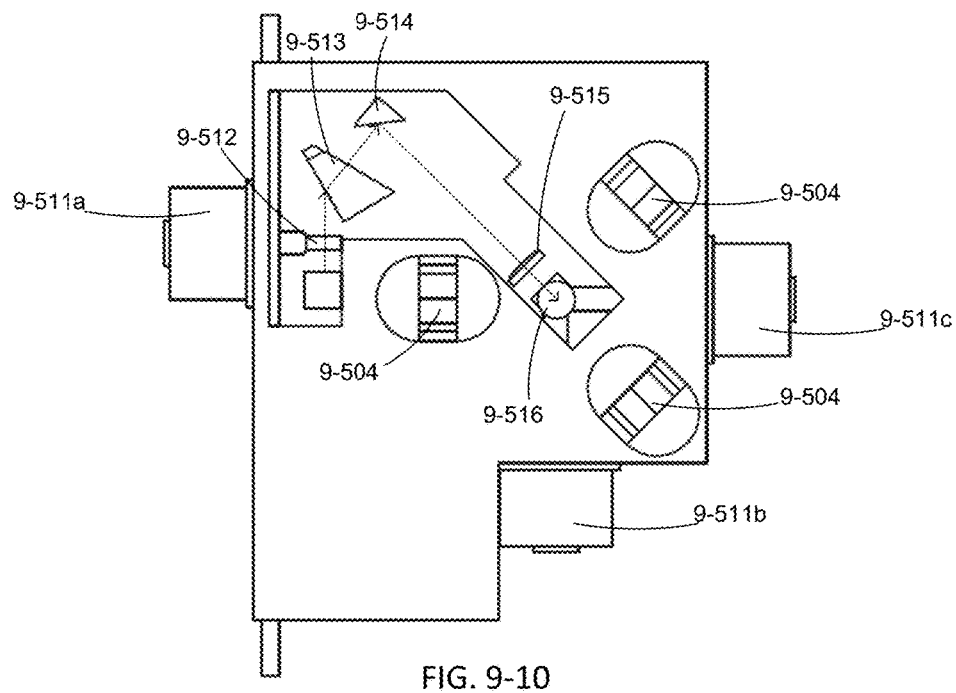
Figures 9, 10, 11:
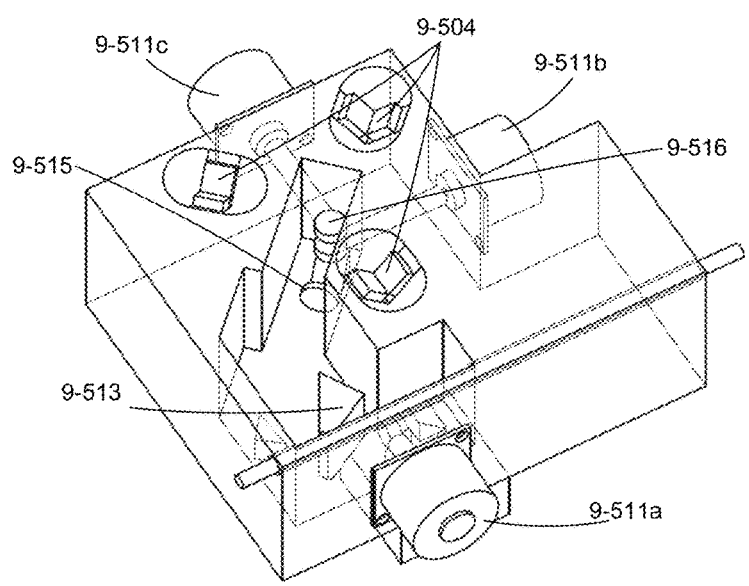
Figures 9, 10, 11, 12:
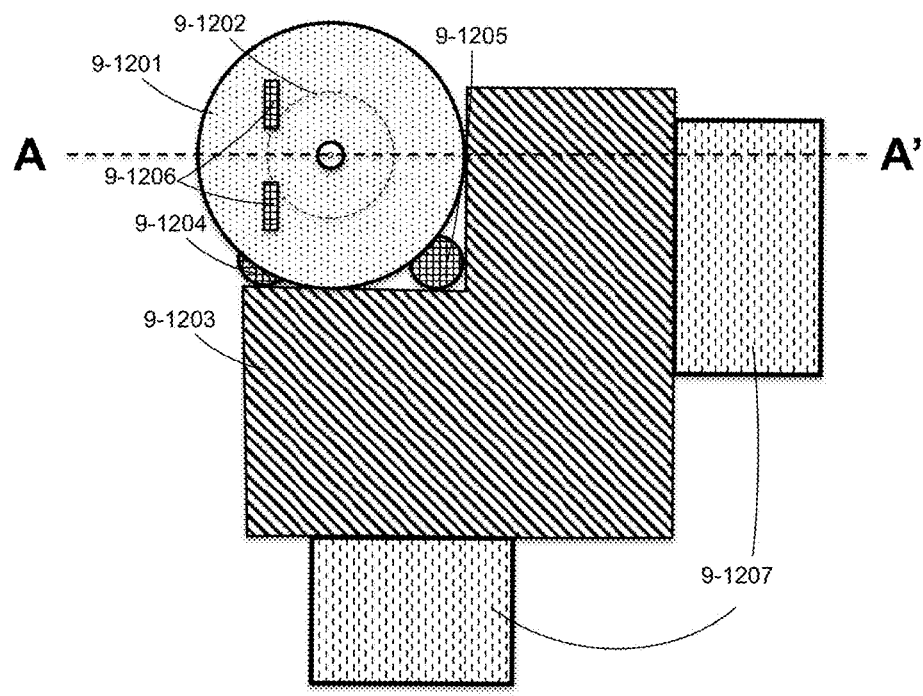
Figures 9, 10, 11, 12, 13:
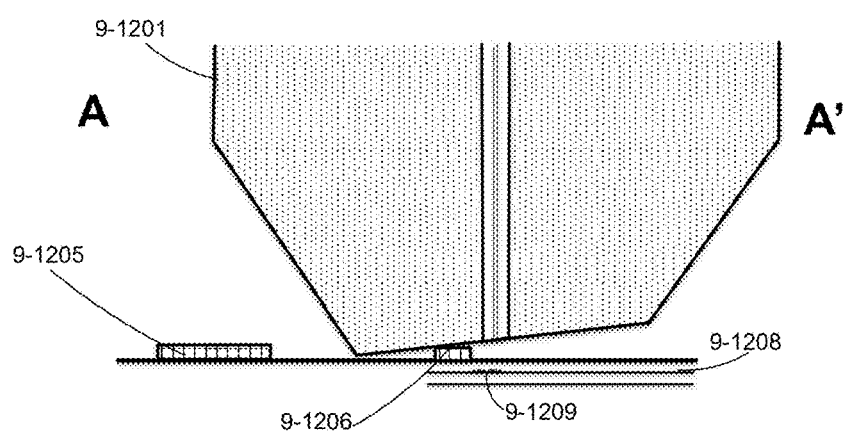
Figures 9, 10, 11, 12, 13, 14:
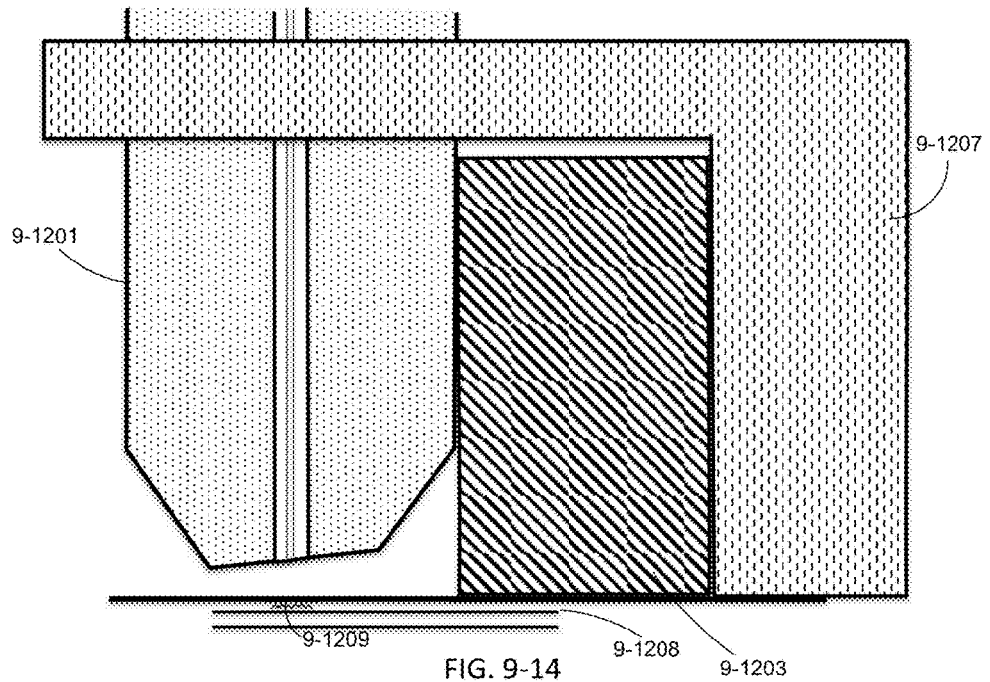
Figures 9, 10, 11, 12, 13, 14, 15:
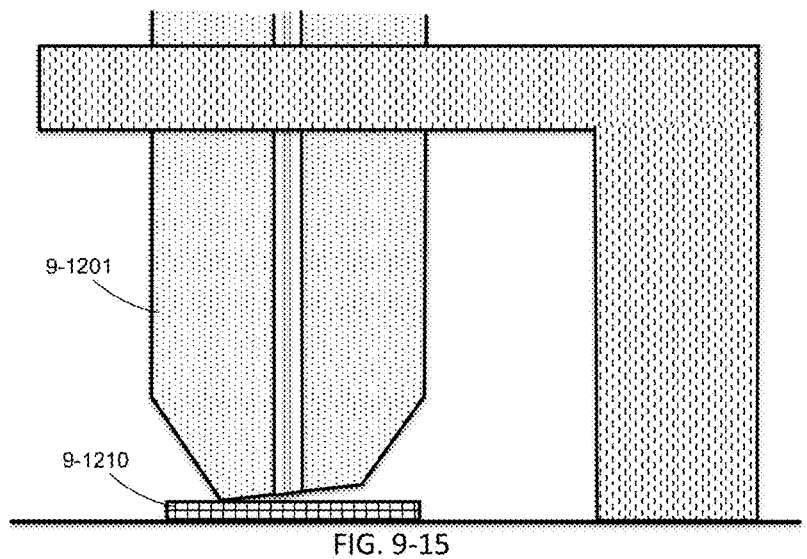
Figures 9, 10, 11, 12, 13, 14, 15, 16:
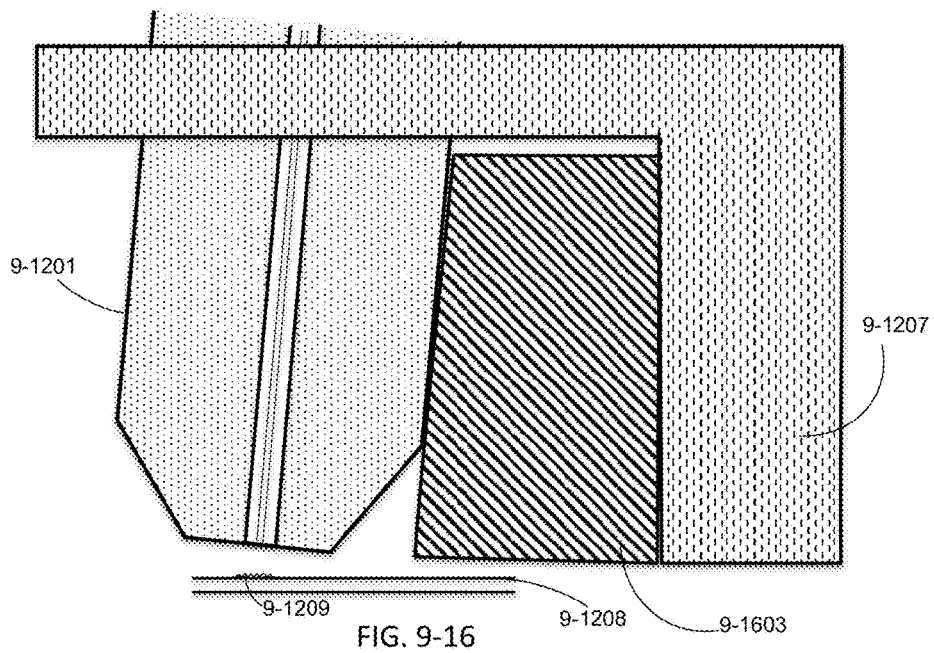
Figures 9, 10, 11, 12, 13, 14, 15, 16, 17:
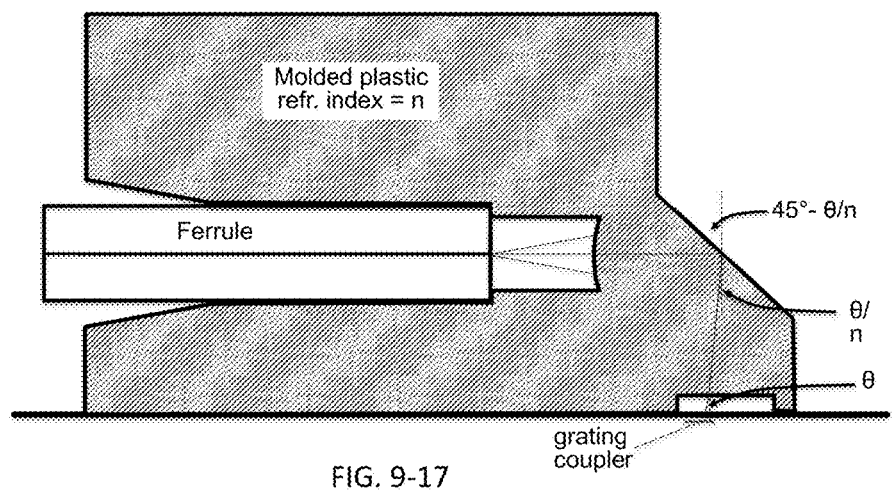
Figures 9, 10, 11, 12, 13, 14, 15, 16, 17, 18:
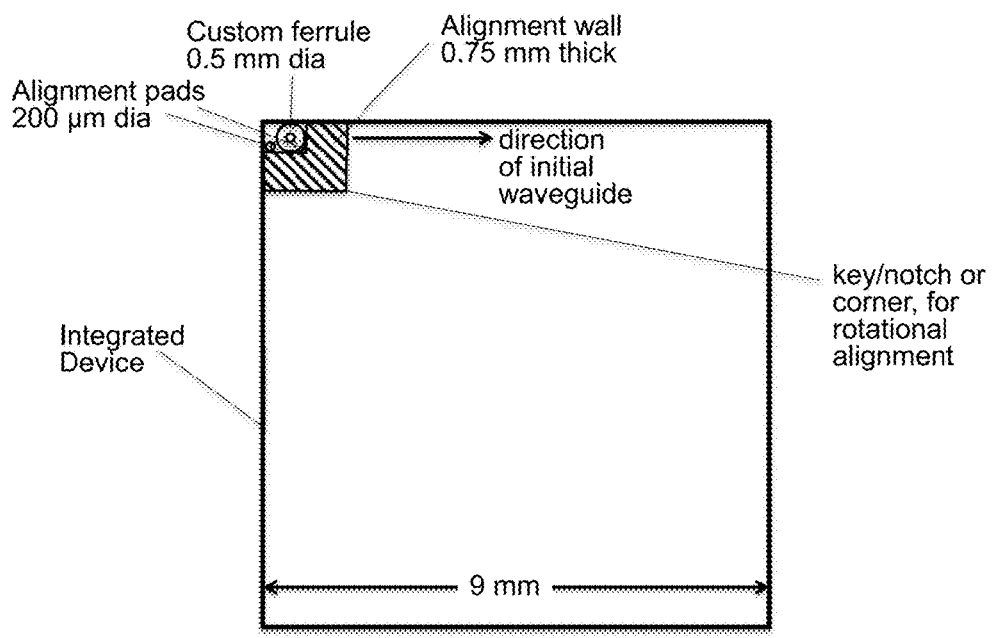
Figures 9, 10, 11, 12, 13, 14, 15, 16, 17, 18, 19:
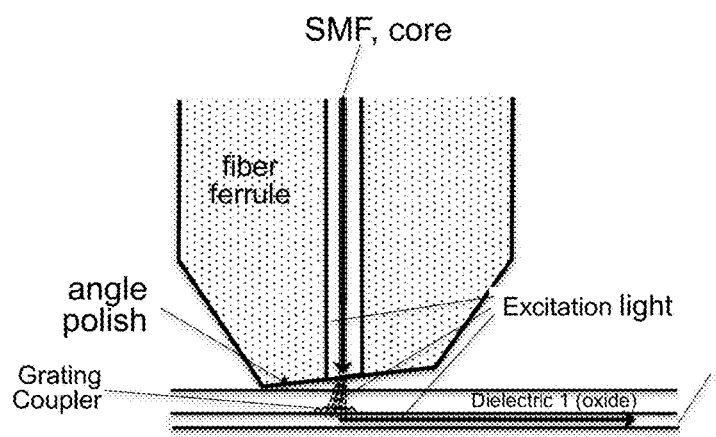
Figures 9, 10, 11, 12, 13, 14, 15, 16, 17, 18, 19, 20:
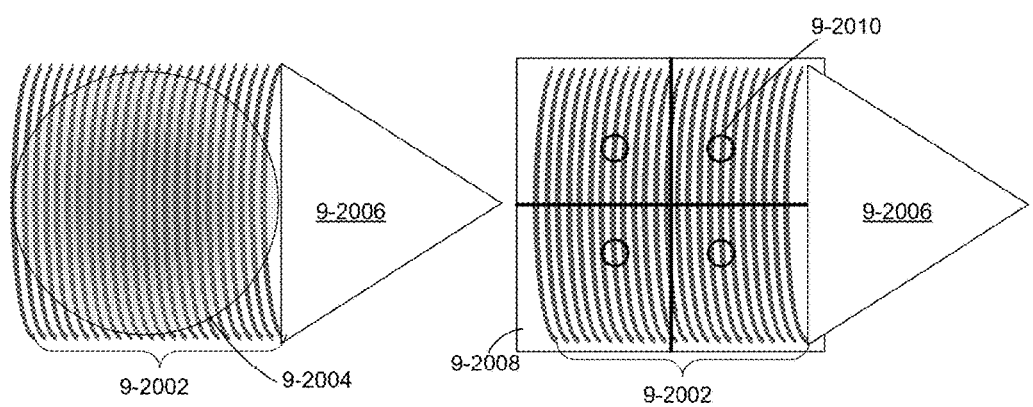
Figures 9, 10, 11, 12, 13, 14, 15, 16, 17, 18, 19, 20, 21:
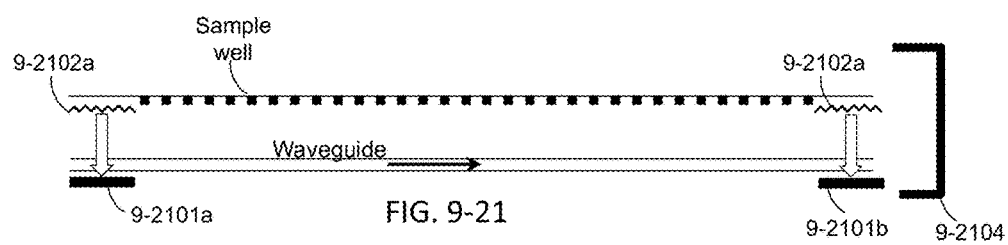
Figures 9, 10, 11, 12, 13, 14, 15, 16, 17, 18, 19, 20, 21, 22:
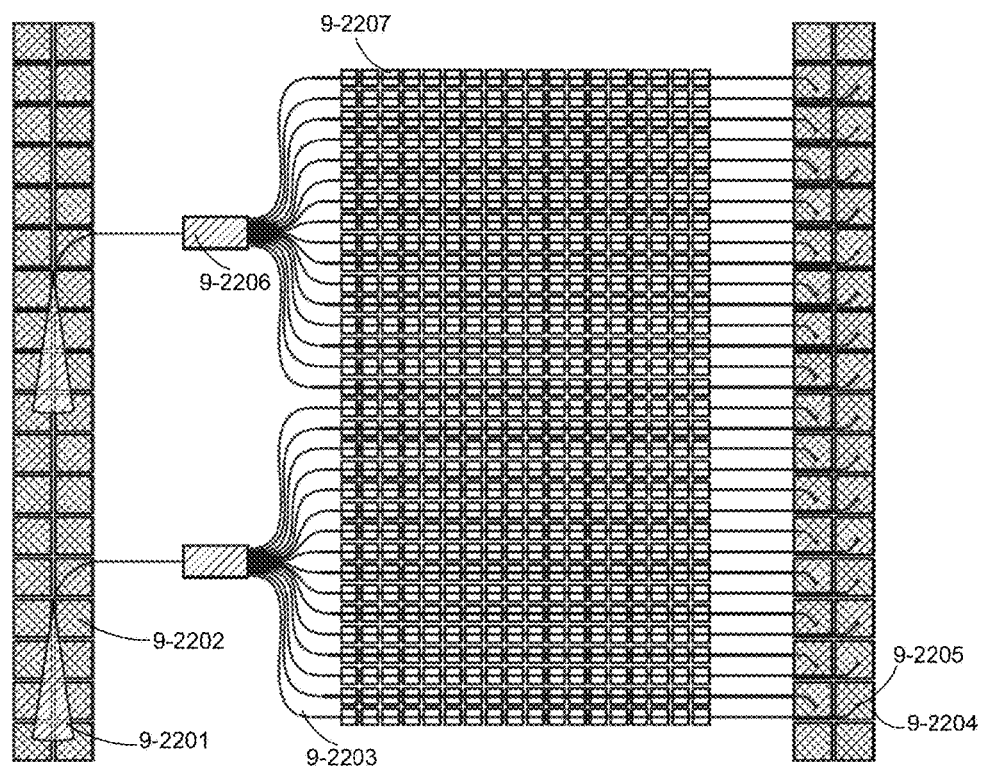
Figures 9, 10, 11, 12, 13, 14, 15, 16, 17, 18, 19, 20, 21, 22, 23:
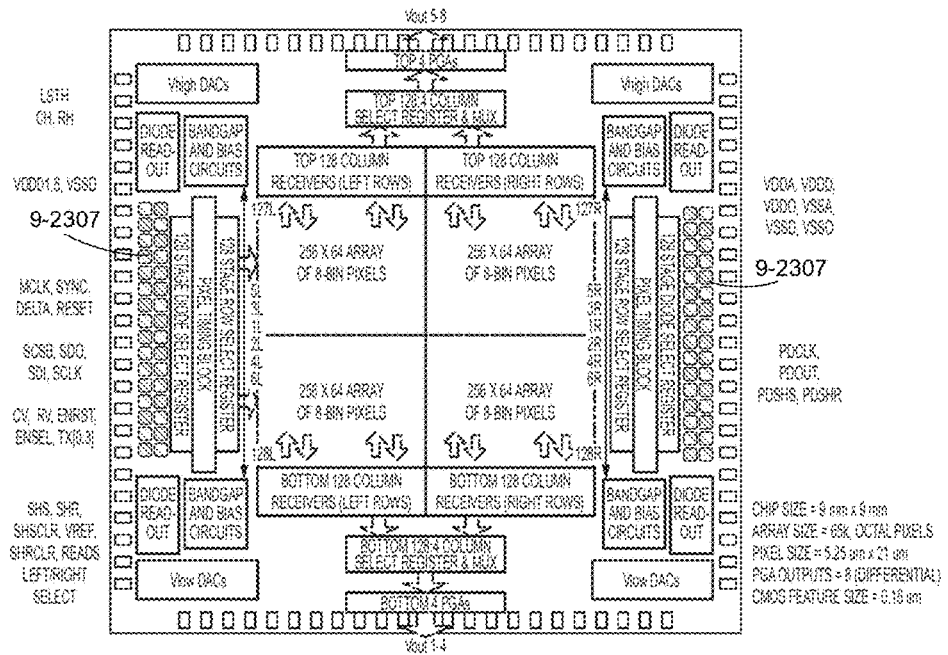
Figures 9, 10, 11, 12, 13, 14, 15, 16, 17, 18, 19, 20, 21, 22, 23, 24:
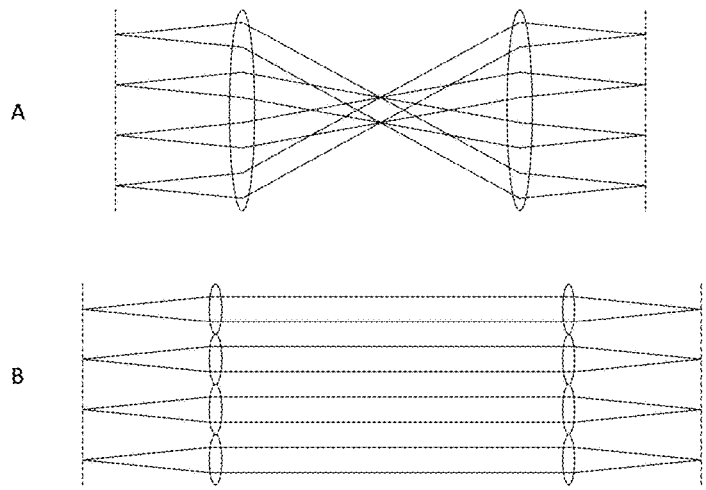
Figures 9, 10, 11, 12, 13, 14, 15, 16, 17, 18, 19, 20, 21, 22, 23, 24, 25, 25A:
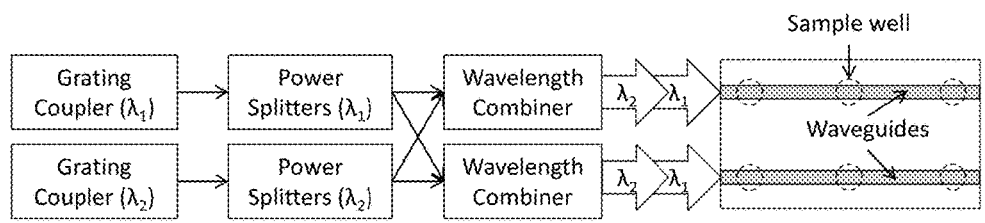
Figures 9, 10, 11, 12, 13, 14, 15, 16, 17, 18, 19, 20, 21, 22, 23, 24, 25, 25B:
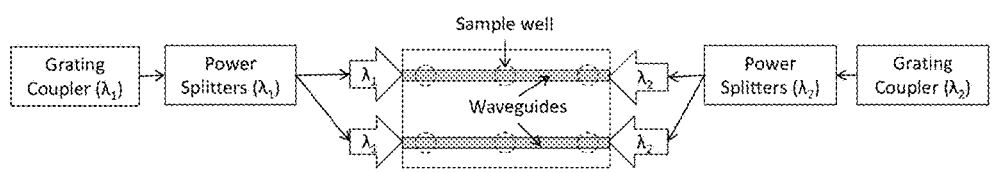
Figures 9, 10, 11, 12, 13, 14, 15, 16, 17, 18, 19, 20, 21, 22, 23, 24, 25, 25C:
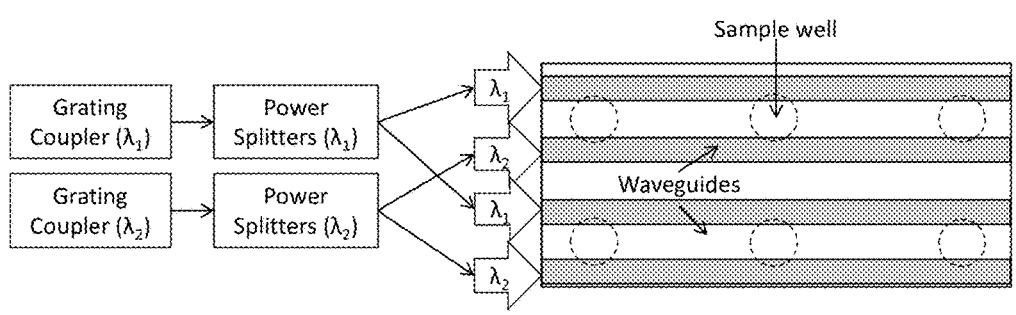
Figures 1, 10:
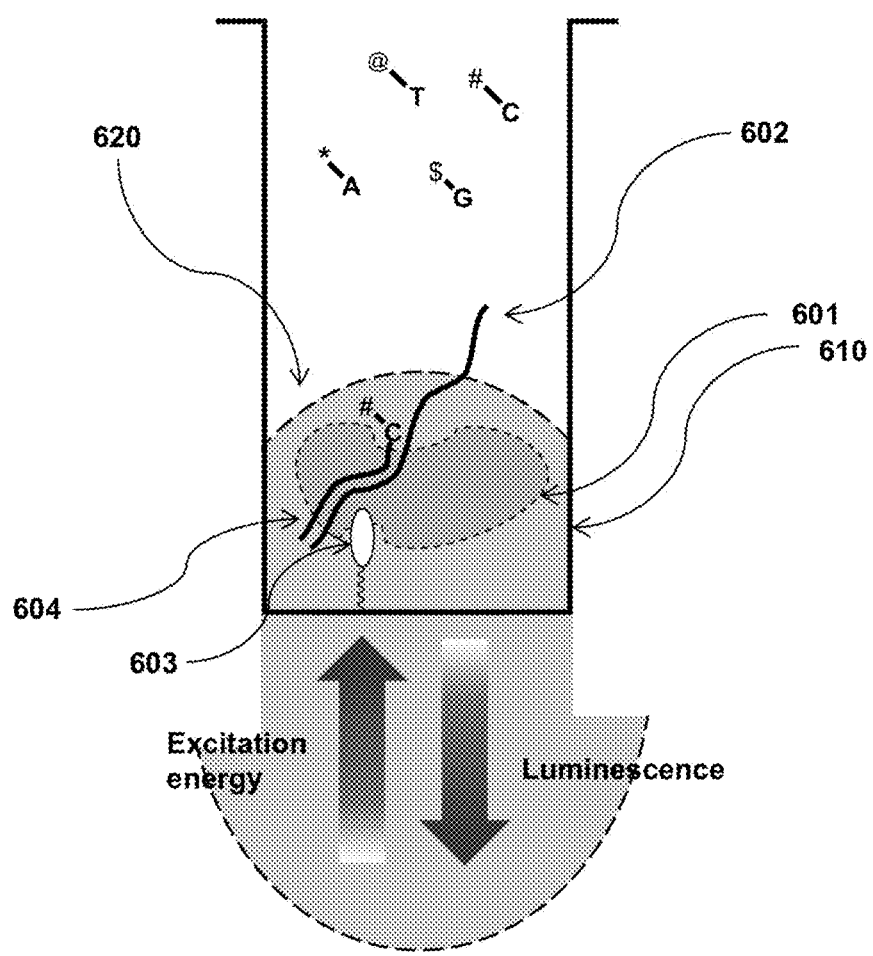
Figures 2, 10:
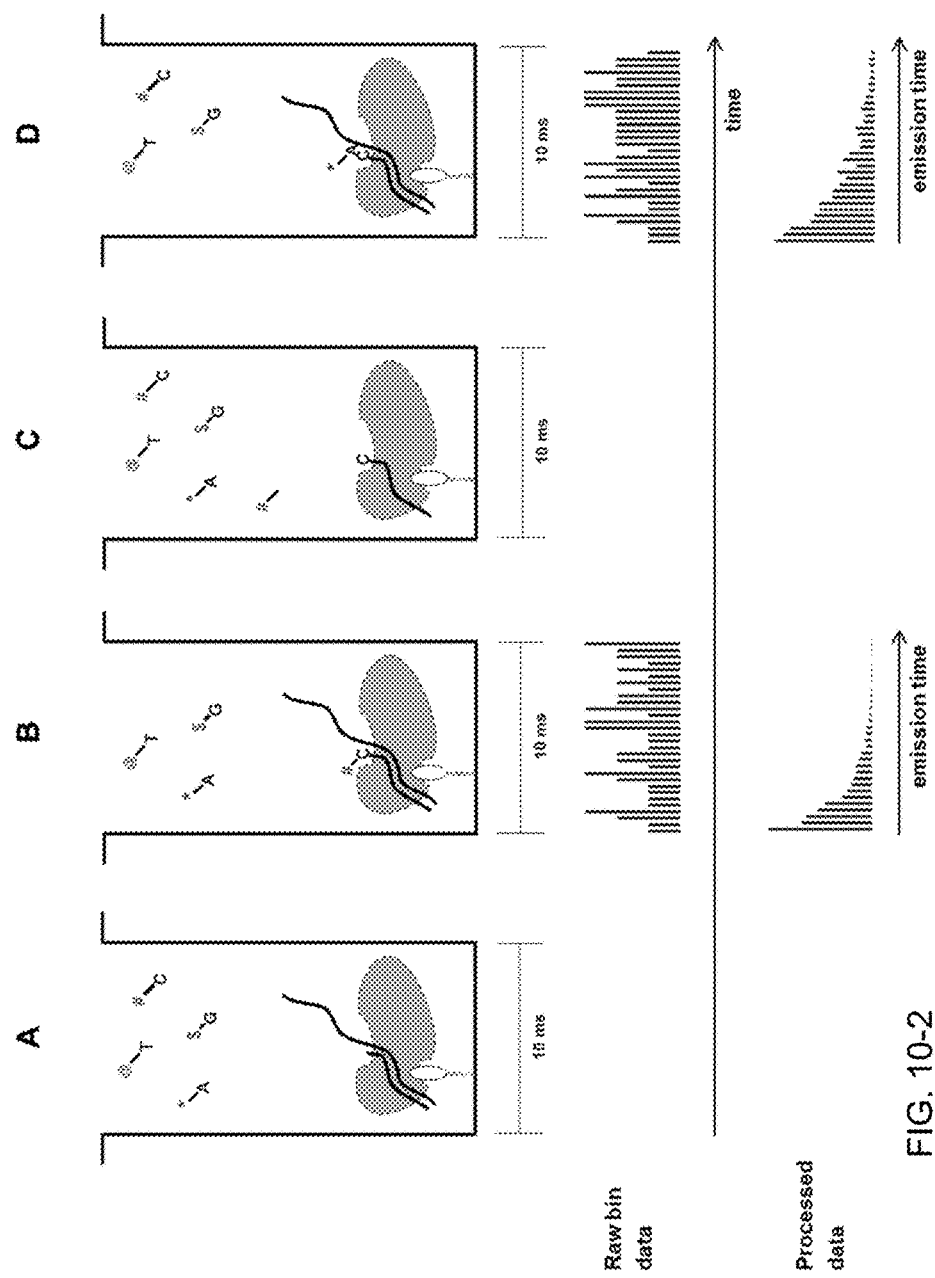
Figures 3, 10:
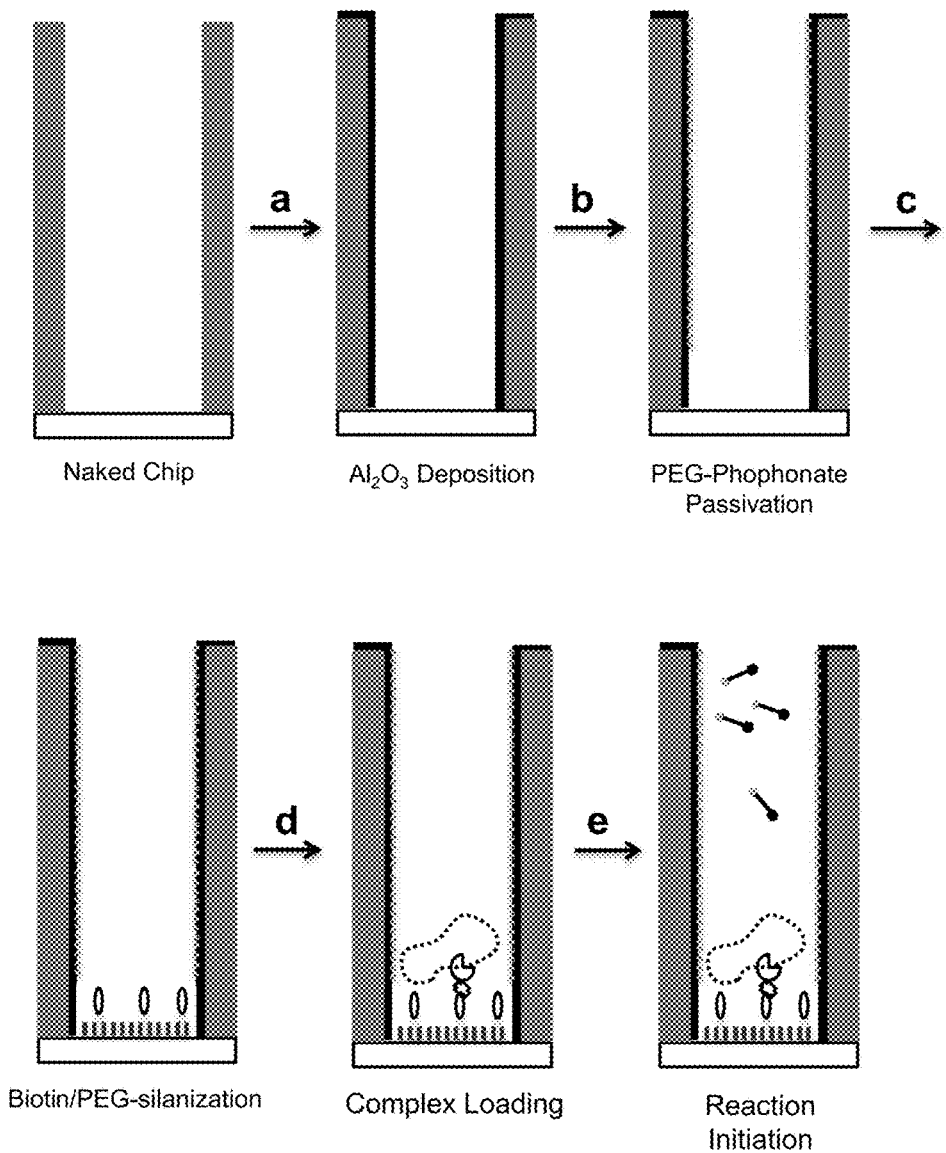
Figures 4, 10:
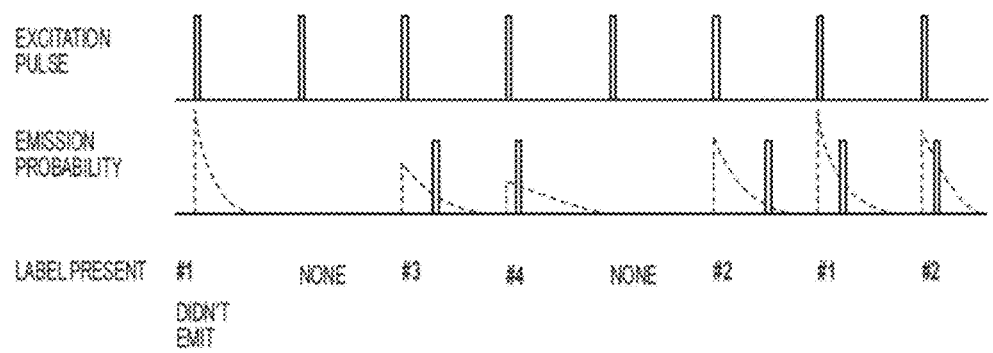
Figures 5, 10:
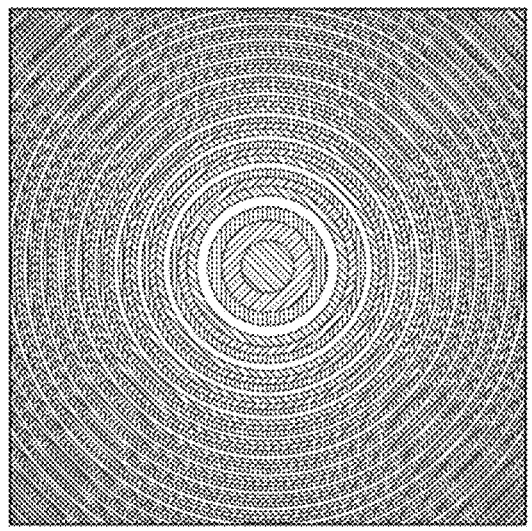
Figures 6, 7, 10:
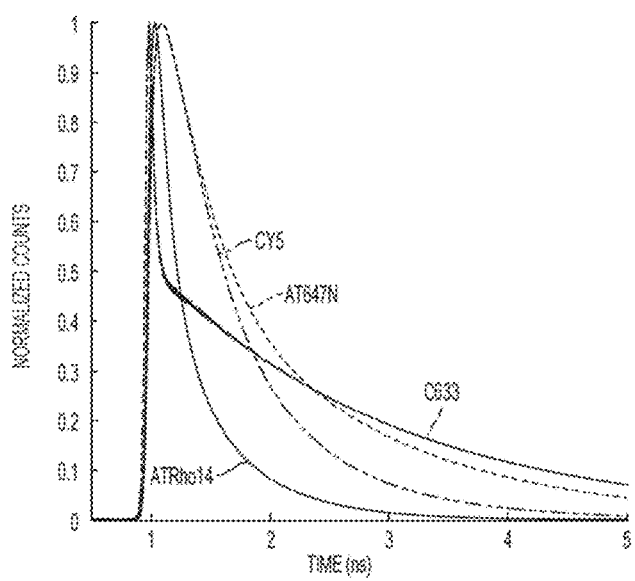
Figures 8, 9, 10:
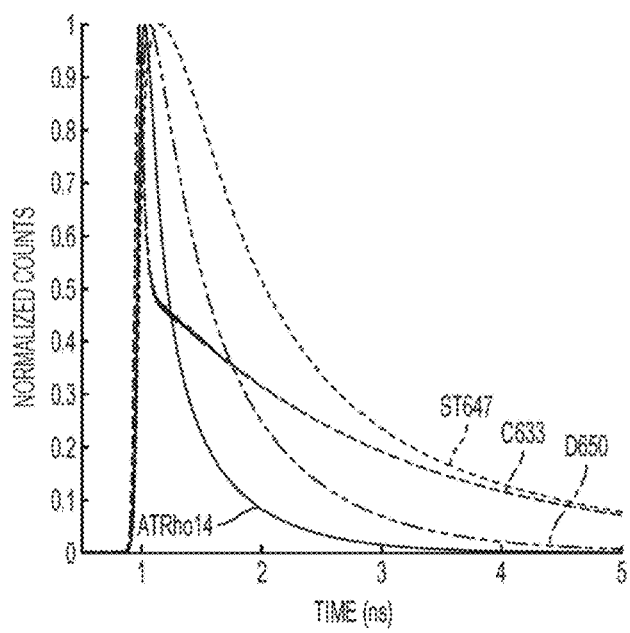
Figure 10:
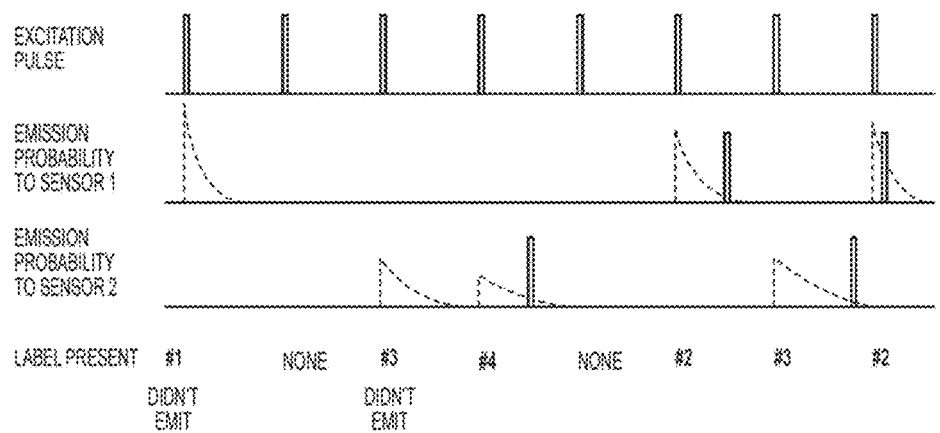
Figures 10, 11:
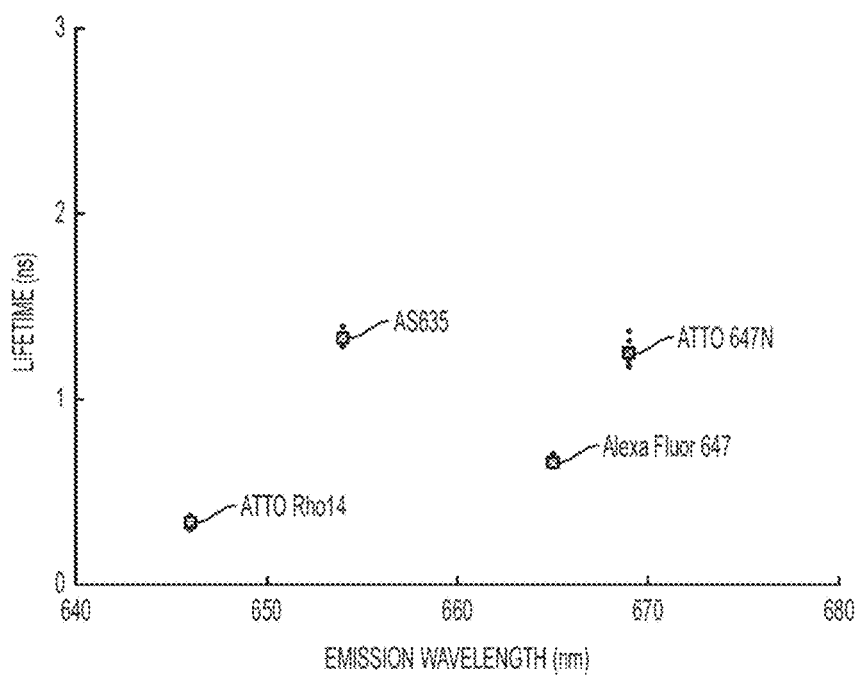
Figures 10, 11, 12:
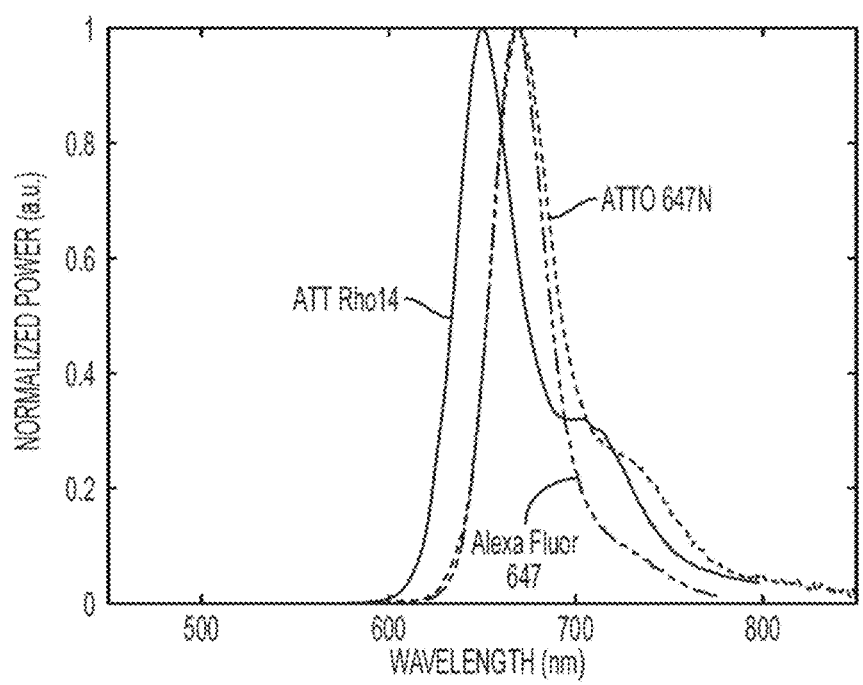
Figures 10, 11, 12, 13:
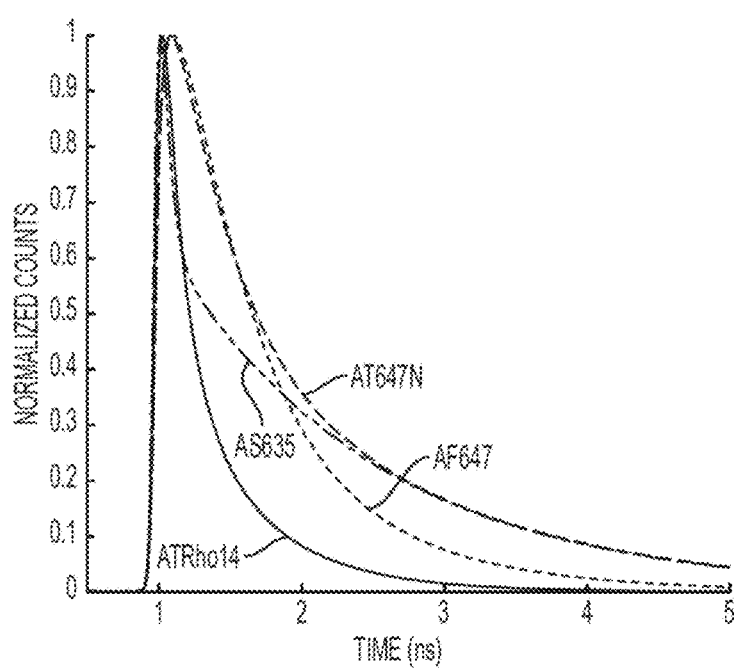
Figures 10, 11, 12, 13, 14, 15, 16, 17:
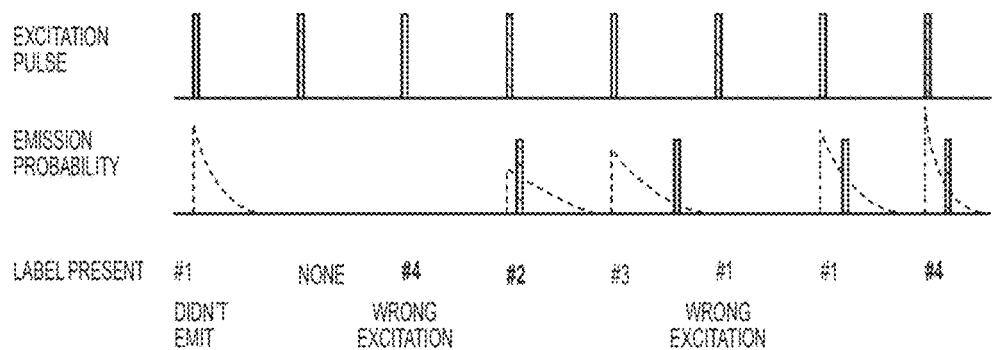
Figures 10, 11, 12, 13, 14, 15, 16, 17, 18:
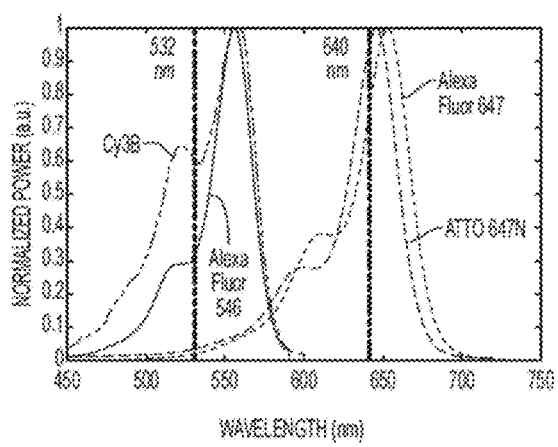
Figures 10, 11, 12, 13, 14, 15, 16, 17, 18, 19, 20:
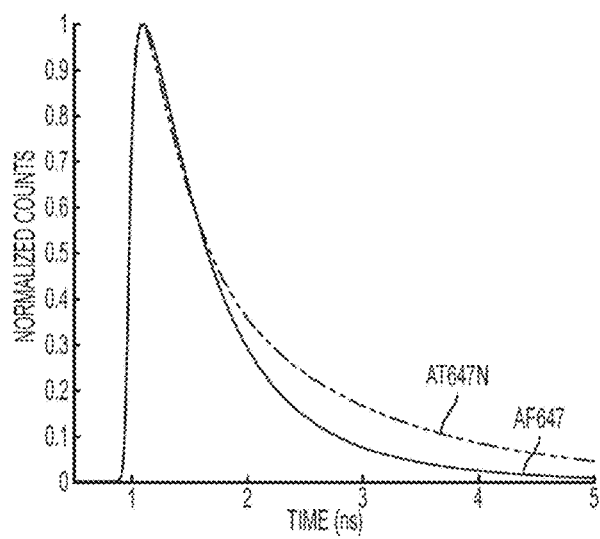
Figures 1, 11:
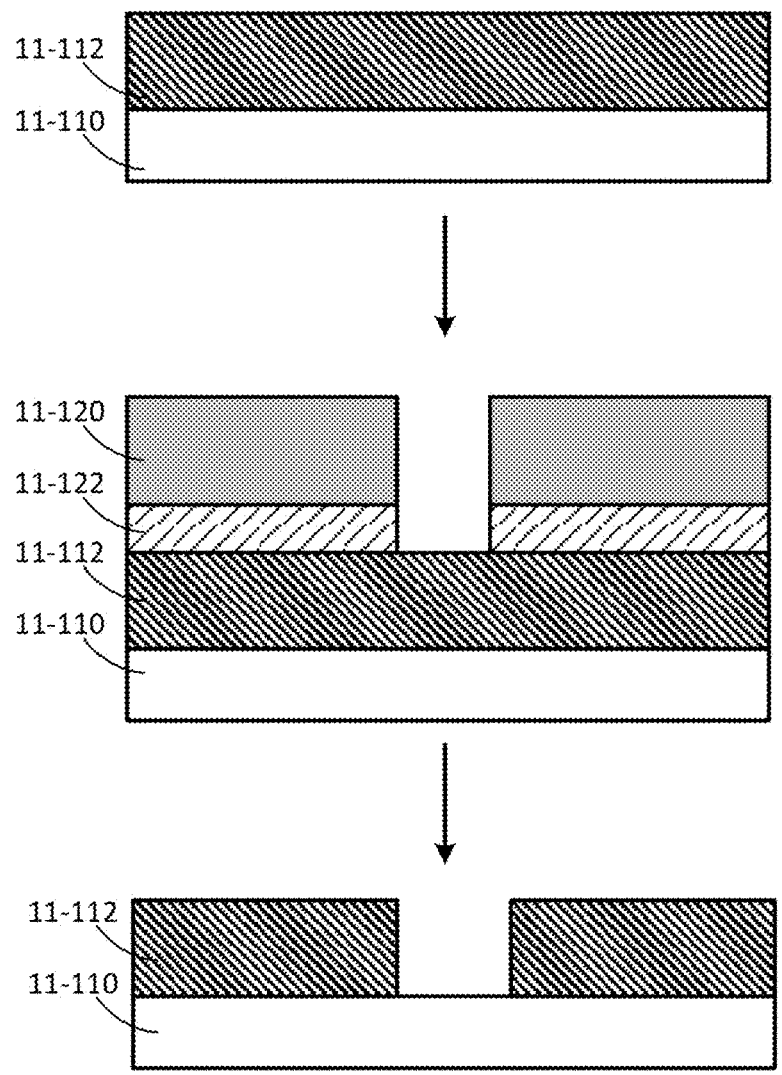
Figures 2, 11:
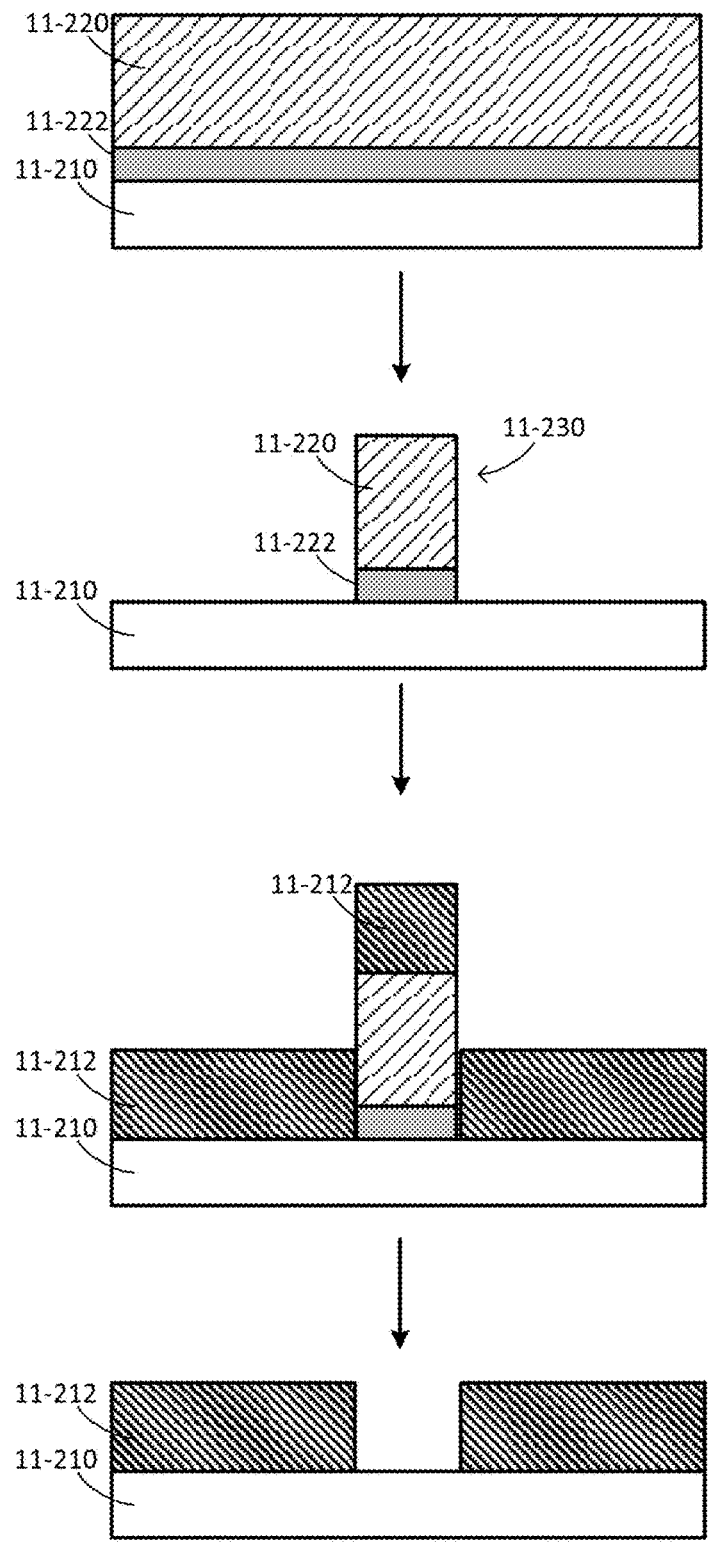
Figures 3, 11:
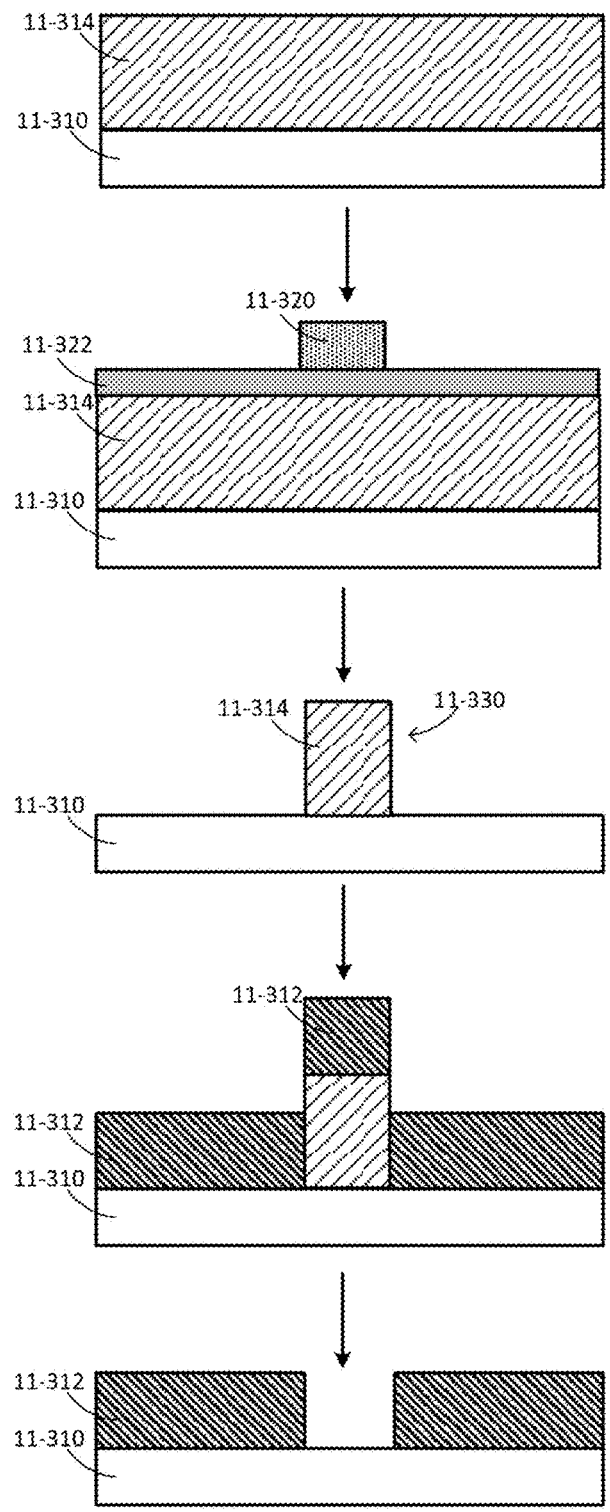
Figures 4A, 11:
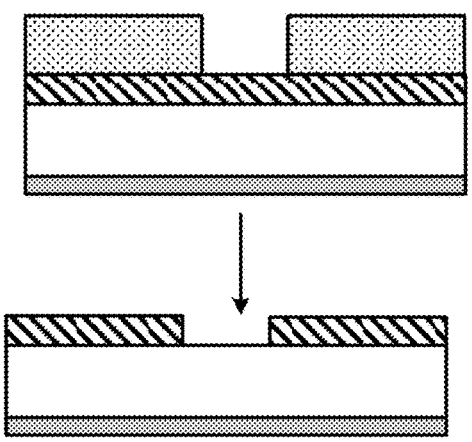
Figures 4B, 11:
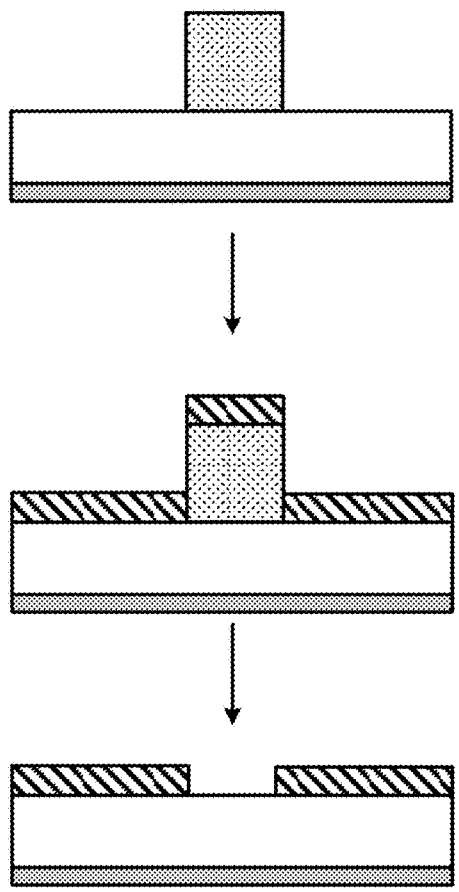
Figures 5, 11:
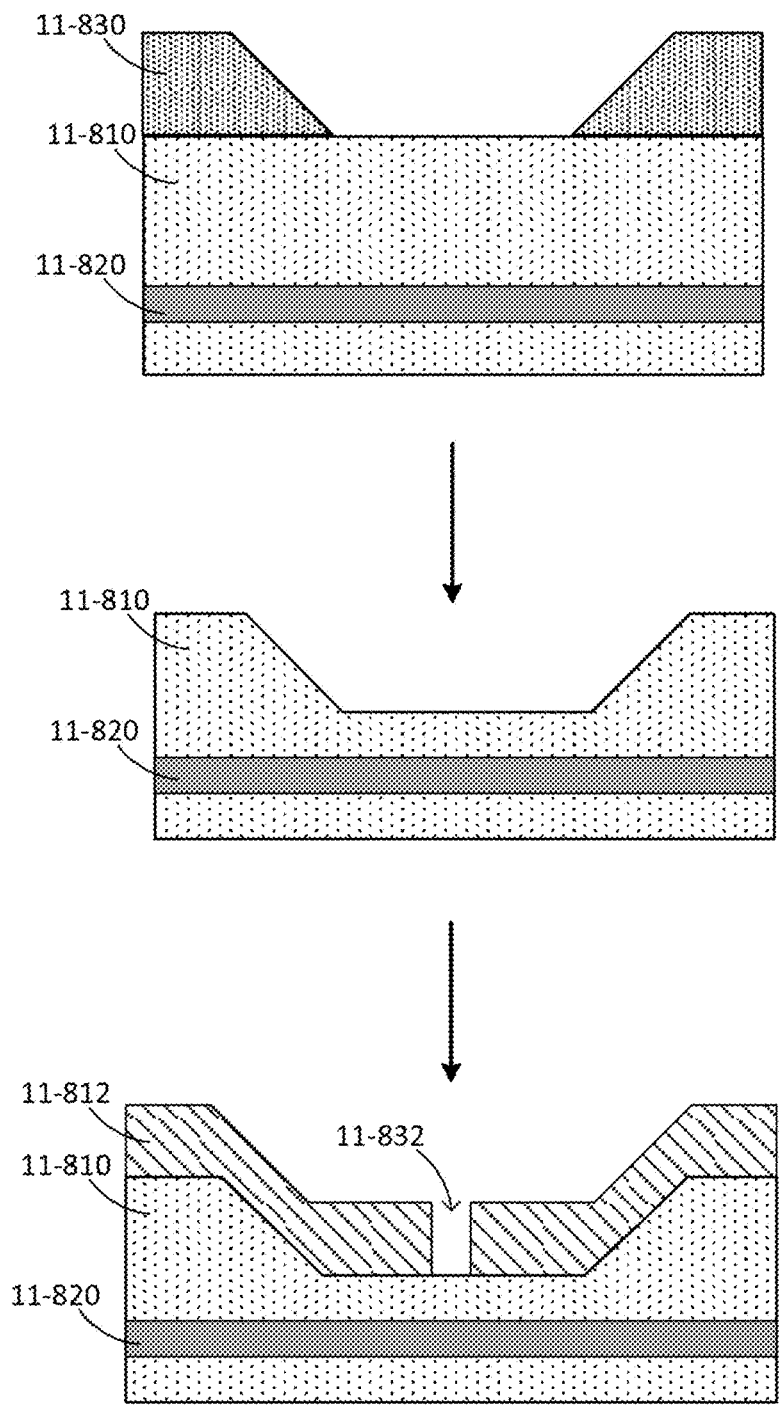
Figures 6, 11:
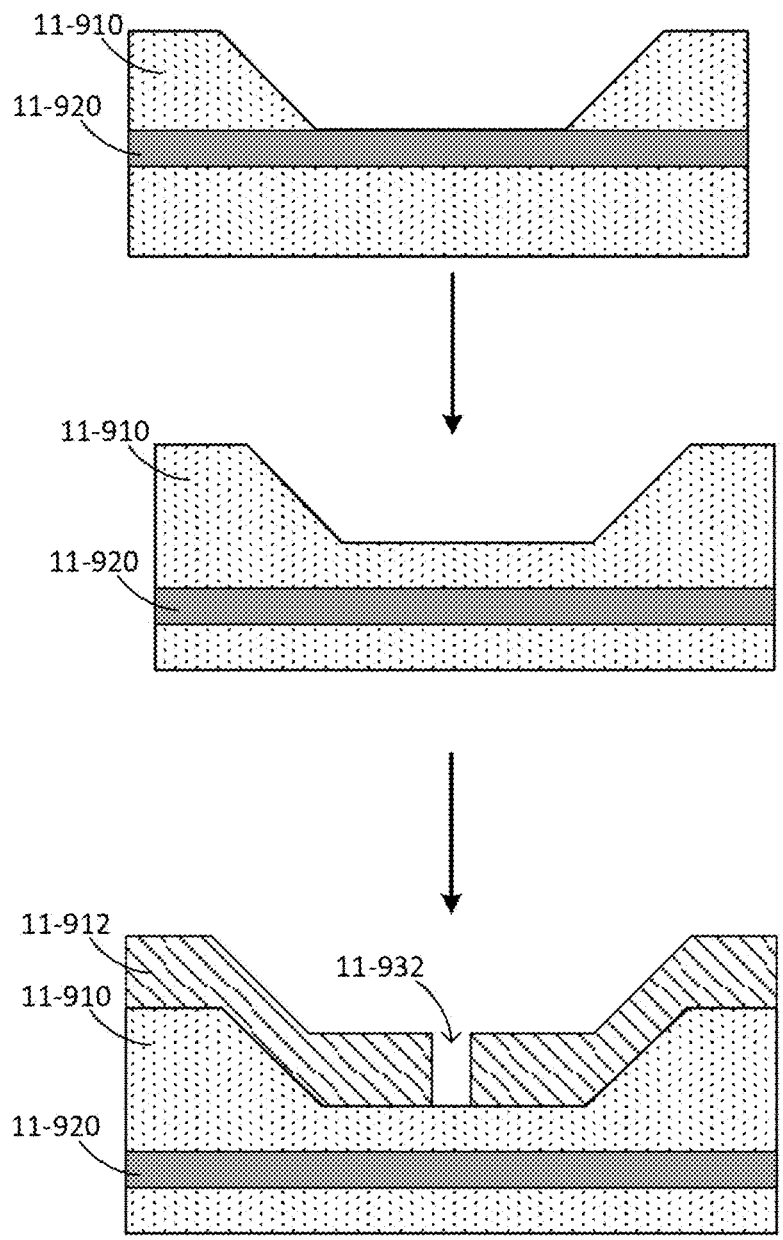
Figures 7, 11:
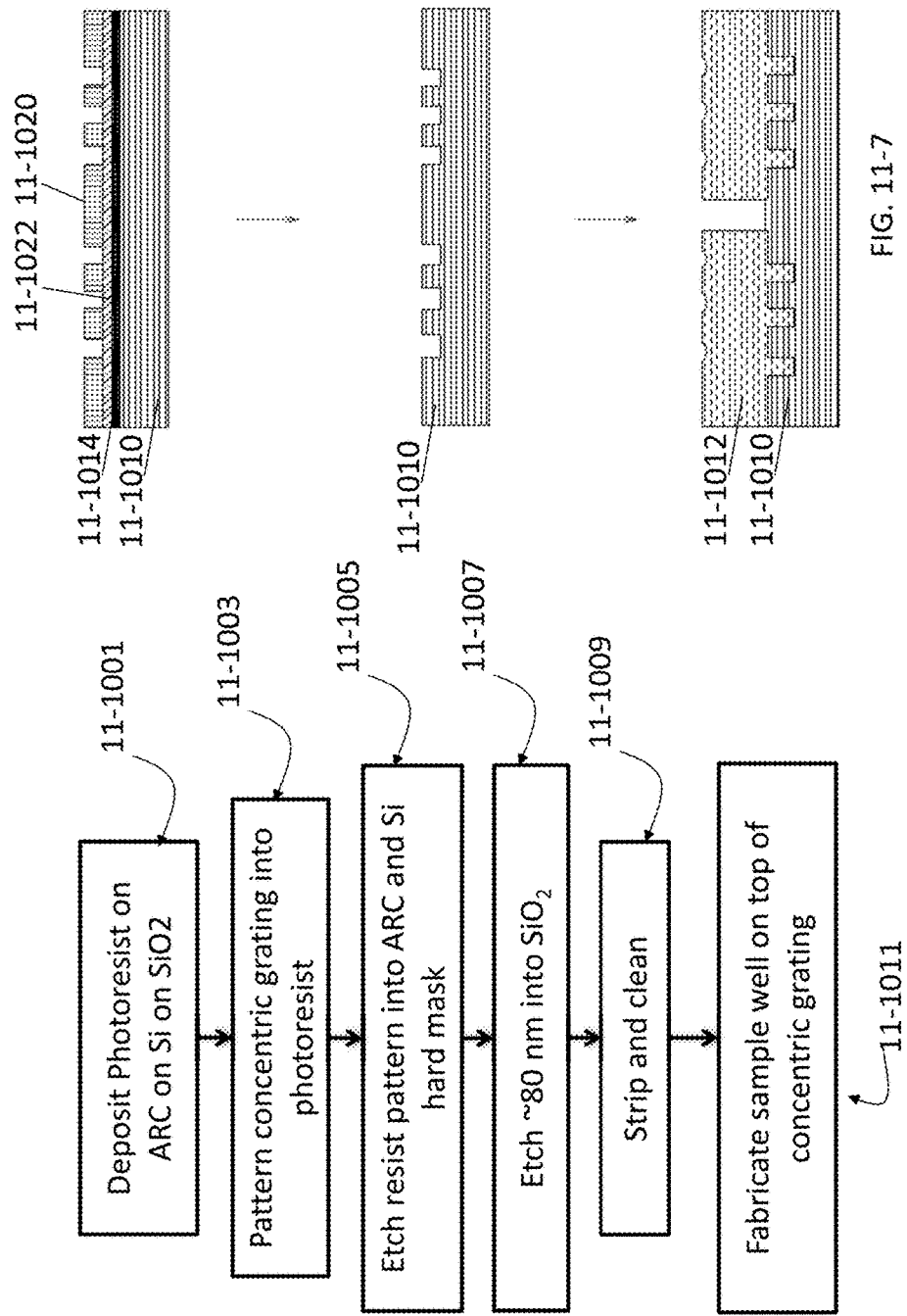
Figures 8, 11:
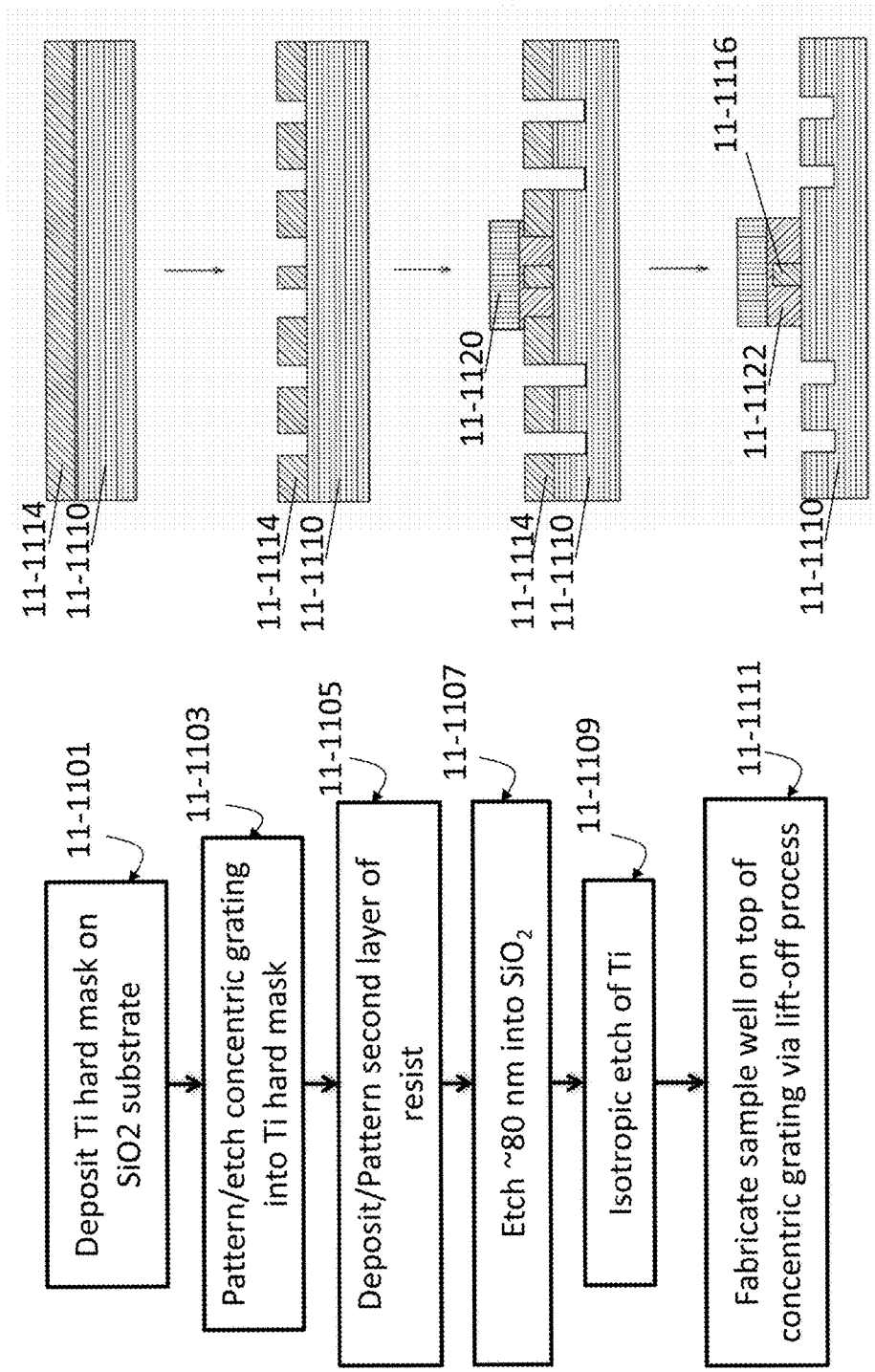
Figures 9, 11:
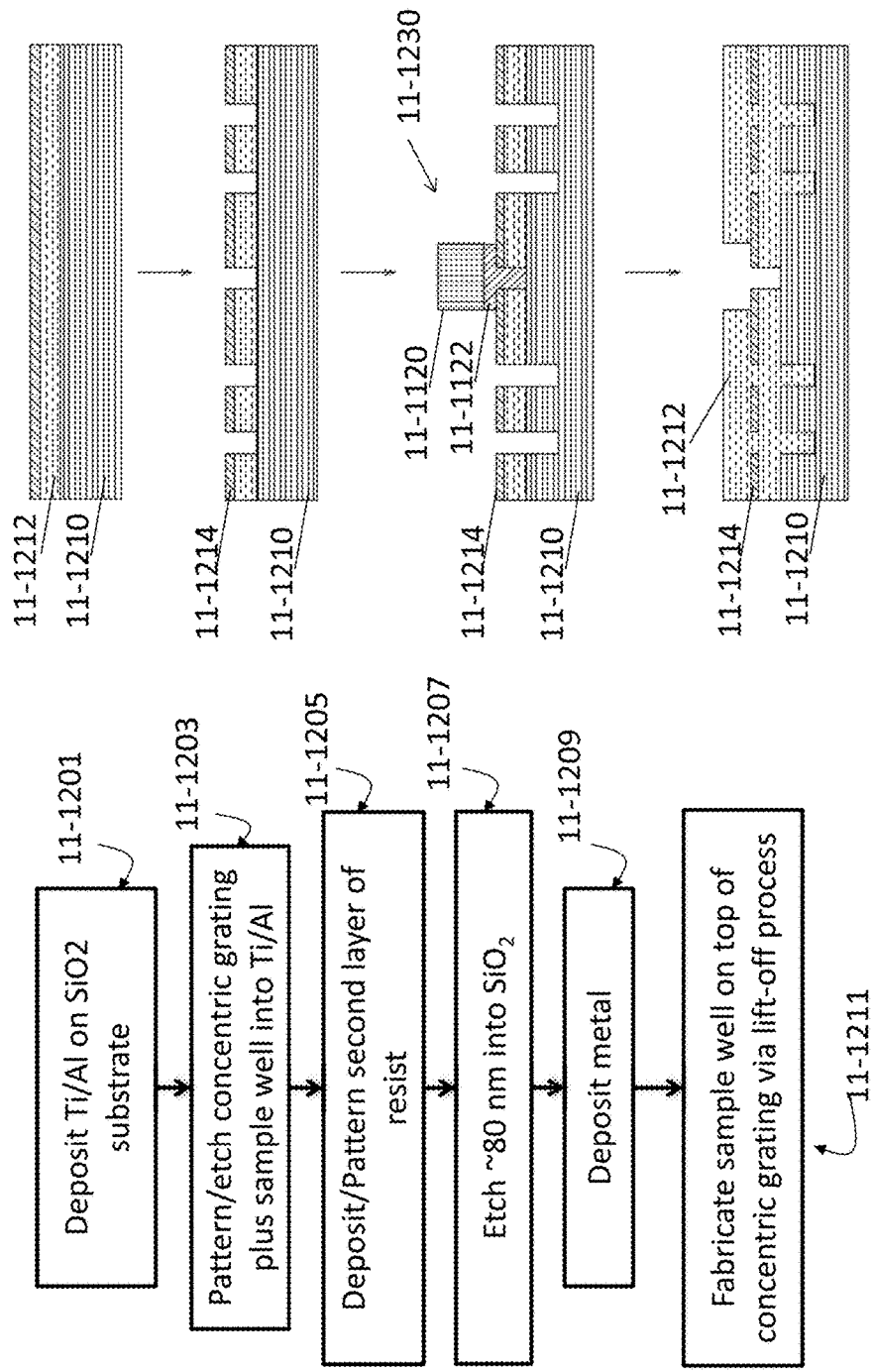
Figures 10, 11:
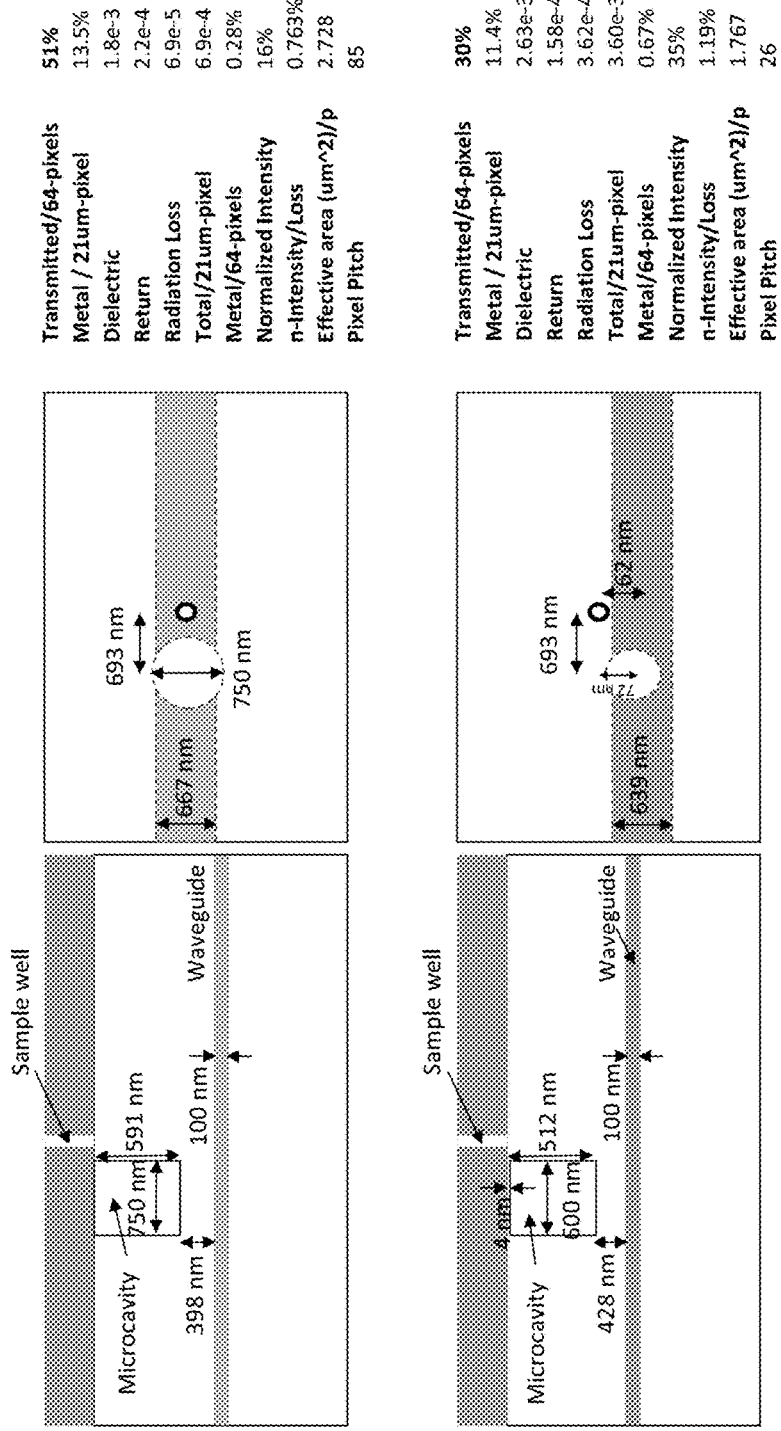
Figure 11:
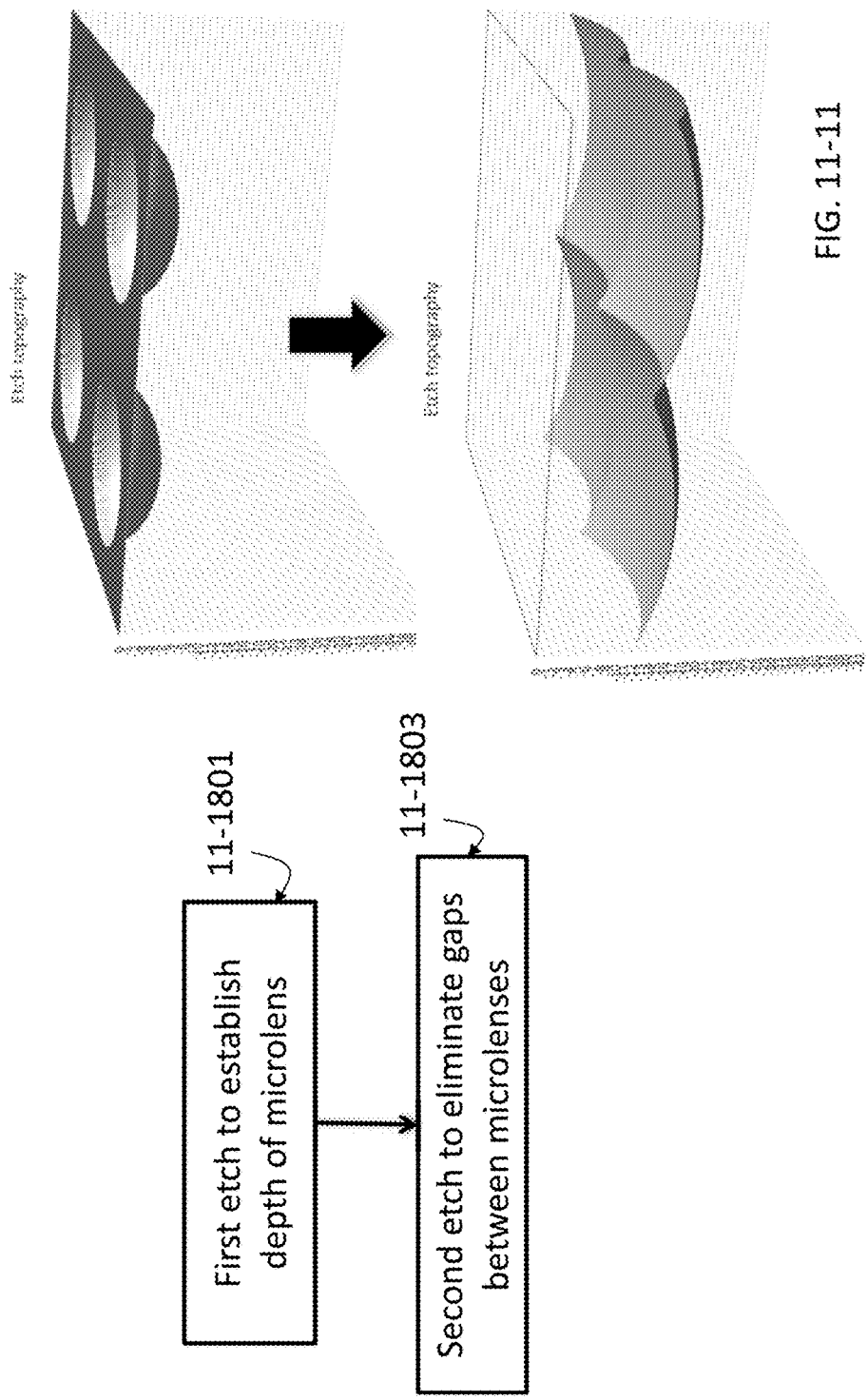
Figures 11, 12:
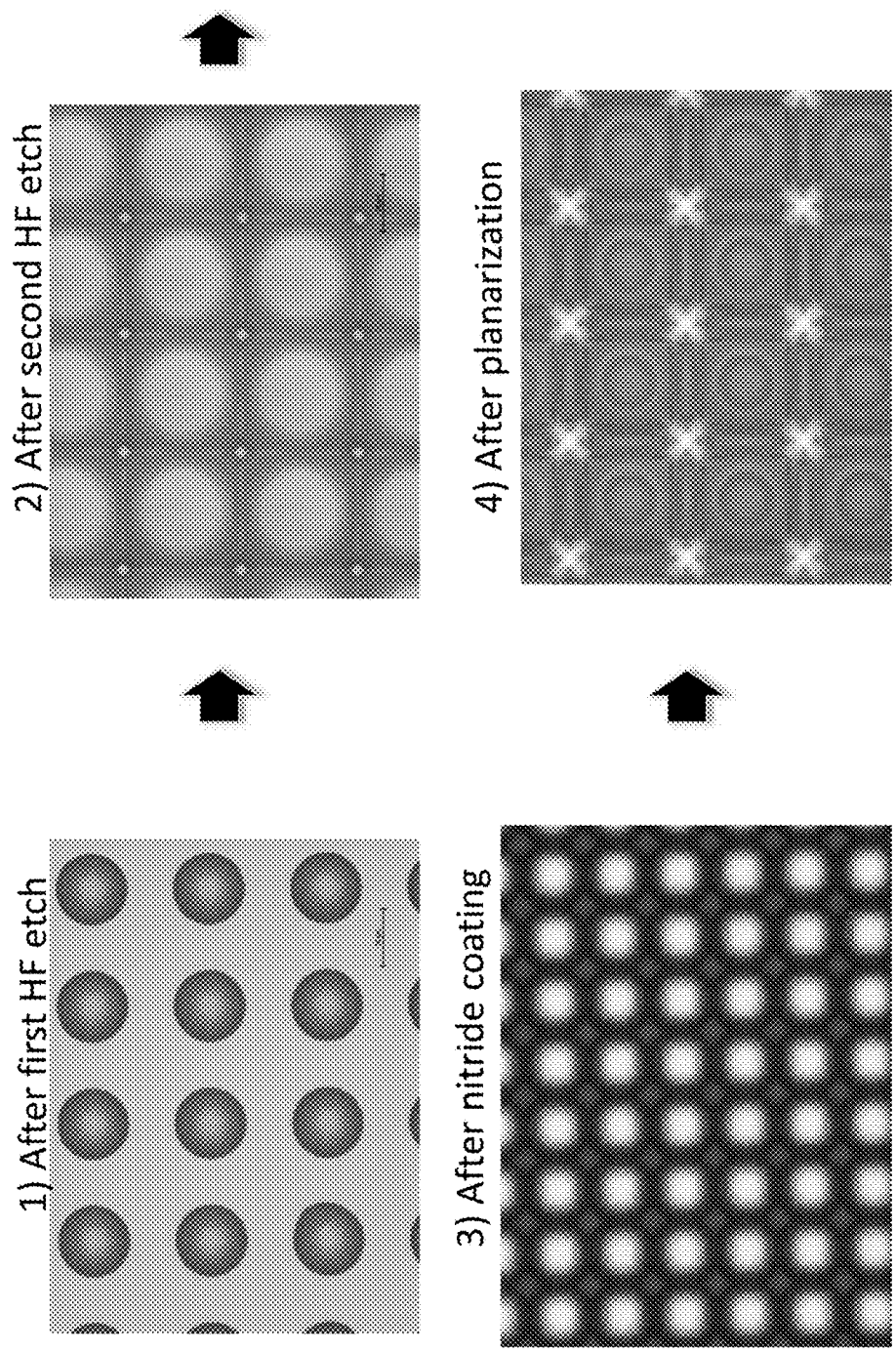
Figures 11, 12, 13:
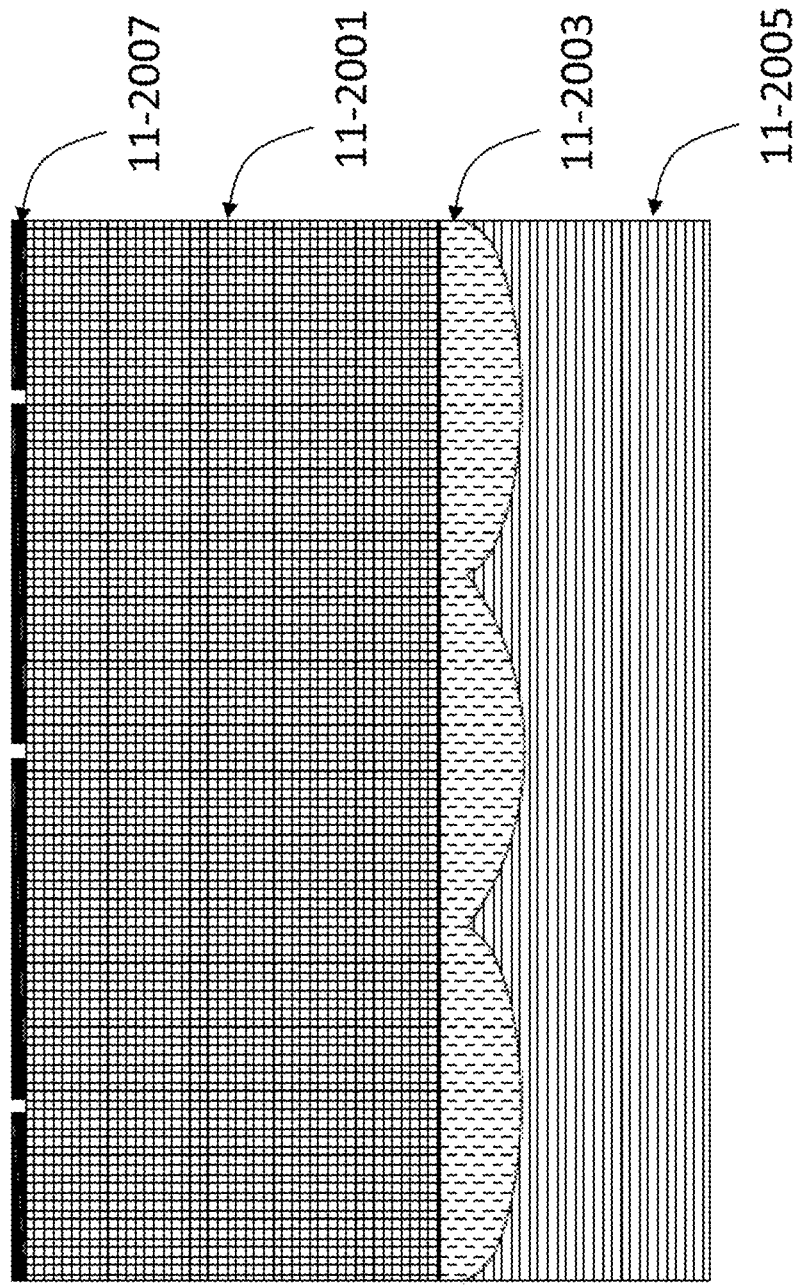
Figures 11, 12, 13, 14:
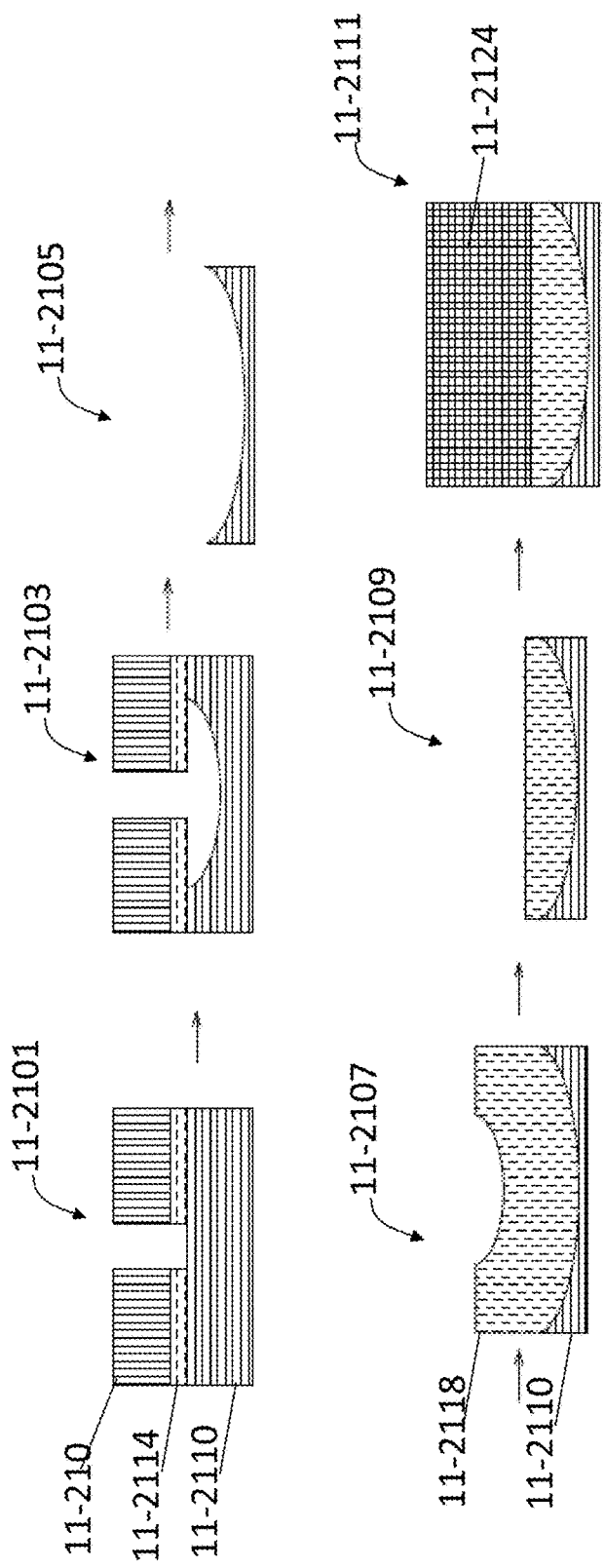
Figures 11, 12, 13, 14, 15:
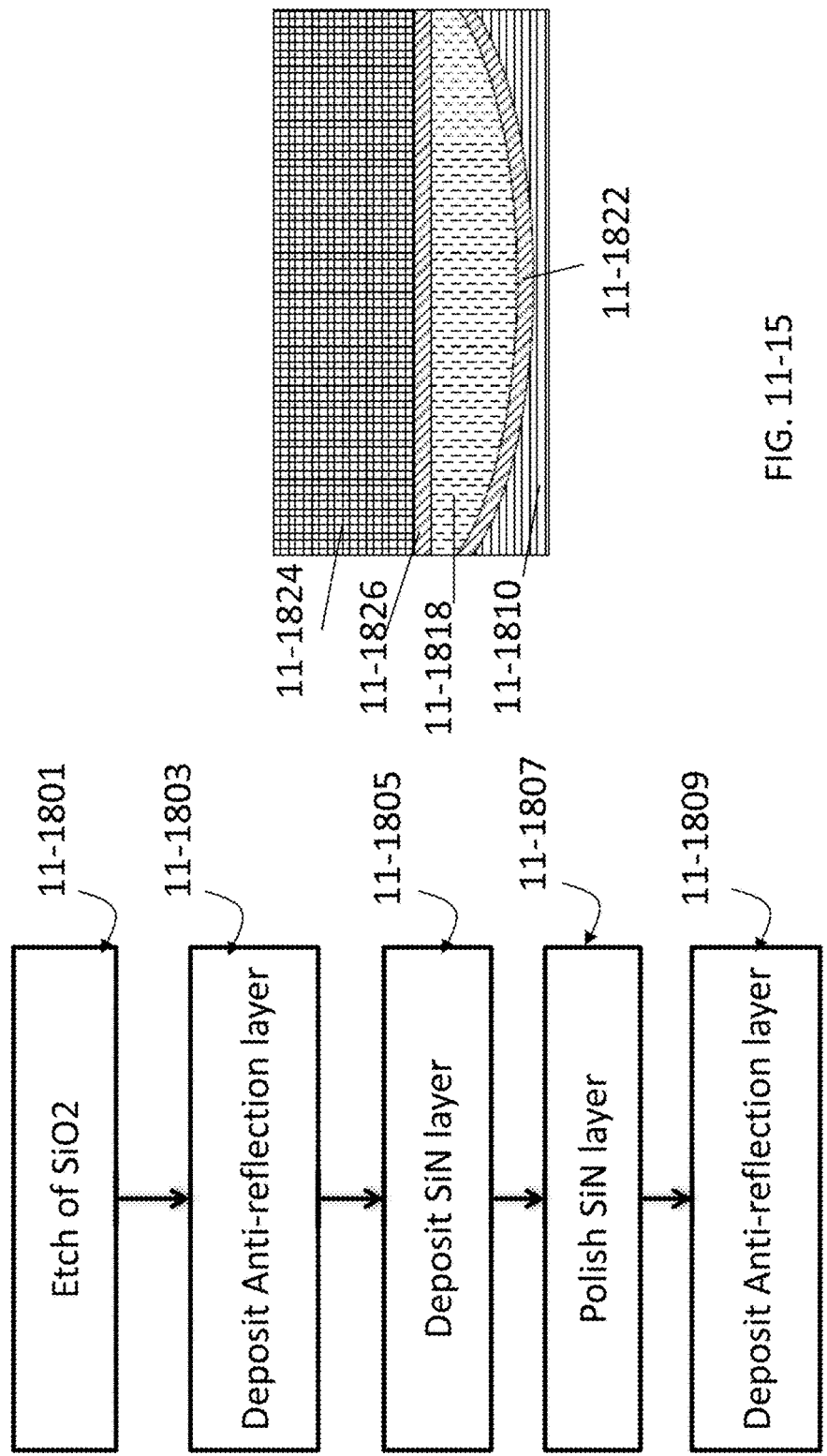
Figures 11, 12, 13, 14, 15, 16:
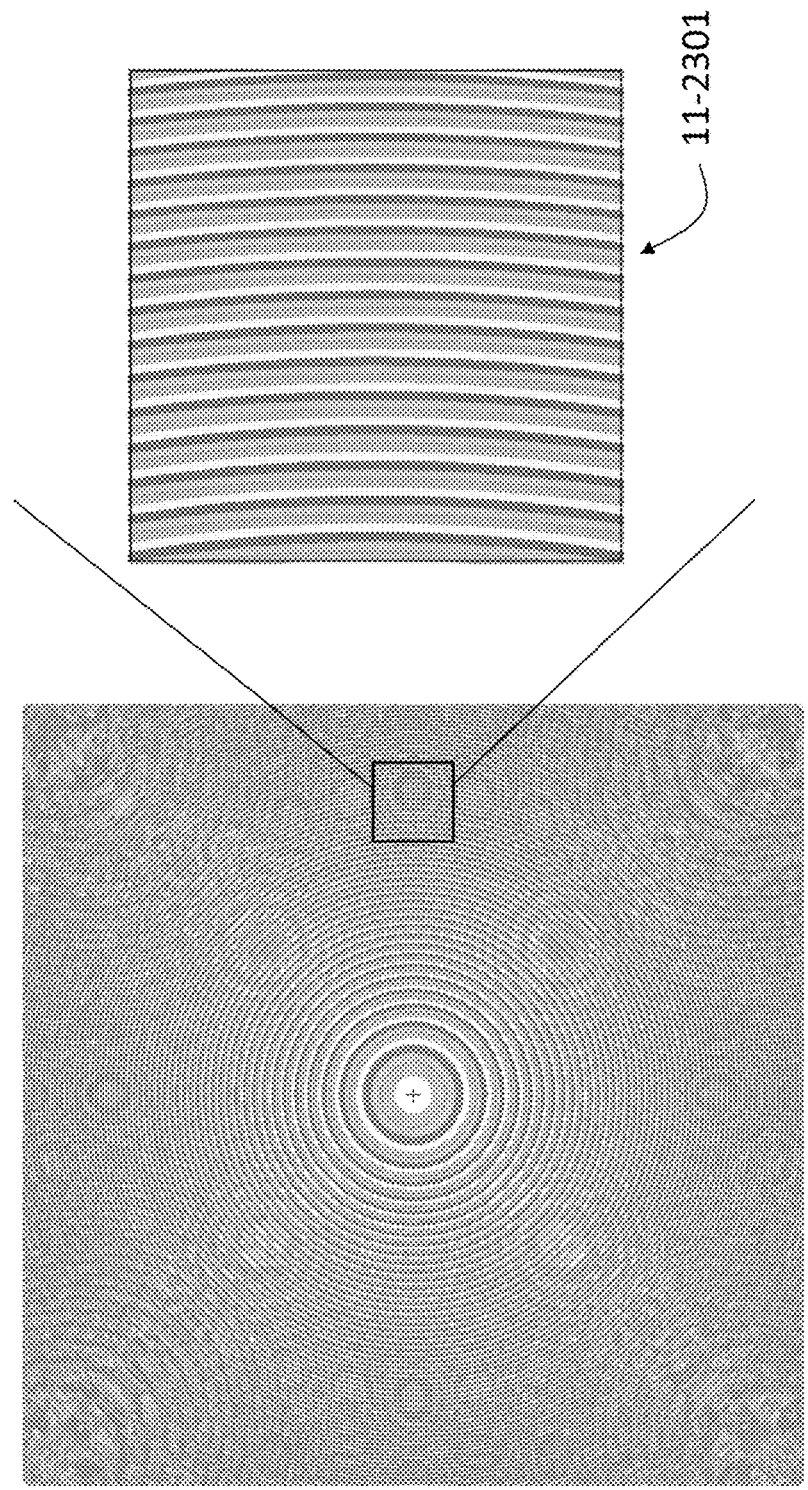
Figures 11, 12, 13, 14, 15, 16, 17:
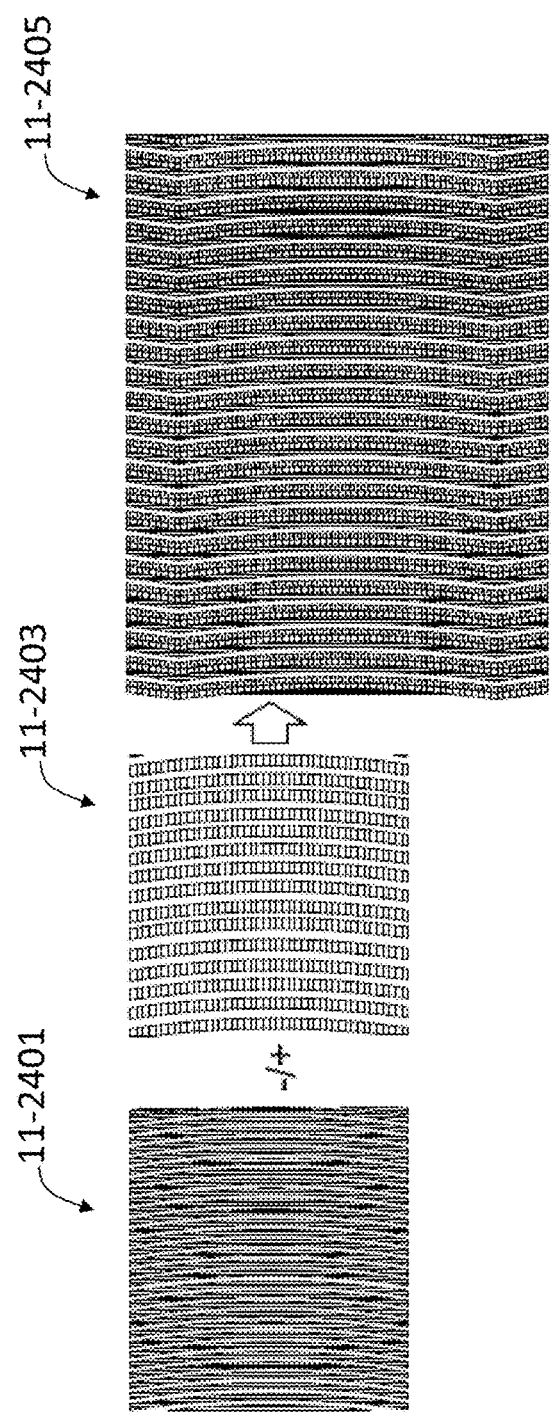
Figures 11, 12, 13, 14, 15, 16, 17, 18:
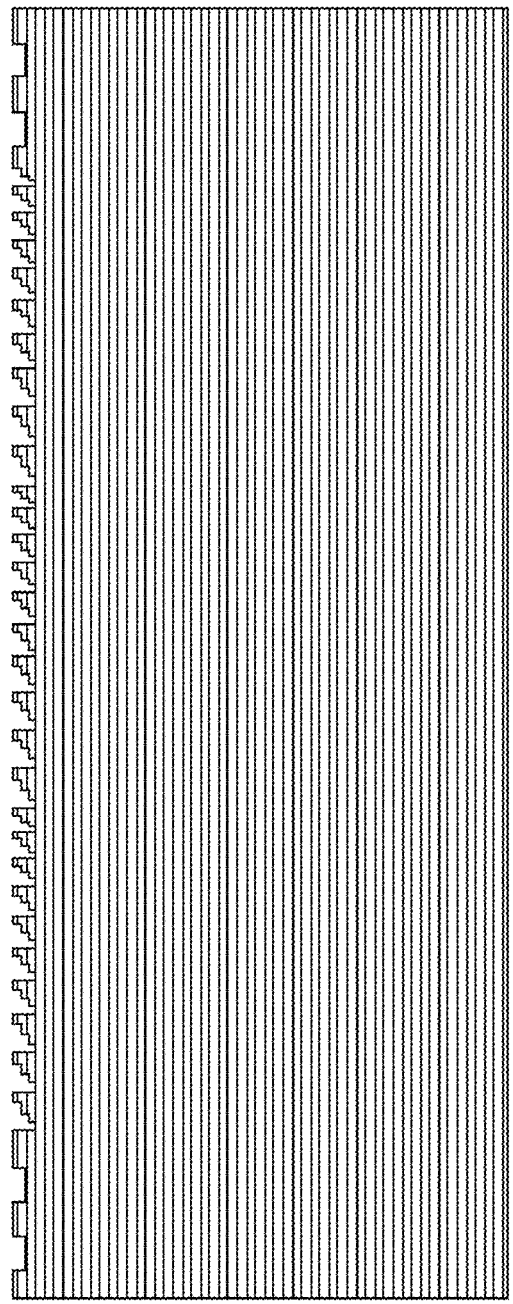
Figures 11, 12, 13, 14, 15, 16, 17, 18, 19:
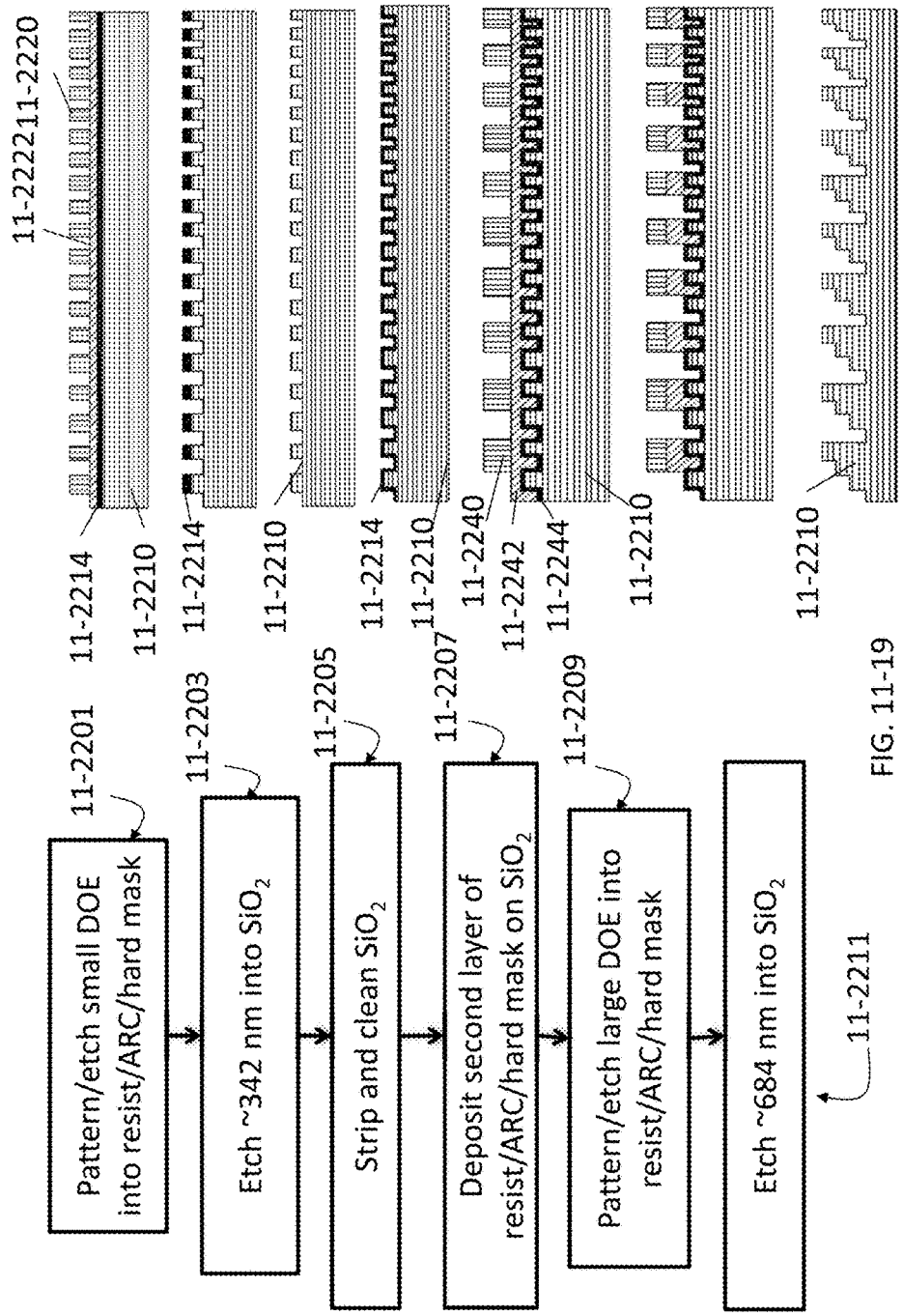
Figures 11, 12, 13, 14, 15, 16, 17, 18, 19, 20:
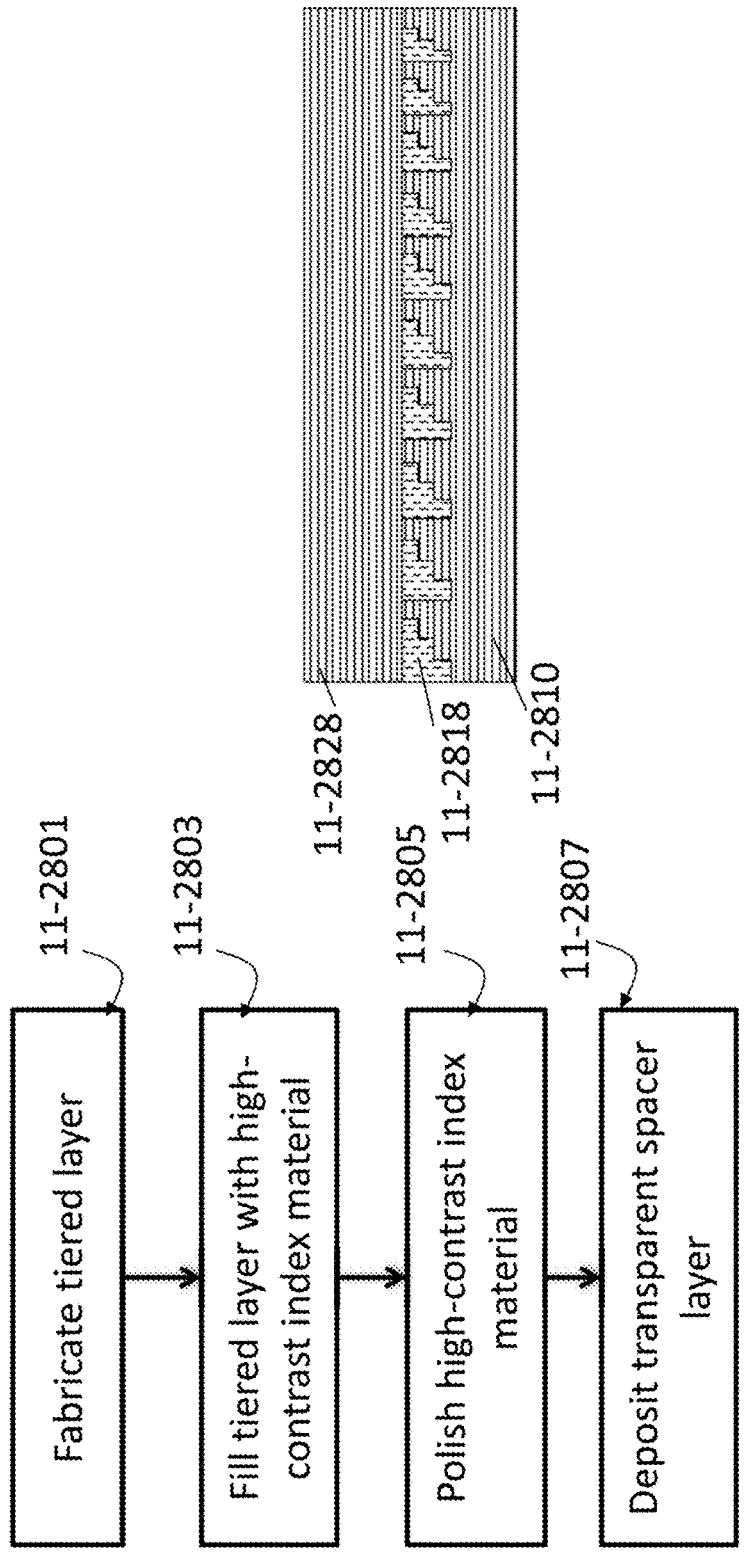
Figures 11, 12, 13, 14, 15, 16, 17, 18, 19, 20, 21:
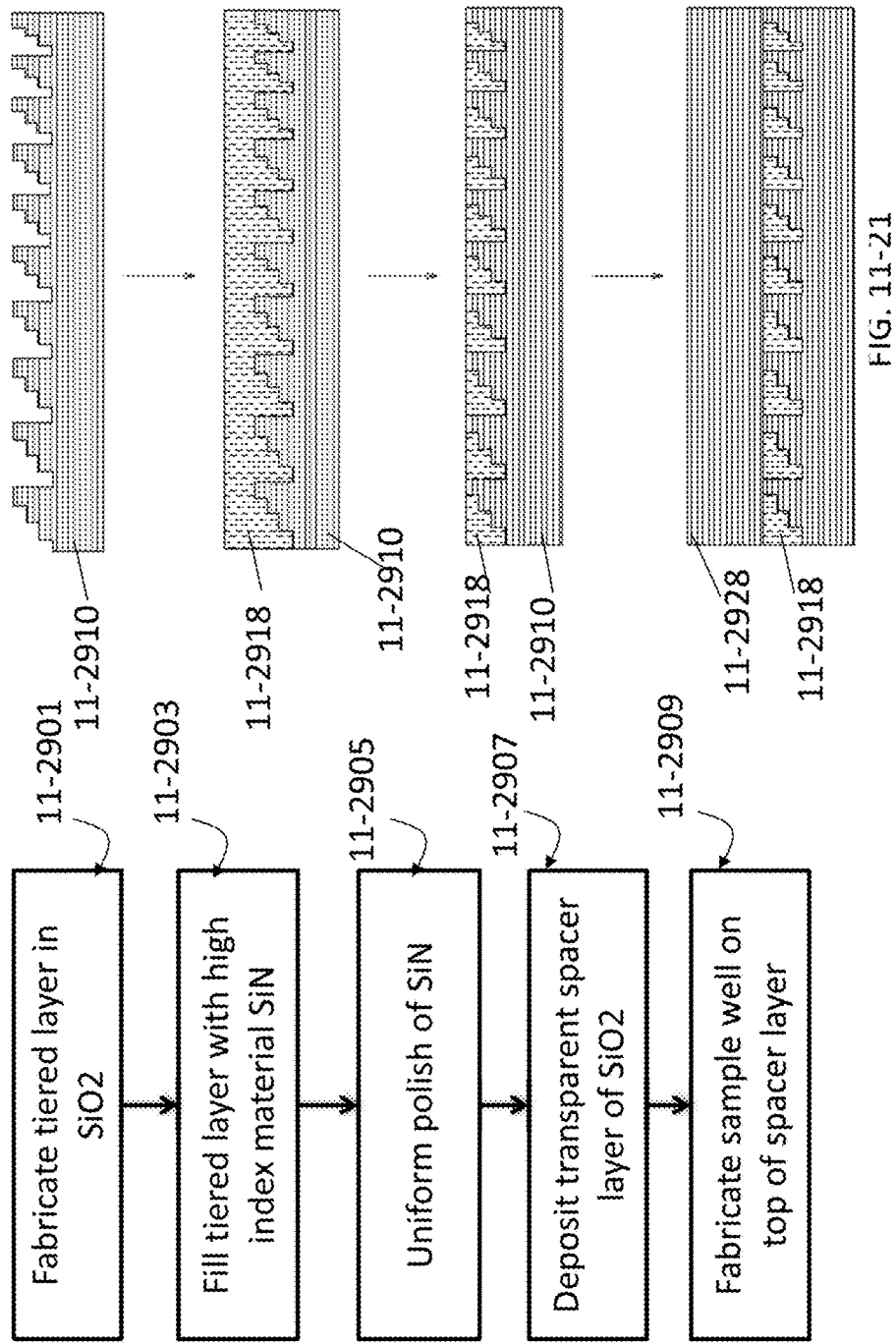
Figures 11, 12, 13, 14, 15, 16, 17, 18, 19, 20, 21, 22:
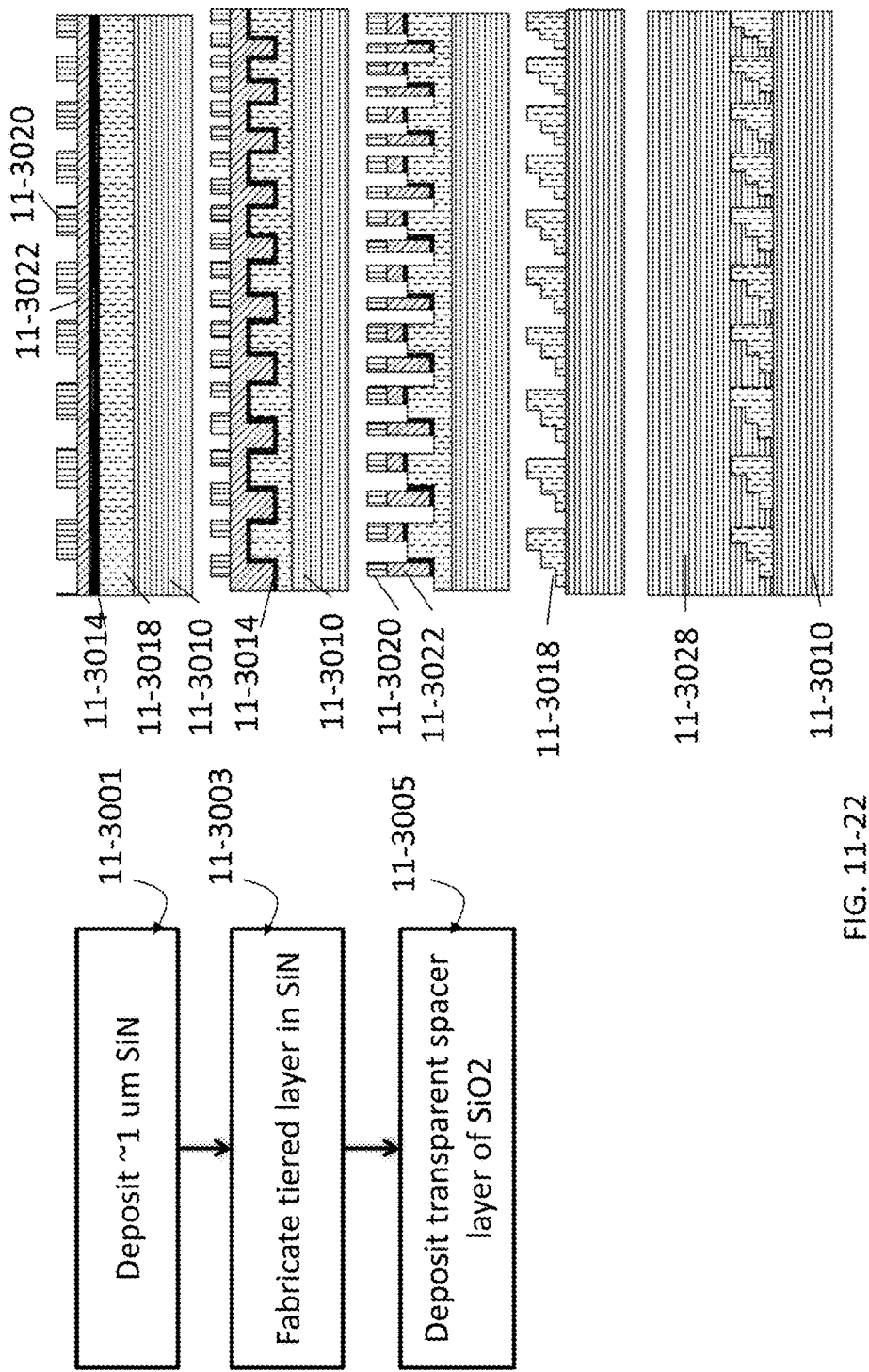

FIG. 8-0B depicts a plot of light intensity as a function of time.

FIG. 8-1 depicts a plot of carrier density as a function of time.

FIG. 8-2 depicts a tailored electrical signal to form an optical output, according to some embodiments.

FIG. 8-3 depicts an optical output from an excitation source, according to some embodiments.

FIG. 8-4 depicts an optical output from an excitation source, according to some embodiments.

FIG. 8-5 depicts performance of a laser diode, according to some embodiments.

FIG. 8-6A depicts a transmission line pulsar, according to some embodiments.

FIG. 8-6B depicts light pulses obtained by a transmission line pulsar, according to some embodiments.

FIG. 8-7 depicts a circuit for obtaining light pulses, according to some embodiments.

FIG. 8-8 depicts a circuit for obtaining light pulses, according to some embodiments.

Figures 5, 6, 7, 8, 9, 9A:
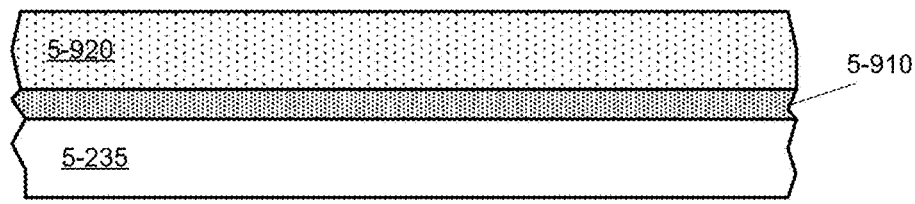

FIG. 8-9A depicts a circuit for obtaining light pulses, according to some embodiments.

Figures 5, 6, 7, 8, 9, 9B:
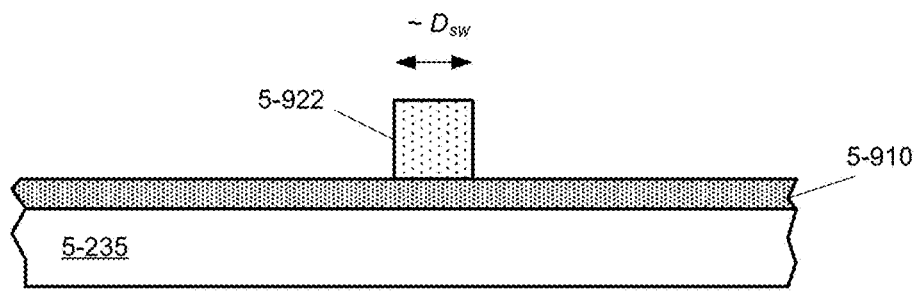
Figures 5, 6, 7, 8, 9, 9C:
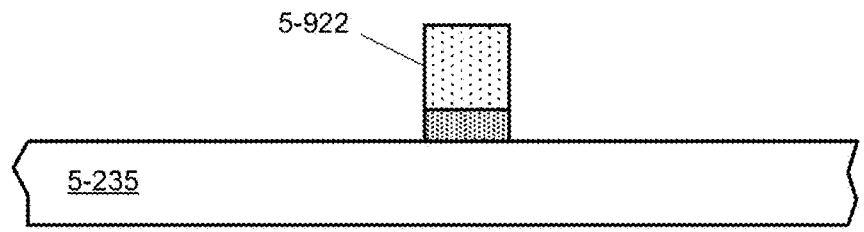
Figures 5, 6, 7, 8, 9, 9D:
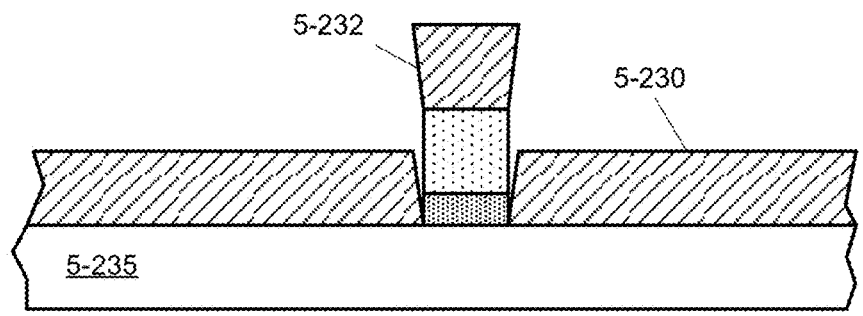
Figures 5, 6, 7, 8, 9, 9E:
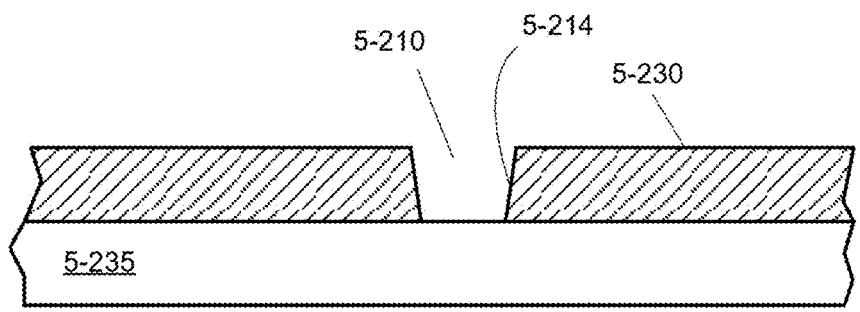
Figures 5, 6, 7, 8, 9, 9F:
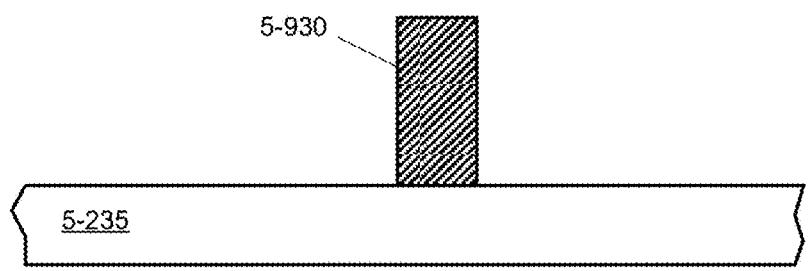

FIG. 8-9B depicts an electrical signal from the circuit shown in FIG. 8-9A.

FIG. 8-10A depicts a circuit for obtaining light pulses, according to some embodiments.

FIG. 8-10B depicts an electrical signal from the circuit shown in FIG. 8-10A.

FIG. 8-11A depicts an arrangement for combining light sources, according to some embodiments.

FIG. 8-11B depicts a plot of performance of the circuit shown in FIG. 8-10A.

FIG. 9-1 depicts an excitation source module and base instrument, according to some embodiments.

FIG. 9-2 depicts an excitation source module and base instrument, according to some embodiments.

FIG. 9-3 depicts optical components for aligning an excitation source to an integrated device, according to some embodiments.

FIG. 9-4 depicts an excitation source module and base instrument, according to some embodiments.

FIG. 9-5 through 9-11 depicts an excitation source module and base instrument, according to some embodiments.

FIG. 9-12 through 9-19 depicts components for passive alignment of an excitation source to an integrated device, according to some embodiments.

FIG. 9-20 depicts monitoring sensors, according to some embodiments.

FIG. 9-21 depicts an integrated device with monitoring sensors, according to some embodiments.

FIG. 9-22 depicts an arrangement of waveguides and monitoring sensors of an integrated device, according to some embodiments.

FIG. 9-23 depicts monitoring sensors of an integrated device, according to some embodiments.

FIG. 9-24 depicts optical components for coupling the excitation energy to the integrated device, according to some embodiments.

FIG. 9-25A depicts components for coupling the excitation energy to the integrated device, according to some embodiments.

FIG. 9-25B depicts components for coupling the excitation energy to the integrated device, according to some embodiments.

FIG. 9-25C depicts components for coupling the excitation energy to the integrated device, according to some embodiments.

Figures 5, 6, 7, 8, 9, 10, 10A:
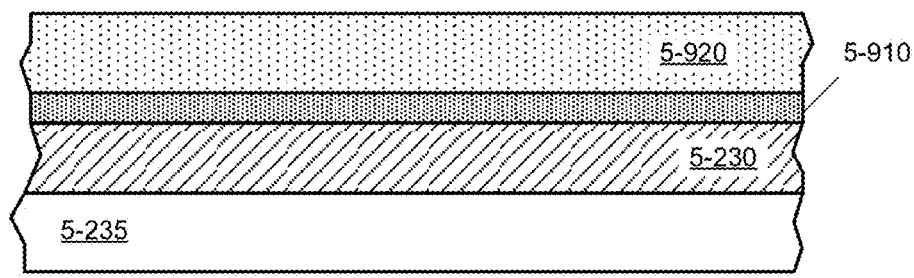
Figures 5, 6, 7, 8, 9, 10, 10B:
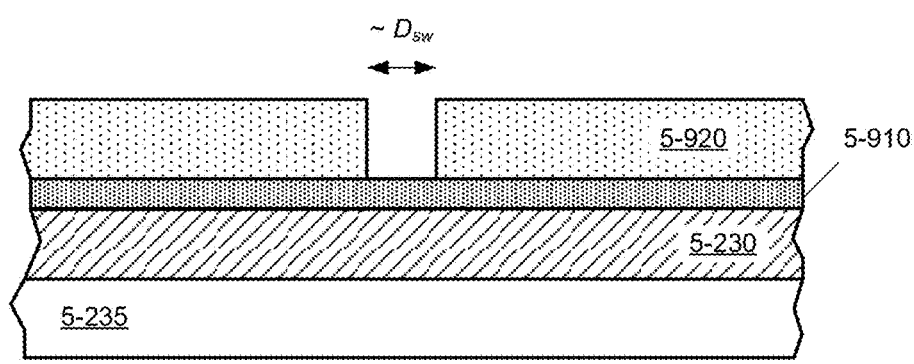
Figures 5, 6, 7, 8, 9, 10, 10C:
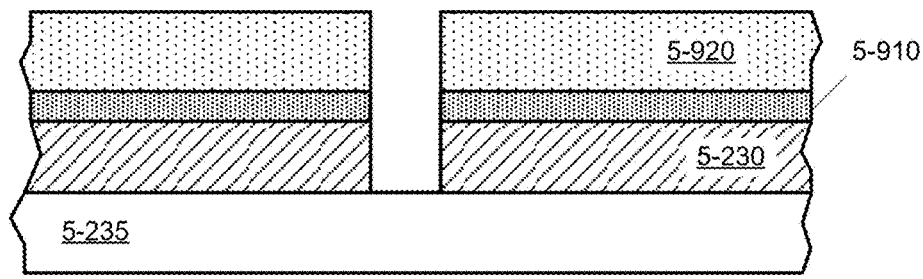
Figures 5, 6, 7, 8, 9, 10, 10D:
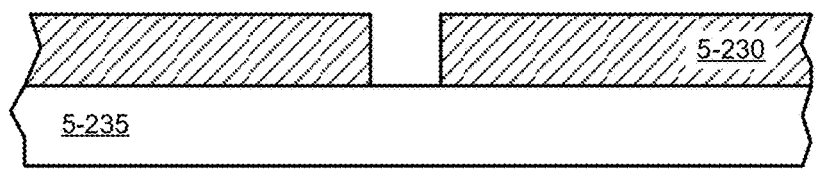

FIG. 10-1 shows a schematic of a sample well containing various components for nucleic acid sequencing, showing a target volume, polymerase complex, target nucleic acid, complimentary strand and primer, and linker for immobilizing.

FIG. 10-2 shows an exemplary experiment of nucleic acid sequencing for four stages of a sequencing reaction; (A) before incorporation of a luminescently labeled nucleotide; (B) a first incorporation event; (C) a period between the first and second incorporation events; and (D) a second incorporation event; along with corresponding examples of raw and processed data during stages (A)-(D).

FIG. 10-3 shows an exemplary process for surface preparation, including the steps of (a) Al2O3 deposition, (b) PEG-phosphonate passivation, (c) Biotin/PEG-silanization, (d) complex loading, and (e) sequencing reaction initiation.

FIG. 10-4 depicts a schematic for performing measurements, according to some embodiments.

FIG. 10-5 depicts a Fresnel lens, according to some embodiments.

FIG. 10-6 depicts a plot of light signal as a function of time, according to some embodiments.

FIG. 10-7 depicts a signal profile for markers across time bins, according to some embodiments.

FIG. 10-8 depicts a plot of light signal as a function of time, according to some embodiments.

FIG. 10-9 depicts a signal profile for markers across time bins, according to some embodiments.

FIG. 10-10 depicts a schematic for performing measurements, according to some embodiments.

Figures 5, 6, 7, 8, 9, 10, 11:
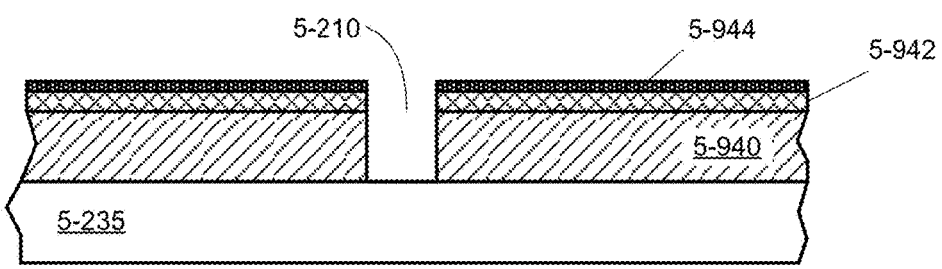

FIG. 10-11 depicts a plot of lifetime as a function of emission wavelength, according to some embodiments.

Figures 5, 6, 7, 8, 9, 10, 11, 12:
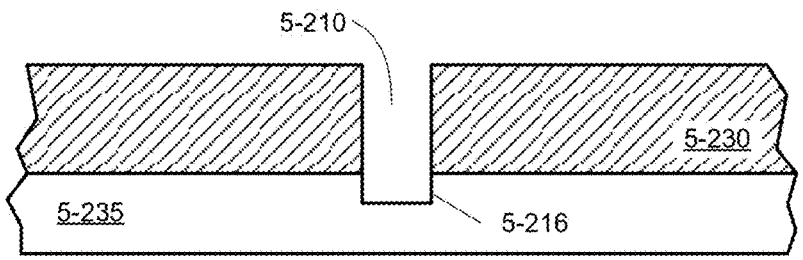

FIG. 10-12 depicts a plot of light signal as a function of wavelength, according to some embodiments.

FIG. 10-13 depicts a plot of light signal as a function of time, according to some embodiments.

FIG. 10-14 depicts a signal profile for markers across time bins for multiple sensors, according to some embodiments.

FIG. 10-15 depicts a plot of light signal as a function of time, according to some embodiments.

FIG. 10-16 depicts a signal profile for a marker across time bins for multiple sensors, according to some embodiments.

FIG. 10-17 depicts a schematic for performing measurements, according to some embodiments.

FIG. 10-18 depicts a plot of light signal as a function of wavelength, according to some embodiments.

FIG. 10-19 depicts a plot of light signal as a function of time, according to some embodiments.

FIG. 10-20 depicts a signal profile for a marker across time bins for multiple sensors, according to some embodiments.

FIG. 11-1 depicts a method for fabricating a sample well, according to some embodiments.

FIG. 11-2 depicts a method for fabricating a sample well, according to some embodiments.

FIG. 11-3 depicts a method for fabricating a sample well, according to some embodiments.

FIG. 11-4A depicts a method for fabricating a sample well, according to some embodiments.

FIG. 11-4B depicts a method for fabricating a sample well, according to some embodiments.

FIG. 11-5 depicts a method for fabricating a sample well layer with dips, according to some embodiments.

FIG. 11-6 depicts a method for fabricating a sample well layer with dips, according to some embodiments.

FIG. 11-7 depicts a method for fabricating a concentric grating, according to some embodiments.

FIG. 11-8 depicts a method for fabricating a concentric grating, according to some embodiments.

FIG. 11-9 depicts a method for fabricating a concentric grating, according to some embodiments.

FIG. 11-10 depicts exemplary microcavity designs, according to some embodiments.

FIG. 11-11 depicts a method for fabricating refractive optics, according to some embodiments.

FIG. 11-12 depicts images of different steps in fabricating refractive optics, according to some embodiments.

Figures 5, 6, 7, 8, 9, 10, 11, 12, 13, 13A:
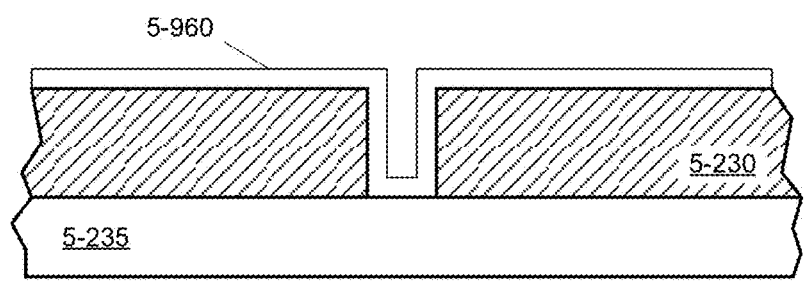
Figures 5, 6, 7, 8, 9, 10, 11, 12, 13, 13B:
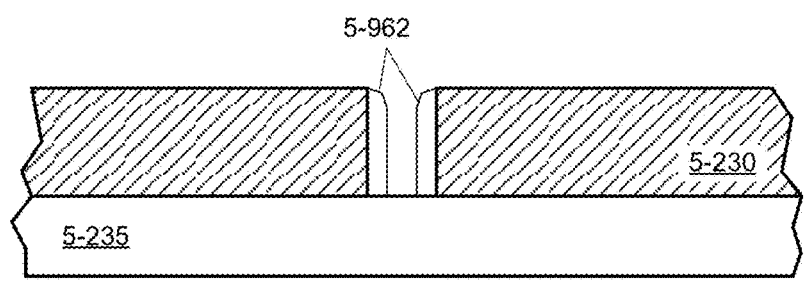
Figures 5, 6, 7, 8, 9, 10, 11, 12, 13, 13C:
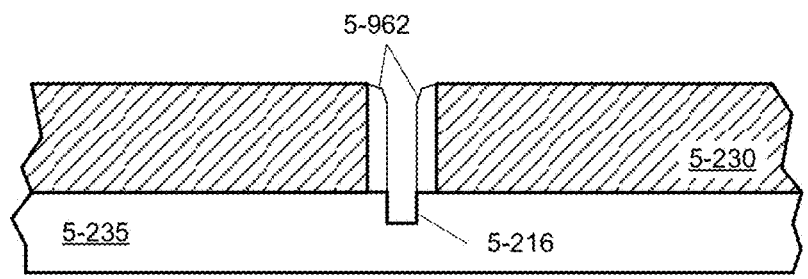
Figures 5, 6, 7, 8, 9, 10, 11, 12, 13, 14, 14A:
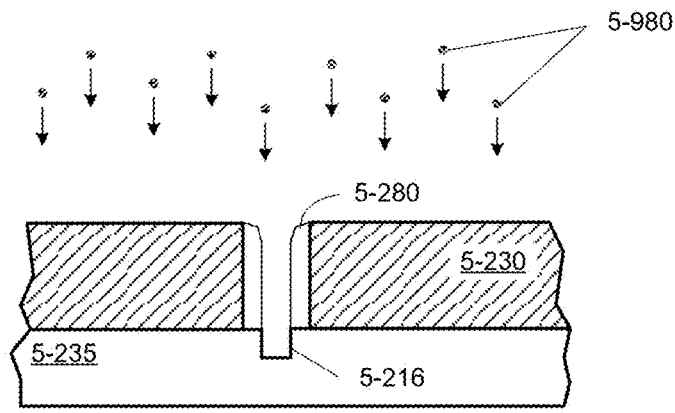
Figures 5, 6, 7, 8, 9, 10, 11, 12, 13, 14, 14B:
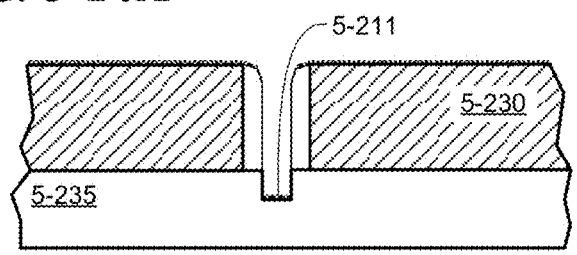
Figures 5, 6, 7, 8, 9, 10, 11, 12, 13, 14, 14C:
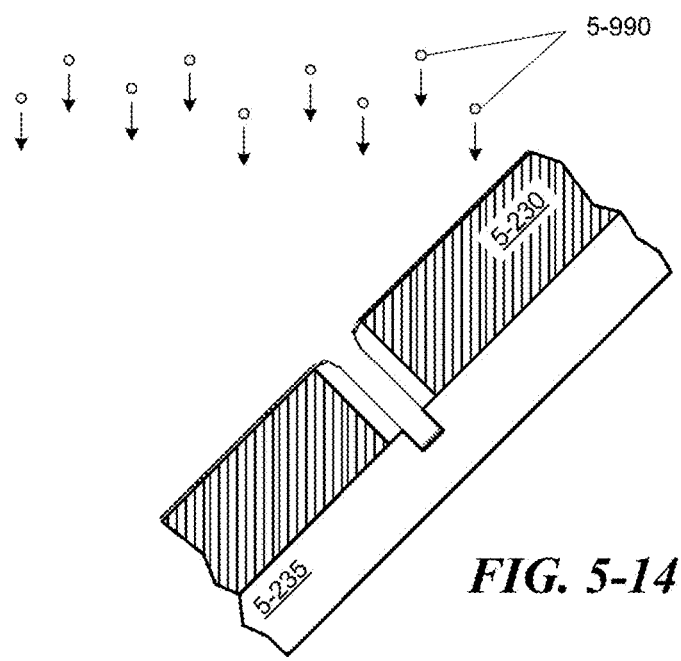
Figures 5, 6, 7, 8, 9, 10, 11, 12, 13, 14, 14D:
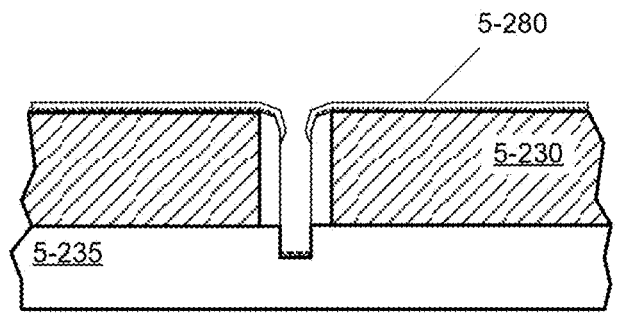
Figures 5, 6, 7, 8, 9, 10, 11, 12, 13, 14, 15:
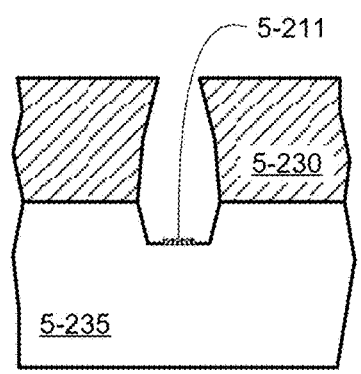
Figures 5, 6, 7, 8, 9, 10, 11, 12, 13, 14, 15, 16:
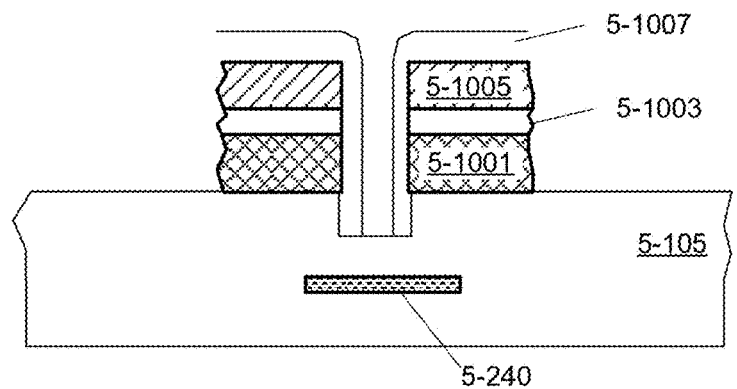

FIG. 11-13 depicts a refractive optic, according to some embodiments.

FIG. 11-14 depicts a method for fabricating refractive optics, according to some embodiments.

FIG. 11-15 depicts a method for fabricating refractive optics, according to some embodiments.

FIG. 11-16 depicts a Fresnel lens, according to some embodiments.

FIG. 11-17 depicts a Fresnel lens, according to some embodiments.

FIG. 11-18 depicts a Fresnel lens, according to some embodiments.

FIG. 11-19 depicts a method for fabricating a Fresnel lens, according to some embodiments.

FIG. 11-20 depicts a method for fabricating a Fresnel lens, according to some embodiments.

FIG. 11-21 depicts a method for fabricating a Fresnel lens, according to some embodiments.

FIG. 11-22 depicts a method for fabricating a Fresnel lens, according to some embodiments.

DETAILED DESCRIPTION

The inventors have recognized and appreciated that a compact, high-speed apparatus for performing detection and quantitation of single molecules or particles could reduce the cost of performing complex quantitative measurements of biological and/or chemical samples and rapidly advance the rate of biochemical technological discoveries. Moreover, a cost-effective device that is readily transportable could transform not only the way bioassays are performed in the developed world, but provide people in developing regions, for the first time, access to essential diagnostic tests that could dramatically improve their health and well-being. For example, embodiments described herein may be used for diagnostic tests of blood, urine and/or saliva that may be used by individuals in their home, or by a doctor in a remote clinic in a developing country.

A pixelated sensor device with a large number of pixels (e.g., hundreds, thousands, millions or more) allows for the detection of a plurality of individual molecules or particles in parallel. The molecules may be, by way of example and not limitation, proteins and/or DNA. Moreover, a high-speed device that can acquire data at more than one hundred frames per second allows for the detection and analysis of dynamic processes or changes that occur over time within the sample being analyzed.

The inventors have recognized and appreciated that one hurdle preventing bioassay equipment from being made more compact was the need to filter the excitation light from causing undesirable detection events at the sensor. Optical filters used to transmit the desired signal light (the luminescence) and sufficiently block the excitation light can be thick, bulky, expensive, and intolerant to variations in the incidence angle of light, preventing miniaturization. The inventors, however, recognized and appreciated that using a pulsed excitation source can reduce the need for such filtering or, in some cases, remove the need for such filters altogether. By using sensors capable of determining the time a photon is detected relative to the excitation light pulse, the signal light can be separated from the excitation light based on the time that the photon is received, rather than the spectrum of the light received. Accordingly, the need for a bulky optical filter is reduced and/or removed in some embodiments.

The inventors have recognized and appreciated that luminescence lifetime measurements may also be used to identify the molecules present in a sample. An optical sensor capable of detecting when a photon is detected is capable of measuring, using the statistics gathered from many events, the luminescence lifetime of the molecule being excited by the excitation light. In some embodiments, the luminescence lifetime measurement may be made in addition to a spectral measurement of the luminescence. Alternatively, a spectral measurement of the luminescence may be completely omitted in identifying the sample molecule. Luminescence lifetime measurements may be made with a pulsed excitation source. Additionally, luminescence lifetime measurements may be made using an integrated device that includes the sensor, or a device where the light source is located in a system separate from the integrated device.

The inventors have also recognized and appreciated that integrating a sample well (which may include a nanoaperture) and a sensor in a single integrated device capable of measuring luminescent light emitted from biological samples reduces the cost of producing such a device such that disposable bioanalytical integrated devices may be formed. Disposable, single-use integrated devices that interface with a base instrument may be used anywhere in the world, without the constraint of requiring high-cost biological laboratories for sample analyses. Thus, automated bioanalytics may be brought to regions of the world that previously could not perform quantitative analysis of biological samples. For example, blood tests for infants may be performed by placing a blood sample on a disposable integrated device, placing the disposable integrated device into a small, portable base instrument for analysis, and processing the results by a computer for immediate review by a user. The data may also be transmitted over a data network to a remote location to be analyzed, and/or archived for subsequent clinical analyses.

The inventors have also recognized and appreciated that a disposable, single-use device may be made more simply and for lower cost by not including the light source on the integrated device. Instead, the light source may include reusable components incorporated into a system that interfaces with the disposable integrated device to analyze a sample.

The inventors have also recognized and appreciated that, when a sample is tagged with a plurality of different types of luminescent markers, any suitable characteristic of luminescent markers may be used to identify the type of marker that is present in a particular pixel of the integrated device. For example, characteristics of the luminescence emitted by the markers and/or characteristics of the excitation absorption may be used to identify the markers. In some embodiments, the emission energy of the luminescence (which is directly related to the wavelength of the light) may be used to distinguish a first type of marker from a second type of marker. Additionally, or alternatively, luminescence lifetime measurements may also be used to identify the type of marker present at a particular pixel. In some embodiments, luminescence lifetime measurements may be made with a pulsed excitation source using a sensor capable of distinguishing a time when a photon is detected with sufficient resolution to obtain lifetime information. Additionally, or alternatively, the energy of the excitation light absorbed by the different types of markers may be used to identify the type of marker present at a particular pixel. For example, a first marker may absorb light of a first wavelength, but not equally absorb light of a second wavelength, while a second marker may absorb light of the second wavelength, but not equally absorb light of the first wavelength. In this way, when more than one excitation light source, each with a different excitation energy, may be used to illuminate the sample in an interleaved manner, the absorption energy of the markers can be used to identify which type of marker is present in a sample. Different markers may also have different luminescent intensities. Accordingly, the detected intensity of the luminescence may also be used to identify the type of marker present at a particular pixel.

One non-limiting example of an application of a device contemplated by the inventors is a device capable of performing sequencing of a biomolecule, such as a nucleic acid or a polypeptide (e.g. protein) having a plurality of amino acids. Diagnostic tests that may be performed using such a device include sequencing a nucleic acid molecule in a biological sample of a subject, such as sequencing of cell free deoxyribonucleic acid molecules or expression products in a biological sample of the subject.

The present application provides devices, systems and methods for detecting biomolecules or subunits thereof, such as nucleic acid molecules. Such detection can include sequencing. A biomolecule may be extracted from a biological sample obtained from a subject. The biological sample may be extracted from a bodily fluid or tissue of the subject, such as breath, saliva, urine or blood (e.g., whole blood or plasma). The subject may be suspected of having a health condition, such as a disease (e.g., cancer). In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30, 50, 100 base pairs (bp) or more) that can be used to identify a larger sequence or region, e.g., that can be aligned to a location on a chromosome or genomic region or gene.

Individual subunits of biomolecules may be identified using markers. In some examples, luminescent markers are used to identify individual subunits of biomolecules. Luminescent markers (also referred to herein as "markers") may be exogenous or endogenous markers.

Exogenous markers may be external luminescent markers used in a reporter and/or tag for luminescent labeling. Examples of exogenous markers may include, but are not limited to, fluorescent molecules, fluorophores, fluorescent dyes, fluorescent stains, organic dyes, fluorescent proteins, enzymes, species that participate in fluorescence resonance energy transfer (FRET), enzymes, and/or quantum dots. Such exogenous markers may be conjugated to a probe or functional group (e.g., molecule, ion, and/or ligand) that specifically binds to a particular target or component. Attaching an exogenous marker to a probe allows identification of the target through detection of the presence of the exogenous marker. Examples of probes may include proteins, nucleic acid (e.g. DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may include mass tags or electrostatic tags.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

While some embodiments may be directed to diagnostic testing by detecting single molecules in a specimen, the inventors have also recognized that some embodiments may use the single molecule detection capabilities to perform nucleic acid (e.g. DNA, RNA) sequencing of one or more nucleic acid segments such as, for example, genes, or polypeptides. Nucleic acid sequencing allows for the determination of the order and position of nucleotides in a target nucleic acid molecule. Nucleic acid sequencing technologies may vary in the methods used to determine the nucleic acid sequence as well as in the rate, read length, and incidence of errors in the sequencing process. For example, some nucleic acid sequencing methods are based on sequencing by synthesis, in which the identity of a nucleotide is determined as the nucleotide is incorporated into a newly synthesized strand of nucleic acid that is complementary to the target nucleic acid molecule. Some sequencing by synthesis methods require the presence of a population of target nucleic acid molecules (e.g., copies of a target nucleic acid) or a step of amplification of the target nucleic acid to achieve a population of target nucleic acids.

Having recognized the need for simple, less complex apparatuses for performing single molecule detection and/or nucleic acid sequencing, the inventors have conceived of a technique for detecting single molecules using sets of markers, such as optical (e.g., luminescent) markers, to label different molecules. A tag may include a nucleotide or amino acid and a suitable marker. Markers may be detected while bound to single molecules, upon release from the single molecules, or while bound to and upon release from the single molecules. In some examples, markers are luminescent tags. Each luminescent marker in a selected set is associated with a respective molecule. For example, a set of four markers may be used to "label" the nucleobases present in DNA—each marker of the set being associated with a different nucleobase to form a tag, e.g., a first marker being associated with adenine (A), a second marker being associated with cytosine (C), a third marker being associated with guanine (G), and a fourth marker being associated with thymine (T). Moreover, each of the luminescent markers in the set of markers has different properties that may be used to distinguish a first marker of the set from the other markers in the set. In this way, each marker is uniquely identifiable using one or more of these distinguishing characteristics. By way of example and not limitation, the characteristics of the markers that may be used to distinguish one marker from another may include the emission energy and/or wavelength of the light that is emitted by the marker in response to excitation and/or the wavelength and/or energy of the excitation light that excites a particular marker. Distinguishing a marker from among the set of four markers uniquely identifies the nucleobase associated with the marker.

Luminescent markers may vary in the wavelength of light they emit, the temporal characteristics of the light they emit (e.g., their emission decay time periods), and their response to excitation energy (e.g., their probability of absorbing an excitation photon). Accordingly, luminescent markers may be identified or discriminated from other luminescent markers based on detecting these properties. Such identification or discrimination techniques may be used alone or in any suitable combination.

In some embodiments, an integrated photodetector as described in the present application can measure or discriminate luminescence lifetimes, such as fluorescence lifetimes. Lifetime measurements are based on exciting one or more markers (e.g., fluorescent molecules), and measuring the time variation in the emitted luminescence. The probability that a marker emits a photon after the marker reaches an excited state decreases exponentially over time. The rate at which the probability decreases may be characteristic of a marker, and may be different for different markers. Detecting the temporal characteristics of light emitted by markers may allow identifying markers and/or discriminating markers with respect to one another. The decrease in the probability of a photon being emitted over time may be represented by an exponential decay function $p(t)=e^{\char`\^}(-t/\tau)$, where $p(t)$ is the probability of photon emission at a time, t, and $\tau$ is a temporal parameter of the marker. The temporal parameter $\tau$ indicates a time after excitation when the probability of the marker emitting a photon is a certain value. The temporal parameter, $\tau$, is a property of a marker that may be distinct from its absorption and emission spectral properties. Such a temporal parameter, $\tau$, is referred to as the luminescence lifetime, the fluorescence lifetime or simply the "lifetime" of a marker.

FIG. 1-1 plots the probability of a photon being emitted as a function of time for two markers with different lifetimes. The marker represented by probability curve B has a probability of emission that decays more quickly than the probability of emission for the marker represented by probability curve A. The marker represented by probability curve B has a shorter temporal parameter, $\tau$, or lifetime than the marker represented by probability curve A. Markers may have lifetimes ranging from 0.1-20 ns, in some embodiments. However, the techniques described herein are not limited as to the lifetimes of the marker(s) used.

The lifetime of a marker may be used to distinguish among more than one marker, and/or may be used to identify marker(s). In some embodiments, lifetime measurements may be performed in which a plurality of markers having different lifetimes is excited by an excitation source. As an example, four markers having lifetimes of 0.5, 1, 2, and 3 nanoseconds, respectively, may be excited by a light source that emits light having a selected wavelength (e.g., 635 nm, by way of example). The markers may be identified or differentiated from each other based on measuring the lifetime of the light emitted by the markers.

Lifetime measurements may use relative intensity measurements by comparing how intensity changes over time, as opposed to absolute intensity values. As a result, lifetime measurements may avoid some of the difficulties of absolute intensity measurements. Absolute intensity measurements may depend on the concentration of markers present and calibration steps may be needed for varying marker concentrations. By contrast, lifetime measurements may be insensitive to the concentration of markers.

Embodiments may use any suitable combination of marker characteristics to distinguish a first marker in a set of markers from the other markers in the same set. For example, some embodiments may use only the timing information of the emission light from the markers to identify the markers. In such embodiments, each marker in a selected set of markers has a different emission lifetime from the other markers in the set and the luminescent markers are all excited by light from a single excitation source. FIG. 1-2A illustrates the emission timing from four luminescent markers according to an embodiment where the four markers exhibit different average emission lifetimes (t). The probability that a marker is measured to have a lifetime of a particular value is referred to herein as the marker's "emission timing." A first emission timing 1-101 from a first luminescent marker has a peak probability of having a lifetime of at $\tau 1$, a second emission timing 1-102 from a second luminescent marker has a peak probability of having a lifetime of at $\tau 2$, a third emission timing 1-103 from a third luminescent marker has a peak probability of having a lifetime of at $\tau 3$, and a fourth emission timing 1-104 from a fourth luminescent marker has a peak probability of having a lifetime of at $\tau 4$. In this embodiment, the lifetime probability peaks of the four luminescent markers may have any suitable values that satisfy the relation $\tau 1 < \tau 2 < \tau 3 < \tau 4$. The four timing emission graphs may or may not overlap due to slight variations in the lifetime of a particular luminescent marker, as illustrated in FIG. 1-2A. In this embodiment, the excitation wavelength at which each of the four markers maximally absorbs light from the excitation source is substantially equal, but that need not be the case. Using the above marker set, four different molecules may be labeled with a respective marker from the marker set, the markers may be excited using a single excitation source, and the markers can be distinguished from one another by detecting the emission lifetime of the markers using an optical system and sensors. While FIG. 1-2A illustrates four different markers, it should be appreciated that any suitable number of markers may be used.

Other embodiments may use any suitable combination of marker characteristics to determine the identity of the marker within a set of markers. Examples of the marker characteristics that may be used include, but are not limited to excitation wavelength, emission wavelength, and emission lifetime. The combination of marker characteristics form a phase space and each marker may be represented as a point within this phase space. Markers within a set of markers should be selected such that the "distance" between each marker within the set is sufficiently large that the detection mechanism can distinguish each marker from the other markers in the set. For example, in some embodiments a set of markers may be selected where a subset of the markers have the same emission wavelength, but have different emission lifetimes and/or different excitation wavelengths. In other embodiments, a set of markers may be selected where a subset of the markers have the same emission lifetime, but have different emission wavelengths and/or different excitation wavelengths. In other embodiments, a set of markers may be selected where a subset of the markers have the same excitation wavelength, but have different emission wavelengths and/or different emission lifetimes.

By way of example and not limitation, FIG. 1-2B illustrates the emission spectra from four luminescent markers according to an embodiment where two of the markers have a first peak emission wavelength and the other two markers have a second peak emission wavelength. A first emission spectrum 1-105 from a first luminescent marker has a peak emission wavelength at $\lambda 1$, a second emission spectrum 1-106 from a second luminescent marker also has a peak emission wavelength at $\lambda 1$, a third emission spectrum 1-107 from a third luminescent marker has a peak emission wavelength at $\lambda 2$, and a fourth emission spectrum 1-108 from a fourth luminescent marker also has a peak emission wavelength at $\lambda 2$. In this embodiment, the emission peaks of the four luminescent markers may have any suitable values that satisfy the relation $\lambda 1 < \lambda 2$. In embodiments such as this where the peak emission wavelength is the same for more than one luminescent marker, a separate characteristic of the markers that have the same emission wavelength must be different. For example, the two markers that emit at $\lambda 1$ may have different emission lifetimes. FIG. 1-3A illustrates this situation schematically in a phase space spanned by the emission wavelength and the emission lifetime. A first marker has an emission wavelength $\lambda 1$ and an emission lifetime t1, a second marker has an emission wavelength $\lambda 1$ and a emission lifetime t4, a third marker has an emission wavelength $\lambda 2$ and a emission lifetime t1, and a fourth marker has an emission wavelength $\lambda 2$ and a emission lifetime τ4. In this way, all four markers in the marker set shown in FIG. 1-3A are distinguishable from one another. Using such a marker set allows distinguishing between four markers even when the absorption wavelengths for the four markers are identical. This is possible using a sensor that can detect the time of emission of the photoluminescence as well as the emission wavelength.

By way of example and not limitation, FIG. 1-2C illustrates the absorption spectra from four luminescent markers according to another embodiment. In this embodiment, two of the markers have a first peak absorption wavelength and the other two markers have a second peak absorption wavelength. A first absorption spectrum 1-109 for the first luminescent marker has a peak absorption wavelength at λ3, a second absorption spectrum 1-110 for the second luminescent marker has a peak absorption wavelength at λ4, a third absorption spectrum 1-111 for the third luminescent marker has a peak absorption wavelength at λ3, and a fourth absorption spectrum 1-112 for the fourth luminescent marker has a peak absorption wavelength at λ4. Note that the markers that share an absorption peak wavelength in FIG. 1-2C are distinguishable via another marker characteristic, such as emission lifetime. FIG. 1-3B illustrates this situation schematically in a phase space spanned by the absorption wavelength and the emission lifetime. A first marker has an absorption wavelength λ3 and an emission lifetime t1, a second marker has an absorption wavelength λ3 and an emission lifetime t4, a third marker has an absorption wavelength λ4 and an emission lifetime t1, and a fourth marker has an absorption wavelength λ4 and an emission lifetime t4. In this way, all four markers in the marker set shown in FIG. 1-3A are distinguishable from one another.

Using such a marker set allows distinguishing between four markers even when the emission wavelengths for the four markers are indistinguishable. This is possible using two excitation sources that emit at different wavelengths or a single excitation source capable of emitting at multiple wavelengths in connection with a sensor that can detect the time of emission of the photoluminescence. If the wavelength of the excitation light is known for each detected emission event, then it can be determined which marker was present. The excitation source(s) may alternate between a first excitation wavelength and a second excitation wavelength, which is referred to as interleaving. Alternatively, two or more pulses of the first excitation wavelength may be used followed by two or more pulses of the second excitation wavelength.

The number of excitation sources or excitation wavelengths used to distinguish the markers is not limited to two, and in some embodiments more than two excitation wavelengths or energies may be used to distinguish the markers. In such embodiments, markers may be distinguished by the intensity or number of photons emitted in response to multiple excitation wavelengths. A marker may be distinguishable from among multiple markers by detecting the number of photons emitted in response to exposing the marker to a certain excitation wavelength. In some embodiments, a marker may be distinguished by illuminating the marker to one of multiple excitation energies at a time and identifying the excitation energy from among the multiple excitation energies where the marker emitted the highest number of photons. In other embodiments, the number of photons emitted from a marker in response to different excitation energies may be used to identify the marker. A first marker that has a higher probability of emitting photons in response to a first excitation energy than a second excitation energy may be distinguished from a second marker that has a higher probability of emitting photons in response to the second excitation energy than the first excitation energy. In this manner, markers having distinguishable probabilities of emitting certain amounts of photons in response to different excitation energies may be identified by measuring the emitted photons while exposing an unknown marker to the different excitation energies. In such embodiments, a marker may be exposed to multiple excitation energies and identification of the marker may be achieved by determining whether the marker emitted any light and/or a particular number of photons emitted. Any suitable number of excitation energy sources may be used. In some embodiments, four different excitation energies may be used to distinguish among different markers (e.g., four different markers). In some embodiments, three different excitation energies may be used to distinguish among different markers. Other characteristics of a marker may be used to distinguish the presence of a marker in combination with the amount of photons emitted in response to different excitation energies, including emission lifetime and emission spectra.

In other embodiments more than two characteristics of the markers in a marker set may be used to distinguish which marker is present. FIG. 1-4 illustrates an illustrative phase space spanned by the absorption wavelength, the emission wavelength and the emission lifetime of the markers. In FIG. 1-4, eight different markers are distributed in phase space. Four of the eight markers have the same emission wavelength, a different four markers have the same absorption wavelength and a different four markers have the same emission lifetime. However, each of the markers is distinguishable from every other marker when all three characteristics of the markers are considered. Embodiments are not limited to any number of markers. This concept can be extended to include any number of markers that may be distinguished from one another using at least these three marker characteristics.

While not illustrated in the figures, other embodiments may determine the identity of a luminescent marker based on the absorption frequency alone. Such embodiments are possible if the excitation light can be tuned to specific wavelengths that match the absorption spectrum of the markers in a marker set. In such embodiments, the optical system and sensor used to direct and detect the light emitted from each marker does not need to be capable of detecting the wavelength of the emitted light. This may be advantageous in some embodiments because it reduces the complexity of the optical system and sensors because detecting the emission wavelength is not required in such embodiments.

As discussed above, the inventors have recognized and appreciated the need for being able to distinguish different luminescent markers from one another using various characteristics of the markers. The type of characteristics used to determine the identity of a marker impacts the physical device used to perform this analysis. The present application discloses several embodiments of an apparatus, device, instrument and methods for performing these different experiments.

The inventors have recognized and appreciated that a low-cost, single-use disposable integrated device that includes optics and sensors may be used in connection with an instrument that includes an excitation source to measure different characteristics of luminescent light emitted from one or markers used to label a biological sample in order to analyze the sample. Using a low-cost integrated device reduces the cost of performing a given bioassay. A biological sample is placed onto the integrated device and, upon completion of the bioassay, may be discarded. The integrated device interfaces with the more expensive, multi-use instrument, which may be used repeatedly with many different disposable integrated devices. A low-cost integrated device that interfaces with a compact, portable instrument may be used anywhere in the world, without the constraint of high-cost biological laboratories requiring laboratory expertise to analyze samples. Thus, automated bioanalytics may be brought to regions of the world that previously could not perform quantitative analysis of biological samples. For example, blood tests for infants may be performed by placing a blood sample on a disposable integrated device, placing the disposable integrated device into the small, portable instrument for analysis, and processing the results by a computer that connects to the instrument for immediate review by a user. The data may also be transmitted over a data network to a remote location to be analyzed, and/or archived for subsequent clinical analyses. Alternatively, the instrument may include one or more processors for analyzing the data obtained from the sensors of the integrated device.

Various embodiments are described in more detail below.

I. Overview of the System

The system includes an integrated device and an instrument configured to interface with the integrated device. The integrated device includes an array of pixels, where a pixel includes a sample well and at least one sensor. A surface of the integrated device has a plurality of sample wells, where a sample well is configured to receive a sample from a specimen placed on the surface of the integrated device. A specimen may contain multiple samples, and in some embodiments, different types of samples. The plurality of sample wells may be designed such that at least a portion of the sample wells are configured to receive one sample from a specimen. In some embodiments, the number of samples within a sample well may be distributed among the sample wells such that some sample wells contain one sample with others contain zero, two or more samples. For example, a specimen may contain multiple single-stranded DNA templates, and a sample well on a surface of an integrated device may receive a single-stranded DNA template. At least a portion of the sample wells of the integrated device may contain a single-stranded DNA template. The specimen may also contain tagged dNTPs which then enter in the sample well and may allow for identification of a nucleotide as it is incorporated into a complementary strand of DNA. In such an example, the "sample" may refer to both the single-stranded DNA and the tagged dNTP currently being incorporated by a polymerase. In some embodiments, the specimen may contain single-stranded DNA templates and tagged dNTPS may be subsequently introduced to a sample well as nucleotides are incorporated into a complementary strand of DNA within the sample well. In this manner, timing of incorporation of nucleotides may be controlled by when tagged dNTPs are introduced to the sample wells of an integrated device.

Excitation energy is provided from an excitation source located separate from the pixel array of the integrated device. The excitation energy is directed at least in part by elements of the integrated device towards one or more pixels to illuminate an illumination region within the sample well. A marker or tag may then emit emission energy when located within the illumination region and in response to being illuminated by excitation energy. In some embodiments, one or more excitation sources are part of the instrument of the system where components of the instrument and the integrated device are configured to direct the excitation energy towards one or more pixels. In other embodiments, one or more excitation sources are located on the integrated device but are located in a separate region from the array of pixels, and components in the integrated device are configured to direct excitation energy from the excitation source region to one or more pixels.

Emission energy emitted by a sample may then be detected by one or more sensors within a pixel of the integrated device. In some embodiments, a plurality of sensors may be sized and arranged to capture a spatial distribution of the emission energy. In some embodiments one or more sensors may be configured to detect a timing characteristics associated with a sample's emission energy (e.g., fluorescence lifetime). Output signals from the one or more sensors may then be used to distinguish a marker from among a plurality of markers, where the plurality of markers may be used to identify a sample within the specimen. In some embodiments, a sample may be excited by multiple excitation energies, and emission energy and/or timing characteristics of the emission energy emitted by the sample in response to the multiple excitation energies may distinguish a marker from a plurality of markers.

A schematic overview of the system 2-100 is illustrated in FIGS. 2-1A and 2-1B. The system comprises both an integrated device 2-102 that interfaces with an instrument 2-104. In some embodiments, instrument 2-104 may include one or more excitation source 2-106. In some embodiments, an excitation source may be external to both instrument 2-104 and integrated device 2-102, and instrument 2-104 may be configured to receive excitation energy from the excitation source and direct it to the integrated device. The integrated device interfaces with the instrument using any suitable socket for receiving the integrated device and holding it in precise optical alignment with the excitation source. The excitation source 2-106 may be configured to provide excitation energy to the integrated device 2-102. Although the excitation source is shown to be located on the instrument in FIG. 2-1B, the excitation source may be located on the integrated device in a region separate from the pixels in some instances. As illustrated schematically in FIG. 2-1B, the integrated device 2-102 has multiple pixels, where each pixel 2-112 is capable of independent analysis of a sample. Such pixels 2-112 may be referred to as "passive source pixels" since a pixel receives excitation energy from a source 2-106 separate from the pixel, where the source excites a plurality of pixels. Each pixel 2-112 has a sample well 2-108 for retaining and analyzing a sample and a sensor 2-110 for detecting emission energy emitted by the sample in response to illuminating the sample with excitation energy provided by the excitation source 2-106. In some embodiments, each sensor 2-110 may include multiple sub-sensors, each sub-sensor configured to detect a different wavelength of emission energy from the sample.

Optical elements for guiding and coupling excitation energy to the sample well 2-108 are located both on integrated device 2-102 and the instrument 2-104. Such source-to-well elements may include a grating coupler located on integrated device 2-102 to couple excitation energy to the integrated device, waveguides to deliver excitation energy to each pixel 2-112, and lenses, plasmonic elements and dielectric coatings on the integrated device to direct excitation energy received from instrument 2-104 to sample well 2-108. Additionally, optical elements located on the integrated device direct emission energy from the sample well towards the sensor. Such well-to-sample elements may include components that direct the emission energy into a radiation pattern where the radiation pattern depends on the emission energy emitted by a sample in a sample well. Sample well 2-108, a portion of the excitation source-to-well optics, and the sample well-to-sensor optics are located on integrated device 2-102. Excitation source 2-106 and a portion of the source-to-well components are located in instrument 2-104. In some embodiments, a single component may play a role in both coupling excitation energy to sample well 2-108 and delivering emission energy from sample well 2-108 to sensor 2-110.

As illustrated in FIG. 2-1B, the integrated device comprises a plurality of pixels, each pixel 2-112 associated with its own individual sample well 2-108 and sensor 2-110. The plurality of pixels may be arranged in an array, and there may be any suitable number of pixels. For example, integrated device 2-102 may include between 100 and 1,000 pixels according to some embodiments, between 1,000 and 10,000 pixels according to some embodiments, between 10,000 and 100,000 pixels according to some embodiments, between 100,000 and 1,000,000 pixels according to some embodiments, and yet between 1,000,000 and 10,000,000 pixels according to some embodiments. In some implementations, there may be fewer or more pixels on integrated device 2-102. Integrated device 2-102 and instrument 2-104 may include multi-channel, high-speed communication links for handling data associated with large pixel arrays (e.g., more than 1000 pixels).

Excitation source 2-106 may be any suitable source that is arranged to deliver excitation energy to at least one sample well. In some embodiments, an array of one or more excitation sources are located adjacent the pixel array on the same integrated device. In other embodiments, one or more excitation sources are on a second substrate mounted in close proximity to the substrate on which the pixel array is formed.

Instrument 2-104 interfaces with integrated device 2-102 through integrated device interface 2-114. Integrated device interface 2-114 may include components to position and/or align integrated device 2-102 to instrument 2-104 to improve coupling of excitation energy from excitation source 2-106 to integrated device 2-102. In some embodiments, excitation source 2-106 includes multiple excitation sources that are combined to deliver excitation energy to integrated device 2-102. The multiple excitation sources may be configured to produce multiple excitation energies or wavelengths. The integrated device interface 2-114 may receive readout signals from the sensors in the pixels located on the integrated device. Additionally, the integrated device interface 2-114 may be designed such that the integrated device attaches to the instrument by securing the integrated device to the integrated device interface 2-114.

The instrument 2-104 includes a user interface 2-116 for controlling the operation of instrument 2-104. The user interface 2-116 is configured to allow a user to input information into the instrument, such as commands and/or settings used to control the functioning of the instrument. In some embodiments, the user interface 2-116 may include buttons, switches, dials, and a microphone for voice commands. Additionally, the user interface 2-116 may allow a user to receive feedback on the performance of the instrument and/or integrated device, such as proper alignment and/or information obtained by readout signals from the sensors on the integrated device. In some embodiments, the user interface 2-116 may provide feedback using a speaker to provide audible feedback, and indicator lights and/or display screen for providing visual feedback. In some embodiments, the instrument 2-104 includes a computer interface 2-118 used to connect with a computing device 2-120. Any suitable computer interface 2-118 and computing device 2-120 may be used. For example, the computer interface 2-118 may be a USB interface or a FireWire interface. The computing device 2-120 may be any general purpose computer, such as a laptop or desktop computer. The computer interface 2-118 facilitates communication of information between the instrument 2-104 and the computing device 2-120. Input information for controlling and/or configuring the instrument 2-104 may be provided through the computing device 2-120 connected to the computer interface 2-118 of the instrument. Additionally, output information may be received by the computing device 2-120 through the computer interface 2-118. Such output information may include feedback about performance of the instrument 2-104 and/or or integrated device 2-112 and information from the readout signals of the sensor 2-110. The instrument 2-104 may also include a processing device 2-122 for analyzing data received from the sensor 2-110 and/or sending control signals to the excitation source 2-106. In some embodiments, the processing device 2-122 may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from the sensor 2-110 may be performed by both the processing device 2-122 and the external computing device 2-120. In other embodiments, the computing device 2-120 may be omitted and processing of data from the sensor 2-110 may be performed solely by processing device 2-122.

A cross-sectional schematic of the integrated device 3-102 illustrating a row of pixels is shown in FIG. 3-1A. Each pixel 3-112 includes a sample well 3-108 and a sensor 3-110. The sensor 3-110 may be aligned and positioned to the sample well 3-112. When an excitation source is coupled to the integrated device, excitation energy is provided to one or more pixels. FIG. 3-1B is a schematic illustrating coupling an excitation source 3-106 to integrated device 3-102. Excitation source 3-106 provides excitation energy 3-130 (shown in dashed lines) in the integrated device 3-102. FIG. 3-1B illustrates the path of excitation energy from excitation energy source 3-106 to a sample well 3-108 in pixel 3-112. Components located off of the integrated device may be used to position and align the excitation source 3-106 to the integrated device. Such components may include optical components including lenses, mirrors, prisms, apertures, attenuators, and/or optical fibers. Additional mechanical components may be included in the instrument configured to allow control of one or more alignment components. Such mechanical components may include actuators, stepper motors, and/or knobs. The integrated device includes components that direct the excitation energy 3-130 towards pixels in the integrated device. Within each pixel 3-112, excitation energy is coupled to the sample well 3-108 associated with the pixel. Although FIG. 3-1B illustrates excitation energy coupling to each sample well in a row of pixels, in some embodiments, excitation energy may not couple to all of the pixels in a row. In some embodiments, excitation energy may couple to a portion of pixels or sample wells in a row of pixels of the integrated device. Excitation energy may illuminate a sample located within a sample well. The sample may reach an excited state in response to being illuminated by the excitation energy.

When a sample is in an excited state, the sample may emit emission energy and the emission energy may be detected by a sensor. FIG. 3-1B schematically illustrates the path of emission energy 3-140 (shown as solid lines) from the sample well 3-108 to the sensor 3-110 of a pixel 3-112. The sensor 3-110 in a pixel 3-112 may be configured and positioned to detect emission energy from sample well 3-108. In some embodiments, the sensor 3-110 may include one or more sub-sensors.

A sample to be analyzed may be introduced into a sample well 3-108 of a pixel 3-112. The sample may be a biological sample or any other suitable sample, such as a chemical sample. The sample may include multiple molecules and the sample well may be configured to isolate a single molecule. In some instances, the dimensions of the sample well may act to confine a single molecule within the sample well, allowing measurements to be performed on the single molecule. An excitation source 3-106 may be configured to deliver excitation energy into the sample well 3-108, so as to excite the sample or at least one luminescent marker attached to the sample or otherwise associated with the sample while it is within an excitation area within the sample well 3-108. In a sample of multiple molecules, a type of luminescent marker may uniquely associate with a molecule type. During or after excitation, the luminescent marker may emit emission energy. When multiple markers are used, they may emit at different characteristic energies. In some embodiments, multiple markers may have different characteristic lifetimes. Additionally, multiple markers may differ in response to multiple excitation energies. Markers for a sample may be discerned by their excitation response, characteristic energies or wavelengths, and/or characteristic lifetimes. Emissions from the sample may radiate from the sample well 3-108 to the sensor 3-110.

Components may focus emission energy towards the sensor and may additionally or alternatively spatially separate emission energies that have characteristic energies or wavelengths. Excitation energy emitted from the excitation source 3-106 may be directed toward the sample well 3-108 in any suitable way and configured to excite at least one sample that is received in the sample well 3-108. According to some embodiments, the excitation source 3-106 may excite the sample, which may luminesce. The excitation source may provide one or more excitation energies to sample well 3-108. In some implementations, the excitation source 3-106 may excite one or more markers that luminesce or emit energy in response to the excitation and that are attached to the sample or otherwise associated with the sample. Emitted luminescent light or energy resulting from the excitation may be directed to a sensor 3-110, which may be configured to detect the intensity and/or timing of the received emission. Non-limiting examples of luminescence are photoluminescence, fluorescence and phosphorescence.

In some embodiments, the integrated device may include components that direct emission energy into a radiation pattern that is dependent on the spectral range of the emission energy. The sensor or sensor region containing multiple sub-sensors may detect a spatial distribution of the emission energy that depends on the radiation pattern. Markers that emit different emission energies and/or spectral ranges may form different radiation patterns. The sensor or sensor region may detect information about the spatial distribution of the emission energy that can be used to identify a marker among the multiple markers.

The emission energy or energies may be detected by the sensor and converted to at least one electrical signal. The electrical signals may be transmitted along conducting lines in the circuitry of the integrated device connected to the instrument through the integrated device interface, such as integrated device interface 2-114 of instrument 2-104 shown in FIG. 2-1B. The electrical signals may be subsequently processed and/or analyzed. Processing or analyzing of electrical signals may occur on a suitable computing device either located on the instrument 2-104 or off instrument, such as computing device 2-120 shown in FIG. 2-1B.

Integrated device 2-210 may appear as depicted in FIG. 2-2. Electronic, optical, and related structures may all be incorporated onto a single substrate 2-200. The integrated device may include an array of pixels 2-205 and integrated electronic circuitry. The integrated electronic circuitry may include drive and read-out circuitry 2-215 coupled to the sensors of the pixel array, and signal processing circuitry. The signal processing circuitry may include analog-to-digital converters 2-217 and one or more field-programmable gate arrays and/or digital signal processors 2-219. Some embodiments may have more circuit components, and some embodiments may have fewer circuit components integrated on the substrate. Although the components of the integrated device are depicted on a single level in FIG. 2-2, the components may be fabricated on multiple levels on the substrate 2-200.

In some embodiments, there may be optical elements (not shown) located on the integrated device that are arranged for guiding and coupling excitation energy from one or more excitation sources to the sample wells. Such source-to-well elements may include plasmonic structures and other microfabricated structures located adjacent the sample wells. Additionally, in some embodiments, there may be optical elements located on the integrated device that are configured for guiding emission energy from the sample wells to corresponding sensors. Such well-to-sample elements may include may include plasmonic structures and other microfabricated structures located adjacent the sample wells. In some embodiments, a single component may play a role in both in coupling excitation energy to a sample well and delivering emission energy from the sample well to a corresponding sensor.

In some implementations, an integrated device may include more than one type of excitation source that is used to excite samples at a sample well. For example, there may be multiple excitation sources configured to produce multiple excitation energies or wavelengths for exciting a sample. In some embodiments, a single excitation source may be configured to emit multiple wavelengths that are used to excite samples in the sample wells. In some embodiments, each sensor at a pixel of the integrated device may include multiple sub-sensors configured to detect different emission energy characteristics from the sample.

In operation, parallel analyses of samples within the sample wells are carried out by exciting the samples within the wells using the excitation source and detecting signals from sample emission with the sensors. Emission energy from a sample may be detected by a corresponding sensor and converted to at least one electrical signal. The resulting signal, or signals, may be processed on the integrated device in some embodiments, or transmitted to the instrument for processing by the processing device and/or computing device. Signals from a sample well may be received and processed independently from signals associated with the other pixels.

When an excitation source delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

In some embodiments, samples may be labeled with one or more markers, and emission associated with the markers is discernable by the instrument. For example the sensor may be configured to convert photons from the emission energy into electrons to form an electrical signal that may be used to discern a lifetime that is dependent on the emission energy from a specific marker. By using markers with different lifetimes to label samples, specific samples may be identified based on the resulting electrical signal detected by the sensor. In some embodiments, components of the integrated device may affect the emission from a sample well to produce a spatial emission distribution pattern that is dependent on the emission wavelength. A corresponding sensor for the sample well may be configured to detect the spatial distribution patterns from a sample well and produce signals that differentiate between the different emission wavelengths, as described in further detail below.

II. Integrated Device

The integrated device may be configured to receive excitation energy from an external excitation energy source. In some embodiments, a region of the device may be used to couple to an excitation energy source located off the integrated device. Components of the integrated device may guide excitation energy from the excitation source coupling region to at least one pixel. In some embodiments, at least one waveguide may be configured to deliver excitation energy to at least one pixel having a sample well. A sample located within the sample well may emit emission energy in response to being illuminated with excitation energy. One or more sensors located within the pixel are configured to receive the emission energy.

Components and/or layers of integrated device 3-200 according to some embodiments shown in FIG. 3-2 include a sample well 3-203, waveguide 3-220, and sensor 3-275 integrated into one device. Sample well 3-203 may be formed in sample well layer 3-201 of integrated device 3-200. In some embodiments, the sample well layer 3-201 may be metal. Sample well 3-203 may have a dimension $D_{fv}$ which may indicate a cross-sectional dimension of the sample well. Sample well 3-203 may act as a nanoaperture and have one or more sub-wavelength dimensions that create a field enhancement effect that increases the intensity of the excitation of the sample in sample well 3-203. Waveguide 3-220 is configured to deliver excitation energy from excitation source 3-230 located off device 3-200 to sample well 3-203. The waveguide 3-220 may be formed in a layer between sample well layer 3-201 and sensor 3-275. The design of integrated device 3-200 allows for sensor 3-275 to collect luminescence emitted from a sample in sample well 3-203. At least some of the time, the sample absorbs excitation energy and emits a photon with an energy less than that of the excitation energy, referred to as emission energy or luminescence.

Having sample well 3-203 and sensor 3-275 on integrated device 3-200 may reduce the optical distance that light travels from the sample well 3-203 to sensor 3-215. Dimensions of integrated device 3-200 or components within the device may be configured for a certain optical distance. Optical properties of the materials of components and/or one or more layers of the device may determine an optical distance between a sample well and a sensor. In some embodiments, the thicknesses of one or more layers may determine the optical distance between the sample well and sensor in a pixel. Additionally or alternatively, the index of refraction of materials that form one or more layers of integrated device 3-200 may determine the optical distance between sample well 3-203 and sensor 3-275 in a pixel. Such an optical distance between the sample well and sensor in a pixel may be less than 1 mm, less than 100 microns, less than 25 microns, and/or less than 10 microns. One or more layers may be present between sample well layer 3-201 and waveguide layer 3-220 to improve coupling of excitation energy from waveguide 3-220 to sample well 3-203. Although integrated device 3-200 shown in FIG. 3-2 illustrates only a single layer 3-210, multiple layers may be formed between sample well 3-203 and waveguide 3-220. Layer 3-210 may be formed with optical properties to improve coupling of excitation energy from waveguide 3-220 to sample well 3-203. Layer 3-210 may be configured to reduce scattering and/or absorption of excitation energy and/or increase luminescence from a sample in sample well 3-203. Layer 3-210 may be optically transparent, according to some embodiments, so that light may travel to and from the sample well 3-203 with little attenuation. In some embodiments, dielectric materials may be used to form layer 3-210. In some embodiments, excitation energy coupling components within layer 3-210 and/or at the interface between layer 3-210 and sample well layer 3-201 may be provided to improve coupling of excitation energy from waveguide 3-220 to sample well 3-203. As an example, energy-collection components 3-215 formed at the interface between sample well layer 3-201 and layer 3-210 may be configured to improve coupling of excitation energy from waveguide 3-220 to sample well 3-203. Energy-collection components 3-215 are optional and, in some embodiments, the configuration of waveguide 3-220 and sample well 3-203 may allow for adequate coupling excitation energy without the presence of excitation energy collection components 3-215.

Luminescent light or energy emitted from a sample in the sample well 3-203 may be transmitted to the sensor 3-275 in a variety of ways, some examples of which are described in detail below. Some embodiments may use optical components to increase the likelihood that light of a particular wavelength is directed to an area or portion of the sensor 3-275 that is dedicated to detecting light of that particular wavelength. The sensor 3-275 may include multiple portions for detecting simultaneously light of different wavelengths that may correspond to emissions from different luminescent markers.

One or more layers may be present between sample well 3-203 and sensor 3-275 that may be configured to improve collection of luminescence from sample well 3-203 to sensor 3-275. Luminescence directing components may be located at the interface between sample well layer 3-201 and layer 3-210. The energy-collection components 3-215 may focus emission energy toward the sensor 3-275, and may additionally or alternatively spatially separate emission energies that have different characteristic energies or wavelengths. Such energy-collection components 3-215 may include a grating structure for directing luminescence towards sensor 3-275. In some embodiments, the grating structure may be a series of concentric rings or "bullseye" grating structure configuration. The concentric circular gratings may protrude from a bottom surface of the sample well layer 3-201. The circular gratings may act as plasmonic elements which may be used to decrease the spread of the signal light and direct the signal light towards associated sensor 3-275. Such a bullseye grating may direct luminescence more efficiently towards sensor 3-275.

Layer 3-225 may be formed adjacent to the waveguide. The optical properties of layer 3-225 may be selected to improve collection of luminescence from the sample well to sensor 3-275. In some embodiments, layer 3-225 may be a dielectric material. A baffle may be formed between sample well layer 3-201 and sensor 3-275. Baffle 3-240 may be configured such that the sensor 3-275 receives luminescence corresponding to sample well 3-203 and reduces luminescence, and reflected/scattered excitation from other sample wells. Filtering elements 3-260 may be positioned and configured to reduce excitation energy from reaching sensor 3-275. In some embodiments, filtering elements 3-260 may include a filter that selectively transmits emission energy of one or more markers used to label a sample. In embodiments with an array of sample wells and an array of sensors where each sample well has a corresponding sensor, a baffle corresponding to each sample well may be formed to reduce luminescence from other sample wells and reflected and/or scattered excitation light from being collected by a sensor corresponding to the sample well.

One or more layers may be formed between waveguide 3-220 and sensor 3-275 to reduce transmission of excitation energy to sensor. In some embodiments, filtering elements may be formed between waveguide 3-220 and sensor 3-275. Such filtering elements may be configured to reduce transmission of excitation energy to sensor 3-275 while allowing luminescence from the sample well to be collected by sensor 3-275.

The emission energy or energies may be detected by the sensor 3-275 and converted to at least one electrical signal. The electrical signal or signals may be transmitted along one or more row or column conducting lines (not shown) to the integrated electronic circuitry on the substrate 3-200 for subsequent signal processing.

The above description of FIG. 3-2 is an overview of some of the components of the apparatus according to some embodiments. In some embodiments, one or more elements of FIG. 3-2 may be absent or in a different location. The components of the integrated device 3-200 and excitation source 3-230 are described in more detail below.

A. Excitation Source Coupling Region

The integrated device may have an excitation source coupling region configured to couple with an external excitation energy source and guide excitation towards at least one pixel in a pixel area of the integrated device. The excitation source coupling region may include one or more structures configured to couple light into at least one waveguide. Any suitable mechanism for coupling excitation energy into a waveguide may be used.

In some embodiments, excitation energy from an external excitation source may couple to a waveguide of an integrated device through edge-coupling. An edge of the integrated device may include an end of the waveguide such that an external excitation source positioned proximate to the end of the waveguide may couple light into the waveguide. In such embodiments, fabrication of the excitation source coupling region may include positioning of an end of a waveguide at an edge of integrated device. FIG. 4-1A illustrates an example of edge-coupling. Optical fiber 4-106, configured to propagate excitation energy, is positioned proximate to an edge of integrated device 4-102 where an end of waveguide 4-104 of integrated device 4-102 is located at the edge such that optical fiber 4-106 may couple light into waveguide 4-104. In such embodiments, monitoring the alignment of optical fiber 4-106 or other excitation source to waveguide 4-104 can improve the amount of light provided by the optical fiber to the waveguide.

In some embodiments, a prism may couple light to the waveguide. Light may be directed and refracted by the prism in order to match the optical phase frequency of the propagating waveguide mode. The refractive index of the material used for the prism may be selected to improve coupling with the waveguide. In some instances, the prism has a high refractive index and a narrow gap relative to the waveguide. In other embodiments, light may couple directly to an end of a waveguide. An edge of the integrated device may be sufficiently well polished to allow focusing and alignment of the light to the waveguide.

The excitation source coupling region of an integrated device may include structural components configured to couple with an external excitation source. An integrated device may include a grating coupler configured to couple with an external excitation source positioned proximate a surface of the integrated device and direct light towards at least one waveguide of the integrated device. Features of the grating coupler, such as the size, shape, and/or grating configurations may be formed to improve coupling of the excitation energy from the excitation source to the waveguide. The grating coupler may include one or more structural components where the spacing between the structural components may act to propagate light. One or more dimensions of the grating coupler may provide desirable coupling of light having a certain characteristic wavelength.

An integrated device may also include a waveguide having a tapered region at an end of the waveguide. One or more dimensions of the waveguide perpendicular to a direction of light propagation in the waveguide may be larger at an end of the waveguide, forming a tapered region of the waveguide. In some embodiments, the tapered region of a waveguide may have a dimension perpendicular to the propagation of light and parallel to a surface of the integrated device that is larger at an end of the waveguide and becomes smaller along the length of the waveguide. In embodiments that include a grating coupler, the tapered region can be positioned proximate to the grating coupler such that the larger end of the tapered region is located closest to the grating coupler. The tapered region may be sized and shaped to improve coupling of light between the grating coupler and the waveguide by expanding one or more dimensions of the waveguide to allow for improved mode overlap of the waveguide with the grating coupler. In this manner, an excitation source positioned proximate the surface of an integrated device may couple light into the waveguide via the grating coupler. Such a combination of grating coupler and waveguide taper may allow for more tolerance in the alignment and positioning of the excitation source to the integrated device.

An exemplary integrated device having a grating coupler and a waveguide with a tapered region is shown in FIG. 4-1B. Integrated device 4-100 has an excitation source coupling region that includes a waveguide with a tapered region 4-114 and a grating coupler 4-116. Tapered region 4-114 has an end with a larger dimension parallel to surface 4-112 of integrated device 4-100 and perpendicular to propagation of light along the waveguide. The end of tapered region 4-114 may be sized and shaped to provide suitable coupling between the grating coupler 4-116 and the waveguide. Optical fiber 4-120, or other suitable excitation source, positioned with respect to grating coupler 4-116 may couple excitation energy to the waveguide.

A grating coupler may be positioned in a region of the integrated device external to the pixels of the integrated device. On a surface of the integrated device, the sample wells of the pixels may occupy a region of the surface separate from the excitation source coupling region. An excitation source positioned proximate to the surface of the excitation source coupling region may couple with the grating coupler. The sample wells may be positioned separate from the excitation source coupling region to reduce interference of light from the excitation source on performance of the pixels. A grating coupler of an integrated device may be formed within one or more layers of the integrated device that include a waveguide. In this manner, an excitation source coupling region of an integrated device may include a grating coupler within the same plane of the integrated device as a waveguide. The grating coupler may be configured for a particular set of beam parameters, including beam width, angle of incidence, and/or polarization of the incident excitation energy.

A cross-sectional view of integrated device 4-200 is shown in FIG. 4-2. Integrated device 4-200 includes at least one sample well 4-222 formed in layer 4-223 of integrated device 4-200. Integrated device 4-200 includes grating coupler 4-216 and waveguide 4-220 formed in substantially the same plane of integrated device 4-200. In some embodiments, grating coupler 4-216 and waveguide 4-220 are formed from the same layer of integrated device 4-200 and may include the same material. Excitation source coupling region 4-201 of integrated device 4-200 includes grating coupler 4-216. As shown in FIG. 4-2, sample well 4-222 is positioned on a surface of integrated device 4-200 external to excitation source coupling region 4-201. Excitation source 4-214 positioned relative to integrated device 4-200 may provide excitation energy incident on surface 4-215 of integrated device 4-200 within excitation source coupling region 4-201. By positioning grating coupler 4-216 within excitation source coupling region 4-201, grating coupler 4-216 may couple with the excitation energy from excitation source 4-214 and couple excitation energy to waveguide 4-220. Waveguide 4-220 is configured to propagate excitation energy to the proximity of one or more sample wells 4-222.

A grating coupler may be formed from one or more materials. In some embodiments, a grating coupler may include alternating regions of different materials along a direction parallel to propagation of light in the waveguide. As shown in FIG. 4-2, grating coupler 4-216 includes structures that are surrounded by material 4-224. The one or more materials that form a grating coupler may have one or more indices of refraction suitable for coupling and propagating light. In some embodiments, a grating coupler may include structures formed from one material surrounded by a material having a larger index of refraction. As an example, a grating coupler may include structures formed of silicon nitride and surrounded by silicon dioxide.

Any suitable dimensions and/or inter-grating spacing may be used to form a grating coupler. Grating coupler 4-216 may have a dimension perpendicular to the propagation of light through the waveguide, such as along the y-direction as shown in FIG. 4-2, of approximately 50 nm, approximately 100 nm, approximately 150 nm, or approximately 200 nm. Spacing between structures of the grating coupler along a direction parallel to light propagation in the waveguide, such as along the z-direction as shown in FIG. 4-2, may have any suitable distance. The inter-spacing grating may be approximately 300 nm, approximately, 350 nm, approximately, 400 nm, approximately 420 nm, approximately 450 nm, or approximately 500 nm. In some embodiments, the inter-grating spacing may be variable within a grating coupler. Grating coupler 4-216 may have one or more dimensions substantially parallel to surface 4-215 of integrated device 4-200 that provide a suitable area for coupling with external excitation source 4-214. The area of grating coupler 4-216 may coincide with one or more dimensions of a beam of light from excitation source 4-214 such that the beam overlaps with grating coupler 4-215. A grating coupler may have an area configured for a beam diameter of approximately 10 microns, approximately 20 microns, approximately 30 microns, or approximately 40 microns.

A cross-sectional view of a portion of an exemplary excitation source coupling region of an integrated device is shown in FIG. 4-3A. Excitation source coupling region includes grating coupler 4-326 and reflection layer 4-336 configured to reflect excitation light that passes through grating coupler 4-326 back towards grating coupler 4-326. Grating coupler 4-326 may include structures that have an inter-grating spacing represented by A along the z-direction shown in FIG. 4-3A. The structures may have a linear, curved, or any other suitable shape. In some embodiments, grating coupler 4-326 may have a dimension along the y-direction similar to waveguide 4-330, as represented by the arrows on either side of waveguide 4-330. Grating coupler 4-326 is surrounded by region 4-324, and the combination of materials that form grating coupler 4-324 and region 4-324 may provide desired coupling of light to waveguide 4-330. The index of refraction of waveguide 4-330, grating coupler 4-326, and/or surrounding material 4-324 may influence the coupling of the excitation energy to the waveguide and overall coupling efficiency of excitation energy to waveguide 4-330. An excitation source coupling region of an integrated device may have more than approximately 50% coupling efficiency. Grating coupler 4-326 may be configured for one or more characteristics of incident beam of excitation energy 4-314, including a characteristic wavelength, beam diameter (represented by arrows), and beam incident angle (represented by θ). Grating coupler 4-326 may be configured for a beam of light having a beam diameter of approximately 10 microns, approximately 20 microns, approximately 30 microns, or approximately 40 microns. Grating coupler 4-326 may be configured for a beam of light having an incident angle of approximately 2 degrees, approximately 5 degrees, or approximately 7 degrees. Grating coupler 4-326 may be configured to couple with excitation energy of a certain polarization, such as TM or TE polarized light.

A simulation of light coupling from a beam into a waveguide via a grating coupler is shown FIG. 4-3B. Waveguide and grating coupler lie along the z-axis at approximately the 0 point of the y-axis. Light beam is an incident angle of approximately 5 degrees from the y-direction and has a diameter of 20 microns. The waveguide used in this simulation has a height (along the y-direction) of 100 nm, and the rating coupler has an inter-grating spacing of 420 nm. The waveguide and the grating coupler structure have an index of refraction of approximately 1.87. The material surrounding the waveguide and grating structure has an index of refraction of approximately 1.45. FIG. 4-3B illustrates light intensity of beam coupled to grating coupler and waveguide and shows the modes of light in the waveguide by the darker regions.

One or more dimensions of the tapered region of a waveguide and relative positioning of the tapered region to the grating coupler may provide sufficient coupling of excitation energy into the waveguide. The curvature and chirp of the tapered region may accommodate convergence and/or divergence of the propagation of incident excitation energy to the waveguide. A planar view of an exemplary waveguide layer that includes a grating coupler 4-316 and tapered waveguide region 4-318 is shown in FIG. 4-3C. Tapered waveguide region 4-318 has a dimension perpendicular to the propagation of light and in the plane of FIG. 4-3C that gradually decreases from right to left to achieve a dimension of waveguide 4-320. Grating coupler 4-316 may have an area within the plane of FIG. 4-3C suitable for coupling with an external excitation source. Alignment of a beam of excitation energy to grating coupler 4-316 such that the beam substantially overlaps with the area of grating coupler 4-316 may improve coupling of excitation energy into waveguide 4-320. The arrangement of tapered region 4-318 relative to grating coupler 4-316 may provide suitable coupling efficiency. The angle of the tapered region 4-318 and grating coupler 4-316 may be selected to improve efficiency of coupling excitation energy from the excitation source to waveguide 4-320 by reducing loss of excitation energy as the dimension of the waveguide perpendicular to light propagation decreases.

An integrated device may include a layer formed on a side of a grating coupler opposite to the excitation source configured reflect light. The layer may reflect excitation energy that passes through the grating coupler towards the grating coupler. By including the layer in an integrated device, coupling efficiency of the excitation energy to the waveguide may be improved. An example of a reflective layer is layer 4-218 of integrated device 4-200 shown in FIG. 4-2 and layer 4-336 shown in FIG. 4-3A. Layer 4-218 is positioned within excitation source coupling region 4-201 of integrated device 4-200 and is configured to reflect light towards grating coupler 4-216. Layer 4-218 is formed proximate to the side of grating coupler 4-216 opposite to the incident excitation energy from excitation source 4-214. Positioning layer 4-218 external to pixels of integrated device 4-200 may reduce interference of layer 4-218 on the performance capabilities of the pixels. Layer may 4-218 may include any suitable material. Layer 4-218 may be substantially reflective for one or more excitation energies. In some embodiments, this layer may include Al, AlCu, and/or TiN.

B. Waveguide

An integrated device may include one or more waveguides arranged to deliver a desired amount of excitation energy to one or more sample wells of the integrated device. A waveguide positioned in the vicinity of one or more sample wells such that as excitation energy propagates along the waveguide a portion of excitation energy couples to the one or more sample wells. A waveguide may couple excitation energy to a plurality of pixels and act as a bus waveguide. For example, a single waveguide may deliver excitation energy to a row or a column of pixels of an integrated device. In some embodiments, a waveguide may be configured to propagate excitation energy having a plurality of characteristic wavelengths. A pixel of an integrated device may include additional structures (e.g., microcavity) configured to direct excitation energy from the waveguide toward the vicinity of the sample well. In some embodiments, a waveguide may carry an optical mode having an evanescent tail configured to extend into a sample well and/or in a region in the vicinity of the sample well. Additional energy-coupling structures located near the sample well may couple energy from the evanescent tail into the sample well.

One or more dimensions of a waveguide of an integrated device may provide desired propagation of excitation energy along the waveguide and/or into one or more sample wells. A waveguide may have a dimension perpendicular to the propagation of light and parallel to a plane of the waveguide, which may be considered as a cross-sectional width. A waveguide may have a cross-sectional width of approximately 0.4 microns, approximately 0.5 microns, approximately 0.6 microns, approximately 0.65 microns, approximately 0.8 microns, approximately 1 micron, or approximately 1.2 microns. A waveguide may have a dimension perpendicular to the propagation of light and perpendicular to a plane of the waveguide, which may be considered as a cross-sectional height. A waveguide may have a cross-sectional height of approximately 0.05 microns, approximately 0.1 microns, approximately 0.15 microns, approximately 0.16 microns, approximately 0.17 microns, approximately 0.2 microns, or approximately 0.3 microns. In some embodiments, a waveguide has a larger cross-sectional width than cross-sectional height. A waveguide may be positioned a certain distance from one or more sample wells within in integrated device, such as distance D shown in FIG. 4-2 between sample well 4-222 and waveguide 4-220, that is approximately 0.3 microns, 0.5 microns, or approximately 0.7 microns.

In an exemplary embodiment, a waveguide may have a cross-sectional width of approximately 0.5 µm and a cross-sectional height of approximately 0.1 µm, and be positioned approximately 0.5 µm below the sample well layer. In another exemplary embodiment, a waveguide may have a cross-sectional width of approximately 1 µm and a cross-sectional height of 0.18 µm, and be positioned 0.3 µm below the sample well layer.

A waveguide may be dimensioned to support a single transverse radiation mode or may be dimensioned to support multi-transverse radiation modes. In some embodiments, one or more dimensions of a waveguide may act such that the waveguide sustains only a single transverse mode and may selectively propagate TE or TM polarization modes. In some implementations, a waveguide may have highly reflective sections formed on its ends, so that it supports a longitudinal standing mode within the waveguide. By supporting one mode, the waveguide may have reduced modal interference effects from cross coupling of modes having different propagation constants. In some embodiments, the highly reflective sections comprise a single, highly reflective surface. In other embodiments, the highly reflective sections comprise multiple reflective structures that, in aggregate, result in a high reflectance. Waveguides may be configured to split excitation energy from a single excitation source having a higher output intensity using waveguide beam splitters to create a plurality of excitation energy beams from a single excitation source. Such beam splitters may include evanescent coupling mechanisms. Additionally or alternatively, photonic crystals may be used in the waveguide structure to improve propagation of excitation energy and/or in the material surrounding the waveguide to reduce scattering of excitation energy.

The position and arrangement of the waveguide with respect to other components in a pixel of the integrated devices may be configured to improve coupling of excitation energy towards a sample well, improve collection of emission energy by the sensor, and/or reduce signal noise introduced by excitation energy. A waveguide may be sized and/or positioned relative to a sample well so as to reduce interference of excitation energy propagating in the waveguide with emission energy emitted from the sample well. Positioning and arrangement of a waveguide in an integrated device may depend on the refractive indices of the waveguide and material surrounding the waveguide. For example, a dimension of the waveguide perpendicular to a direction of light propagation along the waveguide and within a plane of the waveguide may be increased so that a substantial amount of emission energy from a sample well passes through the waveguide as it propagates to the sensor of the pixel. In some implementations, a distance between a sample well and waveguide and/or waveguide thickness may be selected to reduce reflections from one or more interfaces between the waveguide and a surrounding material. According to some embodiments, reflection of emission energy by a waveguide may be reduced to less than about 5% in some embodiments, less than about 2% in some embodiments, and yet less than about 1% in some embodiments.

The capability of a waveguide to propagate excitation energy may depend both on the material for the waveguide and material surrounding the waveguide. In this manner, the waveguide structure may include a core material, such as waveguide 4-220, and a cladding material, such as region 4-224 as illustrated in FIG. 4-2. The material of both the waveguide and surrounding material may allow for propagation of excitation energy having a characteristic wavelength through the waveguide. Material for either the waveguide or the surrounding material may be selected for particular indices of refraction or combination of indices of refraction. The waveguide material may have a lower refractive index than the waveguide surrounding material. Example waveguide materials include silicon nitride ($Si_xN_y$), silicon oxynitride, silicon carbide, tantalum oxide ($TaO_2$), aluminum dioxide. Example waveguide surrounding materials include silicon dioxide ($SiO_2$) and silicon oxide. The waveguide and/or the surrounding material may include one or more materials. In some instances, a desired refractive index for a waveguide and/or surrounding material can be obtained by forming the waveguide and/or surrounding material to include more than one material. In some embodiments, a waveguide comprises silicon nitride and a surrounding material comprises silicon dioxide.

In an exemplary embodiment, a waveguide comprises silicon nitride and has a refractive index of approximately 1.90 and a cross-sectional height of approximately 100 nm, and the surrounding material comprises silicon dioxide and has a refractive index of approximately 1.46. In some embodiments, a waveguide may have a refractive index of approximately 1.88 may be used while the surrounding material has an index of refraction of approximately 1.46. In such embodiments, the lower refractive index for the waveguide may reduce optical loss. In another exemplary embodiment, a waveguide comprises a silicon nitride core and a silicon dioxide cladding and is configured to propagate excitation energy having a characteristic wavelength of 635 nm. The core may have an index of refraction of 1.99 and dimensions of 100 nm by 500 nm.

Waveguides of an integrated device may be formed to have a desired level of uniformity within a waveguide and/or among multiple waveguide. Uniformity within an integrated device can be achieved by fabricating the core and/cladding of a waveguide structure with substantially similar dimensions and/or indices of refraction along one waveguide and among multiple waveguides. Additionally, waveguides may be formed in a repeatable manner across different integrated devices by ensuring a repeatable fabrication process to achieve a certain level of compliance across different devices. Variation in the cross-sectional height of a waveguide and/or multiple waveguides may be less than approximately 2%, less than approximately 3%, or less than approximately 4%. Variation in the index of refraction of a waveguide and/or multiple waveguides may be less than approximately 0.5%, less than approximately 1%, or less than approximately 2%. Variation in the index of refraction of the surrounding material or cladding of a waveguide and/or multiple waveguide may be less than approximately 0.5%, less than approximately 1%, or less than approximately 2%.

A waveguide may be located between a sample well and one or more sensors in a pixel. For example, as shown in FIG. 4-2, waveguide 4-220 is positioned between sample well 4-222 and layer 4-230 which includes at least one sensor. In some embodiments, sample well 4-222 may be located between the waveguide and sensor. A waveguide may be aligned, for example, center-to-center with the sensor such that the center of the waveguide is substantially aligned with the center of the sample well. In some embodiments, the waveguide may be displaced from a center-to-center alignment with the sample well by a certain distance. In some embodiments, two substantially parallel waveguides may deliver excitation energy of a same wavelength or different wavelengths to a pixel, and the sample well may be located between the two waveguides. In some embodiments, a plurality of waveguides at different levels within the integrated device may direct excitation energy towards the vicinity of one or more sample wells located on the integrated device.

One or more waveguides of an integrated device may include bends. Bending of waveguides may provide a desired arrangement of waveguides and/or pixels such that a sufficient amount of excitation energy couples to one or more sample wells of an integrated device. The design of waveguide bends may balance the excitation energy loss due to bending and the spatial extent of the bends. Additionally, with proper design, bends within a waveguide may also be used to filter out part of the propagation light. Designing a portion of a waveguide to have a certain radius of curvature may decrease light of one polarization through the filtering provided by the curvature in the waveguide. Such bending may be used to select for a specific polarization mode, such as TM and TE. In some embodiments, bends may be used to filter out and/or attenuate the TM mode and retain the TE mode. FIG. 4-4 plots the loss of light due to bending as a function of radius of curvature for a bend for waveguide having a cross-sectional height of 100 nm and widths of 300 nm, 400 nm, 500 nm, 700 nm, and 1000 nm. As an example, to achieve a loss of at least 0.1 dB/90 degree bend, a waveguide having a cross-sectional width of 500 nm may have a bend radius of more than approximately 35 microns or a waveguide having a cross-sectional width of 700 nm may have a bend radius of more than approximately 22 microns.

Splitting waveguides from a single waveguide to multiple waveguides may allow for excitation energy to reach multiple rows or columns of sample wells of an integrated device. An excitation source may be coupled to an input waveguide and the input waveguide may be split into multiple output waveguides, where each output waveguide delivers excitation energy to a row or column of sample wells. Any suitable techniques for splitting and/or combining waveguides may be used. Such waveguide splitting and/or combining techniques may include a star splitter or coupler, a Y splitter, and/or an evanescent coupler. Additionally or alternatively, a multi-mode interference splitter (MMI) may be used for splitting and/or combining waveguides. One or more of these waveguide splitting and/or combining techniques may be used for directing excitation energy to a sample well.

An example star coupler 4-500 is illustrated in FIG. 4-5. Light of two different wavelengths may be input to the star coupler using a single waveguide or two waveguides, 4-501 and 4-502, as shown in FIG. 4-5. The size and shape of each input waveguide may be used to separately tune the spread of each of the excitation light beams to match at the output waveguides 4-504 to increase the likelihood that similar power distributions are obtained across the output waveguides 4-504. The star coupler includes a free propagation region 4-503, which may be implemented as a slab waveguide. Free propagation region 4-503 is a highly multi-mode region that allows the input light to propagate essentially freely in the plane of the slab waveguide. The free propagation region 4-503 may be, for example, 300-400 microns in width from the first output waveguide to the last output waveguide.

The coupling of the excitation energy to the output waveguides 4-504 may be tuned using various parameters of the star coupler, including one or more dimensions of individual components of the star coupler. For example, a dimension of the transverse cross-section of each of the input waveguides 4-501 and 4-502, a dimension of the transverse cross-section of each of the output waveguides 4-504, and the distance of each of the output waveguides 4-504 from the input waveguides may be parameters of the star coupler to tune to improve coupling of excitation energy to the output waveguides 4-504. In some embodiments, the star coupler may be formed such that output waveguides 4-504 have substantially equal power distribution relative to one another. In some embodiments, the output waveguides near the outside edge of the star coupler may have a different size than the output waveguides near the center. For example, the waveguides near the edge may have a larger transverse cross-sectional area, thereby collecting more light than the output waveguides near the center of the star coupler, which have a smaller transverse cross-sectional area. In some embodiments, the distance of the output waveguides from the input waveguides may vary. For example, as illustrated in FIG. 4-5, the output waveguides near the edge may have a distance from the input waveguides 4-501 and 4-502 that is smaller than the output waveguides near the center of the star coupler.

Star coupler 4-500 may have any suitable number of output waveguides. In some embodiments, a single star coupler distributes excitation energy to an entire integrated device. Thus, the number of output waveguides is equal to the number of rows of pixels in the integrated device. For example, there may be 128 output waveguides. In other embodiments, more than one star coupler may be used. In such an embodiment, a first star coupler may have 64 output waveguides and a second star coupler may have 64 output waveguides such that a combination of the first and second star couplers provides excitation energy to 128 rows of pixels of an integrated device.

In some embodiments, rather than having an input waveguide, one or more grating couplers may couple excitation energy directly into a free propagation region of a star coupler having a plurality of output waveguides. A single grating coupler may be used to couple a plurality of wavelengths to a free propagation region of the star coupler. To do so, light of differing wavelengths may be incident on the grating coupler at differing angles. In some embodiments, multiple grating couplers may be used to couple excitation energy of different wavelengths. For example, a grating coupler for each excitation wavelength may be used. A grating coupler configured as part of a free propagation region may operate similar to one of grating couplers described above, but rather than coupling light into an input waveguide that propagates light to the star coupler, the light is coupled directly into the slab waveguide that forms a free-propagation region, such as 4-603.

Another exemplary configuration of a star coupler is shown in FIG. 4-6. Light of two wavelengths may be input to the star coupler using grating couplers 4-605 and 4-606 connected to waveguides 4-609 and 4-610, respectively. Grating couplers 4-605 and 4-606 and waveguides 4-609 and 4-610 may be configured to reduce loss of excitation energy by reducing the number of bends and/or selecting for bend angles that improve propagation of excitation energy towards free-propagation region 4-607. Output waveguides 4-608 from the star-coupler may be configured in any suitable way to provide excitation energy to a row of pixels. In the example shown in FIG. 4-6, there are 32 output waveguides. The transverse cross-sectional area of the output waveguides 4-608 proximate to free-propagation region 4-607 may vary such that an output waveguide near an end of free-propagation region 4-607 has a larger transverse cross-sectional area than an output waveguide near the center of free-propagation region 4-607. For example, as shown in FIG. 4-6, output waveguide 4-608a has a larger transverse cross-sectional area than output waveguide 4-608b which is located closer to the center of free-propagation region 4-607. Such variation in transverse cross-sectional areas among output waveguides 4-608 may improve distribution of excitation energy across output waveguides 4-608, and in some embodiments, allow delivery of a substantially similar amount of excitation energy by each output waveguide to a row of pixels. In this manner, multiple rows of pixels may receive a substantially similar amount of excitation energy across the rows of pixels.

The design for waveguide splitting may be selected based on the efficiency of the splitting technique for the number of output waveguides. If the splitting efficiency is high, then more output waveguides may be produced and only a single splitting step may occur. In some embodiments, a single output waveguide from a splitter may correspond to each row of sample wells. Some embodiments include multiple splitting steps to achieve a sufficient number of waveguides configured to deliver excitation energy to a portion of sample wells of an integrated device. In some embodiments, a waveguide may be further split into multiple waveguides using a multi-mode interference splitter (MMI). In a MMI, an input waveguide may be split to multiple output waveguides where one or more dimensions of the MMI may determine the number of output waveguides and/or an amount of excitation energy delivered to an output waveguide. For example, as shown in FIG. 4-7, MMI splitter 4-707 is configured to provide outputs 4-708 from input 4-710. Outputs 4-708 may couple to waveguides configured to propagate excitation energy to rows of sample wells. In some embodiments, MMI splitter 4-707 may have 280 outputs coupled to waveguides configured to propagate excitation energy to 280 rows of sample wells. In some embodiments, a MMI splitter is configured to receive excitation energy from multiple inputs and direct the excitation energy to multiple outputs. As shown in FIG. 4-7, MMI splitter 4-717 is coupled to multiple inputs 4-720 and provides multiple outputs 4-718. In such embodiments, the number of outputs 4-718 may be greater than the number of inputs 4-720. In some embodiments, inputs 4-720 may provide different excitation energies to MMI splitter 4-717. In other embodiments, splitting of waveguides may occur in multiple splitting steps. As an example, splitting may occur using two sets of multi-mode interference splitters where an output waveguide from a first MMI splitter is used as an input for a second MMI splitter. For example, as shown in FIG. 4-7, input waveguide 4-730 is split by MMI splitter 4-727 into a plurality of outputs including output 4-728 coupled to MMI splitter 4-737 configured to provide outputs 4-738. In some embodiments, MMI splitter 4-727 may provide 35 outputs and each of the outputs is split by another MMI splitter, such as 4-737, into eight output waveguides. Since each of the intermediate 35 waveguides is split into eight waveguides, 280 waveguides are formed in this non-limiting example.

In some embodiments, multiple input waveguides may cross-couple in an MMI splitter to form output waveguides for coupling light to sample wells of the integrated device. On such an integrated device, there may be multiple grating couplers to couple with multiple excitation sources. A cross-coupling MMI is included to couple the multiple excitation sources together and form multiple output waveguides, as shown in FIG. 4-7. Each of the multiple input waveguides may originate at one of the grating couplers to couple light from one of the excitation sources to the MMI splitter. Such cross-coupling of multiple excitation sources may improve robustness of the system against excitation source degradation and/or failure. For example, if one of the multiple excitation sources stops producing excitation energy, then the other excitations sources are available to provide sufficient excitation energy for a desired level of performance of the integrated device. A compensation mechanism may also be included to compensate for a decrease in excitation energy by one or more of the multiple excitation sources by increasing the intensity provided by the remaining excitation sources that are functional.

Techniques for splitting and/or combining waveguides may be selected for a reduced loss of excitation energy when the waveguide is split and/or combined, including insertion loss. Insertion loss that occurs due to splitting and/or combining of a waveguide may be approximately less than 10 percent, approximately less than 20 percent, or approximately less than 30 percent. Techniques for splitting waveguides may allow for an approximate uniform splitting of excitation energy among the multiple output waveguides to evenly distribute the excitation energy among each output waveguide. Techniques for combining waveguides may allow for an approximately uniform relative contribution of excitation energy from the multiple input waveguides across the output waveguides. In some embodiments, uniformity among the output waveguides may be approximately less than 10 percent, approximately less than 20 percent, or approximately less than 30 percent. Techniques used for designing the waveguides may be selected for a certain tolerance of fabrication parameters, including waveguide cross-sectional height, cross-sectional width, and/or the index of refraction of the waveguides.

One or more dimensions of a MMI splitter influences the number of output waveguides and/or the efficiency of the waveguide splitting and/or combining. Designing a MMI splitter may include determining the dimensions of a MMI splitter to have a certain number of output waveguides and/or a certain splitting efficiency. FIG. 4-8 illustrates a simulation of the intensity profile for light within an example MMI splitter configured to receive light from an input waveguide and direct light into eight output waveguides. In this example, the input waveguide and the output waveguides have a cross-sectional width of 500 nm, and the dimensions of the MMI splitter are 16.35 microns in width, W, and 84.28 microns in length, L. By measuring the transmitted light at each of the output waveguides, a coupling uniformity and/or efficiency may be measured. For the exemplary MMI splitter shown in FIG. 4-8, the intensity of the eight output waveguides may vary by approximately 0.1%.

In some embodiments, a grating coupler may be configured to direct input light into a plurality of output waveguides. FIG. 4-9A illustrates a slice grating coupler which may be used to couple light having one or more wavelengths into a plurality of output waveguides 4-904. The slice grating is a linear grating structure that is much wider than the wavelength of the light (e.g., hundreds of microns wide). It is formed from alternating layers of dielectric, such as silicon nitride and silicon oxide. In some embodiments, multiple wavelengths can be coupled to the slice grating by launching the different wavelengths at the slice grating such that they are incident at different angles. In some embodiments, the one or more beams incident on the grating coupler has a spot size 4-603 approximately the size of the grating structure itself, as illustrated in FIG. 4-9A.

FIGS. 4-9B and 4-9C illustrate an exemplary slice grating coupler where FIG. 4-9C is a zoomed view of region 4-906 shown in FIG. 4-9B and includes the slice grating coupler 4-903 and output waveguides 4-905. Such a configuration provides both coupling and division of input power of different excitation wavelengths into a plurality of output waveguides. In the example shown in FIG. 4-9B, there are 128 output waveguides 4-905. In embodiments with multiple excitation wavelengths, the grating region 4-906 has a grating pitch designed to provide coupling of the multiple excitation wavelengths to the output waveguides. A waveguide may be powered by a single slice in the grating region where the width of the slice may vary to compensate for varying intensity of the input excitation energy beam on the grating coupler.

C. Sample Well

According to some embodiments, a sample well 5-210 may be formed at one or more pixels of an integrated device. A sample well may comprise a small volume or region formed at a surface of a substrate 5-105 and arranged such that samples 5-101 may diffuse into and out of the sample well from a specimen deposited on the surface of the substrate, as depicted in FIG. 5-1 and FIG. 5-2, which illustrate a single pixel 5-100 of an integrated device. In various embodiments, a sample well 5-210 may be arranged to receive excitation energy from a waveguide 5-240. Samples 5-101 that diffuse into the sample well may be retained, temporarily or permanently, within an excitation region 5-215 of the sample well by an adherent 5-211. In the excitation region, a sample may be excited by excitation energy (e.g., excitation radiation 5-247), and subsequently emit radiation that may be observed and evaluated to characterize the sample.

In further detail of operation, at least one sample 5-101 to be analyzed may be introduced into a sample well 5-210, e.g., from a specimen (not shown) containing a fluid suspension of samples. Excitation energy from a waveguide 5-240 may excite the sample or at least one marker attached to the sample or included in a tag associated with the sample while it is within an excitation region 5-215 within the sample well. According to some embodiments, a marker may be a luminescent molecule (e.g., fluorophore) or quantum dot. In some implementations, there may be more than one marker that is used to analyze a sample (e.g., distinct markers and tags that are used for single-molecule genetic sequencing as described in "Real-Time DNA Sequencing from Single Polymerase Molecules," by J. Eid, et al., *Science* 323, p. 133 (2009), which is incorporated by reference in its entirety). During and/or after excitation, the sample or marker may emit emission energy. When multiple markers are used, they may emit at different characteristic energies and/or emit with different temporal characteristics including different lifetimes. The emission energy from the sample well may radiate or otherwise travel to a sensor 5-260 where the emission energy is detected and converted into electrical signals that can be used to characterize the sample.

According to some embodiments, a sample well 5-210 may be a partially enclosed structure, as depicted in FIG. 5-2. In some implementations, a sample well 5-210 comprises a sub-micron-sized hole or opening (characterized by at least one transverse dimension $D_{sw}$) formed in at least one layer of material 5-230. In some cases, the hole may be referred to as a "nanoaperture." The transverse dimension of the sample well may be between approximately 20 nanometers and approximately 1 micron, according to some embodiments, though larger and smaller sizes may be used in some implementations. A volume of the sample well 5-210 may be between about $10^{-21}$ liters and about $10^{-15}$ liters, in some implementations. A sample well may be formed as a waveguide that may, or may not, support a propagating mode. A sample well may be formed as a waveguide that may, or may not, support a propagating mode. In some embodiments, a sample well may be formed as a zero-mode waveguide (ZMW) having a cylindrical shape (or similar shape) with a diameter (or largest transverse dimension) $D_{sw}$. A ZMW may be formed in a single metal layer as a nano-scale hole that does not support a propagating optical mode through the hole.

Because the sample well 5-210 has a small volume, detection of single-sample events (e.g., single-molecule events) at each pixel may be possible even though samples may be concentrated in an examined specimen at concentrations that are similar to those found in natural environments. For example, micromolar concentrations of the sample may be present in a specimen that is placed in contact with the integrated device, but at the pixel level only about one sample (or single molecule event) may be within a sample well at any given time. Statistically, some sample wells may contain no samples and some may contain more than one sample. However, an appreciable number of sample wells may contain a single sample (e.g., at least 30% in some embodiments), so that single-molecule analysis can be carried out in parallel for a large number of pixels. Because single-molecule or single-sample events may be analyzed at each pixel, the integrated device makes it possible to detect rare events that may otherwise go unnoticed in ensemble averages.

A transverse dimension $D_{sw}$ of a sample well may be between about 500 nanometers (nm) and about one micron in some embodiments, between about 250 nm and about 500 nm in some embodiments, between about 100 nm and about 250 nm in some embodiments, and yet between about 20 nm and about 100 nm in some embodiments. According to some implementations, a transverse dimension of a sample well is between approximately 80 nm and approximately 180 nm, or between approximately one-quarter and one-eighth of the excitation wavelength or emission wavelength. According to other implementations, a transverse dimension of a sample well is between approximately 120 nm and approximately 170 nm. In some embodiments, the depth or height of the sample well 5-210 may be between about 50 nm and about 500 nm. In some implementations, the depth or height of the sample well 5-210 may be between about 80 nm and about 250 nm.

A sample well 5-210 having a sub-wavelength, transverse dimension can improve operation of a pixel 5-100 of an integrated device in at least two ways. For example, excitation energy incident on the sample well from a side opposite the specimen may couple into the excitation region 5-215 with an exponentially decreasing power, and not propagate through the sample well to the specimen. As a result, excitation energy is increased in the excitation region where it excites a sample of interest, and is reduced in the specimen where it would excite other samples that would contribute to background noise. Also, emission from a sample retained at a base of the well (e.g., nearer to the sensor 5-260) is preferably directed toward the sensor, since emission propagating up through the sample well is highly suppressed. Both of these effects can improve signal-to-noise ratio at the pixel. The inventors have recognized several aspects of the sample well that can be improved to further boost signal-to-noise levels at the pixel. These aspects relate to sample well shape and structure, and also to adjacent optical and plasmonic structures (described below) that aid in coupling excitation energy to the sample well and emitted radiation from the sample well.

According to some embodiments, a sample well 5-210 may be formed as a nanoaperture configured to not support a propagating mode for particular wavelengths of interest. In some instances, the nanoaperture is configured where all modes are below a threshold wavelength and the aperture may be a sub-cutoff nanoaperture (SCN). For example, the sample well 5-210 may comprise a cylindrically-shaped hole or bore in a conductive layer. The cross-section of a sample well need not be round, and may be elliptical, square, rectangular, or polygonal in some embodiments. Excitation energy 5-247 (e.g., visible or near infrared radiation) may enter the sample well through an entrance aperture 5-212 that may be defined by walls 5-214 of the sample well at a first end of the well, as depicted in FIG. 5-2. When formed as a SCN, the excitation energy may decay exponentially along a length of the nanoaperture (e.g. in the direction of the specimen). In some implementations, the waveguide may comprise a SCN for emitted radiation from the sample, but may not be a SCN for excitation energy. For example, the aperture and waveguide formed by the sample well may be large enough to support a propagating mode for the excitation energy, since it may have a shorter wavelength than the emitted radiation. The emission, at a longer wavelength, may be beyond a cut-off wavelength for a propagating mode in the waveguide. According to some embodiments, the sample well 5-210 may comprise a SCN for the excitation energy, such that the greatest intensity of excitation energy is localized to an excitation region 5-215 of the sample well at an entrance to the sample well 5-210 (e.g., localized near the interface between layer 5-235 and layer 5-230 as depicted in the drawing). Such localization of the excitation energy can improve localization of emission energy from the sample, and limit the observed emission that emitted from a single sample (e.g., a single molecule).

According to some embodiments, a pixel 5-100 may include additional structures. For example, a pixel 5-100 may include one or more excitation-coupling structure 5-220 that affects coupling of excitation energy to a sample within the sample well. A pixel may also include an emission-directing structure 5-250 that affects directing emission energy from a sample within the sample well to sensor 5-260.

An example of excitation localization near an entrance of a sample well that comprises a SCN is depicted in FIG. 5-3. A numerical simulation was carried out to determine intensity of excitation radiation within and near a sample well 5-210 formed as a SCN. The results show that the intensity of the excitation radiation is about 70% of the incident energy at an entrance aperture of the sample well and drops to about 20% of the incident intensity within about 100 nm in the sample well. For this simulation, the characteristic wavelength of the excitation energy was 633 nm and the diameter of the sample well 5-210 was 140 nm. The sample well 5-210 was formed in a layer of gold metal. Each horizontal division in the graph is 50 nm. As shown by the graph, more than one-half of the excitation energy received in the sample well is localized to about 50 nm within the entrance aperture 5-212 of the sample well.

To improve the intensity of excitation energy that is localized at the sample well, other sample well structures were developed and studied by the inventors. FIG. 5-4 depicts an embodiment of a sample well that includes a cavity or divot 5-216 at an excitation end of the sample well. As can be seen in the simulation results of FIG. 5-3, a region of higher excitation intensity exists just before the entrance aperture 5-212 of the sample well. Adding a divot 5-216 to the sample well allows a sample to move into a region of higher excitation intensity, according to some embodiments. In some implementations, the shape and structure of the divot alters the local excitation field (e.g., because of a difference in refractive index between the layer 5-235 and fluid in the sample well), and can further increase the intensity of the excitation energy in the divot. Divot 5-216 may be formed within layer 5-235 such that a portion of the sample volume that occupies sample well 5-214 and divot 5-216 is surrounded by the material that forms layer 5-216.

The divot may have any suitable shape. The divot may have a transverse shape that is substantially equivalent to a transverse shape of the sample well, e.g., round, elliptical, square, rectangular, polygonal, etc. In some embodiments, the sidewalls of the divot may be substantially straight and vertical, like the walls of the sample well. In some implementations, the sidewalls of the divot may be sloped and/or curved, as depicted in the drawing. The transverse dimension of the divot may be approximately the same size as the transverse dimension of the sample well in some embodiments, may be smaller than the transverse dimension of the sample well in some embodiments, or may be larger than the transverse dimension of the sample well in some embodiments. The divot 5-216 may extend between approximately 10 nm and approximately 200 nm beyond sample well layer 5-230. In some implementations, the divot may extend between approximately 50 nm and approximately 150 nm beyond sample well layer 5-230. In some embodiments, the divot may extend between approximately 150 nm and approximately 250 nm beyond sample well layer 5-230. By forming the divot, the excitation region 5-215 may extend outside the sample well, as depicted in FIG. 5-4.

FIG. 5-5 depicts improvement of excitation energy at the excitation region for a sample well containing a divot (shown in the left simulation image). For comparison, the excitation field is also simulated for a sample well without a divot, shown on the right. The field magnitude has been converted from a color rendering in these plots, and the dark region at the base of the divot represents higher intensity than the light region within the sample well. The dark regions above the sample well represent the lowest intensity. As can be seen, the divot allows a sample 5-101 to move to a region of higher excitation intensity, and the divot also increases the localization of region of highest intensity at an excitation end of the sample well. Note that the region of high intensity is more distributed for the sample well without the divot. In some embodiments, the divot 5-216 provides an increase in excitation energy at the excitation region by a factor of two or more. In some implementations, an increase of more than a factor of two can be obtained depending on the shape and depth of the divot. In these simulations, the layer containing the sample well includes aluminum and has a thickness of approximately 100 nm, the divot has a depth of approximately 50 nm, and the excitation energy wavelength is 635 nm.

FIG. 5-6A depicts another embodiment of a sample well 5-210 in which the sample well is formed above a protrusion 5-615 at a surface of a substrate. A resulting structure for the sample well may increase the excitation energy at the sample by more than a factor of two compared to a sample well shown in FIG. 5-1, and may condense emission from the sample well to a sensor 5-260. According to some embodiments, a protrusion 5-615 is patterned in a first layer 5-610 of material. In some embodiments, the protrusion comprises a waveguide. The protrusion may be formed as a ridge with a rectangular cross-section in some implementations, and a second layer 5-620 of material may be deposited over the first layer of the protrusion. At the protrusion, the second layer may form a shape above the protrusion that approximates a cylindrical portion 5-625, as depicted. In some embodiments, a conductive layer 5-230 (e.g., a reflective metal) may be deposited over the second layer 5-620 and patterned to form a sample well 5-210 in the conductive layer above the protrusion. A divot 5-216 may then be etched into the second layer. The divot 5-216 may extend between about 50 nm and about 150 nm below the conductive layer 5-230. According to some embodiments, the first layer 5-610 and second layer 5-620 may be optically transparent, and may or may not be formed of a same material. In some implementations, the first layer 5-610 may be formed from an oxide (e.g., $SiO_2$) or a nitride (e.g., $Si_3N_4$), and the second layer 5-620 may be formed from an oxide or a nitride.

According to some embodiments, the conductive layer 5-230 above the protrusion 5-615 is shaped approximately as a cylindrical reflector 5-630. The shape of the cylindrical portion may be controlled by selection of the protrusion height h, width or transverse dimension w of the protrusion, and a thickness t of the second layer 5-620. The location of the excitation region and position of the sample can be adjusted with respect to an optical focal point of the cylindrical reflector by selection of the divot depth d. It may be appreciated that the cylindrical reflector 5-630 can concentrate excitation energy at the excitation region 5-215, and can also collect radiation emitted from a sample and reflect and concentrate the radiation toward the sensor 5-260.

Some embodiments relate to an integrated device having a sample well with a divot positioned proximate to a waveguide. FIG. 5-6B shows an integrated device having sample well 5-632 formed in layer 5-630 and layer 5-636. Layer 5-630 may be a metal layer and include one or more metals (e.g., Al). Layer 5-636 may act as a dielectric layer and include one or more dielectric materials (e.g., silicon dioxide). Sample well 5-632 may have a variable dimension in a direction parallel to layer 5-630 and/or layer 5-636. Sample well 5-632 may have a dimension D2 along the z-direction at least within layer 5-630 of the integrated device, and in some embodiments, dimension D2 may be considered a diameter of sample well 5-632. Dimension D2 of sample well 5-632 may be approximately 700 nm, approximately 800 nm, approximately 900 nm, approximately 1 micron, or approximately 1.1 microns. Sample well 5-632 may have a dimension D1 along the z-direction within layer 5-636 of the integrated device and in some embodiments, may be consider a diameter at a surface of sample well 5-632. Dimension D1 may be approximately 100 nm, approximately 150 nm, approximately 200 nm, or approximately 250 nm. The surface of sample well 5-632 having dimension D1 is positioned a dimension d1 along the x-direction from waveguide 5-634. Positioning sample well 5-632 proximate to waveguide 5-634 by distance d1 may allow for improved coupling of excitation energy from waveguide 5-634 to sample well 5-632. Dimension d1 may be approximately 50 nm, approximately 100 nm, approximately 150 nm, approximately 200 nm, or approximately 250 nm.

As noted above, a sample well may be formed in any suitable shape, and is not limited to only cylindrical shapes. In some implementations, a sample well may be conic, tetrahedron, pentahedron, etc. FIG. 5-7A-FIG. 5-7F illustrate some example sample well shapes and structures that may be used in some embodiments. A sample well 5-210 may be formed to have an entrance aperture 5-212 that is larger than an exit aperture 5-218 for the excitation energy, according to some embodiments. The sidewalls of the sample well may be tapered or curved. Forming a sample well in this manner can admit more excitation energy to the excitation region, yet still appreciably attenuate excitation energy that travels toward the specimen. Additionally, emission radiated by a sample may preferentially radiate toward the end of the sample well with the larger aperture, because of favorable energy transfer in that direction.

In some embodiments, a divot 5-216 may have a smaller transverse dimension than the base of the sample well, as depicted in FIG. 5-7B. A smaller divot may be formed by coating sidewalls of the sample well with a sacrificial layer before etching the divot, and subsequently removing the sacrificial layer. A smaller divot may be formed to retain a sample in a region that is more equidistant from the conductive walls of the sample well. Retaining a sample equidistant from the walls of the sample well may reduce undesirable effects of the sample well walls on the radiating sample, e.g., quenching of emission, and/or altering of radiation lifetimes.

FIGS. 5-7C and 5-7D depict another embodiment of a sample well. According to this embodiment, a sample well 5-210 may comprise excitation-energy-enhancing structures 5-711 and an adherent 5-211 formed adjacent the excitation-energy-enhancing structures. The energy-enhancing structures 5-711 may comprise surface plasmon or nano-antenna structures formed in conductive materials on an optically transparent layer 5-235, according to some embodiments. FIG. 5-7C depicts an elevation view of the sample well 5-210 and nearby structure, and FIG. 5-7D depicts a plan view. The excitation-energy-enhancing structures 5-711 may be shaped and arranged to enhance excitation energy in a small localized region. For example, the structures may include pointed conductors having acute angles at the sample well that increase the intensity of the excitation energy within an excitation region 5-215. In the depicted example, the excitation-energy-enhancing structures 5-711 are in the form of a bow-tie. Samples 5-101 diffusing into the region may be retained, temporarily or permanently, by the adherent 5-211 and excited by excitation energy that may be delivered from a waveguide 5-240 located adjacent the sample well 5-210. According to some embodiments, the excitation energy may drive surface-plasmon waves in the energy-enhancing structures 5-711. The resulting surface-plasmon currents may produce high electric fields at the sharp points of the structures 5-711, and these high fields may excite a sample retained in the excitation region 5-215. In some embodiments, a sample well 5-210 depicted in FIG. 5-7C may include a divot 5-216.

Another embodiment of a sample well is depicted in FIG. 5-7E, and shows an excitation-energy-enhancing structure 5-720 formed along interior walls of the sample well 5-210. The excitation-energy-enhancing structure 5-720 may comprise a metal or conductor, and may be formed using an angled (or shadow), directional deposition where the substrate on which the sample well is formed is rotated during the deposition. During the deposition, the base of the sample well 5-210 is obscured by the upper walls of the well, so that the deposited material does not accumulate at the base. The resulting structure 5-720 may form an acute angle 5-722 near the bottom of the structure, and this acute angle of the conductor can enhance excitation energy within the sample well.

In an embodiment depicted in FIG. 5-7E, the material 5-232 in which the sample well is formed need not be a conductor, and may be any suitable dielectric. According to some implementations, the sample well 5-210 and excitation-energy-enhancing structure 5-720 may be formed at a blind hole etched into a dielectric layer 5-235, and a separate layer 5-232 need not be deposited.

In some implementations, a shadow evaporation may be subsequently performed on the structure shown in FIG. 5-7E to deposit a metallic or conductive energy-enhancing structure, e.g., a trapezoidal structure or pointed cone at the base of the sample well, as depicted by the dashed line. The energy-enhancing structure may enhance the excitation energy within the sample well via surface plasmons. After the shadow evaporation, a planarizing process (e.g., a chemical-mechanical polishing step or a plasma etching process) may be performed to remove or etch back the deposited material at the top of the sample well, while leaving the energy-enhancing structure within the well.

In some embodiments, a sample well 5-210 may be formed from more than a single metal layer. FIG. 5-7F illustrates a sample well formed in a multi-layer structure, where different materials may be used for the different layers. According to some embodiments, a sample well 5-210 may be formed in a first layer 5-232 (which may be a semiconducting or conducting material), a second layer 5-234 (which may be an insulator or dielectric), and a third layer 5-230 (which may be a conductor or semiconductor). In some embodiments, a degeneratively-doped semiconductor or graphene may be used for a layer of the sample well. In some implementations, a sample well may be formed in two layers, and in other implementations a sample well may be formed in four or more layers. In some embodiments, multi-layer materials used for forming a sample well may be selected to increase or suppress interfacial excitons which may be generated by excitation radiation incident on the sample well. In some embodiments, multi-layer materials used for forming a sample well may be selected to increase surface-plasmon generation at a base of the sample well or suppress surface-plasmon radiation at a top of the well. In some embodiments, multi-layer materials used for forming a sample well may be selected to suppress excitation radiation from propagating beyond the sample well and multi-layer structure into the bulk specimen. In some embodiments, multi-layer materials used for forming a sample well may be selected to increase or suppress interfacial excitons which may be generated by excitation radiation incident on the sample well.

Various materials may be used to form sample wells described in the foregoing embodiments. According to some embodiments, a sample well 5-210 may be formed from at least one layer of material 5-230, which may comprise any one of or a combination of a conductive material, a semiconductor, and an insulator. In some embodiments, the sample well 5-210 comprises a highly conductive metallic layer, e.g., gold, silver, aluminum, copper. In some embodiments, the layer 5-230 may comprise a multi-layer stack that includes any one of or a combination of gold, silver, aluminum, copper, titanium, titanium nitride, palladium, platinum, and chromium. In some implementations, other metals may be used additionally or alternatively. According to some embodiments, a sample well may comprise an alloy such as AlCu or AlSi.

In some embodiments, the multiple layers of different metals or alloys may be used to form a sample well. In some implementations, the material in which the sample well 5-210 is formed may comprise alternating layers of metals and non-metals, e.g., alternating layers of metal and one or more oxides. In some embodiments, the non-metal may include a polymer, such as polyvinyl phosphonic acid or a polyethylene glycol (PEG)-thiol.

A layer 5-230 in which a sample well is formed may be deposited on or adjacent to at least one optically transparent layer 5-235, according to some embodiments, so that excitation energy (in the form of optical radiation, such as visible or near-infrared radiation) and emission energy (in the form of optical radiation, such as visible or near-infrared radiation) may travel to and from the sample well 5-210 without significant attenuation. For example, excitation energy from a waveguide 5-240 may pass through the at least one optically transparent layer 5-235 to the excitation region 5-215, and emission from the sample may pass through the same layer or layers to the sensor 5-260. This excitation energy may be from the evanescent tail of excitation light guided by the waveguide.

In some embodiments, at least one surface of the sample well 5-210 may be coated with one or more layers 5-211, 5-280 of material that affect the action of a sample within the sample well, as depicted in FIG. 5-8. For example, a thin dielectric layer 5-280 (e.g., alumina, titanium nitride or silica) may be deposited as a passivating coating on sidewalls of the sample well. Such a coating may be implemented to reduce sample adhesion of a sample outside the excitation region 5-215, or to reduce interaction between a sample and the material 5-230 in which the sample well 5-210 is formed. The thickness of a passivating coating within the sample well may be between about 5 nm and about 50 nm, according to some embodiments.

In some implementations, a material for a coating layer 5-280 may be selected based upon an affinity of a chemical agent for the material, so that the layer 5-280 may be treated with a chemical or biological substance to further inhibit adhesion of a sample species to the layer. For example, a coating layer 5-280 may comprise alumina, which may be passivated with a polyphosphonate passivation layer, according to some embodiments. Additional or alternative coatings and passivating agents may be used in some embodiments.

According to some embodiments, at least a bottom surface of the sample well 5-210 and/or divot 5-216 may be treated with a chemical or biological adherent 5-211 (e.g., biotin) to promote retention of a sample. The sample may be retained permanently or temporarily, e.g., for at least a period of time between about 0.5 milliseconds and about 50 milliseconds. In another embodiment, the adherent may promote temporary retention of a sample 5-101 for longer periods. Any suitable adherent may be used in various embodiments, and is not limited to biotin.

According to some embodiments, the layer of material 5-235 adjacent the sample well may be selected based upon an affinity of an adherent for the material of that layer. In some embodiments, passivation of the sample well's sidewalls may inhibit coating of an adherent on the sidewalls, so that the adherent 5-211 preferentially deposits at the base of the sample well. In some embodiments, an adherent coating may extend up a portion of the sample well's sidewalls. In some implementations, an adherent may be deposited by an anisotropic physical deposition process (e.g., evaporation, sputtering), such that the adherent accumulates at the base of a sample well or divot and does not appreciably form on sidewalls of the sample well.

Various fabrication techniques may be employed to fabricate sample wells 5-210 for an integrated device. A few example processes are described below, but the invention is not limited to only these examples.

The sample well 5-210 may be formed by any suitable micro- or nano-fabrication process, which may include, but is not limited to, processing steps associated with photolithography, deep-ultraviolet photolithography, immersion photolithography, near-field optical contact photolithography, EUV lithography, x-ray lithography, nanoimprint lithography, interferometric lithography, step-and-flash lithography, direct-write electron beam lithography, ion beam lithography, ion beam milling, lift-off processing, reactive-ion etching, etc. According to some embodiments, a sample well 5-210 may be formed using photolithography and lift-off processing. Example fabrication steps associated with lift-off processing of a sample well are depicted in FIG. 5-9A-F. Although fabrication of only a single sample well or structure at a pixel is typically depicted in the drawings, it will be understood that a large number of sample wells or structures may be fabricated on a substrate (e.g., at each pixel) in parallel.

According to some embodiments, a layer 5-235 (e.g., an oxide layer) on a substrate may be covered with an anti-reflection coating (ARC) layer 5-910 and photoresist 5-920, as depicted in FIG. 5-9A. The photoresist may be exposed and patterned using photolithography and development of the resist. The resist may be developed to remove exposed portions or unexposed portions (depending on the resist type), leaving a pillar 5-922 that has a diameter approximately equal to a desired diameter for the sample well, $D_{sw}$, as depicted in FIG. 5-9B. The height of the pillar may be substantially different than a desired depth of the sample well. For example, the height of the pillar may be substantially greater than a desired depth of the sample well.

The pattern of the pillar 5-922 may be transferred to the ARC layer 5-910 via anisotropic, reactive ion etching (RIE), for example as shown in FIG. 5-9C. The region may then be coated with at least one material 5-230, e.g., a conductor or metal, which is desired to form the sample well. A portion of the deposited material, or materials, forms a cap 5-232 over the pillar 5-922, as depicted in FIG. 5-9D. The photoresist 5-920 and ARC layer 5-910 may then be stripped from the substrate, using a selective removal process (e.g., using a chemical bath with or without agitation which dissolves at least the resist and releases or "lifts off" the cap). If the ARC layer 5-910 remains, it may be stripped from the substrate using a selective etch, leaving the sample well 5-210 as shown in FIG. 5-9E. According to some embodiments, the sidewalls 5-214 of the sample well may be sloped due to the nature of the deposition of the at least one material 5-230.

As used herein, a "selective etch" means an etching process in which an etchant selectively etches one material that is desired to be removed or etched at a higher rate (e.g., at least twice the rate) than the etchant etches other materials which are not intended to be removed.

Because the photoresist 5-920 and ARC layer 5-910 are typically polymer based, they are considered soft materials which may not be suitable for forming sample wells having high aspect ratios (e.g., aspect ratios greater than about 2:1 with respect to height-to-width). For sample wells having higher aspect ratios, a hard material may be included in the lift-off process. For example, before depositing the ARC layer and photoresist, a layer of a hard (e.g., an inorganic material) may be deposited. In some embodiments, a layer of titanium or silicon nitride may be deposited. The layer of hard material should exhibit preferential etching over the material, or materials, 5-230 in which the sample well is formed. After the photoresist is patterned, a pattern of the pillar may be transferred into the ARC layer and the underlying hard material 5-930 yielding a structure as depicted in FIG. 5-9F. The photoresist and ARC layer may be then stripped, the material(s) 5-230 deposited, and a lift-off step performed to form the sample well.

According to some embodiments, a lift-off process may be used to form a sample well comprising energy-enhancing structures 5-711, as depicted in FIG. 5-7C and FIG. 5-7D.

An alternative process for forming a sample well is depicted in FIG. 5-10A-D. In this process, the sample well may be directly etched into at least one material 5-230. For example, at least one material 5-230 in which a sample well is to be formed may be deposited on a substrate. The layer may be covered by an ARC layer 5-910 and a photoresist 5-920, as illustrated in FIG. 5-10A. The photoresist may be patterned to form a hole having a diameter approximately equal to a desired diameter of the sample well, as depicted in FIG. 5-10B. The pattern of the hole may be transferred to the ARC and through the layer 5-230 using an anisotropic, reactive ion etch, as shown in FIG. 5-10C for example. The photoresist and ARC layer may be stripped, yielding a sample well as depicted in FIG. 5-10D. According to some embodiments, the sidewalls of a sample well formed by etching into the layer of material 5-230 may be more vertical than sidewalls resulting from a lift-off process.

In some embodiments, the photoresist and ARC layer may be used to pattern a hard mask (e.g., a silicon nitride or oxide layer, not shown) over the material 5-230. The patterned hole may then be transferred to the hard mask, which is then used to transfer the pattern into the layer of material 5-230. A hard mask may allow greater etching depths into the layer of material 5-230, so as to form sample wells of higher aspect ratio.

It will be appreciated that the lift-off processes and the direct etching fabrication techniques described above may be used to form a sample well when multiple layers of different materials are used to form a stack of material 5-230 in which the sample well is formed. An example stack is shown in FIG. 5-11. According to some embodiments, a stack of material may be used to form a sample well to improve coupling of excitation energy to the excitation region of a sample well, or to reduce transmission or re-radiation of excitation energy into the bulk specimen. For example, an absorbing layer 5-942 may be deposited over a first layer 5-940. The first layer may comprise a metal or metal alloy, and the absorbing layer may comprise a material that inhibits surface plasmons, e.g., amorphous silicon, TaN, TiN or Cr. In some implementations, a surface layer 5-944 may also be deposited to passivate the surface surrounding the sample well (e.g., inhibit adhesion of molecules).

Formation of a sample well including a divot 5-216 may be done in any suitable manner. In some embodiments, a divot may be formed by etching further into an adjacent layer 5-235, and/or any intervening layer or layers, adjacent the sample well. For example, after forming a sample well in a layer of material 5-230, that layer 5-230 may be used as an etch mask for patterning a divot, as depicted in FIG. 5-12. For example, the substrate may be subjected to a selective, anisotropic reactive ion etch so that a divot 5-216 may be etched into adjacent layer 5-235. For example, in an embodiment where the material 5-230 is metallic and the adjacent layer 5-235 silicon oxide, a reactive-ion plasma etch having a feed gas comprising $CHF_3$ or $CF_4$ may be used to preferentially remove exposed silicon oxide below the sample well and form the divot 5-216. As used herein, "silicon oxide" generally refers to $SiO_x$ and may include silicon dioxide, for example.

In some embodiments, conditions within the plasma (e.g., bias to the substrate and pressure) during an etch may be controlled to determine the etch profile of the divot. For example, at low pressure (e.g., less than about 100 mTorr) and high DC bias (e.g., greater than about 20V), the etching may be highly anisotropic and form substantially straight and vertical sidewalls of the divot, as depicted in the drawing. At higher pressures and lower bias, the etching may be more isotropic yielding tapered and/or curved sidewalls of the divot. In some implementations, a wet etch may be used to form the divot, which may be substantially isotropic and form an approximately spherical divot that may extend laterally under the material 5-230, up to or beyond the sidewalls of the sample well.

FIG. 5-13A through FIG. 5-13C depict process steps that may be used to form a divot 5-216 having a smaller transverse dimension than the sample well 5-210 (for example, a divot like that depicted in FIG. 5-7B). In some implementations, after forming a sample well, a conformal sacrificial layer 5-960 may be deposited over a region including the sample well. According to some embodiments, the sacrificial layer 5-960 may be deposited by a vapor deposition process, e.g., chemical vapor deposition (CVD), plasma-enhanced CVD, or atomic layer deposition (ALD). The sacrificial layer may then be etched back using a first anisotropic etch that is selective to the sacrificial layer 5-960, removes the layer from horizontal surfaces, leaves side wall coatings 5-962 on walls of the sample well, as depicted in FIG. 5-13B. The etch back may be selective and stop on the material 5-230 and adjacent layer 5-235 in some embodiments, or may be a non-selective, timed etch in some embodiments.

A second anisotropic etch that is selective to the adjacent layer 5-235 may be executed to etch a divot 5-216 into the adjacent layer as depicted in FIG. 5-13C. The sacrificial side wall coatings 5-962 may then optionally be removed by a selective wet or dry etch. The removal of the sidewall coatings open up the sample well to have a larger transverse dimension than the divot 5-216.

According to some embodiments, the sacrificial layer 5-960 may comprise the same material as the adjacent layer 5-235. In such embodiments, the second etch may remove at least some of the side wall coating 5-962 as the divot is etched into the adjacent layer 5-235. This etch back of the side wall coating can form tapered sidewalls of the divot in some embodiments.

In some implementations, the sacrificial layer 5-960 may be formed from, or include a layer of, a material that is used to passivate the sidewalls of the sample well (e.g., reduce adhesion of samples at the sidewalls of the sample well). At least some of the layer 5-960 may then be left on the walls of the sample well after formation of the divot.

According to some embodiments, the formation of the sidewall coatings 5-962 occurs after the formation of the divot. In such embodiments, the layer 5-960 coats the sidewalls of the divot. Such a process may be used to passivate the sidewalls of the divot and localize the sample within a center region of the divot.

Process steps associated with depositing an adherent 5-211 at a base of a sample well 5-210, and a passivation layer 5-280 are depicted in FIG. 5-14. According to some embodiments, a sample well may include a first passivation layer 5-280 on walls of the sample well. The first passivation layer may be formed, for example, as described above in connection with FIG. 5-13B or FIG. 5-8. In some embodiments, a first passivation layer 5-280 may be formed by any suitable deposition process and etch back. In some embodiments, a first passivation layer may be formed by oxidizing the material 5-230 in which the sample well is formed. For example, the sample well may be formed of aluminum, which may be oxidized to create a coating of alumina on sidewalls of the sample well.

An adherent 5-980 or an adherent precursor (e.g., a material which preferentially binds an adherent) may be deposited on the substrate using an anisotropic physical deposition process, e.g., an evaporative deposition, as depicted in FIG. 5-14A. The adherent or adherent precursor may form an adherent layer 5-211 at the base of the sample well, as depicted in FIG. 5-14B, and may coat an upper surface of the material 5-230 in which the sample well is formed. A subsequent angled, directional deposition depicted in FIG. 5-14C (sometimes referred to as a shadow deposition or shadow evaporation process) may be used to deposit a second passivation layer 5-280 of passivation material 5-990 over an upper surface of the material 5-230 without covering the adherent layer 5-211. During the shadow deposition process, the substrate may be rotated around an axis normal to the substrate, so that the second passivation layer 5-280 deposits more uniformly around an upper rim of the sample well. A resulting structure is depicted in FIG. 5-14D, according to some embodiments. As an alternative to depositing the second passivation layer, a planarizing etch (e.g., a CMP step) may be used to remove adherent from an upper surface of the material 5-230.

According to some implementations, an adherent layer 5-211 may be deposited centrally at the base of a tapered sample well, as depicted in FIG. 5-15. For example, an adherent, or adherent precursor, may be directionally deposited, as depicted in FIG. 5-14A, in a tapered sample well, formed as described above. Walls of the sample well may be passivated by an oxidation process before or after deposition of the adherent layer 5-211. Adherent or precursor remaining on a surface of the material 5-230 may be passivated as described in connection with FIG. 5-14D. In some embodiments, an adherent on an upper surface of the material 5-230 may be removed by a chemical-mechanical polishing step. By forming an adherent layer, or an adherent layer precursor, centrally at the base of a sample well, deleterious effects on emission from a sample (e.g., suppression or quenching of sample radiation from sample walls, unfavorable radiation distribution from a sample because it is not located centrally with respect to energy coupling structures formed around a sample well, adverse effects on luminescent lifetime for a sample) may be reduced.

In some embodiments, lift-off patterning, etching, and deposition processes used to form the sample well and divot may be compatible with CMOS processes that are used to form integrated CMOS circuits on an integrated device. Accordingly, an integrated device may be fabricated using conventional CMOS facilities and fabrication techniques, though custom or specialized fabrication facilities may be used in some implementations.

Variations of the process steps described above may be used to form alternative embodiments of sample wells. For example, a tapered sample well such as depicted in FIG. 5-7A or FIG. 5-7B may be formed using an angled deposition process depicted in FIG. 5-14C. For the sample well of FIG. 5-7B, the angle of deposition may be changed during the deposition process. For such embodiments, a sample well having substantially straight and vertical sidewalls may first be formed, and then additional material 5-230 deposited by an angled deposition to taper the sidewalls of the sample well.

In some embodiments, a sample well may be formed from a multi-layer stack comprising a plurality of layers. FIG. 5-16 illustrates a sample well with a divot that is formed in the substrate layer 5-105. The sample well in this embodiment is approximately 140-180 nm in diameter with a divot depth of approximately 40-90 nm. The substrate 5-105 may be formed from any suitable material, such as silicon oxide. A first layer 5-1001 may be formed on the surface of the substrate 5-105. This first layer 5-1001 may be formed from any suitable metal, such as aluminum and may be, for example, approximately 60 nm thick. A second layer 5-1003 may be formed on the first layer 5-1001. This second layer 5-1003 may be formed from any suitable metal such as titanium and may be, for example, 10 nm thick. A third layer 5-1005 may be formed on the second layer 5-1003. This third layer 5-1005 may be formed from any suitable ceramic such as titanium nitride and may be, for example, 30 nm thick. A fourth layer 5-1007 may be formed on top of the third layer 5-1005 and also coating the vertical wall of the sample well. This fourth layer 5-1007 may be formed from any suitable material, such as aluminum oxide and may be approximately 5 nm thick.

The sample well of FIG. 5-16 may be formed approximately 350 nm above a waveguide 5-240 configured to carry excitation energy in the form of light pulses to the sample well. The waveguide may be, for example, 250 nm-700 nm wide. In some embodiments, the waveguide is approximately 500 nm wide.

The sample well may be formed in any suitable way. For example, the first three layers (5-1001, 5-1003, and 5-1005) may be formed on the substrate 5-105 as described above. Additionally, a thin layer (approximately 5 nm) of aluminum oxide may be deposited over the first three layers. Then, the sample well and divot may be chemically etched into the layers. A second aluminum oxide layer may be deposited to conformally coat the edges of the sample well, including the bottom of the divot. The second aluminum oxide layer may be deposited by atomic layer deposition, according to some embodiments. Then, the second layer of aluminum oxide may be anisotropically etched from the bottom of the divot to expose the silicon oxide substrate.

D. Coupling Excitation Energy to Sample Well

Coupling of excitation energy to one or more sample wells of the integrated device may occur through one or more techniques. As previously discussed, in some embodiments, a waveguide is positioned to couple with an excitation source to one or more sample wells. As excitation energy propagates along the waveguide, a portion of the excitation energy may be couple to one or more sample wells through a variety of light coupling techniques. For example, the waveguide may guide excitation energy substantially in one direction, and an evanescent wave or tail may form perpendicular to this one direction and, in some instances, be located outside the waveguide structure. Such an evanescent tail may direct a portion of excitation energy towards one or more sample wells. In some embodiments, the sample well layer may be designed and configured to direct excitation energy to a localized region within the sample well. The sample well may be configured to retain a sample within the localized region of the sample well such that excitation energy is directed towards the sample.

FIGS. 6-1A and 6-1B are cross-sectional views of an integrated device and provide an exemplary illustration of using a waveguide to couple excitation energy into a sample well. FIG. 6-1A is a cross-sectional schematic showing a waveguide 6-104 positioned in proximity to a sample well 6-108 in a sample well layer 6-116. Excitation energy propagates along the waveguide in a direction perpendicular to the field of view of FIG. 6-1A. Proximity of a sample well to the waveguide may allow excitation energy to couple into the sample well. FIG. 6-1B illustrates a closer view of the region of the sample well 6-108 and the sample well layer 6-116 and shows excitation energy located within sample well 6-108.

Additionally, one or more components may be formed in an integrated device to improve or enhance coupling of excitation energy into a sample well. These additional components may be formed in a pixel and provide coupling of excitation energy from a waveguide into the pixel and towards the sample well. One or more components located in a pixel may act to tap a portion of the excitation energy from a waveguide into the pixel. Such components may include optical structures such as, grating structures, scattering structures, microcavities and/or nano-antennas. Features or configurations of one or more of these components may be selected for coupling a certain amount of excitation energy to each sample well within a row or column of sample wells. A waveguide configured to provide excitation energy to a row of pixels may couple to a component in each pixel region to provide a portion of the excitation energy to each pixel in the row of pixels. When a waveguide is configured to direct excitation energy from an excitation source towards one or more pixels, the waveguide may be referred to as a bus waveguide.

Components positioned adjacent to a sample well may improve coupling of excitation energy from waveguide to sample well. Such components may be called taps and/or microcavities. A microcavity may deflect a portion of the excitation energy from the waveguide such that excitation energy reaches the sample well. One or more microcavities may be used to couple excitation energy to a sample well. The one or more microcavities may reduce loss of excitation energy from the waveguide, including metallic loss. One or more microcavities may act as a lens to focus excitation energy to the sample well. In some embodiments, one or more microcavities may improve directing luminescence from a marker in the sample well towards the sensor. The microcavities may have a cylindrical, convex, concave, rectangular, spherical, or elliptical configuration or any other suitable shape. A microcavity may be formed from any suitable material. In some embodiments, a microcavity may include silicon nitride.

One or more microcavities may overlap with at least a portion of a waveguide to direct excitation energy towards the sample well when viewed from the top of the integrated device where the sample wells are present. The thickness of a waveguide may be configured to reduce loss of excitation energy and improve coupling of excitation energy to one or more microcavities. In some embodiments, microcavities along a row of sample wells may vary in strength of coupling between the waveguide to each sample well. The microcavities may increase coupling along the propagation direction of the excitation energy in order to accommodate a reduced power in the waveguide as excitation energy is directed out of the waveguide to each sample well. In some embodiments, one or more microcavities are adjacent to the sample well. There may be an offset distance between the location of the center of a sample well and the center of a microcavity. In other embodiments, one microcavity is located below a sample well such that at least a portion of the sample well and a portion of the microcavity overlap when viewed from the top of the integrated device where the sample wells are present.

FIG. 6-2A illustrates a planar view of an exemplary pixel region having waveguide 6-204 positioned proximate to sample well 6-208 such that waveguide 6-204 and sample well 6-208 are non-overlapping. As shown in FIG. 6-2A, microcavity 6-218b has a smaller cross-sectional diameter than microcavity 6-218a. Microcavities 6-218a and 6-218b are positioned relative to waveguide 6-204 and sample well 6-208 to couple excitation energy from waveguide 6-204 to sample well 6-208. Together microcavities 6-218a and 6-218b deflect a portion of excitation energy within the waveguide to the sample well. A portion of microcavity 6-218b is positioned to overlap with waveguide 6-204. Microcavity 6-218b is positioned proximate to microcavity 6-218b to provide sufficient coupling between the two microcavities. Microcavity 6-218a is positioned closer to sample well 6-208 than microcavity 6-218b. In such a configuration microcavities 6-218a and 6-218b may act as a tap to couple a portion of excitation energy from waveguide 6-204 to sample well 6-208. FIG. 6-2B illustrates an elevation view from the perspective along line A-A' shown in FIG. 6-2A. Microcavities 6-218a and 6-218b are positioned adjacent to layer 6-216 forming sample well 6-208. Layer 6-216 may include a metal (e.g., aluminum). In this exemplary embodiment, microcavities 6-218a and 6-218b have cylindrical shapes where an end of the cylinder is positioned at or at least proximate to a surface of layer 6-218. A distance between waveguide 6-204 and an edge of microcavity 6-218a and/or microcavity 6-218b may allow for a desired amount of excitation energy to couple into sample well 6-218. FIG. 6-2C illustrates an elevation view from the perspective along line B-B' shown in FIG. 6-2A. Microcavity 6-218b is positioned to overlap with waveguide 6-204, while microcavity 6-218a is positioned to not overlap with waveguide 6-204.

FIG. 6-3A-D illustrate planar views of further exemplary configurations of one or more microcavities with respect to a sample well and waveguide in an integrated device. The one or more microcavities may overlap with a portion of the waveguide. In some instances, a microcavity is located below the sample well. FIG. 6-3A shows microcavity 6-306 overlapping with sample well 6-308 with respect to waveguide 6-304. FIG. 6-3B shows cavity 6-316b overlapping with sample well 6-318 with respect to waveguide 6-314. In other embodiments, a microcavity is located at a distance offset from the sample well such that the microcavity and sample well do not overlap. FIG. 6-3B shows microcavity 6-318a positioned from sample well 6-318 such that there is no overlapping region between microcavity 6-316a and sample well 6-318. Similarly, FIG. 6-3C shows microcavity 6-326 positioned from sample well 6-328 with respect to waveguide 6-324 such that there is no overlapping region between microcavity 6-316a and sample well 6-318. In some embodiments, multiple microcavities may be positioned offset from a sample well. FIG. 6-3D shows microcavities 6-336a and 6-336b positioned from sample well 6-338 with respect to waveguide 6-334 such that there is no overlapping region between sample well 6-338 and either 6-336a or 6-336b. The microcavity design, position with respect to the sample well, and/or position with respect the waveguide may be determined based on reducing the overall coupling loss and improving coupling efficiency between the waveguide and the sample well.

FIG. 6-4 shows a cross-sectional view of microcavity 6-418 positioned to couple excitation energy from waveguide 6-404 to sample well 6-408 in layer 6-416. One or more dimensions of microcavity 6-418 and/or waveguide 6-404 may provide a desired amount of coupling. A waveguide of an integrated device, such as waveguide 6-404, has cross-sectional height, t, which may be approximately 50 nm, approximately 100 nm, approximately 150 nm, approximately 160 nm, approximately 170 nm, or approximately 200 nm. Microcavity 6-418 has a cross-sectional dimension D, such as diameter if microcavity has a cylindrical shape. Cross-sectional dimension, D, may be approximately 550 nm, approximately 600 nm, approximately 650 nm, approximately 700 nm, approximately 750 nm, or approximately 800 nm. Microcavity 6-418 has cross-sectional height, h, which may be approximately 450 nm, approximately 500 nm, approximately 550 nm, or approximately 600 nm. The position of microcavity 6-418 relative to waveguide 6-408 and sample well 6-408 may allow for coupling of excitation energy from waveguide 6-408 to sample well 6-408. A distance between microcavity 6-418 and waveguide 6-408 that is perpendicular to propagation of light in waveguide 6-408, shown as x in FIG. 6-4, may be approximately 300 nm, approximately 350 nm, approximately 400 nm, approximately 450 nm, or approximately 500 nm. A distance of microcavity 6-418 offset from sample well 6-408, shown as d in FIG. 6-4, may be approximately 500 nm, approximately 550 nm, approximately 600 nm, approximately 650 nm, or approximately 700 nm. Layer 6-416 including sample well 6-408 may have a cross-sectional height, y, of approximately 50 nm, approximately 100 nm, or approximately 150 nm. Sample well 6-408 may have a cross-sectional dimension, such as a diameter, of approximately 75 nm, approximately 100 nm, approximately 125 nm, approximately 150 nm, or approximately 175 nm.

In an exemplary embodiment, waveguide 6-404 has a cross-sectional width of 667 nm and a cross-sectional height of 100 nm. Microcavity 6-418 has a dimension h of 591 nm, a cross-sectional diameter of 750 nm, and is positioned such that distance x from waveguide 6-404 is 398 nm and distance d from sample well 6-408 is 693 nm. Such a pixel configuration may have a total coupling loss of 0.28%, which if implemented in an integrated device having 256 pixels, may have a transmission loss of approximately 51% and a metallic loss of approximately 11%.

In another exemplary embodiment, waveguide 6-404 has a cross-sectional width of 639 nm and a cross-sectional height of 100 nm. Microcavity 6-418 has an ellipsoid shape with one cross-sectional dimension of 600 nm, another cross-sectional dimension of 639 nm, a dimension h of 512 nm. Such a pixel configuration may have a total coupling loss of approximately 0.77%, which if implemented in an integrated device having 64 pixels, may have a transmission loss of approximately 30% and a metal loss of approximately 35%.

FIG. 6-5 illustrates simulation results of propagation of light in a configuration having two microcavities 6-536a and 6-536b relative to sample well 6-538 and waveguide 6-534. As shown in FIG. 6-5, the dark regions correspond to higher intensity of light which extend from waveguide 6-534 to sample well 6-538 and supported by microcavities 6-536a and 6-536b.

In another exemplary embodiment, waveguide has a cross-sectional width of 700 nm and a cross-sectional height of 100 nm. A microcavity is cylindrical with a diameter of 600 nm and has dimension h of 650 nm. The microcavity is positioned in proximity to the waveguide and the sample well such that there is a coupling of 0.148%, a metallic loss of 0.09856%, a return loss of 0.1225%, and a radiation loss of 0.1270%. FIGS. 6-6A to 6-6C illustrate simulations of light propagation through such an embodiment. FIG. 6-6A illustrates a cross-sectional view of sample well 6-638, microcavity 6-636, and waveguide 6-634. Waveguide 6-634 supports a mode of light that propagates along waveguide 6-634, and microcavity 6-636 is positioned to act as a tap to couple some of the excitation energy into sample well 6-638. In FIG. 6-6A, darker regions indicates areas having higher light intensity. FIG. 6-6B illustrates a planar view of microcavity 6-636 and sample well 6-638, where light is directed by microcavity 6-636 towards sample well 6-638. FIG. 6-6C illustrates a transverse cross-sectional view showing light from waveguide 6-634 coupling to sample well 6-638.

FIG. 6-6D illustrates a planar view of simulations for another exemplary configuration having waveguide 6-654, microcavity 6-656, and sample well 6-658. In this configuration, sample well 6-658 overlaps microcavity 6-656, and microcavity 6-658 and waveguide 6-654 overlap. FIG. 6-6D shows of light, where dark regions indicate higher intensity, propagation to sample well 6-658 supported by microcavity 6-656.

Some embodiments relate to a microcavity positioned between a sample well layer and a waveguide such that the microcavity is offset from a surface of the sample well layer. The microcavity may be offset from a surface of the sample well layer in a direction perpendicular to the propagation of light along the waveguide. In some embodiments, the microcavity may also be offset from a location of a sample well such that the sample well and microcavity are non-overlapping. The microcavity may be sized and shaped to provide a desired amount of coupling of excitation energy from the waveguide to the sample well. In some embodiments, the microcavity may have a longer dimension along a direction parallel to a direction of light propagation through the waveguide than in a dimension perpendicular to light propagation through the waveguide.

FIG. 6-7A shows a cross-sectional view of an integrated device having microcavity 6-718 positioned proximate to sample well 6-708 and waveguide 6-704. Sample well 6-708 is formed in sample well layer 6-716. Microcavity has dimension D, which is parallel to the direction of light propagating through waveguide 6-704 and dimension h, which is perpendicular to the direction of light propagating through waveguide 6-704. In some embodiments, dimension D of microcavity 6-718 is larger than dimension h of microcavity 6-718. Microcavity 6-718 may have a dimension h of approximately 100 nm, approximately 150 nm, or approximately 200 nm. Microcavity 6-718 may have a dimension D of approximately 500 nm, approximately, 750 nm, or approximately 1000 nm. Microcavity 6-718 is positioned a distance along the y-direction from a surface of waveguide 6-704 having dimension x1 and a distance along the y-direction from a surface of sample well layer 6-716 having dimension x2. In some embodiments, dimension x2 is smaller than dimension x1. Microcavity 6-718 may be offset from sample well layer 6-716 such that x2 is approximately 200 nm, approximately 300 nm, or approximately 400 nm, in some embodiments.

In some embodiments, microcavity 6-718 is offset from sample well 6-708 by a distance along a direction parallel to a direction of light propagation through waveguide 6-704. Microcavity 6-718 may be offset from sample well 6-708 by a center-to center distance, d. In some embodiments, microcavity 6-718 is offset from sample well 6-708 such that microcavity 6-718 and sample well 6-708 are non-overlapping. In some embodiments, microcavity 6-718 may be positioned such that an edge of microcavity 6-718 proximate to sample well 6-708 is offset from sample well 6-708 by a distance. An offset distance between an edge of microcavity 6-718 and sample well 6-708 may be approximately 50 nm, approximately 100 nm, approximately 150 nm, or approximately 200 nm.

FIG. 6-7B shows a cross-sectional view of intensity of light as excitation energy propagates through waveguide 6-704 and couples to sample well 6-708 in sample well layer 6-716 via microcavity 6-718, similar the configuration shown in FIG. 6-7A. Excitation energy travels along the z-direction through waveguide 6-704. As shown in FIG. 6-7B, a portion of excitation energy (shown as dark lines) reaches sample well 6-708 by coupling to microcavity 6-718. Since excitation energy continues to propagate along waveguide 6-704, microcavity 6-718 acts as a tap by directing a portion of the excitation energy away from waveguide 6-704 and towards sample well 6-708.

FIG. 6-7C shows a planar view of microcavity 6-718 positioned proximate to sample well 6-708. Excitation energy (shown as dark regions) propagates through microcavity and is directed to within sample well 6-708. As shown in FIG. 6-7C, microcavity 6-718 may have a rectangular shape with curved edges that act to direct light towards sample well 6-708. An edge of microcavity 6-718 may have a radius of curvature to allow a desired level of coupling of excitation energy to sample well 6-708. A first edge of microcavity 6-718 proximate to sample well 6-708 may have a smaller radius of curvature than a second edge of microcavity 6-718 opposite the first edge.

Some embodiments relate to an microcavity positioned between a sample well and a waveguide such that the microcavity overlaps with the sample well and is a distance offset from the sample well. The microcavity and sample well may overlap in a direction perpendicular to a direction of light propagation along the waveguide. The microcavity may act to enhance coupling of excitation energy into the sample well. In some embodiments, the microcavity may be aligned to the sample well with a substantial center-to-center alignment between the microcavity and sample well. In some embodiments, the microcavity may be positioned closer to the waveguide than to the sample well. In some embodiments, the microcavity may be positioned on a surface of the waveguide.

FIG. 6-7D shows a cross-sectional view of an integrated device having sample well 6-728, waveguide 6-734, and microcavity 6-738 positioned between sample well 6-728 and waveguide 6-734. Sample well 6-728 is formed in sample well layer 6-738 and may extend beyond sample well layer 6-738 to include a divot in layer 6-732 of the integrated device. Layer 6-732 may have dimension h along the x-direction as shown in FIG. 6-7D. Microcavity 6-738 may be positioned within layer 6-732 such that there is a portion of layer 6-732 between microcavity 6-738 and sample well 6-728 and a portion of layer 6-732 between microcavity 6-738 and waveguide 6-734. As shown in FIG. 6-7D, microcavity 6-738 is positioned a distance along the y-direction from sample well 6-728 having dimension d1. Microcavity 6-738 is positioned a distance along the y-direction from waveguide 6-734 having dimension d2. In some embodiments, dimension d2 is smaller than d1. In some embodiments, microcavity 6-738 is positioned at a surface of sample well 6-728 and within layer 6-732 such that dimension d1 is equal to zero.

One or more dimensions of a waveguide of an integrated device may vary along the length of the waveguide in the direction of light propagation through the waveguide. Varying one or more dimensions along the waveguide may improve coupling efficiency and substantial uniformity in the amount of excitation energy provided by the waveguide to a plurality of sample wells. In some embodiments, the cross-sectional width of a waveguide may vary along a row or column of pixels. The waveguide may include a taper such that the cross-sectional width of the waveguide decreases along the direction of propagation of excitation energy through the waveguide. FIG. 6-8A shows a planar view of waveguide 6-804 in an integrated device. Excitation source 6-802 couples to waveguide 6-804 using one or more techniques described herein (e.g., grating couplers, star couplers, MMI splitters). Waveguide 6-804 is tapered such that a dimension of waveguide 6-804 along the x-direction shown in FIG. 6-8A decreases along a dimension of waveguide 6-804 along the z-direction or a direction light propagation through waveguide 6-804. In this manner, waveguide 6-804 has a larger cross-sectional width (along the x-direction) proximate to incident excitation source 6-802 than at a location further along the length (along the z-direction) of waveguide 6-804. Positioning waveguide 6-804 to couple with sample wells in a row of pixels may provide a configuration sufficient for coupling a desired amount of excitation energy into each sample well. Since a portion of excitation energy is coupled out of waveguide 6-804 for each sample well, the amount of excitation energy propagated by waveguide 6-804 reduces along the z-direction. Along waveguide 6-804, the amount of power reduces as excitation energy is coupled out to the sample wells. By reducing the cross-sectional width of waveguide 6-804 may propagate excitation energy further along waveguide 6-804 than in a waveguide without such a taper.

Figures 6, 7, 8, 8A:
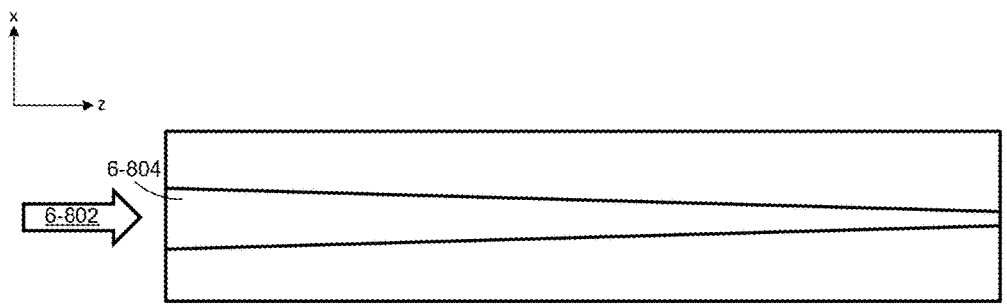
Figures 6, 7, 8, 8B:
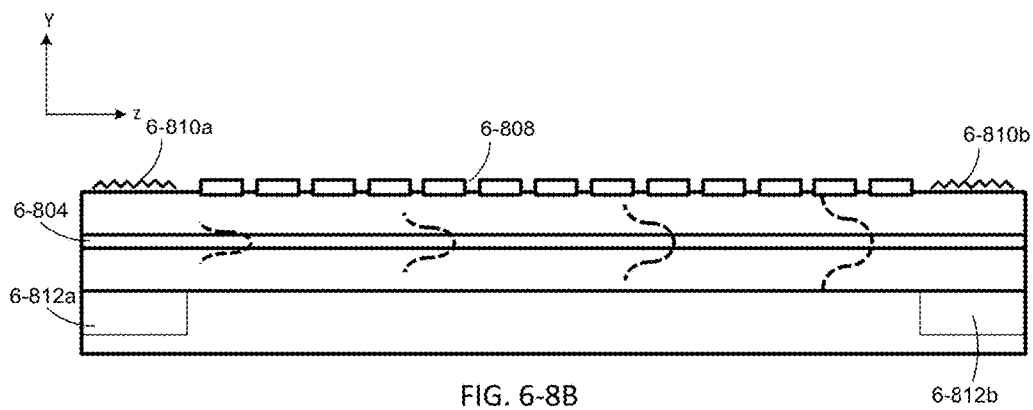
Figures 6, 7, 8, 9, 9A:
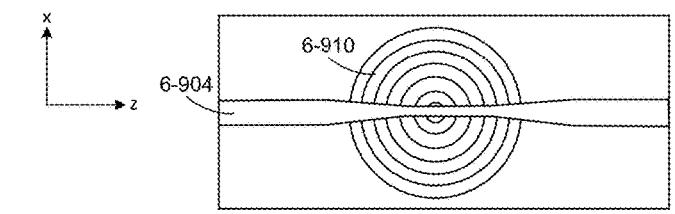
Figures 6, 7, 8, 9, 9B:
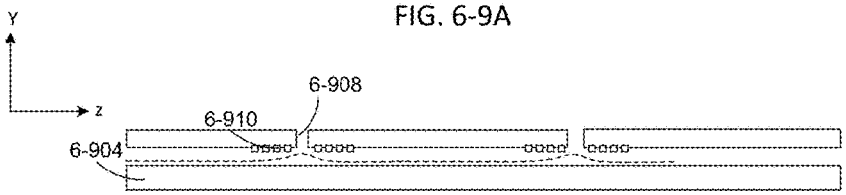
Figures 6, 7, 8, 9, 10:
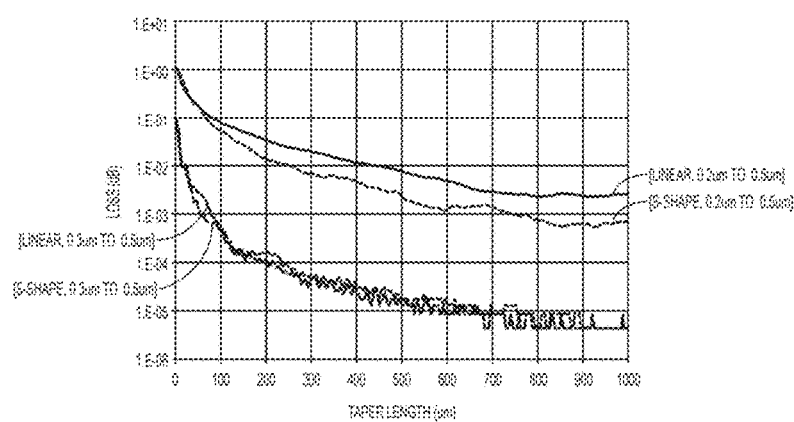
Figures 6, 7, 8, 9, 10, 11, 11A:
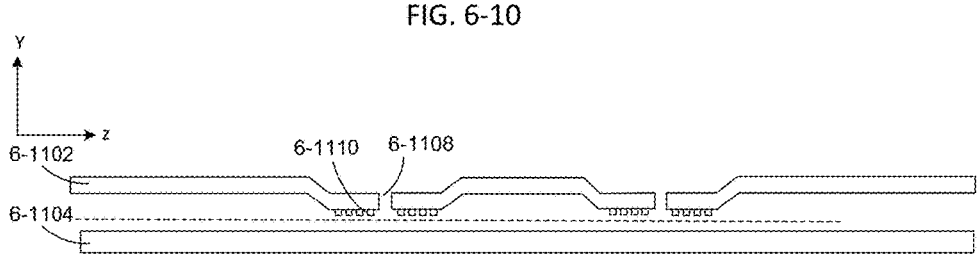
Figures 6, 7, 8, 9, 10, 11, 11B:
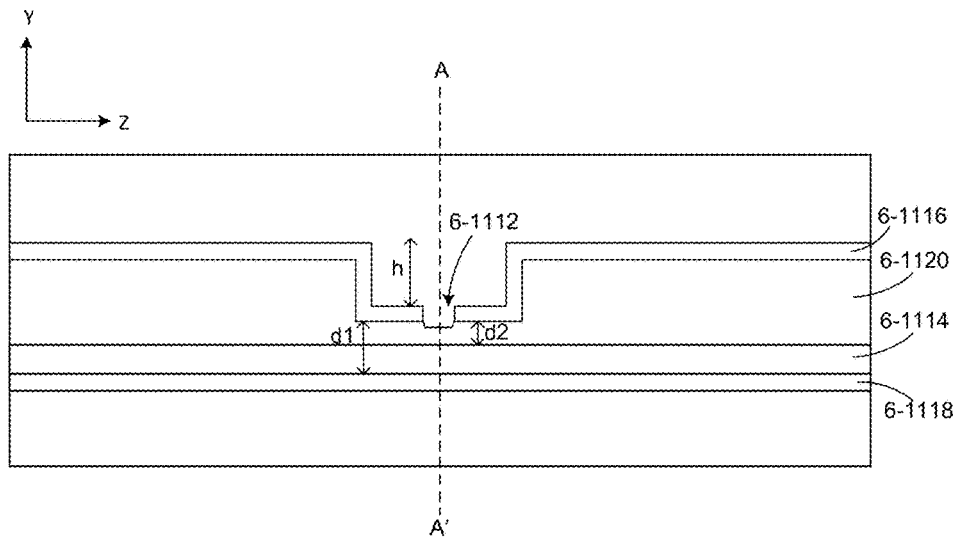
Figures 6, 7, 8, 9, 10, 11, 11C:
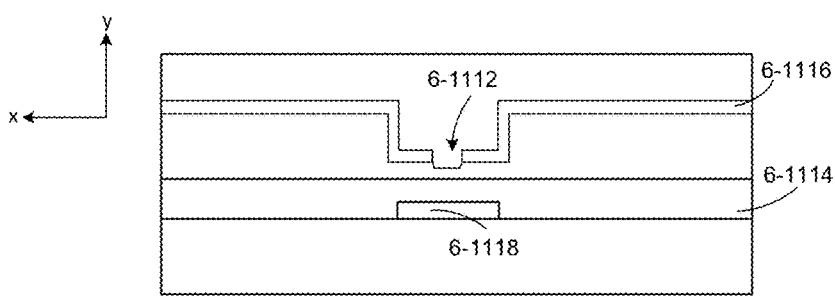
Figures 6, 7, 8, 9, 10, 11, 12:
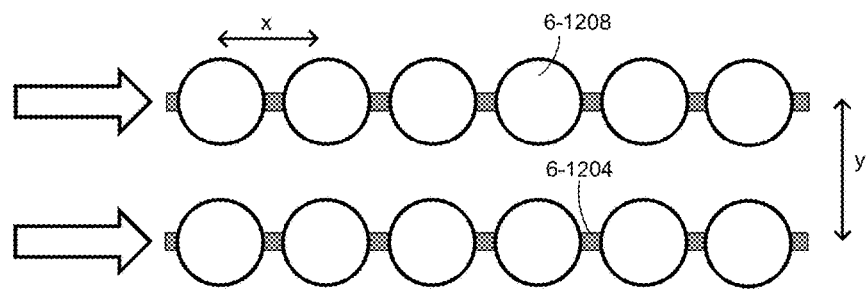
Figures 6, 7, 8, 9, 10, 11, 12, 13:
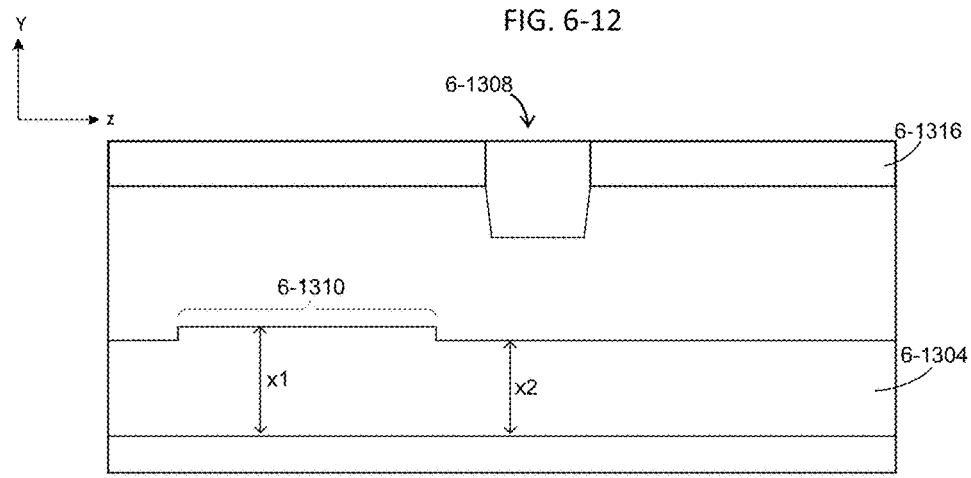
Figures 6, 7, 8, 9, 10, 11, 12, 13, 14:
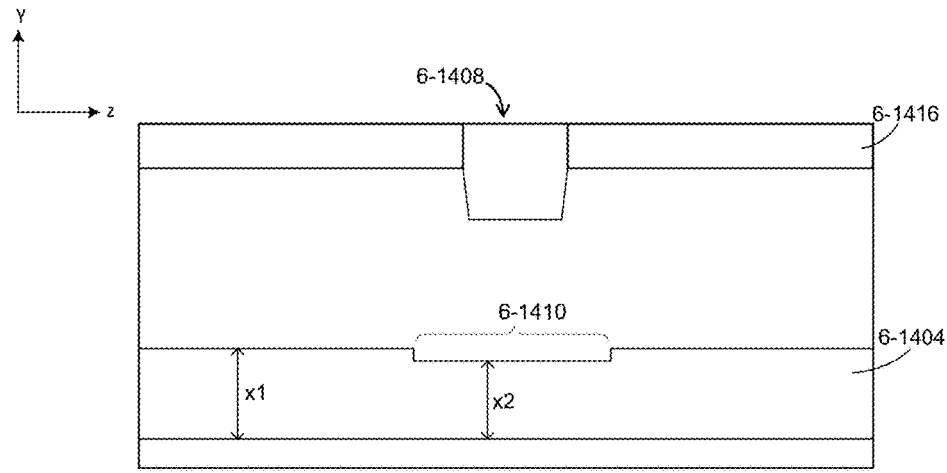

FIG. 6-8B shows a cross-sectional view of waveguide 6-804 shown in FIG. 8A. A dimension of waveguide 6-804 along the y-direction remains substantially similar such that a distance along the y-direction between sample wells 6-808 and waveguide 6-804 is substantially constant along the length of waveguide 6-804. Dotted curved lines illustrate the spread of excitation energy as it propagates along waveguide 6-804 in the z-direction. As the cross-sectional width of waveguide 6-808 narrows, the spread of excitation energy becomes broader and may compensate for reduced power. In this manner, the cross-sectional width of waveguide 6-802 may balance reduction in power of excitation energy propagated by waveguide 6-802 such that a sufficient amount of excitation energy is delivered to each sample well in a row of pixels for a desired performance of an integrated device.

In some embodiments, a tapered waveguide may be configured for a similar coupling efficiency for a row of pixels where pixels in the row include a microcavity and a sample well. A combination of varying one or more dimensions of the tapered waveguide and/or the microcavity may accommodate reduction in power of excitation energy along the length of a waveguide as excitation energy is coupled to each sample well in the row.

In some embodiments, one or more sensors may be positioned relative to a waveguide to measure excitation energy propagating along the waveguide. Additional structures (e.g., gratings) may be positioned to tap out at least a portion of excitation energy to a sensor. As shown in FIG. 6-8B, monitoring sensors 6-812*a* and 6-812*b* are positioned proximate to the ends of waveguide. Gratings 6-810a and 6-810b are positioned on a side of waveguide 6-808 opposite to sensors 6-812a and 6-812b. Gratings 6-810a and 6-810b may be configured to direct excitation energy in waveguide 6-808 towards sensors 6-812a and 6-812b, respectively. The combination of grating 6-810a and sensor 6-812a may monitor excitation energy input into waveguide 6-804. The combination of grating 6-810b and sensor 6-812b may monitor excitation energy, if any, excitation energy at an end of waveguide 6-804 that remains after coupling excitation energy to a row of sample wells 6-808. In this manner, sensors 6-812a and 6-812b may monitor power in waveguide 6-804 at an input end, and output end, and/or any suitable location along waveguide 6-808. Sensors 6-812a and 6-812b may detect information including a level of power at a location along waveguide 6-808. This information may be used to control aspects of components that act to align an excitation source to the integrated device and/or a power of the excitation source.

In some embodiments, a waveguide may couple to a sample well by an evanescent field. In some embodiments, a bullseye grating structure having concentric grating rings positioned proximate to a sample well may improve coupling of excitation energy from the waveguide to the sample well. In some embodiments, the waveguide may include a region having a reduced cross-sectional width in the vicinity of a sample well such that an evanescent field from the excitation energy propagating in the waveguide couples to the sample well. For a row of pixels, a waveguide may include multiple regions having a reduced cross-sectional width along the length of the waveguide to improve coupling uniformity and efficiency among sample wells in the row. In this manner, the waveguide may be considered to have pinched sections at certain locations along the waveguide.

The layer of an integrated device having one or more sample wells may interfere with propagation of light through a waveguide. In some embodiments, the sample well layer is formed of a metal (e.g., aluminum). It may be desirable to position the sample well layer at a certain distance from the waveguide to reduce loss and improve performance of the device. These techniques may allow for a desired performance achieved by positioning the sample well layer at a certain distance from the waveguide while allowing a sample well in the layer to receive a sufficient amount of excitation energy.

FIG. 6-9A shows a planar view of waveguide 6-904 relative to a bullseye grating structure 6-910. Bullseye grating structure 6-910 comprises a plurality of concentric circular gratings centered at a sample well. Waveguide 6-904 includes a pinched region where the cross-sectional width of waveguide 6-904 is smaller at a location proximate to the center of bullseye grating structure 6-910. The pinched region of waveguide 6-904 may be formed by tapering a certain distance along waveguide 6-904. The length of waveguide 6-904 that is tapered may be a suitable amount to reduce excitation energy loss and/or improve coupling efficiency. A waveguide may include multiple pinched regions, where each pinched region is associated with a sample well. The multiple pinched regions may have one or more dimensions that vary along the length of the waveguide to provide suitably uniform power and coupling efficiency to each of the sample wells. FIG. 6-9B shows a cross-sectional view of waveguide 6-904 configured to couple excitation energy to sample well 6-908. Bullseye grating 6-910 is substantially centered at sample well 6-908 and configured to couple excitation energy from waveguide 6-904 to sample well 6-908. The cross-sectional width of waveguide 6-904 has a pinched region proximate to sample well 6-908 such that the spread of the field of excitation energy broadens as the cross-sectional width narrows. The dotted line indicates the extent to which the field of excitation energy extends perpendicularly from waveguide 6-904 in the y-direction. At a location along waveguide 6-904 that overlaps with sample well 6-908, the field of excitation energy is at a certain location to allow coupling of the excitation energy to sample well 6-908.

One or more dimensions of the taper in a pinched region and/or a shape of the taper in the pinched region of a waveguide may provide a desired level of coupling efficiency. FIG. 6-10 illustrates a plot of total loss for different tapering profiles as a function of length over which the taper profile occurs or taper length to indicate the amount of loss caused by the tapering process. As shown by FIG. 10, having a more gradual tapering of the pinched region may improve coupling efficiency by reducing total coupling loss. Tapering the cross-sectional width from 0.5 microns to 0.3 microns for either linear or s-shaped configurations has lower total loss than if the cross-sectional width is tapered from 0.5 microns to 0.2 microns. Additionally, increasing the length over which the cross-sectional width is reduced may improve total coupling loss. In some embodiments, a waveguide may include a pinched region where a cross-sectional width of the waveguide varies from approximately 0.3 microns to approximately 0.5 microns over a length along the waveguide of approximately 20 microns, approximately 40 microns, approximately 50 microns, approximately 60 microns, approximately 80 microns, or approximately 100 microns.

In some embodiments, a waveguide may couple to a sample well by decreasing a distance between a sample well and the waveguide within a region of the sample well. Such a configuration may allow for portions of the waveguide to be positioned a certain distance from a sample well layer to provide a desired efficiency and loss of excitation energy. FIG. 6-11A shows a cross-sectional view of waveguide 6-1104 positioned with respect to layer 6-1102 having sample well 6-1108. Bullseye grating is formed adjacent to layer 6-1102 and substantially centered at sample well 6-1108. In such embodiments, the waveguide has a substantially uniform cross-sectional thickness and the field of excitation energy extending from waveguide 6-1104 is approximately uniform along the length of waveguide 6-1104. By forming layer 6-1102 such that sample well 6-1108 and waveguide 6-1104 have a certain distance along the y-direction, the excitation energy may couple to sample well 6-1108. Bullseye grating 6-1110 may act to further couple excitation energy from waveguide 6-1104 to sample well 6-1108. Other regions along waveguide 6-1104 separate from sample well 6-1108 may have layer 6-1102 at larger distance along the y-direction than in a vicinity proximate to sample well 6-1108. Such a configuration may be considered a sample well dip configuration and, in some embodiments, provide a coupling efficiency of approximately 0.3%.

Some embodiments related to forming one or more layers of material on a waveguide to improve coupling of excitation energy from the waveguide to a sample well. FIG. 6-11B shows a cross-sectional view of sample well 6-1112 formed from sample well layer 6-1116. As shown in FIG. 6-11B, sample well layer 6-1116 includes a region having an opening of sample well layer 6-1116 which forms sample well 6-1112. The region of sample well layer 6-1116 is offset by dimension h from a surface of the integrated device. Dimension h may be greater than approximately 200 nm, approximately 250 nm, approximately 300 nm, approximately 350 nm, or approximately 400 nm. The offset region of sample well layer 6-1116 may be formed by etching a portion of layer 6-1120 and forming sample well layer 6-116 over layer 6-1120. The region of sample well layer 6-1116 that includes sample well 6-1112 is positioned a distance d1 from waveguide 6-1118 along the y-direction. Distance d1 may be approximately 250 nm, approximately 300 nm, approximately 350 nm, approximately 400 nm, or approximately 450 nm. Layer 6-1114 is formed adjacent to waveguide 6-1118. Layer 1114 may have a higher refractive index that layer 6-1120 and a lower refractive index than waveguide 6-1118. In some embodiments, layer 6-1114 includes a plurality of layers having different materials. In an exemplary embodiment, waveguide 6-1118 includes silicon nitride and layer 6-1114 includes aluminum oxide and/or titanium oxide. Layer 6-1114 is positioned a distance d2 from sample well layer 6-1116. Distance d2 may be approximately 50 nm, approximately 100 nm, approximately 150 nm, approximately 200 nm, or approximately 250 nm. FIG. 6-11C shows a cross-sectional view along line A-A' shown in FIG. 6-11B. As shown in FIG. 6-11C, waveguide 6-1118 may have a lateral transverse dimension along the x-direction that overlaps with the offset region of sample well layer 6-1116 that includes sample well 6-1112. Layer 6-1114 may be formed on waveguide 6-1118 such that layer 6-1114 contacts a plurality of sides of waveguide 6-111C.

Additionally or alternatively, the spacing between pixels in a row along a waveguide may be selected to reduce waveguide loss. Each pixel may include a sample well, one or more sensors, and/or a bullseye grating. The spacing between rows of pixels may be selected to accommodate other integrated device components, such as circuitry. FIG. 6-12 shows a planar view of an integrated device having pixels 6-1208 arranged in a rectangular array with waveguides 6-1204 configured to deliver excitation energy to a row of pixels 6-1208. FIG. 6-12 shows a configuration of the pixel array where spacing between pixels in a row, x, is smaller than spacing between rows, y. By positioning pixels in a row at a certain distance, waveguide loss along the waveguide may be reduced. Having a larger spacing between rows may reduce interference of one row of pixels on another row and/or provide suitable spacing to accommodate additional components on the device, including circuitry components.

The whole pixel array of an integrated device may have any suitable number of pixels and any suitable arrangement of pixels. In some embodiments, a pixel array may have a square and/or rectangular configuration. In some embodiments, the array of pixels may be rectangular and have a length parallel to the waveguides that is longer than the length perpendicular to the waveguides. In other embodiments, there may be more waveguides and/or rows of pixels, and the length of each row of pixels parallel to the waveguides may be shorter than the length perpendicular to the waveguide.

Some embodiments relate to an integrated device with a waveguide having a variable dimension in a direction perpendicular to light propagation through the waveguide and perpendicular to a surface of the integrated device with one or more sample wells. In some embodiments, the dimension of the waveguide may vary to be larger in a region proximate to a sample well but non-overlapping with the sample well. In some embodiments, the dimension of the waveguide may decrease in a region of the waveguide that overlaps with the sample well. An integrated device may include a waveguide configured to couple with a row of sample wells, where the variation in the dimension of the waveguide allows for a substantially similar amount of excitation energy to couple to each sample well.

FIG. 6-13 shows a cross-sectional view of an integrated device having sample well 6-1308 formed in sample well layer 6-1316. Waveguide 6-1304 includes region 6-1310 having a dimension x1 along the y-direction x1 that is larger than a portion of waveguide 6-1304 that overlaps with sample well 6-1308 having dimension x2 along the y-direction. As shown in FIG. 6-13, region 6-1310 is offset from sample well 6-1308 and form a ridge in waveguide 6-1304. Region 6-1310 may be sized and shaped to provide a desired amount of excitation energy from waveguide 6-1304 to sample well 6-1308. FIG. 6-14 shows a cross-sectional view of an integrated device having sample well 6-1408 formed in sample well layer 6-1416. Waveguide 6-1404 includes region 6-1410 that overlaps with sample well 6-1408. Waveguide in region 6-1410 has a dimension x2 along the y-direction that is smaller than portions of the waveguide outside of region 6-1410, which have a dimension x1 along the y-direction. In this configuration waveguide 6-1404 includes a dimension smaller within region 6-1410 that overlaps with sample well 6-1408.

Although FIGS. 6-13 and 6-14 show a single sample well, waveguides 6-1304 and 6-1404 may be configured to couple to a row of sample wells and have a region similar to regions 6-1310 and 6-1404 positioned proximate to each sample well. In some embodiments, the regions positioned proximate to the plurality of sample wells in the row may vary in size and/or shape such that a substantially similar amount of excitation energy couples to each sample well. In this manner, regions of a waveguide may be configured to accommodate for decreased excitation energy propagating along the waveguide along a row of sample wells.

E. Directing Emission Energy to Sensor

An integrated device may include one or more components positioned between a sample well and a sensor of a pixel to improve collection of luminescence by the sensor from a sample in the sample well. Such components may improve the signal-to-noise ratio of the luminescence signal to a background signal to provide improved detection of a luminescent marker. Some components may direct luminescence from a sample well to a corresponding sensor in a pixel. In some embodiments, a component may provide both suitable coupling of excitation energy to a sample well and coupling of luminescence out of the sample well. Other components (e.g., filters) may reduce excitation energy and other light not associated with the sample and/or marker from contributing to a signal acquired by the sensor.

A bullseye grating may be formed from concentric grating rings around a sample well. A bullseye grating may couple with a sample well to improve propagation of luminescence out of the sample well. The bullseye grating structure may direct luminescence towards a sensor in a pixel having the sample well. In some embodiments, an effective diameter of the luminescence directed by a bullseye grating is approximately 5 microns.

FIG. 7-1A shows a planar view of bullseye 7-110 configured to direct luminescence from sample well 7-108. Bullseye structure 7-110 includes a plurality of concentric gratings. The concentric gratings may align substantially with the center of sample well 7-108. Waveguide 7-104 may be positioned of overlap with at least a portion of bullseye structure 7-110 and sample well 7-108. Waveguide 7-104 includes a tapered region, which may allow for luminescence to pass to a sensor positioned within the pixel having sample well 7-108 and a desired level of collection of luminescence by the sensor. The tapered region may allow for reduced interference of waveguide 7-104 on the collection of luminescence by the sensor. In some embodiments, a bullseye grating may be configured to direct more than one characteristic luminescence energies or wavelengths towards a sensor. FIG. 7-1B shows a cross-sectional view of bullseye grating configured to direct luminescence from sample well 7-108. The dotted lines indicate the spread of two characteristic wavelengths, $\lambda 1$ and $\lambda 2$, that may be coupled out of sample well 7-108. The two characteristic wavelengths, $\lambda 1$ and $\lambda 2$, may be characteristic wavelengths emitted from different markers used to label a sample. FIG. 7-1C shows a cross-sectional view of bullseye grating 7-110 at a transverse cross-sectional view of waveguide 7-104. Bullseye grating 7-110 and waveguide 7-104 are configured such that luminesce emitted from sample well 7-108 is spread to allow luminescence energy to pass through a region of the integrated device other than waveguide 7-104. Bullseye grating 7-110 may direct luminescence over a certain distance from sample well 7-108 that is greater than if the bullseye grating was not present. In some embodiments, bullseye grating 7-110 may reduce overall scattering of luminescence. Bullseye grating 7-110 may be configured both for coupling excitation energy to sample well 7-108 and to direct luminescence energy out of sample well 7-108.

Microcavities provided for coupling of a waveguide and a sample well to allow propagation of excitation energy to the sample well may also direct luminescence from the sample well to a sensor. FIG. 7-2A shows a cross-sectional view of waveguide 7-204 offset from sample well 7-208. Microcavity 7-211 is configured to direct luminescence from sample well 7-208. FIG. 7-2A shows intensity of luminescence emitted by sample well 7-208 where regions having a higher intensity of luminescence are darker. Microcavity 7-211 may direct luminescence at an angle away from waveguide 7-204 to reduce scattering of the luminescence by waveguide 7-204. FIG. 7-2B illustrates a plot luminescence emitted from a sample well as a function of angle. As shown in FIG. 7-2B, microcavity 7-211 may direct luminescence at an angle of approximately 15 degrees from the y-direction. One or more microcavities may direct luminescence at an angle of approximately 5 degrees, approximately 10 degrees, approximately 15 degrees, approximately 20 degrees, approximately 25 degrees from the y-direction. In some embodiments, a sensor may be offset from the sample well in order to receive the luminescence directed at such an angle. Microcavity 7-211 may also be configured to couple excitation energy from waveguide to the sample well such that microcavity 7-211 provides both coupling of excitation energy to a sample well and directs luminescence out of the sample well. In some embodiments, more than one microcavity may be formed to couple luminescence out of a sample well.

A baffle having an opening centered on a sensor may be formed between a sample well and the sensor. As shown in FIG. 4-2, baffle layer 4-226 is positioned between sample well 4-22 and sensor layer 4-230. A baffle in a pixel may be designed to suppress collection of energy besides luminescence for the pixel. A baffle associated with a sample well and a sensor may allow for luminescence from the sample well to reach the sensor while reducing luminescence from neighboring pixels, excitation energy, and other energy not associated with the luminescence from the sample well associated with the sensor. A dimension of the opening of the baffle may be configured to allow luminescence directed by a bullseye on the same pixel. As shown in FIG. 4-2, baffle 4-226 has openings along the z-direction to allow luminescence to pass through to sensors positioned in layer 4-230. The material of a baffle may be selected for certain optical properties, such as reducing transmission of certain light wavelengths or energies at certain incident angles. In some embodiments, a baffle may be formed by multiple layers of materials having different refractive indices. A baffle may include one or more layers of silicon, silicon nitride ($Si_3N_4$), silicon, titanium nitride (TiN), and aluminum (Al). A layer configured to form a baffle may have a cross-sectional height of approximately 20 nm, approximately 20 nm, approximately 50 nm, approximately 60 nm, approximately 70 nm, approximately 80 nm, or approximately 90 nm.

In an exemplary embodiment, a baffle includes four layers: a layer of silicon nitrate having a cross-sectional thickness of 22.34 nm, a layer of amorphous silicon having a cross-sectional thickness of 81.34 nm, a layer of titanium nitride having a cross-sectional thickness of 30 nm, and a layer of aluminum having a cross-sectional thickness of 50 nm. Absorption and reflectance of an exemplary baffle design is illustrated in FIG. 7-3, which shows absorbance and reflectance at different incident angles of 0, 20, and 35 degrees for both p and s polarizations. As shown in FIG. 7-3, the baffle has varying levels of absorptance for different incident angles to the baffle and has a larger absorptance at larger incidence angles.

Filtering components may be formed between a waveguide and a sensor for reducing collection of excitation energy by the sensor. Any suitable manner for filtering excitation energy may be provided. Techniques for filtering the excitation energy may include filtering based on one or more characteristics of light. Such characteristics may include wavelength and/or polarization. Filtering components may selectively suppress scattered excitation energy while allowing luminescence to pass through to the sensor. Layer 4-228 shown in FIG. 4-2 may include one or more filtering components described herein.

A polarization filter configured to reflect and/or absorb light of a particular polarization may act as a filter for in an integrated device. A polarization filter may be used in systems where excitation energy propagating through a waveguide has a certain polarization and luminescence emitted by a marker may have a different polarization than the excitation energy. The polarization excitation filter may be configured to filter the polarization of the excitation energy and thereby reduce excitation energy from being collected by a sensor. In some embodiments, a polarization filter may be configured to absorb TE-polarized light when the excitation energy provided by the excitation is TE polarized. The polarization filter may consist of a patterned wire-grid polarizer. In some embodiments, the wires in the wire-grid are aluminum. The orientation of the wires may be aligned parallel along a direction perpendicular to the propagation direction of one or more waveguides. When the excitation energy is TE-polarized, the orientation of the wires may be aligned with the oscillating electric field of the TE-polarized excitation energy. Fabrication of such a wire-grid polarizer may provide a suitable filter while negligibly contribute to the thickness of the overall integrated device. Such a wire-grid polarizer may have a loss of scattered excitation energy of approximately greater than 10 dB and a loss of luminescence of approximately 3 dB. In some embodiments, openings in the wire-grid filter where the wires are not present may align with one or more underlying sensors. The openings may have a dimension that is smaller or larger than a dimension of one or more sensors. An opening may allow for luminescence from a sample well of a pixel to be collected by a sensor in the pixel while the surrounding wire-grid pattern may provide filtering of excitation energy.

FIG. 7-4A shows a planar view of a polarization excitation filter having a grid comprising a plurality of wires 7-406. The wire grid has openings 7-408 that form pixel regions in a pixel array of an integrated device. Waveguide 7-404 may be positioned to pass through a row of openings 7-408. FIG. 7-4B shows a cross-sectional view along line A-A' as shown in FIG. 7-4A. Wires 7-406 are positioned between waveguide 7-404 and sensor 7-410. Opening 7-408 in the wires 7-406 is positioned to at least partially overlap with sensor 7-410. In this manner, opening 7-408 and sensor 7-410 may be included in the same pixel of an integrated device. Opening 7-408 may allow luminescence energy to pass through such that sensor 7-410 may detect the luminesce, while reducing the amount of excitation energy detected by sensor 7-410.

An integrated device may include a wavelength filter configured to reflect light of one or more characteristic wavelengths and allow transmission of light having a different characteristic wavelength. In some embodiments, light reflected by a wavelength filter may have a shorter characteristic wavelength than the light transmitted by the wavelength filter. Such a wavelength filter may reflect excitation energy and allow transmission of luminesce since excitation energy used to excite a marker typically has a shorter characteristic wavelength than luminesce emitted by the marker in response reaching an excitation state by the excitation energy.

A wavelength filter may include one or more layers having one or more materials. A wavelength filter may include titanium dioxide ($TiO_2$) and/or silicon dioxide ($SiO_2$). In some embodiments, a wavelength filter may include a stack of multiple layers having alternating layers of a high index of refraction material and a low index of refraction material. The cross-sectional thickness of each layer may be any suitable thickness and, in some instances, may be configured to reflect and/or transmit a particular wavelength of light. The cross-sectional thickness of the layers may be approximately a quarter of the wavelength of the light transmitted by the wavelength filter. A thickness of a layer of a wavelength filter may be approximately 10 nm, approximately 40 nm, approximately 50 nm, approximately 60 nm, approximately 70 nm, approximately 80 nm, approximately 90 nm, approximately 100 nm, approximately 110 nm, approximately 130 nm, or approximately 150 nm. In some embodiments, a layer of an wavelength filter may have less than 1% variation in thickness across the layer, providing suitable thickness uniformity within the wavelength filter.

In some embodiments, the different materials may include alternating layers of titanium dioxide ($TiO_2$) and silicon dioxide ($SiO_2$). Using titanium dioxide and silicon dioxide as the alternating layers in a wavelength filter may reduce the overall thickness of the structure of the wavelength filter.

The stack of alternating layers may have any suitable thickness to provide a desired level of filtering of excitation energy while allowing transmission of luminescence. A wavelength filter may have a thickness of approximately 3 microns, approximately 3.5 microns, approximately 4 microns, or approximately 4.5 microns. A wavelength filter may be formed across multiple pixels of an integrated device.

FIG. 7-5 shows a cross-sectional view of wavelength filter 7-500 of an integrated device. Wavelength filter includes alternating layers of layer 7-501 and layer 7-502. Layer 7-501 and layer 7-502 have different indices of refraction. For example, layer 7-501 may have a higher index of refraction than layer 7-502. Different indices of refraction for layers 7-501 and 7-502 can be achieved by using materials that have different indices of refraction. In some embodiments, layer 7-501 may include silicon dioxide, and layer 7-502 may include titanium dioxide. Wavelength filter 7-500 is formed within pixel region 7-508 having sensor 7-510. Wavelength filter 7-500 may be configured to allow transmission of light having one characteristic wavelength, $\lambda 2$, while substantially reflecting a different characteristic wavelength, $\lambda 1$. A marker may emit luminescence having $\lambda 2$, which can pass through excitation filter 7-500 and be detected by sensor 7-510. Excitation energy may include $\lambda 1$. In this manner, sensor 7-510 may detect a signal substantially relative to luminescence of a marker.

In an exemplary embodiment, a waveguide filter may include 49 layers of alternating $TiO_2$ and $SiO_2$ with a layer of $SiO_2$ on either side of the stack of $TiO_2$ and $SiO_2$ layer. The total thickness of the entire stack is approximately 3.876 microns. FIG. 7-6 plots transmittance as a function of wavelength for p-polarization, average polarization, s-polarization for an incident angle of approximately 10 degrees and transmittance at an incident angle of approximately 0 degrees. The extinction loss may vary significantly over a wavelength range of approximately 21 nm and be approximately 30 dB at approximately 646 nm for an incident angle of approximately 10. The thickness variation for such a filter may be less than approximately 1% in order to reduce artifacts due to thickness uniformity.

Altering the thicknesses of layers within a multi-layer stack of a wavelength filter may change its transmission properties. Changing the thickness of one or more layers in a wavelength filters may alter the wavelength of light the filter transmits. Using such a technique, sections of filtering elements may transmit one wavelength of light while other sections may transmit a different wavelength of light to form a multi-wavelength filter. A section of a multi-wavelength filter may overlap with a sensor configured to receive light transmitted through the section. The stack of alternating layers of a multi-wavelength filter may have two sections where the thickness of the alternating layers is approximately a quarter of a wavelength of light with a spacer having a half wavelength between the two quarter wavelength sections. The spacer may act as a Fabry-Perot resonator. The spacer may have a variable thickness such that it has a thickness in a first region that is larger than a thickness in a second region. The wavelength of light transmitted by the wavelength filter may vary across the filter because of the variation in thickness of the spacer. The first region may allow transmission of light having a first wavelength, and the second region may allow transmission of light having a second wavelength where the first wavelength is longer than the second wavelength. Additionally, the first region of the filter may substantially reflect light having the second wavelength, and the second region of the filter may substantially reflect light having the first wavelength. In this manner, the wavelength filter may provide variation of the wavelength of transmitted light across the wavelength filter provided by the variation in the thickness of the spacer. Such multi-wavelength filters may be used in embodiments where more than one luminescence wavelength is detected. The multi-wavelength filters may reflect excitation energy by greater than 10 dB.

While fabricating such a wavelength filter, the spacer may be formed to the thickness for transmission of the longer wavelength of light and etched in the regions where the shorter wavelength of light is transmitted. The high refractive index layer in regions that transmit the shorter wavelength of light may have a patterned etch region.

FIG. 7-7 shows a cross-sectional view of a multi-wavelength filter 7-700. Pixel 7-707 includes region 7-708 and region 7-709 of multi-wavelength filter 7-700 and sensor 7-710 and sensor 7-711. Multi-wavelength filter 7-700 includes alternating layers of 7-701 and 7-702 and spacer 7-706. Layer 7-701 and layer 7-702 have different indices of refraction. For example, layer 7-701 may have a higher index of refraction than layer 7-702. Different indices of refraction for layers 7-701 and 7-702 can be achieved by using materials that have different indices of refraction. In some embodiments, layer 7-701 may include silicon dioxide, and layer 7-702 may include titanium dioxide. As shown in FIG. 7-7, spacer 7-706 has a variable thickness such that region 7-708 has a smaller thickness than region 7-709. By varying the thickness of spacer 7-706, the wavelength of light transmitted by filter 7-700 varies from region 7-708 to region 7-709. Depending on the region, the thickness of spacer 7-706 may equal approximately half the wavelength of the transmitted light. Spacer 7-706 has a smaller thickness in region 7-708 than in region 7-709 such that transmission of light through region 7-708 has a smaller wavelength than transmission of light through region 7-709. Variation in thickness of region 7-708 and 7-709 may be approximately 5 nm, approximately 10 nm, approximately 15, approximately 20 nm, or approximately 25 nm. As shown in FIG. 7-7, region 7-708 allows transmission of $\lambda 1$, and region 7-709 allows transmission of $\lambda 2$ where $\lambda 2$ is larger than $\lambda 1$. In this manner, sensor 7-710 positioned in region 7-708 may detect $\lambda 1$ and sensor 7-711 positioned in region 7-709 may detect $\lambda 2$. Additionally, multi-wavelength filter 7-706 may be configured to reflect excitation energy by both regions 7-708 and 7-709. As shown in FIG. 7.7, both regions 7-708 and 7-709 reflect $\lambda 3$, which may have a longer wavelength than both $\lambda 1$ and $\lambda 2$.

FIG. 7-8 illustrates a plot of the transmittance of polarized light as a function of wavelength of an exemplary wavelength filter having 13 layers alternating $TiO_2$ and $SiO_2$, with a layer of $SiO_2$ on either side of the stack and a $TiO_2$ spacer having variable thickness. The alternating layers of $TiO_2$ and $SiO_2$ that form quarter wavelength layers have thicknesses of 76.20 nm and 118.51, respectively. The $TiO_2$ spacer has a thickness in one region that is 137.16 nm and a thickness in another region that is approximately 122.16 nm. The total thickness of the entire stack is 1.3 microns. The spacer layer has an etched region that is approximately 15 nm thinner for the shorter wavelength bandpass transmission regions of the filter than the longer wavelength bandpass transmission regions. The transmission regions are centered at approximately 660 nm and 685 nm. Additional cavity spacers may broaden the transmission peaks to be squarer. The extinction loss may be approximately in the range of 10 dB to 15 dB. The thickness variation for such a filter may be less than approximately 1% in order to reduce artifacts due to thickness uniformity.

F. Sensor

Any suitable sensor capable of acquiring time bin information may be used for measurements to detect lifetimes of luminescent markers. For example, U.S. Provisional Patent Application 62/164,506, entitled "INTEGRATED DEVICE FOR TEMPORAL BINNING OF RECEIVED PHOTONS," filed May 20, 2015, describes a sensor capable of determining an arrival time of a photon, and is incorporated by reference in its entirety. The sensors are aligned such that each sample well has at least one sensor region to detect luminescence from the sample well. In some embodiments, the integrated device may include Geiger mode avalanche photodiode arrays and/or single photon avalanche diode arrays (SPADs).

Described herein is an integrated photodetector that can accurately measure, or "time-bin," the timing of arrival of incident photons, and which may be used in a variety of applications, such as sequencing of nucleic acids (e.g., DNA sequencing), for example. In some embodiments, the integrated photodetector can measure the arrival of photons with nanosecond or picosecond resolution, which can facilitate time-domain analysis of the arrival of incident photons.

Some embodiments relate to an integrated circuit having a photodetector that produces charge carriers in response to incident photons and which is capable of discriminating the timing at which the charge carriers are generated by the arrival of incident photons with respect to a reference time (e.g., a trigger event). In some embodiments, a charge carrier segregation structure segregates charge carriers generated at different times and directs the charge carriers into one or more charge carrier storage regions (termed "bins") that aggregate charge carriers produced within different time periods. Each bin stores charge carriers produced within a selected time interval. Reading out the charge stored in each bin can provide information about the number of photons that arrived within each time interval. Such an integrated circuit can be used in any of a variety of applications, such as those described herein.

An example of an integrated circuit having a photodetection region and a charge carrier segregation structure will be described. In some embodiments, the integrated circuit may include an array of pixels, and each pixel may include one or more photodetection regions and one or more charge carrier segregation structures, as discussed below.

FIG. 7-9A shows a diagram of a pixel 7-900, according to some embodiments. Pixel 7-900 includes a photon absorption/carrier generation region 7-902 (also referred to as a photodetection region), a carrier travel/capture region 7-906, a carrier storage region 7-908 having one or more charge carrier storage regions, also referred to herein as "charge carrier storage bins" or simply "bins," and readout circuitry 7-910 for reading out signals from the charge carrier storage bins.

The photon absorption/carrier generation region 7-902 may be a region of semiconductor material (e.g., silicon) that can convert incident photons into photogenerated charge carriers. The photon absorption/carrier generation region 7-902 may be exposed to light, and may receive incident photons. When a photon is absorbed by the photon absorption/carrier generation region 7-902 it may generate photogenerated charge carriers, such as an electron/hole pair. Photogenerated charge carriers are also referred to herein simply as "charge carriers."

An electric field may be established in the photon absorption/carrier generation region 7-902. In some embodiments, the electric field may be "static," as distinguished from the changing electric field in the carrier travel/capture region 7-906. The electric field in the photon absorption/carrier generation region 7-902 may include a lateral component, a vertical component, or both a lateral and a vertical component. The lateral component of the electric field may be in the downward direction of FIG. 7-9A, as indicated by the arrows, which induces a force on photogenerated charge carriers that drives them toward the carrier travel/capture region 106. The electric field may be formed in a variety of ways.

In some embodiments, one or more electrodes may be formed over the photon absorption/carrier generation region 7-902. The electrodes(s) may have voltages applied thereto to establish an electric field in the photon absorption/carrier generation region 7-902. Such electrode(s) may be termed "photogate(s)." In some embodiments, photon absorption/carrier generation region 7-902 may be a region of silicon that is fully depleted of charge carriers.

In some embodiments, the electric field in the photon absorption/carrier generation region 7-902 may be established by a junction, such as a PN junction. The semiconductor material of the photon absorption/carrier generation region 7-902 may be doped to form the PN junction with an orientation and/or shape that produces an electric field that induces a force on photogenerated charge carriers that drives them toward the carrier travel/capture region 7-906. In some embodiments, the P terminal of the PN junction diode may connected to a terminal that sets its voltage. Such a diode may be referred to as a "pinned" photodiode. A pinned photodiode may promote carrier recombination at the surface, due to the terminal that sets its voltage and attracts carriers, which can reduce dark current. Photogenerated charge carriers that are desired to be captured may pass underneath the recombination area at the surface. In some embodiments, the lateral electric field may be established using a graded doping concentration in the semiconductor material.

As illustrated in FIG. 7-9A, a photon may be captured and a charge carrier 7-901A (e.g., an electron) may be produced at time t1. In some embodiments, an electrical potential gradient may be established along the photon absorption/carrier generation region 7-902 and the carrier travel/capture region 7-906 that causes the charge carrier 7-901A to travel in the downward direction of FIG. 7-9A (as illustrated by the arrows shown in FIG. 7-9A). In response to the potential gradient, the charge carrier 7-901A may move from its position at time t1 to a second position at time t2, a third position at time t3, a fourth position at time t4, and a fifth position at time t5. The charge carrier 7-901A thus moves into the carrier travel/capture region 7-906 in response to the potential gradient.

The carrier travel/capture region 7-906 may be a semiconductor region. In some embodiments, the carrier travel/capture region 7-906 may be a semiconductor region of the same material as photon absorption/carrier generation region 7-902 (e.g., silicon) with the exception that carrier travel/capture region 7-906 may be shielded from incident light (e.g., by an overlying opaque material, such as a metal layer).

In some embodiments, and as discussed further below, a potential gradient may be established in the photon absorption/carrier generation region 7-902 and the carrier travel/capture region 7-906 by electrodes positioned above these regions. However, the techniques described herein are not limited as to particular positions of electrodes used for producing an electric potential gradient. Nor are the techniques described herein limited to establishing an electric potential gradient using electrodes. In some embodiments, an electric potential gradient may be established using a spatially graded doping profile. Any suitable technique may be used for establishing an electric potential gradient that causes charge carriers to travel along the photon absorption/carrier generation region 7-902 and carrier travel/capture region 7-906.

A charge carrier segregation structure may be formed in the pixel to enable segregating charge carriers produced at different times. In some embodiments, at least a portion of the charge carrier segregation structure may be formed over the carrier travel/capture region 7-906. As will be described below, the charge carrier segregation structure may include one or more electrodes formed over the carrier travel/capture region 7-906, the voltage of which may be controlled by control circuitry to change the electric potential in the carrier travel/capture region 7-906.

The electric potential in the carrier travel/capture region 7-906 may be changed to enable capturing a charge carrier. The potential gradient may be changed by changing the voltage on one or more electrodes overlying the carrier travel/capture region 7-906 to produce a potential barrier that can confine a carrier within a predetermined spatial region. For example, the voltage on an electrode overlying the dashed line in the carrier travel/capture region 7-906 of FIG. 7-9A may be changed at time t5 to raise a potential barrier along the dashed line in the carrier travel/capture region 7-906 of FIG. 7-9A, thereby capturing charge carrier 7-901A. As shown in FIG. 7-9A, the carrier captured at time t5 may be transferred to a bin "bin0" of carrier storage region 7-908. The transfer of the carrier to the charge carrier storage bin may be performed by changing the potential in the carrier travel/capture region 7-906 and/or carrier storage region 7-908 (e.g., by changing the voltage of electrode(s) overlying these regions) to cause the carrier to travel into the charge carrier storage bin.

Changing the potential at a certain point in time within a predetermined spatial region of the carrier travel/capture region 7-906 may enable trapping a carrier that was generated by photon absorption that occurred within a specific time interval. By trapping photogenerated charge carriers at different times and/or locations, the times at which the charge carriers were generated by photon absorption may be discriminated. In this sense, a charge carrier may be "time binned" by trapping the charge carrier at a certain point in time and/or space after the occurrence of a trigger event. The time binning of a charge carrier within a particular bin provides information about the time at which the photogenerated charge carrier was generated by absorption of an incident photon, and thus likewise "time bins," with respect to the trigger event, the arrival of the incident photon that produced the photogenerated charge carrier.

FIG. 7-9B illustrates capturing a charge carrier at a different point in time and space. As shown in FIG. 7-9B, the voltage on an electrode overlying the dashed line in the carrier travel/capture region 7-906 may be changed at time t9 to raise a potential barrier along the dashed line in the carrier travel/capture region 106 of FIG. 7-9B, thereby capturing carrier 7-901B. As shown in FIG. 7-9B, the carrier captured at time t9 may be transferred to a bin "bin1" of carrier storage region 7-908. Since charge carrier 7-901B is trapped at time t9, it represents a photon absorption event that occurred at a different time (i.e., time t6) than the photon absorption event (i.e., at t1) for carrier 7-901A, which is captured at time t5.

Performing multiple measurements and aggregating charge carriers in the charge carrier storage bins of carrier storage region 7-908 based on the times at which the charge carriers are captured can provide information about the times at which photons are captured in the photon absorption/carrier generation area 7-902. Such information can be useful in a variety of applications, as discussed above.

In some embodiments, the duration of time each time bin captures after an excitation pulse may vary. For example, shorter time bins may be used to detect luminescence shortly after the excitation pulse, while longer time bins may be used at times further from an excitation pulse. By varying the time bin intervals, the signal to noise ratio for measurements of the electrical signal associated with each time bin may be improved for a given sensor. Since the probability of a photon emission event is higher shortly after an excitation pulse, a time bin within this time may have a shorter time interval to account for the potential of more photons to detect. While at longer times, the probability of photon emission may be less and a time bin detecting within this time may be longer to account for a potential fewer number of photons. In some embodiments, a time bin with a significantly longer time duration may be used to distinguish among multiple lifetimes. For example, the majority of time bins may capture a time interval in the range of approximately 0.1-0.5 ns, while a time bin may capture a time interval in the range of approximately 2-5 ns. The number of time bins and/or the time interval of each bin may depend on the sensor used to detect the photons emitted from the sample object. Determining the time interval for each bin may include identifying the time intervals needed for the number of time bins provided by the sensor to distinguish among luminescent markers used for analysis of a sample. The distribution of the recorded histogram may be compared to known histograms of markers under similar conditions and time bins to identify the type of marker in the sample well. Different embodiments of the present application may measure lifetimes of markers but vary in the excitation energies used to excite a marker, the number of sensor regions in each pixel, and/or the wavelength detected by the sensors.

III. Excitation Source

According to some embodiments, one or more excitation sources may be located external to the integrated device, and may be arranged to deliver pulses of light to an integrated device having sample wells. For example, U.S. Provisional Patent Application 62/164,485, entitled "PULSED LASER," filed May 20, 2015 describes a pulsed laser source that may be used as an excitation source, and is incorporated by reference in its entirety. The pulses of light may be coupled to a plurality of sample wells and used to excite one or more markers within the wells, for example. The one or more excitation sources may deliver pulses of light at one or more characteristic wavelengths, according to some implementations. In some cases, an excitation source may be packaged as an exchangeable module that mounts in or couples to a base instrument, into which the integrated device may be loaded. Energy from an excitation source may be delivered radiatively or non-radiatively to at least one sample well or to at least one sample in at least one sample well. In some implementations, an excitation source having a controllable intensity may be arranged to deliver excitation energy to a plurality of pixels of an integrated device. The pixels may be arranged in a linear array (e.g., row or column), or in a 2D array (e.g., a sub-area of the array of pixels or the full array of pixels).

Any suitable light source may be used for an excitation source. Some embodiments may use incoherent light sources and other embodiments may use coherent light sources. By way of non-limiting examples, incoherent light sources according to some embodiments may include different types of light emitting diodes (LEDs) such as organic LEDs (OLEDs), quantum dots (QLEDs), nanowire LEDs, and (in)organic semiconductor LEDs. By way of non-limiting examples, coherent light sources according to some embodiments may include different types of lasers such as semiconductor lasers (e.g., vertical cavity surface emitting lasers (VCSELs), edge emitting lasers, and distributed-feedback (DFB) laser diodes). Additionally or alternatively, slab-coupled optical waveguide laser (SCOWLs) or other asymmetric single-mode waveguide structures may be used. In some implementations, coherent light sources may comprise organic lasers, quantum dot lasers, and solid state lasers (e.g., a Nd:YAG or ND:Glass laser, pumped by laser diodes or flashlamps). In some embodiments, a laser-diode-pumped fiber laser may be used. A coherent light source may be passively mode locked to produce ultrashort pulses. There may be more than one type of excitation source for an array of pixels on an integrated device. In some embodiments, different types of excitation sources may be combined. An excitation source may be fabricated according to conventional technologies that are used to fabricate a selected type of excitation source.

By way of introduction and without limiting the invention, an example arrangement of a coherent light source is depicted in FIG. 8-0A. The drawing illustrates an analytical instrument 8-100 that may include an ultrashort-pulsed laser excitation source 8-110 as the excitation source. The ultrashort pulsed laser 8-110 may comprise a gain medium 8-105 (which may be a solid-state material is some embodiments), a pump source for exciting the gain medium (not shown), and at least two cavity mirrors 8-102, 8-104 that define ends of an optical laser cavity. In some embodiments, there may be one or more additional optical elements in the laser cavity for purposes of beam shaping, wavelength selection, and/or pulse forming. When operating, the pulsed-laser excitation source 8-110 may produce an ultrashort optical pulse 8-120 that circulates back-and-forth in the laser cavity between the cavity's end mirrors 8-102, 8-104 and through the gain medium 8-105. One of the cavity mirrors 8-104 may partially transmit a portion of the circulating pulse, so that a train of optical pulses 8-122 is emitted from the pulsed laser 8-110 to subsequent component 8-160, such as an optical component and integrated device. The emitted pulses may sweep out a beam (indicated by the dashed lines) that is characterized by a beam waist w.

Measured temporal intensity profiles of the emitted pulses 8-122 may appear as depicted in FIG. 8-0B. In some embodiments, the peak intensity values of the emitted pulses may be approximately equal, and the profiles may have a Gaussian temporal profile, though other profiles such as a sech profile may be possible. In some cases, the pulses may not have symmetric temporal profiles and may have other temporal shapes. In some embodiments, gain and/or loss dynamics may yield pulses having asymmetric profiles. The duration of each pulse may be characterized by a full-width-half-maximum (FWHM) value, as indicated in FIG. 8-0B. Ultrashort optical pulses may have FWHM values less than 100 picoseconds.

The pulses emitting from a laser excitation source may be separated by regular intervals T. In some embodiments, T may be determined by active gain and/or loss modulation rates in the laser. For mode-locked lasers, T may be determined by a round-trip travel time between the cavity end mirrors 8-102, 8-104. According to some embodiments, the pulse separation time T may be between about 1 ns and about 100 ns. In some cases, the pulse separation time T may be between about 0.1 ns and about 1 ns. In some implementations, the pulse separation time T may be between about 100 ns and about 2 μs.

In some embodiments, an optical system 8-140 may operate on a beam of pulses 8-122 from a laser excitation source 8-110. For example, the optical system may include one or more lenses to reshape the beam and/or change the divergence of the beam. Reshaping of the beam may include increasing or decreasing the value of the beam waist and/or changing a cross-sectional shape of the beam (e.g., elliptical to circular, circular to elliptical, etc.). Changing the divergence of the beam may comprise converging or diverging the beam flux. In some implementations, the optical system 8-140 may include an attenuator or amplifier to change the amount of beam energy. In some cases, the optical system may include wavelength filtering elements. In some implementations, the optical system may include pulse shaping elements, e.g., a pulse stretcher and/or pulse compressor. In some embodiments, the optical system may include one or more nonlinear optical elements, such as a saturable absorber for reducing a pulse length. According to some embodiments, the optical system 8-140 may include one or more elements that alter the polarization of pulses from a laser excitation source 8-110.

In some implementations, an optical system 8-140 may include a nonlinear crystal for converting the output wavelength from an excitation source 8-110 to a shorter wavelength via frequency doubling or to a longer wavelength via parametric amplification. For example, an output of the laser may be frequency-doubled in a nonlinear crystal (e.g., in periodically-poled lithium niobate (PPLN)) or other non-poled nonlinear crystal. Such a frequency-doubling process may allow more efficient lasers to generate wavelengths more suitable for excitation of selected fluorophores.

The phrase "characteristic wavelength" or "wavelength" may refer to a central or predominant wavelength within a limited bandwidth of radiation produced by an excitation source. In some cases, it may refer to a peak wavelength within a bandwidth of radiation produced by an excitation source. A characteristic wavelength of an excitation source may be selected based upon a choice of luminescent markers or probes that are used in a bioanalysis device, for example. In some implementations, the characteristic wavelength of a source of excitation energy is selected for direct excitation (e.g., single photon excitation) of a chosen fluorophore. In some implementations, the characteristic wavelength of an excitation source is selected for indirect excitation (e.g., multi-photon excitation or harmonic conversion to a wavelength that will provide direct excitation). In some embodiments, excitation radiation may be generated by a light source that is configured to generate excitation energy at a particular wavelength for application to a sample well. In some embodiments, a characteristic wavelength of the excitation source may be less than a characteristic wavelength of corresponding emission from the sample. For example, an excitation source may emit radiation having a characteristic wavelength between 500 nm and 700 nm (e.g., 515 nm, 532 nm, 563 nm, 594 nm, 612 nm, 632 nm, 647 nm). In some embodiments, an excitation source may provide excitation energy centered at two different wavelengths, such as 532 nm and 593 nm for example.

In some embodiments, a pulsed excitation source may be used to excite a luminescent marker in order to measure an emission lifetime of the luminescent marker. This can be useful for distinguishing luminescent markers based on emission lifetime rather than emission color or wavelength. As an example, a pulsed excitation source may periodically excite a luminescent marker in order to generate and detect subsequent photon emission events that are used to determine a lifetime for the marker. Lifetime measurements of luminescent markers may be possible when the excitation pulse from an excitation source transitions from a peak pulse power or intensity to a lower (e.g., nearly extinguished) power or intensity over a duration of time that is less than the lifetime of the luminescent marker. It may be beneficial if the excitation pulse terminates quickly, so that it does not re-excite the luminescent marker during a post-excitation phase when a lifetime of the luminescent marker is being evaluated. By way of example and not limitation, the pulse power may drop to approximately 20 dB, approximately 40 dB, approximately 80 dB, or approximately 120 dB less than the peak power after 250 picoseconds. In some implementations, the pulse power may drop to approximately 20 dB, approximately 40 dB, approximately 80 dB, or approximately 120 dB less than the peak power after 100 picoseconds.

An additional advantage of using ultrashort excitation pulses to excite luminescent markers is to reduce photobleaching of the markers. Applying continuous excitation energy to a marker may bleach and/or damage a luminescent marker over time. Even though a peak pulse power of the excitation source may be considerably higher than a level that would rapidly damage a marker at continuous exposure, the use of ultrashort pulses may increase the amount of time and number of useful measurements before the marker becomes damaged by the excitation energy.

When using a pulsed excitation source to discern lifetimes of luminescent markers, the time between pulses of excitation energy may be as long as or longer than a longest lifetime of the markers in order to observe and evaluate emission events after each excitation pulse. For example, the time interval T (see FIG. 8-0B) between excitation pulses may be longer than any emission lifetime of the examined fluorophores. In this case, a subsequent pulse may not arrive before an excited fluorophore from a previous pulse has had a reasonable amount of time to fluoresce. In some embodiments, the interval T needs to be long enough to determine a time between an excitation pulse that excites a fluorophore and a subsequent photon emitted by the fluorophore after termination of excitation pulse and before the next excitation pulse.

Although the interval between excitation pulses T should be long enough to observe decay properties of the fluorophores, it is also desirable that T is short enough to allow many measurements to be made in a short period of time. By way of example and not limitation, emission lifetimes of fluorophores used in some applications may be in the range of about 100 picoseconds to about 10 nanoseconds. Accordingly, excitation pulses used to detect and/or discern such lifetimes may have durations (FWHM) ranging from about 25 picoseconds to about 2 nanoseconds, and may be provided at pulse repetition rates ranging from about 20 MHz to about 1 GHz.

In further detail, any suitable techniques for modulating the excitation energy to create a pulsed excitation source for lifetime measurements may be used. Direct modulation of an excitation source, such as a laser, may involve modulating the electrical drive signal of the excitation source so the emitted power is in the form of pulses. The input power for a light source, including the optical pumping power, and excited-state carrier injection and/or carrier removal from a portion of the gain region, may be modulated to affect the gain of the gain medium, allowing the formation of pulses of excitation energy through dynamic gain shaping. Additionally, the quality (Q) factor of the optical resonator may be modulated by various means to form pulses using Q-switching techniques. Such Q-switching techniques may be active and/or passive. The longitudinal modes of a resonant cavity of a laser may be phase-locked to produce a series of pulses of emitted light through mode-locking. Such mode-locking techniques may be active and/or passive. A laser cavity may include a separate absorbing section to allow for modulation of the carrier density and control of the absorption loss of that section, thus providing additional mechanisms for shaping the excitation pulse. In some embodiments, an optical modulator may be used to modulate a beam of continuous wave (CW) light to be in the form of a pulse of excitation energy. In other embodiments, a signal sent to an acoustic optic modulator (AOM) coupled to an excitation source may be used to change the deflection, intensity, frequency, phase, and/or polarization of the outputted light to produce a pulsed excitation energy. AOMs may also be used for continuous wave beam scanning, Q-switching, and/or mode-locking. Although the above techniques are described for creating a pulsed excitation source, any suitable way to produce a pulsed excitation source may be used for measuring lifetimes of luminescent markers.

In some embodiments, techniques for forming a pulsed excitation source suitable for lifetime measurements may include modulation of an input electrical signal that drives photon emission. Some excitation sources (e.g., diode lasers and LEDs) convert an electrical signal, such as an input current, into a light signal. The characteristics of the light signal may depend on characteristics of the electrical signal. In producing a pulsed light signal, the electrical signal may vary over time in order to produce a variable light signal. Modulating the electrical signal to have a specific waveform may produce an optical signal with a specific waveform. The electrical signal may have a sinusoidal waveform with a certain frequency and the resulting pulses of light may occur within time intervals related to the frequency. For example, an electrical signal with a 500 MHz frequency may produce a light signal with pulses every 2 nanoseconds. Combined beams produced by distinct pulsed excitation sources, whether similar or different from each other, may have a relative path difference below 1 mm.

In some excitation sources, such as laser diodes, the electrical signal changes the carrier density and photons are produced through the recombination of electron and hole pairs. The carrier density is related to the light signal such that when the carrier density is above a threshold, a substantial number of coherent photons are generated via stimulated emission. Current supplied to a laser diode may inject electrons or carriers into the device, and thereby increase the carrier density. When the carrier density is above a threshold, photons may be generated at a faster rate than the current supplying the carriers, and thus the carrier density may decrease below the threshold and photon generation reduces. With the photon generation reduced, the carrier density begins to increase again, due to continued current injection and the absorption of photons, and eventually increases above the threshold again. This cycle leads to oscillations of the carrier density around the threshold value for photon generation, resulting in an oscillating light signal. These dynamics, known as relaxation oscillations, can lead to artifacts in the light signal due to oscillations of the carrier density. When current is initially supplied to a laser, there may be oscillations before the light signal reaches a stable power due to oscillations in the carrier density. When forming a pulsed excitation source, oscillations of the carrier density may introduce artifacts for a pulsed light signal. For example, the plot in FIG. 8-1 illustrates how the carrier density may have relaxation oscillations and a corresponding light signal with oscillating power through modulation by gain switching. Artifacts from such relaxation oscillations may broaden a pulsed light signal and/or produce a tail in the light signal, limiting the lifetimes that can be detected by such a pulsed light source since the excitation signal may overlap with emitted photons by a luminescent marker.

In some embodiments, techniques for shortening the time duration of an excitation pulse may be used to reduce the excitation energy required to detect luminescent markers and thereby reduce or delay bleaching and other damage to the luminescent markers. Techniques for shortening the time duration of the excitation pulse may be used to reduce the power and/or intensity of the excitation energy after a maximum value or peak of the excitation pulse, allowing the detection of shorter lifetimes. Such techniques may electrically drive the excitation source in order to reduce the excitation power after the peak power. This may suppress a tail of the pulse as shown in FIG. 8-2. An electrical driving signal may be tailored to drive the intensity of the pulse of excitation energy to zero as quickly as possible after the peak pulse. An example of a tailored electrical driving signal combined with gain switching is shown in FIG. 8-2. Such a technique may involve reversing the sign of an electrical driving signal after the peak power is produced. Such a tailored electrical driving signal may produce an optical output shown in FIG. 8-2. The electrical signal may be tailored to quickly reduce the carrier density after the first relaxation oscillation or first oscillation of the optical signal. By reducing the carrier density after the first oscillation, a light pulse of just the first oscillation may be generated. The electrical signal may be configured to generate a short pulse that turns the light signal off quickly by reducing the number of photons emitted after a peak in the signal, such as shown by the plot in FIG. 8-3 showing the optical output of such an electrical signal. A picosecond laser diode system may be designed to emit light pulses, according to some embodiments. FIG. 8-4 illustrates a plot of an exemplary light pulse with a peak of 985 mW, a width of 84.3 picoseconds, and a signal reduced by approximately 24.3 dB approximately 250 picoseconds after the peak. In some embodiments, saturable absorbers, including semiconductor saturable absorbers (SESAMs) may be used to suppress the optical tail. In such embodiments, using the saturable absorbers may suppress the optical tail by 3-5 dB or, in some instances, greater than 5 dB. Reducing the effects of a tail in the excitation pulse may reduce and/or eliminate any requirements on additional filtering of the excitation energy, increase the range of lifetimes that can be measured, and/or enable faster pulse rates. Increasing the excitation pulse rate may enable more experiments to be conducted in a given time, which may decrease the time needed to acquire enough statistics to identify a lifetime for a marker labeling a sample object.

Additionally, two or more of these techniques may be used together to generate pulsed excitation energy. For example, pulsed excitation energy emitted from a directly modulated source may be further modified using optical modulation techniques. Techniques for modulating the excitation pulse and tailoring the electrical pulse driving signal may be combined in any suitable way to optimize a pulsed excitation energy for performing lifetime measurements. A tailored electrical drive signal may be applied to a pulsed excitation energy from a directly modulated source.

In some embodiments, a laser diode having a certain number of wire bonds may be used as a pulsed excitation source. Laser diodes with more wire bonds may reduce the inductance of the excitation source. Laser diodes having a lower inductance may enable the current into the laser to operate at a higher frequency. As shown in FIG. 8-5, when driven by an 18V pulse in a 50 ohm transmission line, the laser source with 3 ohm series resistance and 36 wire bonds has a higher current at higher frequencies than the laser sources with fewer wire bonds. Selecting a packaging method to minimize inductance may improve the power supplied to the excitation source at higher frequencies, enabling shorter excitation pulses, faster reductions of optical power after the peak, and/or increased pulse repetition rate for detecting luminescent markers.

In some embodiments, a transmission line in combination with an excitation source may be used for generating light pulses. The transmission line may match the impedance of a laser diode in order to improve performance and/or quality of light pulses. In some embodiments, the transmission line impedance may be 50 ohms. In some instances, the terminating resistance may be similar to the resistance of the line in order to avoid reflections. Alternatively or additionally, the terminating impedance may be similar to the impedance of the line in order to avoid reflections. The terminating impedance may less than the impedance of the line in order to reflect a negative pulse. In other embodiments, the terminating impedance may have a capacitive or inductive component in order to control the shape of the negative reflection pulse. In other embodiments, the transmission line may allow for a higher frequency of pulses. FIG. 8-6A illustrates an example prototype of a transmission line pulsar, and FIG. 8-6B illustrates exemplary light pulses obtained with such a transmission line. Using a transmission line may produce electrical pulses having a frequency within a range of 40 MHz to 500 MHz. A transmission line may be used in combination with a tailored electrical signal described above in order to produce a pulsed light source with light pulses having a certain time duration and a specific time interval.

Techniques for tailoring the electrical signal to improve the production of light pulses may include connecting the excitation source to a circuit with a negative bias capability. In some embodiments, a negative bias may be provided on an excitation source after a light pulse emits to reduce emission of a tail in the light pulse. FIG. 8-7 illustrates an exemplary circuit containing a current source, diode laser, resistor, capacitor, and switch that may be implemented to reduce the presence of a tail in a light pulse. Such a circuit may create a constant current that bypasses the diode laser when the switch is closed, or in a conducting state. When the switch is open, the switch may have a high resistance and current may flow through the diode laser. Light pulses may be generated by opening and closing the switch to provide intermittent current to the diode laser. In some instances, the resistor may be sufficiently high and the capacitor sufficiently small such that there is a voltage across the capacitor when the switch is open and the diode laser emits light. When the switch is closed, the voltage across the capacitor will reverse bias the diode laser. Such a reverse bias may reduce or eliminate the presence of a tail in the light pulse. In such instances, the switch may be configured to close after the peak of the light pulse in order to reduce the laser power shortly after the peak light pulse. The value of the resistor in the circuit may be selected such that the charge on the capacitor will discharge before the switch is subsequently opened and/or a subsequent light pulse is generated by the laser diode.

Additional circuit components may be provided to tailor an electrical signal of a laser diode in order to produce light pulses. In some embodiments, multiple capacitors, resistors, and voltages may be connected as a network circuit to control the waveform of an electrical signal supplied to a laser diode. A controlled waveform may be created by switching a number of voltages, V1, V2, . . . , VN with corresponding signals S1, S2, . . . , SN when there are N capacitor sub-circuits. An exemplary network circuit of four capacitor sub-circuits is shown in FIG. 8-8 where a controlled electrical waveform may be created by switching voltages V1, V2, V3, and V4 with signals S1, S2, S3, and S4, respectively. In some embodiments, voltages V1, V2, V3, and V4 may be variable. In the example shown in FIG. 8-8, V4 is negative to the laser and may create a reverse bias depending on signal S4. Timing of the frequency of light pulses emitted by the laser, the duration of each light pulse, and features of each light pulse may be adjusted with the signal inputs S1, S2, S3, and S4. In some embodiments, additional resistance may be added to lower the peak current. In such instances, the resistance may be added after one or more of the switches S1, S2, S3, S4. Although FIG. 8-8 shows one configuration with four capacitors and four voltages, any suitable configuration and any suitable number of additional circuit components may be provided to produce a tailored electrical signal to the laser diode to generate light pulses for lifetime measurements.

In some embodiments, an electrical signal for generating light pulses may use a circuit having discrete components, including radio frequency (RF) and/or microwave components. Discrete components that may be included in such a circuit are DC blocks, adaptors, logic gates, terminators, phase shifters, delays, attenuators, combiners, and/or RF amplifiers. Such components may be used to create a positive electrical signal having a certain amplitude followed by a negative electrical signal with another amplitude. There may be a delay between the positive and negative electrical signals. FIG. 8-9A illustrates an exemplary circuit having one RF amplifier that may be used to produce a tailored electrical signal as an output pulse, such as the pulse profile shown in FIG. 8-9B, that may be supplied to an excitation source, such as a laser diode, to emit a light pulse. In other embodiments, a circuit may produce multiple electrical signals combined to form an electrical pulse signal configured to drive an excitation source. Such a circuit may produce a differential output which may be used to increase the power of the light pulse. By adjusting the discrete components of the circuit, the electrical output signal may be adjusted to produce a light pulse suitable for lifetime measurements. In an example shown in FIG. 8-10A, two RF amplifiers are used to produce an output pulse signal having a profile shown in FIG. 8-10B consisting of a positive electrical signal pulse and a corresponding negative electrical signal pulse where the positive and negative electrical signal pulses overlap and have a similar width.

In some embodiments, excitation sources may be combined to generate light pulses for lifetime measurements. Synchronized pulsed sources may be coupled to a circuit or load over a certain distance. In some embodiments, excitation sources may be coupled in parallel to a circuit. The excitation sources may be from the same source or from multiple sources. In some embodiments with multiple sources, the multiple sources may vary in type of excitation source. When combining sources, it may be important to consider the impedance of the circuit and the excitation sources in order to have sufficient power supplied to the excitation sources. Combination of sources may be achieved by using one or more of the above-described techniques for producing a pulsed excitation source. FIG. 8-11A illustrates a schematic for combining four different sources having one or more impedance values. FIG. 8-11B shows a plot of current, power efficiency, and voltage as a function of impedance. This exemplary embodiment shows 4 sources delivering power on 50 ohms transmission lines and that optimal power delivery occurs when the impedance of the load equals the ratio of the impedance of the individual lines to the number of sources.

An excitation source may include a battery or any other power supply arranged to provide power to the excitation source. For example, an excitation source may be located in a base instrument and its operating power may be received through an integrated bioanalysis device to which it is coupled (e.g., via conducting power leads). An excitation source may be controlled independently of or in collaboration with control of an integrated bioanalysis device. As just one example, control signals for an excitation source may be provided to the excitation source wirelessly or via a wired interconnection (e.g., a USB interconnect) with a personal computer and/or the integrated bioanalysis device.

In some implementations, an excitation source may be operated in a time-gated and/or synchronized manner with one or more sensors of an integrated device. For example, an excitation source may be turned on to excite a luminescent marker, and then turned off. The sensor may be turned off while the excitation source is turned on, and then may be turned on for a sampling interval after the excitation source is turned off. In some embodiments, the sensor may be turned on for a sampling interval while the excitation source is turned on.

IV. Alignment of Excitation Source to Integrated Device

Positioning of excitation energy from one or more excitation sources to a grating coupler on an integrated device may occur using any suitable techniques. In some embodiments, excitation energy may be directed from an excitation source through one or more optical components to a grating coupler. In such embodiments, the excitation energy may be projected onto the integrated device. Alignment of such an excitation source may occur actively by positioning the excitation source and/or optical components. In other embodiments, an excitation source may be aligned to a grating coupler through components that position the excitation source relative to the grating coupler. Positioning of such an excitation energy source may occur through passive alignment of an optical fiber configured to provide excitation energy within a ferrule. In such embodiments, the excitation source may be connected directly or indirectly to the integrated device.

A. Active Alignment

Alignment of one or more excitation sources to an integrated device may occur once before excitation energy is delivered to a sample well and/or multiple times while the integrated device is used for an analysis. Any suitable techniques for alignment and/or stabilization of one or more excitation sources may be used to couple excitation energy to the integrated device. In some embodiments, the external excitation source may be aligned to the integrated device and then fixed in position without further adjustment throughout the duration while the integrated device is used for analysis. In other embodiments, a feedback mechanism is provided to improve the alignment of the excitation source to the integrated device. The feedback mechanism may be used in combination with an operator using a manual alignment mechanism to align the excitation source based on a feedback signal. In other instances, an automatic alignment mechanism may automatically adjust the alignment of the excitation source to the integrated device based on a feedback signal. Automatic alignment may occur before operation of the integrated device occurs and/or before acquiring a measurement. Automatic alignment may also occur during operation of the integrated device while measurements are acquired. In some instances, the time when automatic alignment occurs may correspond to times when the sensor is not actively acquiring measurements. Readjusting the alignment of the excitation source to the integrated device may improve stability of the excitation source and/or consistency in sensor measurements over time among one or more samples.

The alignment may be actively controlled in multiple dimensions based on a feedback signal. The multiple dimensions may include the x-y lateral positions of the excitation energy beam to the grating coupler, the angle of incidence of the beam along the direction of the grating coupler, the z direction of focus of the beam, and/or an orthogonal angle of incidence of the beam perpendicular to the direction of the grating coupler. The excitation source may be connected to the integrated device through a frame mount. Such an alignment mechanism may be performed using one or more servo-controlled optical elements. The active alignment mechanism may increase the overall coupling efficiency of the excitation source to the one or more waveguides in the integrated device. Such an alignment mechanism may decrease additional costs associated with a disposable integrated device as compared to other alignment methods, and/or reduce the footprint on the integrated device required by other alignment approaches. Additionally, an active alignment mechanism may reduce the training needed for an operator to operate such an integrated device and/or system.

The components performing the alignment may depend on the configuration of the excitation source and the integrated device. In some embodiments, an integrated device and an excitation source may be configured into separate modules. A base instrument may include a dark box with a lid and a socket to connect the integrated device to electrical circuitry in order to detect an electrical signal from the sensor on the integrated device. An excitation source module may include one or more excitation sources, socket connections for the one or more excitation sources, and/or optical components to direct light to the integrated device. When a laser is used as an excitation source, the excitation source module may be referred to as a laser module.

In some embodiments, optical components couple the excitation source to the integrated device in free space. The mirror and/or additional optical components may direct excitation energy from the excitation source to the waveguide. Optical components may increase the depth of focus of the excitation source. FIG. 9-1 illustrates base instrument 9-112 configured to receive integrated device 9-102. Base instrument 9-112 includes mirror 9-114 arranged to direct excitation energy (shown as dashed lines) received from excitation source module 9-110 and direct excitation energy towards a region of integrated device 9-102, such as a surface proximate a grating coupler. Excitation source module 9-110 includes excitation source 9-106 and adjustment mechanism 9-108. Alignment mechanism 9-108 may modulate the x, y, z positions, the x and y incidence angles, and the z positioning or focus of excitation source 9-206 to align the excitation source and/or optical components in order to improve coupling of the excitation energy to the integrated device. Such optical components may include mirrors, reflectors, lenses, prisms, gratings, and/or tiltable windows, such as the example set of optical components arranged in FIG. 9-3. Alignment of excitation source 9-106 may be determined through feedback (shown as solid arrow) from integrated device 9-102 and received by excitation source module 9-110 through socket 9-116 that couples to integrated device 9-102. Electrical signals received by socket 9-116 may indicate the alignment of excitation source 9-106. Such electrical signals may be used in an active feedback process by sending electrical signals received from integrated device 9-102 to excitation source module 9-110 and provide a signal to alignment mechanism 9-108 indicating adjustment of one or more parameters of alignment mechanism 9-108 and/or excitation source 9-106. When the electrical signal is received by excitation source module 9-110, alignment mechanism 9-108 may consist of adjusting the position of excitation source 9-106 and/or optical components. Such an alignment process may occur automatically and/or manually.

In some embodiments, a mirror is provided as part of the excitation source module. FIG. 9-2 illustrates a schematic of excitation source module 9-210 that includes mirror 9-214 configured to direct excitation energy (shown in dashed lines) to integrated device 9-202. Base instrument 9-212 is configured to receive integrated device 9-202 and excitation source module 9-210 such that mirror 9-214 is positioned to direct excitation energy from excitation source 9-206 to integrated device 9-202. Alignment module 9-206 may modulate one or more parameters of excitation source 9-206 and/or mirror 9-214 based on a feedback signal (shown as solid arrow) received by excitation source module 9-210 from socket 9-216 configured to couple to 9-202. The feedback signal may provide an indication of the alignment of excitation energy to a region (e.g., grating coupler) of integrated device 9-202. Alignment mechanism 9-208 may modulate the x, y, z positions, the x and y incidence angles, and the z positioning or focus of excitation source 9-206 and/or optical components to improve coupling of the excitation energy to the integrated device. Such optical components may include mirrors, reflectors, lenses, prisms, gratings, and/or tiltable windows, such as the example set of optical components arranged in FIG. 9-3.

In some embodiments, excitation energy from the excitation source module is coupled to the base instrument through an optical fiber, such as in the example shown in FIG. 9-4. The optical fiber connects an excitation energy output from the excitation source model to an input in the base instrument. In some embodiments, the optical fiber is a single mode fiber. Optical components within the base instrument direct the excitation energy to the integrated device. Alignment of the excitation energy to the integrated device may occur through such optical components. Feedback from an electrical signal received by the integrated device may direct adjustment of one or more optical components within the base instrument to improve the alignment of the excitation energy to the integrated device.

Another example of an excitation module that rests on top of integrated device is illustrated in FIGS. 9-5 to 9-11. The excitation source module contains one or more excitation sources in addition to optical and alignment components for delivering excitation energy to one or more grating couplers on the integrated device positioned at 9-501. Alignment components are included in module 9-502 and are positioned over integrated device 9-501. Coarse alignment of the excitation source to the integrated device may occur by placing steel ball bearings on the surface of the integrated device and forming, on the excitation source module, magnetized grooves that automatically register the steel ball bearings. As shown in FIG. 9-6, there are three steel ball bearings 9-503 bonded to the integrated device surface 9-501 and the excitation source module has three magnetized radial v-grooves 9-504 that automatically register the three ball bearings to stabilize positioning of the excitation source module to the integrated device, including all three translational and all three rotational degrees of freedom. The excitation source module 9-502 may include a hinge pin 9-505 to tilt the module away from integrated device in an up position to provide access to the integrated device. FIG. 9-6 shows the excitation source module in the up position.

FIG. 9-7 shows the same excitation source module in the down position when the steel ball bearings are registered by the magnetized grooves. On the top surface of the excitation source module there is a circuit board 9-506 with an excitation source, in this example a laser diode. The circuit board 9-506 with the laser diode, collimating lens 9-508, and heat sink 9-507 are shown in further detail in FIG. 9-8. The printed circuit board may have circuitry for driving and supporting the laser diode. There may be a focusable collimating lens to focus light from the laser diode. Additionally, there is a heat sink surrounding the laser diode for heat dissipation. The excitation source module has an entrance port 9-509 for the collimated laser beam, as shown in FIG. 9-9. The entrance port is surrounded by a heat conducting block 9-510 to receive the laser diode heat sink. Additionally, rotary actuators 9-511a, 9-511b, and 9-511c are provided on the excitation source module to control the x-y position and incidence angle of the delivered beam to the integrated device. The rotary actuators may be any suitable actuator that produces a rotary motion or torque, including stepper motors and servos. The rotary actuators control plane parallel plates that act as tiltable windows along the light path. The tilt of each of the plates is controlled by the corresponding rotary actuator. When using a point light source, such as a laser diode, introducing a plane parallel plate before a focusing lens in the light path adjusts the angle of incidence while introducing a plane parallel plate after the focusing lens adjust the x-y position of the beam. Optical components inside the excitation source module direct and modulate light from the laser diode, as illustrated in a cross-sectional view shown in FIG. 9-10. The path of the light beam is denoted by dotted lines. The light beam enters from the top surface of the excitation source module, which is into the plane of view from behind, and is reflected by a 45 degree prism to propagate to the top of the plane view of FIG. 9-10. A rotary actuator 9-511a with a plane parallel plate 9-512 is provided along the light path before an anamorphic prism 9-513 with an adjustable angle of incidence. The anamorphic prism stretches or shrinks the beam in one direction to adjust the cross-section of the beam from an elliptical profile to be substantially more circular in profile. The amount of beam stretching or shrinking is controlled by the angle of incidence of the prism. The light beam then reflects off another prism 9-514 to pass through a focusing lens 9-515 to bring the beam to focus on the integrated device. The light beam then passes through two more rotary actuator driven tiltable windows 9-516 that adjust the x-y position of the beam on the integrated device and the light beam propagates perpendicularly out of the plane of view towards the viewer in FIG. 9-10. An additional viewpoint illustrating the positioning of the three rotary actuators within the excitation source module is shown in FIG. 9-11.

Alignment along the excitation energy path from an excitation source to an integrated device may be performed at any suitable time after an integrated device is positioned within a base instrument. In some embodiments, the alignment of the excitation source and/or optical components in either the excitation source module or the base instrument is initially obtained and there is no subsequent re-alignment process. Such an alignment procedure may be called an initial static alignment. An initial static alignment process may be manual, automated, or a combination of a manual and automated process. In some embodiments, the alignment of the excitation source and/or optical components may undergo multiple re-alignments in a continuous, active alignment process. A continuous active alignment process may be automatic based on a feedback electrical signal from the integrated device. In some embodiments, the alignment process may include an initial manual alignment followed by a continuous active alignment.

Various possible parameters of the beam of excitation energy may be adjusted during an alignment process. Such parameters may include x-y-z positions, focus, angle with respect to the waveguide, angle perpendicular to the waveguide, and/or the magnification, aspect ratio, and/or astigmatism content of the beam. Variations for projected excitation energy beam alignment to the integrated device are summarized in FIG. 9-12.

B. Passive Alignment

Positioning of one or more excitation sources may occur through passive alignment of an optical fiber, which carries excitation energy, to an integrated device. Passive alignment techniques may include a series of components that securely position the optical fiber with respect to the grating coupler in order to couple excitation energy to a waveguide. The components are made of any suitable material, including plastic and metal. Passive alignment components are any suitable size in order to accommodate an optical fiber of a certain size. Additionally, the components may be designed for ease of connecting and disconnecting an optical fiber to an integrated device.

In some embodiments, some of the passive alignment components may form a receptacle for connecting and positioning of a ferrule for an optical fiber which carries excitation energy and aligns the ferrule with respect to an integrated device. The receptacle may be made of any suitable material, such as plastic or metal. The receptacle may be sized to frame the ferrule.

Passive alignment components may include mechanical reference components to achieve positioning of an optical fiber to an integrated device. The mechanical reference components may improve precision in positioning of the optical fiber with respect to a grating coupler on the integrated device. The mechanical reference components may be located on a surface of the integrated device. In some instances, mechanical references components set an angle of alignment of the ferrule to a surface of the integrated device. Mechanical reference components may set a distance from the surface of the integrated device such than the fiber ferrule does not contact the integrated device's surface. Additionally or alternatively, mechanical reference components may provide an indicator for a user to identify when correct alignment is achieved. As an example, a mechanical reference may provide a visual indication of correct alignment of the fiber ferrule within the receptacle. In some embodiments, a clip may be attached to the fiber ferrule to achieve correct rotational positioning of the fiber ferrule with respect to one or more passive alignment components.

Illustrated in FIGS. 9-12 to 9-16 are exemplary passive alignment components that may form a receptacle and/or mechanical references for a fiber ferrule. The fiber ferrule has a ferrule wall 9-1201 and a single-mode fiber (SMF) core 9-1202. In some embodiments, the fiber ferrule may have a diameter of 0.5 mm. As shown in FIG. 9-12, a planar cross-section view of an exemplary receptacle may include a component 9-1203 with two alignment walls to form a receptacle and contact the fiber ferrule when the fiber ferrule is positioned within the receptacle. The alignment walls may form a corner with an angle of 90 degrees. In some embodiments, one of the alignment walls may be optionally angled at 5 degrees from perpendicular to the surface of the integrated device. Mechanical reference components may position the fiber ferrule within the receptacle. In some embodiments, mechanical reference components on the surface of the integrated device may include a first mechanical reference cylinder aligned with the corner of the receptacle formed by the two alignment walls and a second mechanical reference cylinder aligned with a side of the alignment wall component. The first mechanical reference cylinder 9-1205 may be termed "corner pad" and the second mechanical reference cylinder 9-1204 may be termed "side pad." The mechanical reference cylinders may be formed by electroplating gold on the surface of the integrated device. Additional mechanical reference components may include one or more z-stop pads 9-1206 positioned on the surface of the integrated device to maintain a distance between the end of the fiber ferrule and the surface of the integrated device. The z-stop pads may be formed by electroplating gold on the surface of the integrated device. In some embodiments, a molded plastic clip 9-1207 may be attached to the fiber ferrule to provide rotational alignment with respect to the alignment wall component to position the ferrule into the corner of the two alignment walls by attaching to the alignment wall component. The molded plastic integrated device may also be configured to position the ferrule a distance from the surface of the integrated device, providing a z-stop when inserting the ferrule into the receptacle.

FIG. 9-13 illustrates a cross-section along line A-A' shown in FIG. 9-12 of an embodiment of a passive receptacle where the fiber ferrule is aligned with respect to the integrated device surface 9-1208. The end of the fiber ferrule may be angled to 8 degrees perpendicular to the direction of the fiber core. Such an angle may be formed by polishing the end of the fiber ferrule. One or more z-stop pads and/or a corner pad may be provided on the surface of the integrated device. While positioned in the receptacle, the fiber core may overlap with the grating coupler 9-1209 in the integrated device in order to couple excitation energy to a waveguide.

Another embodiment of alignment of the fiber ferrule is shown in FIG. 9-14 illustrating a cross-section along line A-A' shown in FIG. 9-12. In this embodiment, a molded plastic clip 9-1207 is attached to the fiber ferrule 9-1201 to provide positioning of the fiber ferrule 9-1201 with respect to the alignment wall component 9-1203 such that the ferrule is in contact with the alignment walls and forced into the 90 degree corner between the two alignment walls. The molded plastic clip attached to the fiber ferrule may also provide a z-stop for the fiber ferrule by having a section that extends from the end of the fiber ferrule such that when the molded plastic clip is in contact with the integrated device the end of the fiber ferrule is positioned a distance from the surface of the integrated device.

In another embodiment, a step is formed on the metal surface of the integrated device to provide a z-stop when positioning the fiber ferrule. FIG. 9-15 illustrates a cross-section view of such an embodiment along line A-A' of FIG. 9-12. As the fiber ferrule 9-1201 is positioned, the end of the fiber ferrule contacts step 9-1210 and positions the fiber ferrule with respect to the integrated device surface.

FIG. 9-16 illustrates an embodiment where one of the alignment walls 9-1603 has a 5 degree angle with respect to perpendicular to the integrated device surface. When positioned in such a receptacle, the fiber ferrule contacts the angled alignment wall such that the fiber core is also at an angle perpendicular to the integrated device surface. The end of the fiber ferrule may be perpendicular to the direction of the fiber core. In such an embodiment, the end of the fiber ferrule may have no angle polished since the angle of the optical fiber to the integrated device surface is achieved by the angle of the alignment wall.

In some embodiments, a fiber ferrule may be positioned in a molded plastic component substantially parallel to the surface of the integrated device and the molded plastic component may have one or more lenses to direct light. Excitation energy from such a fiber ferrule may propagate from the optical fiber through the molded plastic component to couple with a grating coupler on the integrated device surface. The molded plastic component may be made from a material having an index of refraction to direct the excitation energy towards the grating coupler. Additionally, the molded plastic may be formed with edge angles to direct the excitation energy towards the grating coupler. When positioned in the molded plastic component, the fiber ferrule may be aligned within the molded plastic component such that through a combination of the index of refraction and one or more edge angles of the molded plastic component the excitation energy may be directed towards the grating coupler on the integrated device. FIG. 9-17 illustrates an exemplary molded plastic component configured to fit a fiber ferrule with a diameter of 500 microns. Excitation energy from the optical fiber propagates through a collimating surface to an angled surface and reflects from the angled surface, propagating through the molded plastic of a certain refractive index, to the grating coupler. The angle of incidence of the excitation energy at integrated device surface may depend on the angle of the angled surface and the index of refraction of the material. In some embodiments, the angled surface may be angled at 45 degrees minus the ratio of the angle of incidence to the index of refraction in order to align the excitation energy to the integrated device.

FIG. 9-18 illustrates an exemplary arrangement of a fiber ferrule, an alignment wall component, and an integrated device. The fiber ferrule is positioned within the alignment wall component in a corner of the integrated device. The fiber ferrule has a diameter of 0.5 mm. The alignment walls are 0.75 mm thick. Alignment pads are positioned inside the receptacle and are 200 microns in diameter. When positioned in such a receptacle, excitation energy from the optical fiber may couple with an initial waveguide aligned in a direction of the integrated device having a certain length. In some embodiments, the initial waveguide is aligned in the direction of the integrated device with a length of approximately 9 mm.

FIG. 9-19 illustrates coupling of the excitation energy from the fiber core to a waveguide via the grating coupler. In some embodiments, the excitation energy beam may expand to 15 microns in diameter. The radius of curvature of the grating coupler features may be approximately 81 microns where the grating coupler refocuses the excitation beam. The grating coupler may then refocus excitation energy towards a horn and ultimately a waveguide.

In some embodiments, passive alignment may occur through a beam projected onto a coupler. Projecting a beam of excitation energy may occur when there is sufficient stability of the optical apparatus to allow proper alignment. During manufacture, alignment of a beam may be set such that when a integrated device is correctly positioned the beam couples to the grating coupler on the integrated device. The integrated device may be inserted using techniques that require accurate alignment of an inserted integrated device to a laser module that includes the excitation source. As an example, alignment of an inserted integrated device may be achieved passively through the use of kinematic balls and rods. In this case, balls, positioned on the integrated device, allow the laser module to register the integrated device and further align the integrated device to the laser module after the integrated device is placed in proximity by the user. In some embodiments, the positional accuracy of the integrated device is within the beam diameter. As an example, placing balls on a integrated device may allow positioning of a 20 µm beam to an accuracy within 5 µm. In some instances, the angle of the beam to the grating coupler may have accuracy to within a few milliradians. Additionally, the spacing of the balls on the integrated device may be adjusted to allow for improved manual placement of the integrated device with respect to the light module. As an example, spacing of the balls to have more than a 5 mm separation may allow for milliradian accuracy on manual placement. Such passive alignment techniques may lower the overall cost for the system and reduce a need for active alignment techniques that may interfere with operation of the system.

C. Excitation Energy Monitoring Sensors

A variety of monitoring sensors may be formed within the integrated substrate and configured to monitor the intensity and/or power of excitation energy at different locations within the integrated device. An electrical signal produced by such monitoring sensors may be used in a feedback process during operation of the integrated device. The electrical signal from the monitoring signals may also indicate a reduced quality of the excitation energy propagated through the integrated device, producing an error signal for an operator. This may include an indication that an excitation source has or is failing. In some instances, the monitoring sensors may provide a feedback signal during alignment of the excitation energy to the grating coupler. The monitoring sensors may be any suitable sensor, including light sensors such as photodetectors and photodiodes.

Monitoring sensors may be provided to monitor the excitation energy along a waveguide. Sensors may be provided at the beginning of the waveguide where the excitation energy initially couples with the waveguide, at the end of the waveguide after the waveguide has coupled with a row of sample wells, and/or anywhere along the length of the waveguide. A grating coupler may be formed to improve coupling of the excitation energy out of the waveguide in order to be detected by a sensor. The information from the monitoring sensors may be used to control parts of the system and/or as inputs for signal processing.

In some embodiments, a monitoring sensor is positioned underneath the grating coupler to receive excitation energy that passes through the grating coupler. The signal based on the intensity of the excitation energy detected by such a sensor may be used to position and align the excitation energy beam to the grating coupler. In some instances, multiple monitoring sensors are located underneath the grating coupler. A non-transparent layer of material, such as metal, having multiple holes may be located between the grating coupler and the multiple sensors. Each hole in the non-transparent layer may overlap with each sensor such that excitation energy that passes through the hole is detected by the sensor. By detecting excitation energy that passes through each hole by the multiple sensors, the position of the excitation energy beam on the grating may be determined. FIG. 9-20 shows an example of such an arrangement where four holes 9-2010 in a metal layer are positioned to let light pass to four sensors 9-2008, which may be considered a quadrant photodetector. As excitation energy 9-2004 couples to the grating coupler 9-2002 and into tapered waveguide 9-2006, some of the excitation energy may pass through the holes 9-2010 in the metal layer to one or more of sensors 9-2008. The metal layer may act as a reflecting layer in regions without holes 9-2010 and may improve coupling of excitation energy 9-2004 to grating coupler 9-2002 and tapered waveguide 9-2006. The signal from the sensors 9-2008 may provide a vector for alignment feedback, with sufficient information to deduce both the magnitude and the sign required for each adjustment in the feedback loop. In some instances, alignment feedback may be provided with each pulse of excitation energy. Alignment may be achieved when the beam of excitation energy is centered on the four sensors.

In some embodiments, one or more sensors associated with each pixel may be used for monitoring and/or alignment of the excitation energy. The power or intensity of the excitation energy may be set to a low value, such as a 'low-power' mode and positioning of the excitation source may be performed by adjusting one or more of the x-y-z positions and/or angles relative to the waveguide in the integrated device. Improving alignment of the excitation energy may occur by positioning the beam of excitation energy where the intensity signal detected by the photodetectors increases to a certain value. In some instances, adjusting parameters of the excitation source may be performed to determine an intensity signal above a certain value, indicating sufficient alignment for operation.

In some embodiments, monitor sensors may be located at the end of each waveguide to detect the amount of light propagated along each waveguide. A grating associated with each monitor sensor may be positioned such that the grating and monitor sensor are located on opposite sides of the waveguide. An example of sensors 9-2101a and 9-2101b and gratings 9-2102a and 9-2102b provided at both ends of a waveguide is shown in FIG. 9-21. In some instances, signals at both ends of the waveguide may be used for further signal processing to compensate for excitation energy loss along the waveguide. When a waveguide is configured to provide excitation energy to multiple sample wells, compensation for overall excitation energy loss along the length of the waveguide may be used to deliver at least a certain amount of excitation energy to each sample well. Additionally, absorptive elements 9-2104 at the end of a waveguide may be positioned to reduce scattering of any light remaining in the waveguide, as shown in FIG. 9-22.

Additionally or alternatively, monitor sensors may be located at specific positions along the path of a waveguide. Such monitor sensors may be positioned before multi-mode interference splitters, after multi-mode interference splitters, before one or more sample wells, and/or after one or more sample wells. Such locations for monitor sensors may be selected based on where excitation energy loss may occur and/or where monitoring of excitation energy loss may be a factor in overall operation of the integrated device.

In some embodiments, sensors may be located on either side of a pixel array of the integrated device to monitor input excitation energy and output excitation energy from one or more waveguides. The integrated device may have one or more grating couplers for coupling the input excitation energy into one or more waveguides. The input waveguides may be split into multiple waveguides, where each split waveguide delivers excitation energy to a row of sample wells. On one side, the sensors may monitor position of the input excitation energy on the grating coupler. The sensors on the other side may measure the excitation energy from the end of one or more waveguides after a row of sample wells. In some embodiments, alignment of the excitation source to the integrated device may consist of initially centering the excitation energy beam on the grating coupler using signals from the input sensors indicating the beam's x-y positioning and further adjusting excitation energy beam parameters, such as focus and/or an incidence angle, from signals from an output sensor at the end of each waveguide. In some instances, signals from the output sensors may be used as a calibration step that may be determined for each integrated device prior to using the integrated device for analysis. Additionally, signals from the output sensors may be used to normalize measurements obtained with the integrated device.

FIGS. 9-22 and 9-23 illustrate exemplary arrangements of monitoring sensors where there are two columns of sensors on either side of the pixel array. Each sensor has a center-to-center spacing of twice the pixel pitch in the x and y directions. Such an arrangement of sensors may accommodate different configurations of grating couplers. One of the sets of two columns monitor the input excitation energy where a set of four sensors in a square arrangement are used as a quadrant detector, as discussed above with reference to FIG. 9-20. A grating coupler 9-2201 may be positioned over four sensors 9-2202 in the input columns with a layer opaque to the excitation energy in between the grating coupler and the sensors. In such a configuration, the fours sensors may be used to monitor the positioning of the excitation energy beam on the grating coupler. For example, the intensity measured by the four sensors may be used for monitoring x-y positioning of the excitation energy beam and alignment onto the grating coupler. The two columns on the output side may monitor the excitation energy out of individual waveguides. As illustrated in FIGS. 9-22, a sensor 9-2204 in the output columns is connected to an individual waveguide 9-2203. A grating coupler 9-2205 may be used to couple the excitation energy from waveguide to the output sensor. An output sensor may monitor the excitation energy directed into a waveguide by measuring the power coupled at the end each waveguide after a row of sample wells. FIG. 9-22 illustrates an exemplary arrangement of grating couplers for the input waveguides on the input monitoring sensors, splitting, by component 9-2206, of the input waveguides into waveguides that deliver excitation energy to sample wells 9-2207, and grating couplers at the ends of the waveguides positioned on output sensors, where each output sensor is used to monitor a waveguide. FIG. 9-23 illustrates an exemplary arrangement of an integrated device with two columns of monitoring sensors 9-2307 on either side of the pixel array to provide an alignment readout of the excitation energy as discussed above.

D. Multiple Excitation Sources

Multiple excitation sources may provide light having different energies or wavelengths to the plurality of sample wells. Each of the multiple excitation sources may provide light having a different characteristic wavelength or energy. One or more markers may be identified based on whether light from an excitation source excites a marker such that the marker emits a photon. In this manner, markers may be identified based on their absorption spectra by measuring the response of a sample after illuminating the sample with light from the different excitation sources. For example, a sample having a marker may be illuminated with light from a first excitation source followed by light from a second excitation source. If the marker emits luminescence in response to being illuminated by light from the first excitation source, then the marker may have an absorption spectrum that overlaps with the characteristic wavelength of the first excitation source.

In some embodiments, it is possible to use a plurality of excitation sources for the excitation energy. This plurality of sources may be, for example, implemented as a diode laser bar comprising multiple diode laser emitters. In the manufacture of laser diodes, multiple emitters are commonly fabricated lithographically on a single substrate, and then diced into single-emitter pieces for individual packaging. But it is also possible to dice the substrate into pieces with a plurality of emitters. In some embodiments, the emitters are nearly identical, and may be spaced equally from each other to lithographic tolerances, typically of the order of 0.1 micrometer.

To couple the light from multiple emitters onto the integrated device, it is possible to image each emitter onto a separate grating coupler on the integrated device. FIG. 9-24 shows two ways of coupling the excitation energy to the integrated device. In both examples shown in FIG. 9-24, the array of emitters is along the dotted line at the left, and the array of grating couplers is along the dotted line at the right. The diagrams illustrate arrays of four emitters and four grating couplers, but any number of emitters and couplers is possible.

In the top example of FIG. 9-24A, two lenses are used, with the left-hand lens being at least as large as the array of emitters, and the right-hand lens being at least as large as the array of grating couplers. This example illustrates the case of unity magnification, but any appropriate magnification can be used, as long as each lens is one focal length from its corresponding array, and as long as the distance between the lenses is the sum of their focal lengths.

In the bottom example of FIG. 9-24B, arrays of lenses are used to image the emitters to the grating couplers. Each array of lenses can be implemented as a monolithic or polylithic array of spherical or aspherical lenses, or as a monolithic or polylithic array of cylindrical or acylindrical lenses in the plane of the diagram, supplemented by a single cylindrical or acylindrical lens in the orthogonal direction. This example illustrates the case of unity magnification, but any appropriate magnification can be used, as long as the appropriate beam-expanding or beam-compacting lenses are inserted between the arrays of lenses.

Sample wells and waveguides may be arranged in an integrated device in any suitable way to allow coupling of excitation energy from multiple excitation sources with a plurality of sample wells. Multiple excitation sources may provide light of different characteristic wavelengths to the plurality of sample wells. A waveguide positioned to receive light from the multiple excitation sources may deliver the light to one or more sample wells. An integrated device may include additional components (e.g., power splitter, wavelength combiner) that allow light from multiple excitation sources to be delivered to multiple sample wells.

Some embodiments relate to an integrated device having a waveguide configured to propagate more than one characteristic wavelengths of light received from one end of the waveguide. Sample wells positioned proximate to the waveguide may couple a portion of the light from the waveguide. FIG. 9-25A shows an exemplary schematic for coupling light from two excitation sources in an integrated device. A first excitation source provides light having a first characteristic wavelength, $\lambda 1$. A second excitation source provides light having a second characteristic wavelength, $\lambda 2$. The integrated device includes two grating couplers: a first grating coupler configured to couple light from the first excitation source having $\lambda 1$, and a second grating coupler configured to couple light from the second excitation source having $\lambda 2$. The integrated device includes two power splitters, each coupled to one of the grating couplers. The power splitter coupled to the first grating coupler is sized and shaped to provide multiple outputs configured to propagate light having $\lambda 1$. The power splitter coupled to the second grating coupler is sized and shaped to provide multiple outputs configured to propagate light having $\lambda 2$. A wavelength combiner receives an output from both of the power splitters as inputs and is sized and shaped to have an output configured to couple both $\lambda 1$ and $\lambda 2$ into a waveguide. In this manner, sample wells positioned proximate to the waveguide may receive both $\lambda 1$ and $\lambda 2$ from the first and second excitation sources.

Some embodiments relate to an integrated device having a waveguide configured to propagate more than one characteristic wavelengths of light received from opposite ends of the waveguide. Sample wells positioned proximate to the waveguide may couple a portion of the light from the waveguide. FIG. 9-25B shows an exemplary schematic for coupling light from two excitation sources in an integrated device. A waveguide in the integrated device are configured to receive light having a first characteristic wavelength, $\lambda 1$, from one end of the waveguide and light having a second characteristic wavelength, $\lambda 2$, from another end of the waveguide. The integrated device includes two grating couplers: a first grating coupler configured to couple light from the first excitation source having $\lambda 1$, and a second grating coupler configured to couple light from the second excitation source having $\lambda 2$. The integrated device includes two power splitters, each coupled to one of the grating couplers. The power splitter coupled to the first grating coupler is sized and shaped to provide an output configured to propagate light having $\lambda 1$ and couple with a first end of a waveguide. The power splitter coupled to the second grating coupler is sized and shaped to provide to provide an output configured to propagate light having $\lambda 2$ and couple with a second end of the waveguide.

Some embodiments relate to an integrated device having two waveguides positioned relative to a sample well such that light propagating in each of the two waveguides is couple to the sample well. The two waveguides are coupled to different excitation sources that provide light having different characteristic wavelengths. FIG. 9-25C shows an exemplary schematic for coupling light from two excitation sources in an integrated device. A first waveguide is configured to propagate light having a first characteristic wavelength, $\lambda 1$. A second waveguide is configured to propagate light having a second characteristic wavelength, $\lambda 2$. A sample well is positioned to couple light having $\lambda 1$ from the first waveguide and light having $\lambda 2$ from the second waveguide. The first waveguide may receive light from an excitation source by a combination of a grating coupler and/or a power splitter configured to propagate light having $\lambda 1$. The second waveguide may receive light from an excitation source by a combination of a grating coupler and/or power splitter configured to propagate light having $\lambda 2$.

V. Example Measurements with the Integrated Device and Excitation Source

Measurements for detecting, analyzing, and/or probing molecules in a sample may be obtained using any combination of the integrated device or integrated device and an excitation source described in the present application. The excitation source may be a pulsed excitation source or, in some instances, a continuous wave source. A luminescent marker tagged to a specific sample may indicate the presence of the sample. Luminescent markers may be distinguished by an excitation energy, luminescence emission wavelength, and/or the lifetime of emission energy emitted by a marker. Markers with similar luminescence emission wavelength may be identified by determining the lifetime for each marker. Additionally, markers with similar lifetimes may be identified by the luminescence emission wavelength for each marker. By using markers, where markers are identified by a combination of the temporal and/or spectral properties of the emitted luminescence, a quantitative analysis and/or identification of markers and associated samples may be performed.

Lifetime measurements may be used to determine that a marker is present in a sample well. The lifetime of a luminescent marker may be identified by performing multiple experiments where the luminescent marker is excited into an excited state and then the time when a photon emits is measured. The excitation source is pulsed to produce a pulse of excitation energy and directed at the marker. The time between the excitation pulse and a subsequent photon emission event from a luminescent marker is measured. By repeating such experiments with a plurality of excitation pulses, the number of instances a photon emits within a particular time interval may be determined. Such results may populate a histogram representing the number of photon emission events that occur within a series of discrete time intervals or time bins. The number of time bins and/or the time interval of each bin may be adjusted to identify a particular set of lifetimes and/or markers.

What follows is a description of example measurements that may be made to identify luminescent markers in some embodiments. Specifically, examples of distinguishing luminescent markers using only a luminescent lifetime measurement, a joint spectral and luminescent lifetime measurement, and only a luminescent lifetime measurement, but using two different excitation energies are discussed. Embodiments are not limited to the examples detailed below. For example, some embodiments may identify the luminescent markers using only spectral measurements. Further details of example measurements may be found in U.S. Provisional Patent Application 62/164,482, entitled "METHODS FOR NUCLEIC ACID SEQUENCING," filed May 20, 2015, which is incorporated by reference in its entirety.

Any suitable luminescent markers may be used. In some embodiments, commercially available fluorophores may be used. By way of example and not limitation, the following fluorophores may be used: Atto Rho14 ("ATRho14"), Dylight 650 ("D650"), SetaTau 647 ("ST647"), CF 633 ("C633"), CF 647 ("C647"), Alexa fluor 647 ("AF647"), BODIPY 630/650 ("B630"), CF 640R ("C640R") and/or Atto 647N ("AT647N").

Additionally and/or optionally, luminescent markers may be modified in any suitable way to increase the speed and accuracy of the sample analysis process. For example, a photostabilizer may be conjugated to a luminescent marker. Examples of photostabilizers include but are not limited to oxygen scavengers or triplet-state quenchers. Conjugating photostabilizers to the luminescent marker may increase the rate of photons emitted and may also reduce a "blinking" effect where the luminescent marker does not emit photons. In some embodiments, when a biological event occurs on the millisecond scale, an increased rate of photon emission may increase the probability of detection of the biological event. Increased rates of photon events may subsequently increase the signal-to-noise ratio of luminescence signal and increase the rate at which lifetime measurements are made, leading to a faster and more accurate sample analysis.

Furthermore, the environment in a sample well of an integrated device may be tuned to engineer the lifetime of the markers as needed. This can be achieved by recognizing that the lifetime of a marker is effected by the density of state of the marker, which can be tuned using the environment. For example, the farther a marker is from the bottom metal layer of the sample well, the longer the lifetime. Accordingly, to increase the lifetime of a marker, the depth of a bottom surface of a sample well, such as a divot, may extend a certain distance from a metal layer. Also, the materials used to form the sample well can affect the lifetime of the markers. While different markers typically have their lifetimes shifted in the same direction (e.g., either longer or shorter), the affect may scale differently for different markers. Accordingly, two markers that cannot be distinguished via lifetime measurements in free-space may be engineered to be distinguishable by fabricating the sample well environment to adjust the lifetimes of the various markers.

A. Single Molecule Detection and Sequencing

According to an aspect of the present application, a single molecule can be identified (e.g., distinguished from other possible molecules in a reaction sample) based on one or more properties of a series of photons that are emitted from the molecule when it is exposed to a plurality of separate light pulses. In some embodiments, the molecule is labelled with a luminescent marker. In some embodiments, the luminescent marker is a fluorophore. In some embodiments, the luminescent marker can be identified or distinguished based on a property of the luminescent marker. Properties of a luminescent marker (e.g., a fluorophore) include, but are not limited to luminescent lifetimes, absorption spectra, emission spectra, luminescence quantum yield, and luminescent intensity, and combinations of two or more thereof.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified form a bodily fluid or tissue of the subject, and amplified through nucleic acid amplification, such as polymerase chain reaction (PCR). Then, the one or more nucleic acids molecules or subunits thereof can be identified, such as through sequencing. However, in some embodiments nucleic acid samples can be evaluated (e.g., sequenced) as described in this application without requiring amplification.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

During sequencing, a polymerizing enzyme may couple (e.g., attach) to a priming location of a target nucleic acid molecule. The priming location can be a primer that is complementary to the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support, such as a sample well. In some embodiments, a sequencing primer may be immobilized to a solid support and hybridization of the target nucleic acid molecule also immobilizes the target nucleic acid molecule to the solid support. Via the action of an enzyme (e.g., a polymerase) capable of adding or incorporating a nucleotide to the primer, nucleotides can be added to the primer in 5' to 3', template bound fashion. Such incorporation of nucleotides to a primer (e.g., via the action of a polymerase) can generally be referred to as a primer extension reaction. Each nucleotide can be associated with a detectable marker as part of a tag that can be detected and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). Moreover, some sequencing by synthesis methods can include the presence of a population of target nucleic acid molecules (e.g, copies of a target nucleic acid) and/or a step of amplification of the target nucleic acid to achieve a population of target nucleic acids.

The single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

The sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent marker associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light can be attributed to a particular dNTP incorporated. The sequence obtained from the collection of detected luminescent markers can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphophates with at least 4, 5, 6, 7, 8, 9, or 10 phosphate groups). Such ribonucleotides and deoxyribonucleotides can form various types of tags by using a linker to attach a marker to a ribonucleotide or a deoxyribonucleotide.

Signals emitted upon the incorporation of nucleosides can be stored in memory and processed at a later point in time to determine the sequence of the target nucleic acid template. This may include comparing the signals to a reference signals to determine the identities of the incorporated nucleosides as a function of time. Alternative or in addition to, signal emitted upon the incorporation of nucleoside can be collected and processed in real time (i.e., upon nucleoside incorporation) to determine the sequence of the target nucleic acid template in real time.

Nucleic acid sequencing of a plurality of single-stranded target nucleic acid templates may be completed where multiple sample wells are available, as is the case in devices described elsewhere herein. Each sample well can be provided with a single-stranded target nucleic acid template and a sequencing reaction can be completed in each sample well. Each of the sample wells may be contacted with the appropriate reagents (e.g., dNTPs, sequencing primers, polymerase, co-factors, appropriate buffers, etc.) necessary for nucleic acid synthesis during a primer extension reaction and the sequencing reaction can proceed in each sample well. In some embodiments, the multiple sample wells are contacted with all appropriate dNTPs simultaneously. In other embodiments, the multiple sample wells are contacted with each appropriate dNTP separately and each washed in between contact with different dNTPs. Incorporated dNTPs can be detected in each sample well and a sequence determined for the single-stranded target nucleic acid in each sample well as is described above.

Embodiments directed toward single molecule RNA sequencing may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

Sequence reads can be used to reconstruct a longer region of a genome of a subject (e.g., by alignment). Reads can be used to reconstruct chromosomal regions, whole chromosomes, or the whole genome. Sequence reads or a larger sequence generated from such reads can be used to analyze a genome of a subject, such as to identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms (DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

In some embodiments, the molecules are identified or distinguished based on luminescent lifetime. In some embodiments, the molecules are identified or distinguished based on luminescent intensity. In some embodiments, the molecules are identified or distinguished based on the wavelength of the delivered excitation energy necessary to observe an emitted photon. In some embodiments, the molecules are identified or distinguished based on the wavelength of an emitted photon. In some embodiments, the molecules are identified or distinguished based on both luminescent lifetime and the wavelength of the delivered excitation energy necessary to observe an emitted photon. In some embodiments, the molecules are identified or distinguished based on both a luminescent intensity and the wavelength of the delivered excitation energy necessary to observe an emitted photon. In some embodiments, the molecules are identified or distinguished based on luminescent lifetime, luminescent intensity, and the wavelength of the delivered excitation energy necessary to observe an emitted photon. In some embodiments, the molecules are identified or distinguished based on both luminescent lifetime and the wavelength of an emitted photon. In some embodiments, the molecules are identified or distinguished based on both a luminescent intensity and the wavelength of an emitted photon. In some embodiments, the molecules are identified or distinguished based on luminescent lifetime, luminescent intensity, and the wavelength of an emitted photon.

In certain embodiments, different types of molecules in a reaction mixture or experiment are labeled with different luminescent markers. In some embodiments, the different markers have different luminescent properties which can be distinguished. In some embodiments, the different markers are distinguished by having different luminescent lifetimes, different luminescent intensities, different wavelengths of emitted photons, or a combination thereof. The presence of a plurality of types of molecules with different luminescent markers may allow for different steps of a complex reaction to be monitored, or for different components of a complex reaction product to be identified. In some embodiments, the order in which the different types of molecules react or interact can be determined.

In certain embodiments, the luminescent properties of a plurality of types of molecules with different luminescent markers are used to identify the sequence of a biomolecule, such as a nucleic acid or protein. In some embodiments, the luminescent properties of a plurality of types of molecules with different luminescent markers are used to identify single molecules as they are incorporated during the synthesis of a biomolecule. In some embodiments, the luminescent properties of a plurality of types of nucleotides with different luminescent markers are used to identify single nucleotides as they are incorporated during a sequencing reaction. In some embodiments, methods, compositions, and devices described in the application can be used to identify a series of nucleotides that are incorporated into a template-dependent nucleic acid sequencing reaction product synthesized by a polymerase enzyme.

In certain embodiments, the template-dependent nucleic acid sequencing product is carried out by naturally occurring nucleic acid polymerases. In some embodiments, the polymerase is a mutant or modified variant of a naturally occurring polymerase. In some embodiments, the template-dependent nucleic acid sequence product will comprise one or more nucleotide segments complementary to the template nucleic acid strand. In one aspect, the application provides a method of determining the sequence of a template (or target) nucleic acid strand by determining the sequence of its complementary nucleic acid strand.

In another aspect, the application provides methods of sequencing target nucleic acids by sequencing a plurality of nucleic acid fragments, wherein the target nucleic acid comprises the fragments. In certain embodiments, the method comprises combining a plurality of fragment sequences to provide a sequence or partial sequence for the parent target nucleic acid. In some embodiments, the step of combining is performed by computer hardware and software. The methods described herein may allow for a set of related target nucleic acids, such as an entire chromosome or genome to be sequenced.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome. In some embodiments, the sequence of an entire genome is determined. However, in some embodiments, sequence information for a subset of a genome (e.g., one or a few chromosomes, or regions thereof) or for one or a few genes (or fragments thereof) are sufficient for diagnostic, prognostic, and/or therapeutic applications.

In some embodiments, the target nucleic acid molecule used in single molecule sequencing is a single-stranded target nucleic acid (e.g. deoxyribonucleic acid (DNA), DNA derivatives, ribonucleic acid (RNA), RNA derivatives) template that is added or immobilized to a sample well containing at least one additional component of a sequencing reaction (e.g., a polymerase such as, a DNA polymerase, a sequencing primer) immobilized or attached to a solid support such as the bottom of the sample well. In some cases, a sequencing primer can be annealed to a target nucleic acid molecule that may or may not be immobilized to a solid support, such as a sample well (e.g., nanoaperture). In some embodiments, a sequencing primer may be immobilized to a solid support and hybridization of the target nucleic acid molecule also immobilizes the target nucleic acid molecule to the solid support. In some embodiments, a polymerase is immobilized to a solid support and soluble primer and target nucleic acid are contacted to the polymerase. However, in some embodiments a complex comprising a polymerase, a target nucleic acid and a primer is formed in solution and the complex is immobilized to a solid support (e.g., via immobilization of the polymerase, primer, and/or target nucleic acid).

Under appropriate conditions, a polymerase enzyme that is contacted to an annealed primer/target nucleic acid can add or incorporate one or more nucleotides onto the primer, and nucleotides can be added to the primer in a 5' to 3', template bound fashion. Such incorporation of nucleotides onto a primer (e.g., via the action of a polymerase) can generally be referred to as a primer extension reaction. Each nucleotide can be associated with a detectable marker that can be detected and identified (e.g., based on its luminescent lifetime, emission spectra, absorption spectra, and/or other characteristics) and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some embodiments, sequencing by synthesis methods can include the presence of a population of target nucleic acid molecules (e.g., copies of a target nucleic acid) and/or a step of amplification of the target nucleic acid to achieve a population of target nucleic acids. However, in some embodiments sequencing by synthesis is used to determine the sequence of a single molecule in each reaction that is being evaluated (and nucleic acid amplification is not required to prepare the target template for sequencing). In some embodiments, a plurality of single molecule sequencing reactions are performed in parallel (e.g., on a single integrated device or chip) according to aspects of the present application.

Embodiments are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp.

The target nucleic acid molecule or the polymerase can be attached to a sample wall, such as at the bottom of the sample well directly or through a linker. The sample well (e.g., nanoaperture) also can contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent markers, such as fluorophores. In some embodiments, each class of dNTPs (e.g. adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent marker such that detection of light emitted from the marker indicates the identity of the dNTP that was incorporated into the newly synthesized nucleic acid. Emitted light from the luminescent marker can be detected and attributed to its appropriate luminescent marker (and, thus, associated dNTP) via any suitable device and/or method, including such devices and methods for detection described elsewhere herein. The luminescent marker may be conjugated to the dNTP at any position such that the presence of the luminescent marker does not inhibit the incorporation of the dNTP into the newly synthesized nucleic acid strand or the activity of the polymerase. In some embodiments, the luminescent marker is conjugated to the terminal phosphate (the gamma phosphate) of the dNTP.

In some embodiments, the sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent marker associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light (e.g., having a particular emission lifetime, intensity, and/or combination thereof) can be attributed to a particular dNTP incorporated. The sequence obtained from the collection of detected luminescent markers can then be used to determine the sequence of the single-stranded target nucleic acid template via sequence complementarity.

As an example, FIG. 10-1 schematically illustrates the setup of a single molecule nucleic acid sequencing method. The example is not meant to limit the invention in any way.

610 is a sample well (e.g., nanoaperture) configured to contain a single complex comprising a nucleic acid polymerase 601, a target nucleic acid 602 to be sequenced, and a primer 604. In this example, a bottom region of sample well 610 is depicted as a target volume 620. In FIG. 10-1 the complex comprising polymerase 601 is confined in target volume 620. The complex may optionally be immobilized by attachment to a surface of the sample well. In this example the complex is immobilized by a linker 603 comprising one or more biomolecules (e.g., biotin) suitable for attaching the linker to the polymerase 601.

The volume of the sample well also contains a reaction mixture with suitable solvent, buffers, and other additives necessary for the polymerase complex to synthesize a nucleic acid strand. The reaction mixture also contains a plurality of types of luminescently labeled nucleotides. Each type of nucleotide is represented by the symbols *-A, @-T, $-G, #-C, wherein A, T, G, and C represent the nucleotide base, and the symbols *, @, $, and # represent a unique luminescent marker attached to each nucleotide, through linker -. In FIG. 10-1, a #-C nucleotide is currently being incorporated into the complementary strand 602. The incorporated nucleotide is located within the target volume 620.

FIG. 10-1 also indicates with arrows the concept of an excitation energy being delivered to a vicinity of the target volume, and luminescence being emitted towards a detector. The arrows are schematic, and are not meant to indicate the particular orientation of excitation energy delivery or luminescence. Some luminescences may emit on a vector which is not directed to the detector (e.g., towards the sidewall of the sample well) and may not be detected.

FIG. 10-2 schematically illustrates a sequencing process in a single sample well over time. Stages A through D depict a sample well with a polymerase complex as in FIG. 10-1. Stage A depicts the initial state before any nucleotides have been added to the primer. Stage B depicts the incorporation event of a luminescently labeled nucleotide (#-C). Stage C, depicts the period between incorporation events. In this example, nucleotide C has been added to the primer, and the label and linker previously attached to the luminescently labeled nucleotide (#-C) has been cleaved. Stage D depicts a second incorporation event of a luminescently labeled nucleotide (*-A). The complementary strand after Stage D consists of the primer, a C nucleotide, and an A nucleotide.

Stage A and C, both depict the periods before or between incorporation events, which are indicated in this example to last for about 10 milliseconds. In stages A and C, because there is no nucleotide being incorporated, there is no luminescently labeled nucleotide in the target volume (not drawn in FIG. 10-2), though background luminescence or spurious luminescence from a luminescently labeled nucleotide which is not being incorporated may be detected. Stage B and D show incorporation events of different nucleotides (#-C, and *-A, respectively). In this example these events are also indicated to last for about 10 milliseconds.

The row labeled "Raw bin data" depicts the data generated during each Stage. Throughout the example experiment, a plurality of pulses of light is delivered to the vicinity of the target volume. For each pulse a detector is configured to record any emitted photon received by the detector, and assign the detected photon to a time bin based on the time duration since the last pulse of excitation energy. In this example there are 3 bins, and the "Raw bin data" records a value of 1 (shortest bars), 2 (medium bars), or 3 (longest bars), corresponding to the shortest, middle, and longest bins, respectively. Each bar indicates detection of an emitted photon.

Since there is no luminescently labeled nucleotide present in the target volume for Stage A or C, there are no photons detected. For each of Stage B and D a plurality of luminescences is detected during the incorporation event. Luminescent marker # has a shorter luminescence lifetime than luminescent marker *. The Stage B data is thus depicted as having recorded lower average bin values, than Stage D where the bin values are higher.

The row labeled "Processed data" depicts raw data which has been processed to indicate the number (counts) of emitted photons at times relative to each pulse. In this example the data is only processed to determine luminescent lifetime, but the data may also be evaluated for other luminescent properties, such as luminescent intensity or the wavelength of the absorbed or emitted photons. The exemplary processed data approximates an exponential decay curve characteristic for the luminescence lifetime of the luminescent marker in the target volume. Because luminescent marker # has a shorter luminescence lifetime than luminescent marker *, the processed data for Stage B has fewer counts at longer time durations, while the processed data for Stage D has relatively more counts at longer time durations.

The example experiment of FIG. 10-2 would identify the first two nucleotides added to the complementary strand as CA. For DNA, the sequence of the target strand immediately after the region annealed to the primer would thus be identified as GT. In this example the nucleotides C and A could be distinguished from amongst the plurality of C, G, T, and A, based on luminescent lifetime alone. In some embodiments, other properties, such as the luminescent intensity or the wavelength of the absorbed or emitted photons may be necessary to distinguish one or more particular nucleotides.

B. Luminescent Properties

As described herein, a luminescent molecule is a molecule that absorbs one or more photons and may subsequently emit one or more photons after one or more time durations. The luminescence of the molecule is described by several parameters, including but not limited to luminescent lifetime, absorption and/or emission spectra, luminescent quantum yield, and luminescent intensity.

The emitted photon from a luminescent emission event will emit at a wavelength within a spectral range of possible wavelengths. Typically the emitted photon has a longer wavelength (e.g., has less energy or is red-shifted) compared to the wavelength of the excitation photon. In certain embodiments, a molecule is identified my measuring the wavelength of an emitted photon. In certain embodiments, a molecule is identified by measuring the wavelength of a plurality of emitted photons. In certain embodiments, a molecule is identified by measuring the emission spectrum.

Luminescent lifetime refers to a time duration (e.g., emission decay time) associated with an excitation event and an emission event. In some embodiments, luminescent lifetime is expressed as the constant in an equation of exponential decay. In some embodiments, wherein there are one or more pulse events delivering excitation energy, the time duration is the time between the pulse and the subsequent emission event.

Luminescent quantum yield refers to the fraction of excitation events at a given wavelength or within a given spectral range that lead to an emission event, and is typically less than 1. In some embodiments, the luminescent quantum yield of a molecule described herein is between 0 and about 0.001, between about 0.001 and about 0.01, between about 0.01 and about 0.1, between about 0.1 and about 0.5, between about 0.5 and 0.9, or between about 0.9 and 1. In some embodiments, a molecule is identified by determining or estimating the luminescent quantum yield.

As used herein for single molecules luminescent intensity refers to the number of emitted photons per unit time that are emitted by a molecule which is being excited by delivery of a pulsed excitation energy. In some embodiments, the luminescent intensity refers to the detected number of emitted photons per unit time that are emitted by a molecule which is being excited by delivery of a pulsed excitation energy, and are detected by a particular sensor or set of sensors.

In one aspect, the application provides a method of determining the luminescent lifetime of a single luminescent molecule comprising: providing the luminescent molecule in a target volume; delivering a plurality of pulses of an excitation energy to a vicinity of the target volume; and detecting a plurality of luminescences from the luminescent molecule. In some embodiments, the method further comprises recording a plurality of time durations between each pair of pulses and luminescences and evaluating the distribution of the plurality of time durations between each pair of pulses and luminescences.

C. Luminescently Labeled Nucleotides

In one aspect, methods and compositions described herein comprises one or more luminescently labeled nucleotide. In certain embodiments, one or more nucleotides comprise deoxyribose nucleosides. In some embodiments, all nucleotides comprises deoxyribose nucleosides. In certain embodiments, one or more nucleotides comprise ribose nucleosides. In some embodiments, all nucleotides comprise ribose nucleosides. In some embodiments, one or more nucleotides comprise a modified ribose sugar or ribose analog (e.g., a locked nucleic acid). In some embodiments, one or more nucleotides comprise naturally occurring bases (e.g., cytosine, guanine, adenine, thymine, uracil). In some embodiments, one or more nucleotides comprise derivatives or analogs of cytosine, guanine, adenine, thymine, or uracil.

In certain embodiments, a method comprises the step of exposing a polymerase complex to a plurality of luminescently labeled nucleotides. In certain embodiments, a composition or device comprises a reaction mixture comprising a plurality of luminescently labeled nucleotides. In some embodiments, the plurality of nucleotides comprises four types of nucleotides. In some embodiments, the four types of nucleotides each comprise one of cytosine, guanine, adenine, and thymine. In some embodiments, the four types of nucleotides each comprise one of cytosine, guanine, adenine, and uracil.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

A nucleotide generally includes a nucleoside and at least 1, 2, 3, 4, 5, 6, 7, 8, 9, 10, or more phosphate (PO3) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable markers (e.g., fluorophores).

A nucleoside polyphosphate can have 'n' phosphate groups, where 'n' is a number that is greater than or equal to 2, 3, 4, 5, 6, 7, 8, 9, or 10. Examples of nucleoside polyphosphates include nucleoside diphosphate and nucleoside triphosphate. A nucleotide can be a terminal phosphate labeled nucleoside, such as a terminal phosphate labeled nucleoside polyphosphate. Such marker can be a luminescent (e.g., fluorescent or chemiluminescent) marker, a fluorogenic marker, a colored marker, a chromogenic marker, a mass tag, an electrostatic marker, or an electrochemical marker. A marker can be coupled to a terminal phosphate through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a marker from the terminal phosphate, such as with the aid of a polymerization enzyme. Examples of nucleotides and linkers are provided in U.S. Pat. No. 7,041,812, which is entirely incorporated herein by reference.

D. Markers

In certain embodiments, the incorporated molecule is a luminescent molecule, e.g., without attachment of a distinct luminescent marker. Typical nucleotide and amino acids are not luminescent, or do not luminesce within suitable ranges of excitation and emission energies. In certain embodiments, the incorporated molecule comprises a luminescent marker. In certain embodiments, the incorporated molecule is a luminescently labeled nucleotide. In certain embodiments, the incorporated molecule is a luminescently labeled amino acid or luminescently labeled tRNA. In some embodiments, a luminescently labeled nucleotide comprises a nucleotide and a luminescent marker. In some embodiments, a luminescently labeled nucleotide comprises a nucleotide, a luminescent marker, and a linker. In some embodiments, the luminescent marker is a fluorophore.

For nucleotide sequencing, certain combinations of luminescently labeled nucleotides may be preferred. In some embodiments, at least one of the luminescently labeled nucleotides comprises a cyanine dye, or analog thereof. In some embodiments, at least one luminescently labeled nucleotides comprises a rhodamine dye, or analog thereof. In some embodiments, at least one of the luminescently labeled nucleotides comprises a cyanine dye, or analog thereof, and at least one luminescently labeled nucleotides comprises a rhodamine dye, or analog thereof.

In certain embodiments, the luminescent marker is a dye selected from Table FL-1. The dyes listed in Table FL-1 are non-limiting, and the luminescent markers of the application may include dyes not listed in Table FL-1. In certain embodiments, the luminescent markers of one or more luminescently labeled nucleotides is selected from Table FL-1. In certain embodiments, the luminescent markers of four or more luminescently labeled nucleotides is selected from Table FL-1.

TABLE FL-1

| Exemplary fluorophores. Fluorophores |
|---|
| 5/6-Carboxyrhodamine 6G |
| 5-Carboxyrhodamine 6G |
| 6-Carboxyrhodamine 6G |
| 6-TAMRA |
| Abberior Star 440SXP |
| Abberior Star 470SXP |
| Abberior Star 488 |
| Abberior Star 512 |
| Abberior Star 520SXP |
| Abberior Star 580 |
| Abberior Star 600 |
| Abberior Star 635 |
| Abberior Star 635P |
| Abberior Star RED |
| Alexa Fluor 350 |
| Alexa Fluor 405 |
| Alexa Fluor 430 |
| Alexa Fluor 480 |
| Alexa Fluor 488 |
| Alexa Fluor 514 |
| Alexa Fluor 532 |
| Alexa Fluor 546 |
| Alexa Fluor 555 |
| Alexa Fluor 568 |
| Alexa Fluor 594 |
| Alexa Fluor 610-X |
| Alexa Fluor 633 |
| Alexa Fluor 647 |
| Alexa Fluor 660 |
| Alexa Fluor 680 |
| Alexa Fluor 700 |
| Alexa Fluor 750 |
| Alexa Fluor 790 |
| AMCA |
| ATTO 390 |
| ATTO 425 |
| ATTO 465 |
| ATTO 488 |
| ATTO 495 |
| ATTO 514 |
| ATTO 520 |
| ATTO 532 |
| ATTO 542 |
| ATTO 550 |
| ATTO 565 |
| ATTO 590 |
| ATTO 610 |
| ATTO 620 |
| ATTO 633 |
| ATTO 647 |
| ATTO 647N |
| ATTO 655 |
| ATTO 665 |
| ATTO 680 |
| ATTO 700 |
| ATTO 725 |
| ATTO 740 |
| ATTO Oxa12 |
| ATTO Rho101 |
| ATTO Rho11 |
| ATTO Rho12 |
| ATTO Rho13 |

TABLE FL-1-continued

Exemplary fluorophores.
Fluorophores

ATTO Rho14
ATTO Rho3B
ATTO Rho6G
ATTO Thio12
BD Horizon V450
BODIPY 493/501
BODIPY 530/550
BODIPY 558/568
BODIPY 564/570
BODIPY 576/589
BODIPY 581/591
BODIPY 630/650
BODIPY 650/665
BODIPY FL
BODIPY FL-X
BODIPY R6G
BODIPY TMR
BODIPY TR
C5.5
C7
CAL Fluor Gold 540
CAL Fluor Green 510
CAL Fluor Orange 560
CAL Fluor Red 590
CAL Fluor Red 610
CAL Fluor Red 615
CAL Fluor Red 635
Cascade Blue
CF350
CF405M
CF405S
CF488A
CF514
CF532
CF543
CF546
CF555
CF568
CF594
CF620R
CF633
CF633-V1
CF640R
CF640R-V1
CF640R-V2
CF660C
CF660R
CF680
CF680R
CF680R-V1
CF750
CF770
CF790
Chromeo 642
Chromis 425N
Chromis 500N
Chromis 515N
Chromis 530N
Chromis 550A
Chromis 550C
Chromis 550Z
Chromis 560N
Chromis 570N
Chromis 577N
Chromis 600N
Chromis 630N
Chromis 645A
Chromis 645C
Chromis 645Z
Chromis 678A
Chromis 678C
Chromis 678Z
Chromis 770A
Chromis 770C
Chromis 800A
Chromis 800C
Chromis 830A TABLE FL-1-continued Exemplary fluorophores.
Fluorophores Chromis 830C
Cy3
Cy3.5
Cy3B
Cy5
DyLight 350
DyLight 405
DyLight 415-Co1
DyLight 425Q
DyLight 485-LS
DyLight 488
DyLight 504Q
DyLight 510-LS
DyLight 515-LS
DyLight 521-LS
DyLight 530-R2
DyLight 543Q
DyLight 550
DyLight 554-R0
DyLight 554-R1
DyLight 590-R2
DyLight 594
DyLight 610-B1
DyLight 615-B2
DyLight 633
DyLight 633-B1
DyLight 633-B2
DyLight 650
DyLight 655-B1
DyLight 655-B2
DyLight 655-B3
DyLight 655-B4
DyLight 662Q
DyLight 675-B1
DyLight 675-B2
DyLight 675-B3
DyLight 675-B4
DyLight 679-C5
DyLight 680
DyLight 683Q
DyLight 690-B1
DyLight 690-B2
DyLight 696Q
DyLight 700-B1
DyLight 730-B1
DyLight 730-B2
DyLight 730-B3
DyLight 730-B4
DyLight 747
DyLight 747-B1
DyLight 747-B2
DyLight 747-B3
DyLight 747-B4
DyLight 755
DyLight 766Q
DyLight 775-B2
DyLight 775-B3
DyLight 775-B4
DyLight 780-B1
DyLight 780-B2
DyLight 780-B3
DyLight 800
DyLight 830-B2
Dyomics-350
Dyomics-350XL
Dyomics-360XL
Dyomics-370XL
Dyomics-375XL
Dyomics-380XL
Dyomics-390XL
Dyomics-405
Dyomics-415
Dyomics-430
Dyomics-431
Dyomics-478
Dyomics-480XL
Dyomics-481XL TABLE FL-1-continued Exemplary fluorophores.
Fluorophores Dyomics-485XL
Dyomics-490
Dyomics-495
Dyomics-505
Dyomics-510XL
Dyomics-511XL
Dyomics-520XL
Dyomics-521XL
Dyomics-530
Dyomics-547
Dyomics-547P1
Dyomics-548
Dyomics-549
Dyomics-549P1
Dyomics-550
Dyomics-554
Dyomics-555
Dyomics-556
Dyomics-560
Dyomics-590
Dyomics-591
Dyomics-594
Dyomics-601XL
Dyomics-605
Dyomics-610
Dyomics-615
Dyomics-630
Dyomics-631
Dyomics-632
Dyomics-633
Dyomics-634
Dyomics-635
Dyomics-636
Dyomics-647
Dyomics-647P1
Dyomics-648
Dyomics-648P1
Dyomics-649
Dyomics-649P1
Dyomics-650
Dyomics-651
Dyomics-652
Dyomics-654
Dyomics-675
Dyomics-676
Dyomics-677
Dyomics-678
Dyomics-679P1
Dyomics-680
Dyomics-681
Dyomics-682
Dyomics-700
Dyomics-701
Dyomics-703
Dyomics-704
Dyomics-730
Dyomics-731
Dyomics-732
Dyomics-734
Dyomics-749
Dyomics-749P1
Dyomics-750
Dyomics-751
Dyomics-752
Dyomics-754
Dyomics-776
Dyomics-777
Dyomics-778
Dyomics-780
Dyomics-781
Dyomics-782
Dyomics-800
Dyomics-831
eFluor 450
Eosin
FITC
Fluorescein TABLE FL-1-continued Exemplary fluorophores.
Fluorophores HiLyte Fluor 405
HiLyte Fluor 488
HiLyte Fluor 532
HiLyte Fluor 555
HiLyte Fluor 594
HiLyte Fluor 647
HiLyte Fluor 680
HiLyte Fluor 750
IRDye 680LT
IRDye 750
IRDye 800CW
JOE
LightCycler 640R
LightCycler Red 610
LightCycler Red 640
LightCycler Red 670
LightCycler Red 705
Lissamine Rhodamine B
Napthofluorescein
Oregon Green 488
Oregon Green 514
Pacific Blue
Pacific Green
Pacific Orange
PET
PF350
PF405
PF415
PF488
PF505
PF532
PF546
PF555P
PF568
PF594
PF610
PF633P
PF647P
Quasar 570
Quasar 670
Quasar 705
Rhoadmine 123
Rhodamine 6G
Rhodamine B
Rhodamine Green
Rhodamine Green-X
Rhodamine Red
ROX
Seta 375
Seta 470
Seta 555
Seta 632
Seta 633
Seta 650
Seta 660
Seta 670
Seta 680
Seta 700
Seta 750
Seta 780
Seta APC-780
Seta PerCP-680
Seta R-PE-670
Seta646
SeTau 380
SeTau 405
SeTau 425
SeTau 647
Square 635
Square 650
Square 660
Square 672
Square 680
Sulforhodamine 101
TAMRA
TET
Texas Red TABLE FL-1-continued Exemplary fluorophores.
Fluorophores TMR
TRITC
Yakima Yellow
Zenon
Zy3
Zy5
Zy5.5
Zy7

In certain embodiments, the luminescent marker may be (Dye 101) or (Dye 102), of formulae:

(Dye 101)

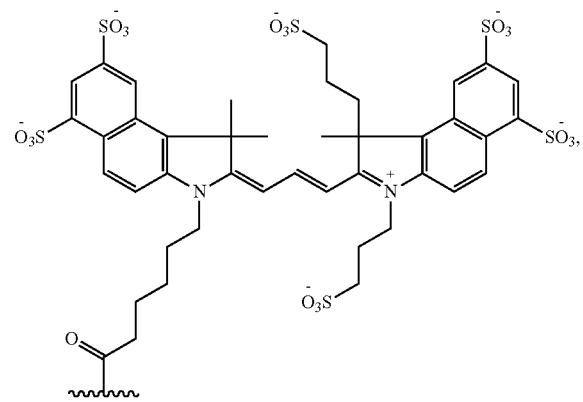

(Dye 102)

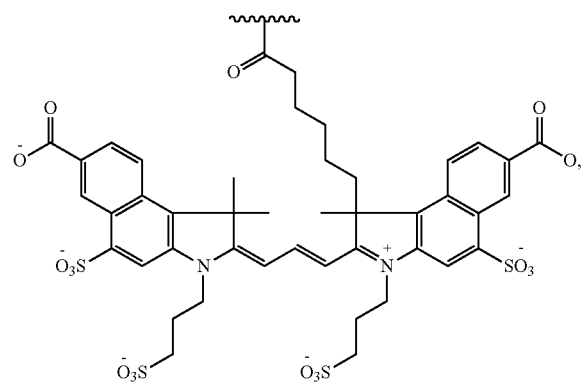

or an analog thereof. In some embodiments, each sulfonate or carboxylate is independently optionally protonated. In some embodiments, the dyes above are attached to the linker or nucleotide by formation of an amide bond at the indicated point of attachment.

In certain embodiments, at least one type, at least two types, at least three types, or at least four of the types of luminescently labeled nucleotides comprise a luminescent marker selected from the group consisting of 6-TAMRA, 5/6-Carboxyrhodamine 6G, Alex Fluor 546, Alexa Fluor 555, Alexa Fluor 568, Alexa Fluor 610, Alexa Fluor 647, Aberrior Star 635, ATTO 647N, ATTO Rho14, Chromis 630, Chromis 654A, Chromeo 642, CF514, CF532, CF543, CF546, CF546, CF555, CF568, CF633, CF640R, CF660C, CF660R, CF680R, Cy3, Cy3B, Cy3.5, Cy5, Cy5.5, Dyomics-530, Dyomics-547P1, Dyomics-549P1, Dyomics-550, Dyomics-554, Dyomics-555, Dyomics-556, Dyomics-560, Dyomics-650, Dyomics-680, DyLight 554-R1, DyLight 530-R2, DyLight 594, DyLight 635-B2, DyLight 650, DyLight 655-B4, DyLight 675-B2, DyLight 675-B4, DyLight 680, HiLyte Fluor 532, HiLyte Fluor 555, HiLyte Fluor 594, LightCycler 640R, Seta 555, Seta 670, Seta700, SeTau 647, and SeTau 665, or are of formulae (Dye 101) or (Dye 102), as described herein.

In some embodiments, at least one type, at least two types, at least three types, or at least four of the types of luminescently labeled nucleotides comprise a luminescent marker selected from the group consisting of Alexa Fluor 532, Alexa Fluor 546, Alexa Fluor 555, Alexa Fluor 594, Alexa Fluor 610, CF532, CF543, CF555, CF594, Cy3, DyLight 530-R2, DyLight 554-R1, DyLight 590-R2, DyLight 594, and DyLight 610-B1, or are of formulae (Dye 101) or (Dye 102).

In some embodiments, a first and second type of luminescently labeled nucleotide comprise a luminescent marker selected from the group consisting of Alexa Fluor 532, Alexa Fluor 546, Alexa Fluor 555, CF532, CF543, CF555, Cy3, DyLight 530-R2, and DyLight 554-R1, and a third and fourth type of luminescently labeled nucleotide comprise a luminescent marker selected from the group consisting of Alexa Fluor 594, Alexa Fluor 610, CF594, DyLight 590-R2, DyLight 594, and DyLight 610-B1, or are of formulae (Dye 101) or (Dye 102).

E. Linkers

A luminescent marker may be attached to the molecule directly, e.g., by a bond, or may be attached via a linker. In certain embodiments, the linker comprises one or more phosphates. In some embodiments, a nucleoside is connected to a luminescent marker by a linker comprising one or more phosphates. In some embodiments, a nucleoside is connected to a luminescent marker by a linker comprising three or more phosphates. In some embodiments, a nucleoside is connected to a luminescent marker by a linker comprising four or more phosphates.

In certain embodiments, a linker comprises an aliphatic chain. In some embodiments a linker comprises $-(CH_2)_n-$, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises $-(CH_2CH_2O)_n-$, wherein n is an integer from 1 to 20, inclusive. In some embodiments, a linker comprises $-(CH_2CH_2O)_n-$, wherein n is an integer from 1 to 10, inclusive. In certain embodiments, a linker comprises $-(CH_2CH_2O)_4-$. In certain embodiments, a linker comprises one or more arylenes. In some embodiments, a linker comprises one or more phenylenes (e.g., para-substituted phenylene). In certain embodiments, a linker comprises a chiral center. In some embodiments, a linker comprises proline, or a derivative thereof. In some embodiments, a linker comprises a proline hexamer, or a derivative thereof. In some embodiments, a linker comprises coumarin, or a derivative thereof. In some embodiments, a linker comprises naphthalene, or a derivative thereof. In some embodiments, a linker comprises anthracene, or a derivative thereof. In some embodiments, a linker comprises a polyphenylamide, or a derivative thereof. In some embodiments, a linker comprises chromanone, or a derivative thereof. In some embodiments, a linker comprises 4-aminopropargyl-L-phenylalanine, or a derivative thereof. In certain embodiments, a linker comprises a polypeptide.

In some embodiments, a linker comprises an oligonucleotide. In some embodiments, a linker comprises two annealed oligonucleotides. In some embodiments, the oligonucleotide or oligonucleotides comprise deoxyribose nucleotides, ribose nucleotide, or locked ribose nucleotides. In certain embodiments, a linker comprises a photostabilizer.

F. Sample Well Surface Preparation

In certain embodiments, a method of detecting one or luminescently labeled molecule is performed with the molecules confined in a target volume. In some embodiments, the target volume is a region within a sample well (e.g., a nanoaperture). In certain embodiments, the sample well comprises a bottom surface comprising a first material and sidewalls formed by a plurality of metal or metal oxide layers. In some embodiments, the first material is a transparent material or glass. In some embodiments, the bottom surface is flat. In some embodiments, the bottom surface is a curved well. In some embodiments, the bottom surface includes a portion of the sidewalls below the sidewalls formed by a plurality of metal or metal oxide layers. In some embodiments, the first material is fused silica or silicon dioxide. In some embodiments, the plurality of layers each comprise a metal (e.g., Al, Ti) or metal oxide (e.g., $Al_2O_3$, $TiO_2$, TiN).

G. Passivation

In some embodiments when one or more molecule or complex is immobilized on a surface, it is desirable to passivate other surfaces of the device to prevent immobilization at an undesired location. In some embodiments, the molecule or complex is immobilized on a bottom surface of a sample well and the sidewalls of the sample well are passivated. In some embodiments, the sidewalls are passivated by the steps of: depositing a metal or metal oxide barrier layer on the sidewall surfaces; and applying a coating to the barrier layer. In some embodiments, the metal oxide barrier layer comprises aluminum oxide. In some embodiments, the step of depositing comprises depositing the metal or metal oxide barrier layer on the sidewall surfaces and the bottom surface. In some embodiments, the step of depositing further comprises etching metal or metal oxide barrier layer off of the bottom surface.

In some embodiments, the barrier layer coating comprises phosphonate groups. In some embodiments, the barrier layer coating comprises phosphonate groups with an alkyl chain. In some embodiments, the barrier layer coating comprises a polymeric phosphonate. In some embodiments, the barrier layer coating comprises polyvinylphosphonic acid (PVPA). In some embodiments, the barrier layer coating comprises phosphonate groups with a substituted alkyl chain. In some embodiments, the alkyl chain comprises one or more amides. In some embodiments, the alkyl chain comprises one or more poly(ethylene glycol) chains. In some embodiments, the coating comprises phosphonate groups of formula:

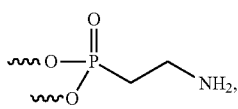

-continued

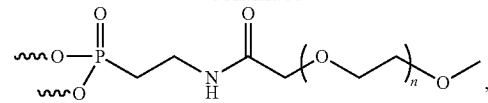

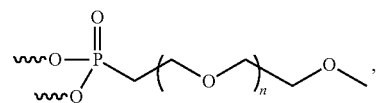

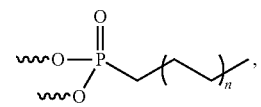

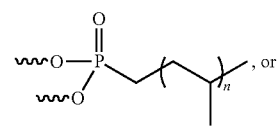, or

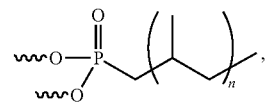

wherein n is an integer between 0 and 100, inclusive, and ⌇ is hydrogen or a point of attachment to the surface. In some embodiments n is an integer between 3 and 20, inclusive. In some embodiments, the barrier layer coating comprises a mixture of different types of phosphonate groups. In some embodiments, the barrier layer coating comprises a mixture of phosphonate groups comprising poly(ethylene glycol) chains of different PEG weight.

In certain embodiments, the barrier layer comprises nitrodopa groups. In certain embodiments, the barrier layer coating comprises groups of formula:

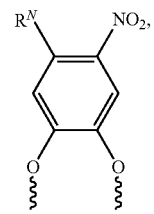

wherein $R^N$ is an optionally substituted alkyl chain and ⌇ is hydrogen or a point of attachment to the surface. In some embodiments, $R^N$ comprises a polymer. In some embodiments, $R^N$ comprises a poly(lysine) or a poly(ethylene glycol). In some embodiments, the barrier layer comprises a co-polymer of poly(lysine) comprising lysine monomers, wherein the lysine monomers independently comprise PEG, nitrodopa groups, phosphonate groups, or primary amines. In certain embodiments, the barrier layer comprises a polymer of formula (P):

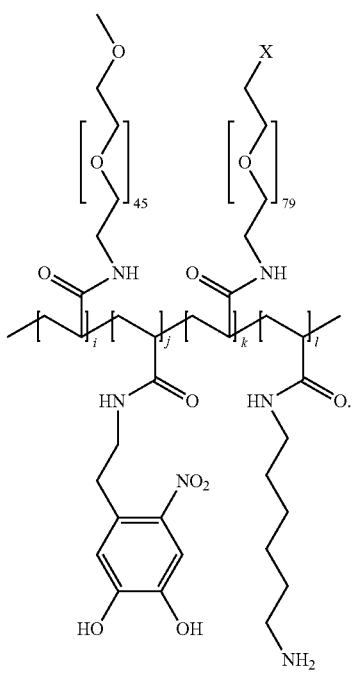

(P)

In some embodiments, X is —OMe, a biotin group, phosphonate, or silane. In some embodiments, each of i, j, k, and l is independently an integer between 0 and 100, inclusive.

H. Polymerase Immobilization

In some embodiments, when one or more molecule or complex is immobilized on a surface the surface is functionalized to allow for attachment of one or more of the molecules or complexes. In some embodiments, the functionalized surface is a bottom surface of a sample well. In certain embodiments, the functionalized surface comprises a transparent glass. In certain embodiments, the functionalized surface comprises fused silica or silicon dioxide. In some embodiments, the functionalized surface is functionalized with a silane. In some embodiments, the functionalized surface is functionalized with an ionically charged polymer. In some embodiments, the ionically charged polymer comprises poly(lysine). In some embodiments, the functionalized surface is functionalized with poly(lysine)-graft-poly(ethylene glycol). In some embodiments, the functionalized surface is functionalized with biotinlyated bovine serum albumin (BSA).

In certain embodiments, the functionalized surface is functionalized with a coating comprising nitrodopa groups. In certain embodiments, the coating comprises groups of formula:

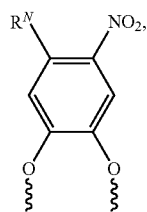

wherein $R^N$ is an optionally substituted alkyl chain and ⌇⌇⌇ is hydrogen or a point of attachment to the surface. In some embodiments, $R^N$ comprises a polymer. In some embodiments, $R^N$ comprises a poly(lysine) or a poly(ethylene glycol). In some embodiments, $R^N$ comprises a biotinylated poly(ethylene glycol). In some embodiments, the coating comprises a co-polymer of poly(lysine) comprising lysine monomers, wherein the lysine monomers independently comprise PEG, biotinylated PEG, nitrodopa groups, phosphonate groups, or silanes. In certain embodiments, the coating comprises a polymer of formula (P):

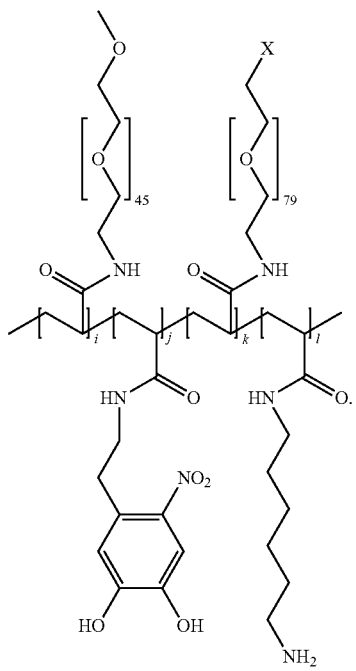

(P)

In some embodiments, X is —OMe, a biotin group, phosphonate, or silane. In some embodiments, each of i, j, k, and l is independently an integer between 0 and 100, inclusive.

In some embodiments, the functionalized surface is functionalized with a silane comprising an alkyl chain. In some embodiments, the functionalized surface is functionalized with a silane comprising an optionally substituted alkyl chain. In some embodiments, the surface is functionalized with a silane comprising a poly(ethylene glycol) chain. In some embodiments, the functionalized surface is functionalized with a silane comprising a coupling group. For example the coupling group may comprise chemical moieties, such as amine groups, carboxyl groups, hydroxyl groups, sulfhydryl groups, metals, chelators, and the like. Alternatively, they may include specific binding elements, such as biotin, avidin, streptavidin, neutravidin, lectins, SNAP-Tags™ or substrates therefore, associative or binding peptides or proteins, antibodies or antibody fragments, nucleic acids or nucleic acid analogs, or the like. Additionally, or alternatively, the coupling group may be used to couple an additional group that is used to couple or bind with the molecule of interest, which may, in some cases include both chemical functional groups and specific binding elements. By way of example, a coupling group, e.g., biotin, may be deposited upon a substrate surface and selectively activated in a given area. An intermediate binding agent, e.g., streptavidin, may then be coupled to the first coupling group. The molecule of interest, which in this particular example would be biotinylated, is then coupled to the streptavidin.

In some embodiments, the functionalized surface is functionalized with a silane comprising biotin, or an analog thereof. In some embodiments, the surface is functionalized with a silane comprising a poly(ethylene) glycol chain, wherein the poly(ethylene glycol) chain comprises biotin. In certain embodiments, the functionalized surface is functionalized with a mixture of silanes, wherein at least one type of silane comprises biotin and at least one type of silane does not comprise biotin. In some embodiments, the mixture comprises about 10 fold less, about 25 fold less, about 50 fold less, about 100 fold less, about 250 fold less, about 500 fold less, or about 1000 fold less of the biotinylated silane than the silane not comprising biotin.

FIG. 10-3 depicts a non-limiting exemplary process for preparing the sample well surface from the fabricated chip (e.g., integrated device) to initiation of a sequencing reaction. The sample well is depicted with a bottom surface (unshaded rectangle) and sidewalls (shaded vertical rectangles). The sidewalls may be comprised of multiple layers (e.g., Al, $Al_2O_3$, Ti, $TiO_2$, TiN). In step (a) the sidewalls are deposited with a barrier layer of $Al_2O_3$. The $Al_2O_3$ barrier layer is then coated, in step (b), with a PEG phosphonate groups, for example, by treating the surface with one or more PEG-phosphonic acids. In step (c), the bottom surface is functionalized, for example, with a mixture of PEG-silane and biotinylated-PEG-silane. The ovals represent individual biotin groups which may provide sites for an attachment of a single molecule or complex, such as a polymerase complex. In step (d), a polymerase complex is attached to a biotin group on the bottom surface. The polymerase may be attached by way of a binding agent, such as streptavidin, and a biotin tag on the polymerase complex. The polymerase complex may further comprise a template nucleic acid and primer (not shown). Step (e) depicts the initiation of a sequencing reaction by exposure of the immobilized polymerase complex to luminescently labeled nucleotides.

I. Polymerases

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme.

Embodiments directed towards single molecule nucleic acid extension (e.g., for nucleic acid sequencing) may use any polymerase that is capable of synthesizing a nucleic acid complementary to a target nucleic acid molecule. In some embodiments, a polymerase may be a DNA polymerase, an RNA polymerase, a reverse transcriptase, and/or a mutant or altered form of one or more thereof.

Embodiments directed towards single molecule nucleic acid sequencing may use any polymerase that is capable of synthesizing a nucleic acid complementary to a target nucleic acid. Examples of polymerases include, but are not limited to, a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. Non-limiting examples of DNA polymerases and their properties are described in detail in, among other places, DNA Replication 2nd edition, Kornberg and Baker, W. H. Freeman, New York, N.Y. (1991).

Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent marker conjugated to the dNTP is a fluorophore, its presence is signaled by excitation and a pulse of emission is detected during or after the step of incorporation. For detection markers that are conjugated to the terminal (gamma) phosphate of the dNTP, incorporation of the dNTP into the newly synthesized strand results in release the beta and gamma phosphates and the detection marker, which is free to diffuse in the sample well, resulting in a decrease in emission detected from the fluorophore.

In some embodiments, the polymerase is a polymerase with high processivity. However, in some embodiments, the polymerase is a polymerase with reduced processivity. Polymerase processivity generally refers to the capability of a polymerase to consecutively incorporate dNTPs into a nucleic acid template without releasing the nucleic acid template. In some embodiments, the polymerase is a polymerase with low 5'-3' exonuclease activity and/or 3'-5' exonuclease. In some embodiments, the polymerase is modified (e.g., by amino acid substitution) to have reduced 5'-3' exonuclease activity and/or 3'-5' activity relative to a corresponding wild-type polymerase. Further non-limiting examples of DNA polymerases include 9°Nm™ DNA polymerase (New England Biolabs), and a P680G mutant of the Klenow exo-polymerase (Tuske et al. (2000) JBC 275(31): 23759-23768). In some embodiments, a polymerase having reduced processivity provides increased accuracy for sequencing templates containing one or more stretches of nucleotide repeats (e.g., two or more sequential bases of the same type).

Embodiments directed toward single molecule RNA extension (e.g., for RNA sequencing) may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above and elsewhere herein. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

The processivity, exonuclease activity, relative affinity for different types of nucleic acid, or other property of a nucleic acid polymerase can be increased or decreased by one of skill in the art by mutation or other modification relative to a corresponding wild-type polymerase.

J. Lifetime Measurements

Lifetime measurements may be performed using one excitation energy wavelength to excite a marker in a sample well. A combination of markers having distinct lifetimes are selected to distinguish among the individual markers based on the lifetime measurements. Additionally, the combination of markers are able to reach an excited state when illuminated by the excitation source used. An integrated device configured for lifetime measurements using one excitation may include multiple pixels positioned along a row where each sample well is configured to couple with the same waveguide. A pixel includes a sample well and a sensor. One or more microcavities or a bullseye grating may be used to couple the waveguide to the sample well for each pixel.

A pulsed excitation source may be one of the pulsed excitation sources using the techniques described above. In some instances, the pulsed excitation source may be a semiconductor laser diode configured to emit pulses through direct modulated electrical pumping of the laser diode. The power of the pulses is less than 20 dB of the pulse peak power at approximately 250 picoseconds after the peak. The time interval for each excitation pulse is in the range of 20-200 picoseconds. The time duration between each excitation pulse is in the range of 1-50 nanoseconds. A schematic of how example measurements may be performed is shown in FIG. 10-4. Since one excitation energy is used, an excitation filter suitable for reducing transmission of the excitation energy to the sensor may be formed in the integrated device, such as the wavelength excitation filter discussed above.

The sensor for each pixel has at least one photosensitive region per a pixel. The photosensitive region may have dimensions of 5 microns by 5 microns. Photons are detected within time intervals of when they reach the sensor. Increasing the number of time bins may improve resolution of the recorded histogram of photons collected over a series of time bins and improve differentiation among different luminescent markers. In some embodiments, focusing elements may be integrated with the sensor in order to improve collection of photons emitted by a marker in an associated sample well. Such focusing elements may include a Fresnel lens as shown in FIG. 10-5. When the sensor is configured to detect a particular wavelength, the four luminescent markers may emit luminescence similar to the particular wavelength. Alternatively, the four luminescent markers may emit luminescence at different wavelengths.

An example set of four luminescent markers that are distinguishable based on lifetime measurements are ATRho14, Cy5, AT647N, and CF633 as shown by the plot in FIG. 10-6. These four markers have varying lifetimes and produce distinguishing histograms when at least four time bins are used. FIG. 10-7 outlines a signal profile for each of these markers across 16 time bins. The signal profile is normalized for each marker. The time bins vary in time interval in order to provide a unique signal profile for each of the markers. FIGS. 10-8 and 10-9 illustrates signal profiles, both continuous and discrete, respectively, of another exemplary set of markers, ATTO Rho14, D650, ST647, and CF633, that are distinguishable based on lifetime measurements. Other sets of markers include ATTO Rho14, C647, ST647, CF633; Alexa Fluor647, B630, C640R, CF633; and ATTO Rho14, ATTO 647N, AlexaFluor647, CF633.

K. Spectral-Lifetime Measurements

Lifetime measurements may be combined with spectral measurements of one or more luminescent markers. Spectral measurements may depend on the wavelength of luminescence for individual markers and are captured using at least two sensor regions per pixel. An exemplary structure of the integrated device includes pixels that each have a sensor with two distinct regions, each region configured to detect a different wavelength. A multi-wavelength filter, such as the one shown and described in FIG. 7-7, may be used to selectively transmit light of different wavelength to each sensor region. For example, one sensor region and filter combination may be configured to detect red light while another sensor region and filter combination may be configured to detect green light.

Combining both lifetime measurements with spectral measurements may be performed using one excitation energy wavelength to excite a marker in a sample well. A combination of markers is selected having at least two distinct luminescence wavelengths where the markers emitting at a wavelength have distinct lifetimes are selected to distinguish among the individual markers based on the lifetime and spectral measurements. Additionally, the combination of markers is selected to be able to reach an excited state when illuminated by the excitation source used.

The excitation source is a pulsed excitation source, and may be one of the excitation sources using the techniques described above. In some instances, the pulsed excitation source may be a semiconductor laser diode configured to emit pulses through direct modulated electrical pumping of the laser diode. The power of the pulses are less than 20 dB the peak power after 250 picoseconds after the peak. The time duration for each excitation pulse is in the range of 20-200 picoseconds. The time interval between each excitation pulse is in the range of 1-50 nanoseconds. A schematic of how example measurements may be performed is shown in FIG. 10-10. Since one excitation energy is used, an excitation filter suitable for reducing transmission of the excitation energy to the sensor may be used, such as the wavelength excitation filter discussed above with reference to FIG. 7-5.

The sensor for each pixel has at least two photosensitive regions per pixel. In some embodiments there are two photosensitive regions per a pixel. In other embodiments, there are four photosensitive regions per a pixel. Each photosensitive region is configured to detect a different wavelength or range of wavelengths. Photons are detected within time intervals of when they reach the sensor. Increasing the number of time bins may improve resolution of the recorded histogram of photons collected over a series of time bins and improve differentiation among different luminescent markers by their individual lifetimes. In some embodiments, there are two time bins per a region of the sensor. In other embodiments, there are four time bins per a region of the sensor.

An example set of four luminescent markers that are distinguishable based on lifetime measurements are ATTO Rho14, AS635, Alexa Fluor647, and ATTO 647N. These four markers have two that emit at one similar wavelength and another similar wavelength. Within each pair of markers that emit at a similar wavelength, the pair of markers have different lifetimes and produce distinguishing histograms when at least four time bins are used. In this example, ATTO Rho14 and AS635 emit similar luminescence wavelengths and have distinct lifetimes. Alexa Fluor 647 and ATTO 647N emit similar luminescence wavelengths, different from the wavelengths emitted by ATTO Rho 14 and AS635, and have distinct lifetimes. FIG. 10-11 shows a plot lifetime as a function of emission wavelength for this set of markers to illustrate how each of these markers is distinguishable based on a combination of lifetime and emission wavelength. FIG.

10-12 shows a plot of power as a function of wavelength for ATT Rho14, Alexa Fluor 647, and ATT) 647N. FIG. 10-13 shows plots of fluorescence signal over time for each one of these markers when present in a sample well with a diameter of 135 nm. FIG. 10-14 illustrates the signal profile for these markers across four photosensitive regions and each region captures four time bins. The signal profiles are normalized and are used to distinguish among the different markers by the relative number of photons captured by a photosensitive region for each of the four time bins. Other sets of four fluorophores for such spectral-lifetime measurements are ATRho14, D650, ST647, CF633; ATTO Rho14, C647, ST647, CF633; Alexa Fluor 647, B630, C640R, CF633; and ATTO Rho 14, ATTO 647N, Alexa Fluor 647, CF633. FIG. 10-15 shows a plot of the signal profile of intensity over time for ATRho14, D650, ST647, and C633. FIG. 10-16 illustrates the signal profile for ATRho14.

L. Lifetime-Excitation Energy Measurements

Lifetime measurements combined with using at least two excitation energy wavelengths may be used to distinguish among multiple markers. Some markers may excite when one excitation wavelength is used and not another. A combination of markers having distinct lifetimes is selected for each excitation wavelength to distinguish among the individual markers based on the lifetime measurements. In this embodiment, an integrated device may be configured to have each pixel with a sensor having one region and the external excitation source may be configured to provide two excitation energy wavelengths are electrically modulated pulsed diode lasers with temporal interleaving.

The excitation source is a combination of at least two excitation energies. The excitation source is a pulsed excitation source and may be one or more of the excitation sources using the techniques described above. In some instances, the pulsed excitation source may be two semiconductor laser diode configured to emit pulses through direct modulated electrical pumping of the laser diode. The power of the pulses are 20 dB less than the pulse peak power at 250 picoseconds after the peak. The time interval for each excitation pulse is in the range of 20-200 picoseconds. The time interval between each excitation pulse is in the range of 1-50 nanoseconds. One excitation wavelength is emitted per a pulse and by knowing the excitation wavelength a subset of markers with distinct lifetimes is uniquely identified. In some embodiments, pulses of excitation alternate among the different wavelengths. For example, when two excitation wavelengths are used subsequent pulses alternate between one wavelength and the other wavelength. A schematic of how example measurements may be performed is shown in FIG. 10-17. Any suitable technique for combining multiple excitation sources and interleaving pulses having different wavelengths may be used. Examples of some techniques for delivering pulses of more than one excitation wavelength to a row of sample wells are illustrated are described herein. In some embodiments, there is a single waveguide per a row of sample wells and there are two excitation sources that are combined such that pulses of excitation energy alternate between the two excitation wavelengths. In some embodiments, there are two waveguides per a row of sample wells and each waveguide is configured to carry one of two excitation wavelengths. In other embodiments, there is a single waveguide per a row of pixels and one wavelength couples to one end of the waveguide and another wavelength couples to the other end.

The sensor for each pixel has at least one photosensitive region per a pixel. The photosensitive region may have dimensions of 5 microns by 5 microns. Photons are detected within time intervals of when they reach the sensor. Increasing the number of time bins may improve resolution of the recorded histogram of photons collected over a series of time bins and improve differentiation among different luminescent markers. The sensor has at least two time bins.

An example set of four luminescent markers that are distinguishable based on lifetime measurements are Alexa Fluor 546, Cy3B, Alexa Fluor 647, and ATTO 647N. As shown in FIG. 10-18, Alexa Fluor 546 and Cy3B excite at one wavelength, such as 532 nm, and have distinct lifetimes. Alexa Fluor 647 and ATTO 647N excite at another wavelength, 640 nm, and have distinct lifetimes as shown in FIG. 10-19. Distinguishable normalized signal profiles across 16 time bins for ATTO647N and CF633, which are both excited at 640 nm, are shown in FIG. 10-20. By detecting a photon after a known excitation wavelength, one of these two pairs of markers may be determined based on the previous excitation wavelength and each marker for a pair is identified based on lifetime measurements.

VI. Fabrication Steps

The above integrated device may be fabricated in any suitable way. What follows is a description of the fabrication of various components of the integrated device, which may be combined in any way with techniques known in the art, to create a suitable integrated device.

A. Sample Well Fabrication Process

A sample well (e.g., nanoaperature) may be fabricated in any suitable way. In some embodiments, a sample well may be fabricated using standard photolithography processes and etching techniques. A sample well may be formed in a layer having a metal (e.g., Al, TiN) or any suitable material compatible with photolithography processing. FIG. 11-1 illustrates an exemplary method for fabricating a sample well of an integrated device. Layer 11-112 forms a sample well and may include a metal such as Al or TiN. Layer 11-110 may act as a dielectric layer and may be formed from any suitable dielectric substrate, such as $SiO_2$ or silicon nitride. One step of the method includes depositing layer 11-112 directly on substrate 11-110. In some embodiments, additional layers may be deposited between layer 11-112 and layer 11-110. Layer 11-112 may be deposited at any suitable thickness, and in some embodiments, the thickness may determine the height of the resulting sample well. The thickness of layer 11-112 may be approximately 50 nm, approximately 100 nm, or approximately 150 nm. An anti-reflection coating (ARC) 11-122 is then deposited on top of layer 11-112. Etch mask 11-120 (e.g., photoresist etch mask) is deposited on ARC 11-122. Conventional photolithographic techniques are used to pattern a hole in etch mask 11-120 and ARC layer 11-122. The hole patterned by etch mask 11-120 may have a diameter of approximately 50 nm, approximately 100 nm, or approximately 150 nm. The hole pattern is then transferred to underlying layer 11-112 using an etch, for example, reactive ion etching techniques, to form the sample well. Etching may stop at the surface of layer 11-110, or etching may create a divot in layer 11-110 under the hole in layer 11-112. Conventional techniques are used to strip etch mask 11-120 and ARC 11-122 off of layer 11-112. The sample well may have a diameter oft approximately 50 nm, approximately 100 nm, or approximately 150 nm.

Alternatively, a sample well may be fabricated using standard photolithography processes and lift-off techniques. FIG. 11-2 illustrates an exemplary method of forming a sample well using lift-off techniques. Sample well is formed in layer 11-212, which may include a metal (e.g., Al, Au, Cr). Layer 11-212 is formed over substrate layer 11-210, which may include any suitable material such as a dielectric (e.g., SiO$_2$). Deposition of layer 11-212 may occur separately from and after the photolithographic process. The first step in the lift-off fabrication process shown in FIG. 11-2 may involve depositing anti-reflection coating (ARC) 11-222 on substrate 11-210 followed by photoresist etch mask 11-220 directly on top of substrate 11-210.

Conventional photolithographic techniques are used to pattern the photoresist such that a pillar 11-230 of resist is left behind. The pillar may have any suitable size and shape that may correspond to a resulting sample well. The pillar may have a diameter of approximately 50 nm, approximately 100 nm, or approximately 150 nm. Such techniques may include dissolving the resist and the ARC layer around the pillar off of the substrate. The following step may involve depositing layer 11-212 directly on top of the pillar of resist and the substrate, creating a capped pillar. In other embodiments, additional layers may be deposited before or after deposition of layer 11-212. As a non-limiting example, TiN may be deposited on layer 11-212 formed of Al, optionally followed by a deposition of Al$_2$O$_3$. Layer 11-212 may be deposited at any suitable thickness, and in some embodiments may have a thickness of approximately 50 nm, approximately 100 nm, or approximately 150 nm. To form the sample well, the capped pillar may be stripped by a solvent in the case that photoresist is used or by selective etching in the case that silicon dioxide or silicon nitride hard etch masks are used. The sample well may have a diameter oft approximately 50 nm, approximately 100 nm, or approximately 150 nm. Alternatively, a sample well may be fabricated using standard photolithography processes and an alternate lift-off technique. FIG. 11-3 illustrates an exemplary embodiment of forming a sample well of an integrated device. A hard etch mask layer 11-314 is deposited on substrate 11-310. Hard etch mask layer 11-314 may include Ti or any other suitable material. Substrate 11-310 may include a dielectric (e.g., SiO$_2$) or any other suitable material. A layer of ARC 11-322 is then deposited onto the hard etch mask layer 11-314 followed by photoresist layer 11-320. Conventional photolithographic techniques are used to pattern the photoresist such that a pillar 11-320 of resist is formed. This photoresist pillar pattern is used as an etch mask for etching the ARC layer 11-322 and hard etch mask layer 11-314. Photoresist layer 11-320 and ARC 11-322 is then stripped, and pillar 11-330 of hard etch mask is left behind. Conventional techniques may be used to dissolve the remaining photoresist and the ARC layer off the pillar. The following step may involve depositing layer 11-312 directly on top of pillar 11-330 creating a capped pillar. To form the sample well, the capped pillar is stripped by a hydrogen peroxide etch, or other suitable etch, which erodes layer 11-314, "lifts off" the cap and results in a sample well in layer 11-312.

In some embodiments, the sample well may be fabricated to attenuate plasmon transmission through the sample well in any suitable way. For example, the sample well may be fabricated in a multi-layered stack. The multi-layered stack may include, but is not limited to, a metal layer deposited on a substrate, an absorbing layer and/or a surface layer. The surface layer may be a passivation layer. The multi-layer stack may be fabricated in any suitable way. Conventional patterning and etching techniques may be used. A metal layer may be deposited onto a substrate. Alternatively, an absorbing layer may be deposited onto the metal layer. Alternatively, a surface passivation layer may be deposited onto the absorbing layer/metal layer stack. A photoresist and anti-reflection layer may be deposited onto the top layer of the multilayer stack. The photoresist layer may be patterned with the dimensions of the sample well. The multi-layer stack may be directly etched to form the sample well.

The absorbing layers may include any suitable absorbing materials. Non-limiting examples include silicon nitride, TiN, aSi, TaN, Ge and/or Cr. Variants of the named materials are also possible, such as Si$_3$N$_4$. The metal layer and the surface layer may be made of any suitable materials. For example, Al, AlSi, or AlCu may be used for the metal layer. The surface layer may be made of Al or Al$_2$O$_3$, for example. The sample well in the multilayer stack may be fabricating using the processes described above.

Additionally and/or alternatively, a reflective layer may be deposited directly on top of the substrate before depositing the multi-layered stack to control the focus of the light beam during photolithography. A reflective layer may be deposited directly on top of the substrate and patterned with the dimensions of the sample well. Optionally, a layer of anti-reflection coating followed by a layer of photoresist may be deposited on top of the patterned reflective coating layer and patterned to leave a pillar of ARC and photoresist at a location on the substrate. A multilayer stack may then be deposited on top of the pillar, reflective layer, and substrate. The capped pillar may be removed using a lift-off process, as described above, forming a sample well at the location of the substrate where the piller had been.

Similarly, a Ti pillar may be used to create the sample well. The first step may involve depositing a layer of Ti on the substrate, followed by a layer of anti-reflection coating and a layer of photoresist. The Ti layer may be patterned and etched to form a Ti pillar. The multilayer stack may be deposited on top of the Ti pillar and substrate. Finally, the Ti pillar may be removed forming a sample well at a location of the substrate corresponding to where the Ti pillar had been.

Any suitable deposition methods may be used. For example, PVD, CVD, sputtering, ALD, e-beam deposition and/or thermal evaporation may be used to deposit one or more layers. The deposition environment may be controlled to prevent oxidation of the layers in between depositions. For example, the environment may be kept at a high vacuum and/or low-oxygen state during and between depositions of one or more layers.

B. Sample Well Layer with Dips

The sample well layer may include dips such than the sample well (e.g., nanoaperture) is positioned at a certain distance to the waveguide. Any suitable technique for forming dips in the sample well layer may be used. One technique includes grayscale lithography used to form a resist with topography followed by etching to transfer the topography to the oxide layer. After the oxide layer has the dip topography, the sample well and/or other structures may be formed. FIG. 11-5 illustrates an exemplary embodiment of forming a sample well layer with dips. Waveguide 11-820 is formed within surrounding material layer 11-810, and resist 11-830 is patterned on a surface of surrounding material layer 11-810. The patterning of resist 11-830 may have any suitable size or shape. The surface of layer 11-810 is etched to form a desired dip shape based on the patterning of resist 11-830. Sample well layer 11-812 is deposited on the etched surface of layer 11-810 by any combination of the techniques described herein to form a sample well layer 11-810 with a portion having sample well 11-832 positioned a distance from waveguide 11-820 to provide suitable coupling between waveguide 11-820 and sample well 11-832.

Another technique for forming a sample well layer with dips may include using grayscale lithography to form topography into an oxide layer to expose the waveguide and then oxide is deposited with a controlled thickness, followed by formation of the sample well and/or other structures. FIG. 11-6 illustrates an exemplary embodiment of forming a sample well layer with dips. Waveguide 11-920 is formed within surrounding material layer 11-910. The surface of layer 11-910 is etched to expose waveguide 11-920 using grayscale lithography. Layer 11-910 is reformed with controlled thickness. Components such as surface plasmonic structures (not shown) may be formed. Sample well layer 11-912 forming sample well 11-932 is formed over layer 11-910.

In some embodiments, the entire array of sample wells are formed in a dip region of the substrate. For example, the distance between the bottom metal layer of the sample well and the the waveguide may be approximately 600 nm outside the region where the sample wells are formed, but may be reduced to approximately 350 nm where the sample well array is located. In this way, where a plurality of integrated devices are being formed on a wafer, the location of each integrated device on the wafer may be visually identified by the dip in the top surface of the wafer associated with each individual integrated device being formed.

C. Concentric Grating (Bullseye) Fabrication Process

A concentric grating, or bullseye, may be fabricated in any suitable way. In some embodiments, a concentric grating may be fabricated using standard photolithography processes and etching techniques. Any suitable dielectric material, such as $SiO_2$ or silicon nitride, may be used to form the concentric grating. In the embodiment illustrated in FIG. 11-7, a $SiO_2$ layer 11-1010 is used to make the concentric grating. The first step in the fabrication process may involve depositing a hard etch mask 11-1014 directly on top of the $SiO_2$ layer 11-1010. The next step of 11-1001 in the fabrication process may involve depositing a photoresist layer 11-1020 directly on top of an anti-reflection coating (ARC) layer 11-1022 onto the hard etch mask, which may include silicon. Conventional photolithographic techniques are used to create the bullseye pattern in the hard etch mask such as by patterning the concentric grating into the photoresist by step 11-1003 and etching the resist pattern into the ARC layer and hard etch mask by step 11-1005. The bullseye pattern is then transferred to the underlying $SiO_2$ layer using etching, for example reactive ion etching techniques to form the concentric grating by step 11-1007. The thickness of the concentric grating can be any suitable thickness. In the embodiment illustrated in FIG. 11-7, the etch depth is approximately 80 nm. Conventional techniques are used to strip the resist and etch mask residues and clean the surface of the concentric grating by step 11-1009. The sample well in layer 11-1012 may be fabricated directly on top of the concentric grating using the lift-off or etch processes by step 11-1011. In other embodiments, other layers may be deposited between the concentric grating and the sample well.

Alternatively, in some embodiments, the sample well may be positioned central to the concentric grating. This precise alignment of the sample well may be achieved in any suitable way. In the embodiment illustrated in FIG. 11-8, positioning of the sample well is achieved using a self-aligned fabrication process. The first step may involve forming the concentric grating according to the techniques described above. However, in FIG. 11-8, a Ti hard etch mask 11-1114 is deposited on top of the $SiO_2$ substrate 11-1110 by step 11-1101. The bullseye pattern is transferred to the Ti layer using etching, for example reactive ion etching, by step 11-1103. A layer of resist 11-1120 and a layer of anti-reflection coating (ARC) 11-1122 are deposited over the two center gaps in the Ti layer to cover the gaps and the center Ti pillar by step 11-1105. The bullseye pattern is then transferred to the $SiO_2$ substrate using conventional etching techniques to form the concentric grating by step 11-1107. The Ti layer is then removed using an isotropic wet etch by step 11-1109, for example, using peroxide, but leaving the center Ti pillar 11-1116 in place. The layer of resist is then stripped using conventional techniques. The metal sample well layer is then deposited on top of the concentric grating and the Ti pillar. Lastly, the metal-capped Ti pillar is removed using a lift-off process leaving a sample well precisely centered relative to the concentric grating by step 11-1111.

The precise alignment of the sample well may be achieved in various other ways. In the embodiment illustrated in FIG. 11-9, positioning of the sample well is achieved using an alternate self-aligned fabrication process. The first step may involve depositing the sample well layer (e.g., Al, Ti) 11-1212 directly on top of the $SiO_2$ concentric grating substrate 11-1210 by step 11-1201. A hard etch mask 11-1214 may then be deposited on top of layer 11-1212. The bullseye pattern is transferred to layer 11-1212 using conventional etching techniques by step 11-1203. A layer of resist 11-1220 and a layer of anti-reflection coating 11-1222 are deposited over the center gap in layer 11-1212 to cover the position where the sample well is to be formed by step 11-1205. The bullseye pattern is then transferred to the $SiO_2$ substrate using conventional etching techniques to form the concentric grating by step 11-1207. An additional metal layer is deposited on top of the layer 11-1212 such that the metal fills the cavities in the $SiO_2$ substrate 11-1210 and covers the resist layer 11-1214 by step 11-1209. In the embodiment illustrated in FIG. 11-9, Al is used as the additional metal layer but other suitable metals compatible with photolithographic processes may be used. Lastly, the metal-capped resist pillar 11-1230 is removed using a lift-off process leaving a nanoaperture precisely centered relative to the concentric grating by step 11-1211.

D. Microcavity Fabrication Process

A microcavity may be fabricated in any suitable way. In some embodiments, a microcavity may be fabricated using standard photolithography processes and etching techniques. The microcavity may include silicon nitride. The first step in the fabrication process may involve depositing silicon nitride on an oxide film. The silicon nitride layer may be patterned and etched to form the microcavity structure. After the silicon nitride is etched, an oxide is deposited over the silicon nitride feature and polished flat, such as via CMP. The sample well layer with a sample well may be fabricated above or near the microcavity. The microcavity may be offset from the sample well. FIG. 11-10 illustrates two possible fabrication designs for an offset microcavity structure.

E. Reflector Layer Below Waveguide Grating Coupler

The reflector layer underneath the grating coupler may be formed in any suitable way. The reflector layer may be a metal layer at a controlled distance from the waveguide grating coupler in order to improve excitation energy coupling into the waveguide. An exemplary fabrication process includes forming a recess in an oxide layer at the grating coupler location using lithography and/or etching. The reflector material is deposited and fills the trench. A resist layer is formed over the reflector and lithography and etching is used to remove excess reflector material. Oxide is formed over the reflector, such as through PECVD, to form a planar surface for waveguide fabrication.

F. Excitation Filter

An excitation filter may be formed by alternating layers of high and low index refractive material. Any suitable low refractive index materials may be used. Example low refractive index materials include silicon dioxide formed using PVD, PECVD, LPCVD, ALD, and/or evaporation techniques. Any suitable high refractive index material may be used. Example high refractive index materials include silicon, silicon nitride, titanium dioxide, and tantalum pentoxide.

G. Baffle

A baffle may be formed in a pixel between the sensor and the sample well to block and/or absorb stray light, such as excitation light from the waveguide, from being detected by the sensor. One technique is to deposit an absorbing layer over a raised section of the oxide layer, where the raised section overlays the sensor, followed by polishing via CMP. Another technique is to deposit an absorptive thin film over the oxide layer and then use lithography and etching techniques to form holes in the absorptive layer over the sensor.

H. Lens Fabrication Process: Refractive Lens

A refractive lens array may be created in any suitable way to improve efficiency of focusing of excitation into and collection of emission light from the sample well. In some embodiments, a refractive lens array may be a "gapless" array to minimize "dead zones" on the lens array. In the embodiment illustrated in FIG. 11-11, a refractive microlens array is shown with no gaps between individual lenses. In some embodiments, fabricating a "gapless" array may involve two etching steps. A first etch may establish the depth of the microlens topography by step 11-1801. A second etch may follow the first etch to eliminate the planar gaps between the individual microlenses by step 11-1803 such that one lens stops at the edge where another lens begins. The sum of the first and second etches defines the focal length. In the embodiment illustrated in FIG. 11-12, a top view of a microlens array is shown after the first HF etch (1), after the second HF etch (2), after the microlens array is coated with a higher refractive index material silicon nitride (3), and after the high refractive index material is polished and planarized (4).

Each refractive lens in the refractive lens array may be fabricated in any suitable way. An example refractive lens array is illustrated in FIG. 11-13 where a nanoaperture layer 11-2007 is fabricated on top of a transparent spacer layer 11-2001, which is on top of a dielectric lens layer 11-2003, which is on top of a substrate 11-2005. In some embodiments, a refractive lens may be fabricated using standard photolithography processes and etching techniques. Any suitable dielectric material, such as $SiO_2$ or silicon nitride, may be used to form the refractive lens. In the embodiment illustrated in FIG. 11-14, silicon nitride is used to fill in the $SiO_2$ substrate topography. The first step 11-2101 in the fabrication process may involve depositing a hard etch mask 11-2114 directly on top of a $SiO_2$ substrate 11-2110. Any suitable metal may be used for the hard etch mask 11-2114 that does not dissolve during the same etching process used for the $SiO_2$ layer. For example, Cr is used, but other metals are possible. The next step may involve applying a photoresist layer 11-2120 on top of the hard etch mask 11-2114. Conventional photolithographic techniques are used to create a circular pattern in the hard etch mask by step 11-2103. The circular pattern is then transferred to the underlying Cr layer using conventional etching techniques, such as reactive ion etching techniques, for example. The $SiO_2$ layer is etched using any suitable selective etching technique which can etch the $SiO_2$ but not the hard etch mask. For example, an isotropic wet etch using HF is used to create a concave surface in the $SiO_2$ layer. The hard etch mask 11-2114 is then removed using conventional etching techniques by step 11-2105. Optionally, a second wet etch using HF is performed to eliminate the gaps between lenses. To create the refractive lens, the cavity in the $SiO_2$ layer is filled with a high refractive index material layer 11-2118, such as silicon nitride, by step 11-2107. Finally, the top surface of the lens is planarized with conventional techniques by step 11-2109, such as chemical mechanical polishing, for example. A spacer layer 11-2124 may be deposited on top of the layer 11-2118 by step 11-2111. For example, a spacer layer made of ORMOCER™ may be spun-coat on top of the silicon nitride layer. Alternatively, a layer of $SiO_2$ may be deposited. The sample well may be fabricated directly on top of the refractive lens. In other embodiments, other layers may be deposited between the refractive lens and the sample well.

Alternatively, each refractive lens may include an anti-reflection layer to further improve optical efficiency. In some embodiments, an anti-reflection layer may coat a bottom, top, or all sides of a lens. In the embodiment illustrated in FIG. 11-15, an $SiO_2$ cavity 11-1810 is etch by step 11-1801, an anti-reflection layer 11-1822 is deposited on the etched cavity by step 11-1803, and a silicon nitride layer 11-1818 is deposited to fill the cavity by st. The silicon nitride layer is polished via CMP by step 11-1807 and a second antireflection layer 11-1826 is deposited on top of the polished silicon nitride layer by step 11-1809. Additional layers may be deposited on top of the antireflection layer, such as the spacer layer described above and shown as layer 11-1824 in FIG. 11-18. The anti-reflection layers may have the following parameters: index of refraction, $n_C$=sqrt($n_{oxide}$, $n_{nitride}$)=sqrt(1.46*1.91)=1.67; range of refractive index from 1.67 to 1.75; and, thickness $t=\lambda/(4*n_C)$=675 nm/(1.670*4)=101.1 nm. The anti-reflection layer may be deposited in any suitable way. For example, PECVD may be used. Alternatively, LPCVD may be used.

I. Lens Fabrication Process: Fresnel Lens

A diffractive optical element (DOE) may have any suitable shape and may be fabricated in any suitable way to improve the focusing of luminescence on the CMOS sensors and the sorting of the luminescence photons. In some embodiments, the DOE may include a section of a Fresnel lens. As illustrated in FIGS. 11-16 to 11-20, the DOE is characterized as a square section offset from the center of a Fresnel lens. As illustrated in FIG. 11-17, the DOE may comprise two unit cell layers where the first layer 11-2301 contains "small" features and the second layer 11-2303 contains "large" features. The unit cell layers may have any suitable pitch, and may further have varying pitch according to the optical design of the Fresnel lens. As illustrated in the example in FIG. 11-17, the small DOE layer has a pitch of 220 nm and the large DOE layer has a pitch of 440 nm. The large DOE layer may be overlaid onto the small DOE layer (or vice versa) to create a multilevel diffractive optic. FIG. 11-17 illustrates an example of an offset Fresnel array 11-2405 where large fiducial markers surround the offset Fresnel lens. Additionally, the offset Fresnel array may be positioned on top of the sensor to provide focusing and spectral separation of luminescence into the sensor.

Alternatively, a diffractive optical element (DOE) may be embedded underneath the nanoaperture to improve the focusing of the excitation energy into and collection of luminescence from the nanoaperture. In some embodiments, the embedded Fresnel lens positioned underneath the nanoaperture and the offset Fresnel lens positioned over the sensor may have a tiered structure with a variable period and variable step size. In other embodiments, only the offset Fresnel lens positioned over the sensor may have a variable period and variable step size. These diffractive lenses may be fabricated using standard photolithography processes and etching techniques. As illustrated in FIG. 11-18, the diffractive lens pattern 11-2501 is characterized as having a tiered structure comprising large steps (large pattern) and small steps (small pattern) on each larger step, both having a decreasing period when viewed from left to right. The fabrication process for the variable-period stepped diffractive lens may involve etching the large steps first, followed by etching the small steps as illustrated in FIG. 11-19, which may protect the corners of the large steps during the second etch. An alternate approach is to etch the small steps first on a flat substrate, followed by etching the large steps, as illustrated in FIG. 11-23. Any suitable dielectric material, such as $SiO_2$ or silicon nitride, $TiO_2$ or $Ta_2O_5$, may be used to form the fill-in layer for the diffractive lens and the tiered layer. In the embodiment illustrated in FIG. 11-26, silicon nitride is used to make the fill-in layer and $SiO_2$ is used to make the tiered layer.

The first step in the fabrication process of the tiered $SiO_2$ layer may involve depositing a hard etch mask 11-2214 directly on top of a $SiO_2$ layer 11-2210 followed by an anti-reflection layer 11-2222 followed by a photoresist layer 11-2220 by step 11-2201. Any suitable material may be used for the hard etch mask. For example, a-Si may be used for the hard etch mask shown in FIG. 11-26, but other materials are possible. The next step may involve applying an ARC and/or a photoresist layer on top of the a-Si hard etch mask. Conventional photolithographic techniques may be used to create the variable-period large binary pattern. The patterns are transferred to the underlying $SiO_2$ layer using conventional etching techniques, such as reactive ion etching techniques, for example. As shown in FIG. 11-19, $SiO_2$ layer 11-2210 is etched by step 11-2203. $SiO_2$ layer 11-2210 is striped and cleaned by step 11-2205 using conventional techniques.

The etch depth of a large diffractive lens step can be any suitable depth that accomplishes the desired focal length. In the embodiment illustrated in FIG. 11-19, this etch depth into the $SiO_2$ layer is approximately 684 nm for the large step. Conventional techniques are then used to strip the resist and etch mask residues and clean the surface of the $SiO_2$ layer. The next step may involve etching the small steps on each large step. In the embodiment illustrated in FIG. 11-19, each large steps comprises four smaller steps.

A second Si hard etch mask 11-2244 is then deposited on the patterned $SiO_2$ layer 11-2310 by step 11-2207. An ARC layer 11-2342 is then deposited on top of the Si layer 11-2610 followed by a photoresist etch mask layer 11-2640. The second variable-period small binary pattern is transferred to the photoresist and/or the ARC layer by step 11-2209, and $SiO_2$ layer 11-2210 is etch by to form a Fresnel lens.

In an alternative embodiment, the fabrication steps are similar to that described in FIG. 11-19, however, two small steps are etched per large step leaving four steps in total. In other embodiments, any number of steps may be used. The small steps are then etched into the $SiO_2$ layer 11-2210. The thickness of a small diffractive lens step can be any suitable thickness.

Additional stages in the fabrication process following creation of the tiered $SiO_2$ layer 11-2810 by step 11-2801 may involve filling the cavities by step 11-2803 with any suitable high index lens material 11-2818, such as silicon nitride, for example, and depositing a transparent layer 11-2828 to create an "embedded Fresnel lens", as illustrated in FIG. 11-20. The tiered structure used for the "embedded Fresnel lens" may have approximately the same and/or smaller size features as the tiered structure used for the offset Fresnel lens. Any method of depositing the silicon nitride may be used such as PECVD, for example. Optionally, the silicon nitride layer may be uniformly polished down until the top step of the $SiO_2$ material is exposed by step 11-2805. Alternatively, the silicon nitride layer 11-2818 is uniformly polished but the $SiO_2$ material is not exposed. In the embodiment illustrated in FIG. 11-21, the tiered structure 11-2910 is formed by step 11-2901, and filled with a high index material 11-2918 by step 11-2903, and polished by step 11-2905. A second layer 11-2928 of $SiO_2$ is then deposited via PECVD on top of the polished silicon nitride layer 11-2918 and polished via CMP by step 11-2907. In some embodiments, the spacer layer 11-2928 may have a thickness equal to the focal length in that spacer layer material. Additionally, other suitable transparent spacer layers may be deposited on top of the silicon nitride layer by step 11-2909. The sample well layer may then be fabricated on top of the transparent spacer layer and/or additional layers.

Alternatively, in the embodiment illustrated in FIG. 11-22, the tiered layer 11-3018 for the diffractive lens is made of silicon nitride. The silicon nitride layer 11-3018 may be deposited at any suitable thickness on top of substrate 11-3010 followed by etch mask 11-3014, ARC layer 11-3022 and photoresist layer 11-3020. In the embodiment illustrated in FIG. 11-22, the silicon nitride layer is approximately 1 um thick by step 11-3001. The fabrication processes may be similar to the one described above in regards to creating the tiered, variable-period diffractive lens layer in $SiO_2$. Optionally, a different hard mask may be used to create the silicon nitride tiered layer by step 11-3003. The silicon nitride tiered layer may have approximately the same and/or smaller size features as the $SiO_2$ tiered layer. After the silicon nitride tiered layer is made, the silicon nitride layer may be coated in any suitable dielectric material 11-3028. In the embodiment illustrated in FIG. 11-30, the silicon nitride layer is coated with transparent (e.g., $SiO_2$) layer 11-3028 by step 11-3005. The $SiO_2$ layer may be deposited using conventional deposition processes such as PECVD, for example. The $SiO_2$ layer may then be polished to create a flat, planar surface. The sample well layer may then be fabricated on top of the $SiO_2$ layer and/or additional layers.

Certain features of the diffractive optic may require a certain degree of uniformity and/or accuracy during the fabrication process to yield a structure with the desired optical properties. For example, the etch depth of the large and small steps may require a certain degree of accuracy. In some embodiments, an etch depth within 50 or 10% of the target may be required to achieve the desired power efficiency into the focal spot sample well. Additionally, the etching of the lens features may require a certain degree of uniformity. For example, etch uniformity within 5% (or 50 nm) is required to achieve the desired focal length.

Any of the lenses described above may be fabricated using any suitable deposition and etching processes to create improved optical properties. By way of example and not limitation, PECVD may be used. The deposition parameters may be tuned in any suitable way to reduce autoluminescence, reduce lens absorption of luminescence, and/or create a high index of refraction. For example, a reduced autoluminescence and lens absorption may be achieved by reducing the density of Si—Si bonds, which may form silicon nanocrystals, during deposition of silicon nitride. In some embodiments, the input gases and their ratios may be modified to reduce the density of Si—Si bonds and silicon nanocrystals. For example, $SiH_4$ and $N_2$ may be used and their ratios adjusted in any suitable way to reduce the density of Si nanocrystals. In other embodiments, $SiH_4$ and $NH_3$ may be used and their ratios adjusted in any suitable way to reduce the density of Si—Si bonds and silicon nanocrystals. For example, the ratio of $NH_3$ to $SiH_4$ may be at least 10:1. Additionally, tuning the frequencies that control the plasma during PECVD may be used to improve optical properties. For example, the low frequency (e.g. below 0.5 MHz) to high frequency (e.g. above 10 MHz) ratio may be at least 1:1.

Additionally, the above described deposition parameters may tune the lens index of refraction to improve optical properties. In some embodiments, the index of refraction for a silicon nitride lens may be less than n=1.92 and associated with a wavelength of 633 nm for a suitable low autoluminescence effect and/or a suitable low absorption loss. The tuned qualities described above may be related to, proportional, correlated, associated with and/or dependent each other. For example, an index of refraction of n=1.92 is indicative of a low luminescence and low absorption loss which is related to a low density of Si—Si bonds and silicon nanocrystals for a lens made of silicon nitride.

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An integrated device comprising:
    a plurality of sample wells arranged on a surface of the integrated device;
    at least one waveguide configured to deliver excitation energy to a vicinity of a portion of the plurality of sample wells;
    a grating coupler positioned beneath the surface, wherein the grating coupler is configured to receive excitation energy incident on the surface from an external optical source and couple the excitation energy into the at least one waveguide; and
    a reflector layer positioned to reflect light passing through the grating coupler towards the grating coupler, wherein the reflector layer includes at least one opening, and the integrated device further comprises at least one monitoring sensor positioned to receive light through the at least one opening.

2. The integrated device of claim 1, wherein the grating coupler is positioned in a region of the integrated device separate from the plurality of sample wells.

3. The integrated device of claim 1, wherein the grating coupler has a width that tapers in a direction towards the at least one waveguide.

4. The integrated device of claim 1, wherein the at least one waveguide is tapered in a dimension perpendicular to a direction of light propagation along the at least one waveguide.

5. The integrated device of claim 1, wherein the integrated device further comprises:
    a plurality of sensors configured to receive light from the plurality of sample wells.

6. The integrated device of claim 5, wherein the integrated device further comprises:
    at least one baffle layer positioned between the plurality of sensors and the at least one waveguide, wherein the at least one baffle layer includes openings corresponding to individual sample wells of the plurality of sample wells.

7. The integrated device of claim 6, wherein the at least one baffle layer is further positioned between the grating coupler and a layer of the integrated device that includes the plurality of sensors.

8. The integrated device of claim 5, wherein the integrated device further comprises:
    at least one filter positioned between the at least one waveguide and the plurality of sensors.

9. The integrated device of claim 8, wherein the at least one filter is configured to suppress transmission of the excitation energy.

10. The integrated device of claim 8, wherein the at least one filter includes a polarization filter.

11. The integrated device of claim 1, wherein the at least one monitoring sensor is configured to generate a signal indicative of alignment of an optical source to the grating coupler.

12. The integrated device of claim 1, wherein the integrated device further comprises at least one metal layer and the plurality of sample wells extend below the at least one metal layer.

13. The integrated device of claim 1, wherein individual sample wells of the plurality of sample wells have tapered sidewalls.

14. A method of forming an integrated device, the method comprising:
    forming a plurality of sample wells arranged on a surface;
    forming at least one waveguide configured to deliver excitation energy to a vicinity of a portion of the plurality of sample wells;
    forming a grating coupler positioned beneath the surface, wherein the grating coupler is configured to receive excitation energy incident on the surface from an external optical source and couple the excitation energy into the at least one waveguide;
    forming a reflector layer positioned to reflect light passing through the grating coupler towards the grating coupler, wherein the reflector layer includes at least one opening; and forming at least one monitoring sensor positioned to receive light through the at least one opening.

15. The method of claim 14, wherein the method further comprises:
forming a plurality of sensors configured to receive light from the plurality of sample wells;
forming at least one baffle layer positioned between the plurality of sensors and the at least one waveguide; and
forming openings in the at least one baffle layer that correspond to individual sample wells of the plurality of sample wells.

16. The method of claim 14, wherein the method further comprises:
forming a plurality of sensors configured to receive light from the plurality of sample wells; and
forming at least one filter positioned between the at least one waveguide and the plurality of sensors.

17. The method of claim 14, wherein forming the plurality of sample wells further comprises forming at least one metal layer and forming the plurality of sample wells through the at least one metal layer to extend below the at least one metal layer.

* * * * *